United States Patent
Wang et al.

(10) Patent No.: US 12,350,322 B2
(45) Date of Patent: Jul. 8, 2025

(54) PEPTIDE IMMUNOGENS TARGETING INTERLEUKIN 6 (IL-6) AND FORMULATIONS THEREOF FOR IMMUNOTHERAPY OF DISEASES IMPACTED BY IL-6 DYSREGULATION

(71) Applicant: UNITED BIOMEDICAL, INC., Hauppauge, NY (US)

(72) Inventors: Chang Yi Wang, Cold Spring Harbor, NY (US); Feng Lin, Hauppauge, NY (US); Jiun Bo Chen, Taipei (TW); Shuang Ding, Hauppauge, NY (US)

(73) Assignee: United Biomedical, Inc., Hauppauge, NY (US)

( * ) Notice: Subject to any disclaimer, the term of this patent is extended or adjusted under 35 U.S.C. 154(b) by 722 days.

(21) Appl. No.: 17/419,163

(22) PCT Filed: Dec. 28, 2019

(86) PCT No.: PCT/US2019/068854
§ 371 (c)(1),
(2) Date: Jun. 28, 2021

(87) PCT Pub. No.: WO2020/140106
PCT Pub. Date: Jul. 2, 2020

(65) Prior Publication Data
US 2022/0105163 A1 Apr. 7, 2022

Related U.S. Application Data

(60) Provisional application No. 62/786,192, filed on Dec. 28, 2018.

(51) Int. Cl.
| | | |
|---|---|---|
| A61K 39/00 | (2006.01) | |
| A61K 39/008 | (2006.01) | |
| A61P 29/00 | (2006.01) | |
| C07K 16/24 | (2006.01) | |

(52) U.S. Cl.
CPC ...... *A61K 39/008* (2013.01); *A61K 39/00114* (2018.08); *A61P 29/00* (2018.01); *C07K 16/248* (2013.01); *A61K 2039/505* (2013.01); *A61K 2039/545* (2013.01); *A61K 2039/55505* (2013.01); *A61K 2039/55561* (2013.01); *A61K 2039/55566* (2013.01); *A61K 2039/6031* (2013.01); *A61K 2039/627* (2013.01); *A61K 2039/804* (2018.08); *A61K 2039/884* (2018.08)

(58) Field of Classification Search
CPC ...................... A61K 39/0008; A61K 39/00114
See application file for complete search history.

(56) References Cited

U.S. PATENT DOCUMENTS

| | | |
|---|---|---|
| 9,102,752 B2 | 8/2015 | Wang |
| 9,834,603 B2 | 12/2017 | Garcia-Martinez et al. |
| 2006/0147417 A1 | 7/2006 | Ashman et al. |
| 2010/0297177 A1 | 11/2010 | Buening et al. |
| 2014/0271690 A1 | 9/2014 | Wang |
| 2014/0322161 A1 | 10/2014 | Desallais et al. |
| 2017/0333539 A1 | 11/2017 | Desallais et al. |

FOREIGN PATENT DOCUMENTS

| | | |
|---|---|---|
| CN | 105198982 A | 12/2015 |
| JP | 2020514668 A | 5/2020 |
| MX | 2009012812 A | 2/2010 |
| RU | 2509574 C2 | 3/2014 |
| WO | 2018232369 A1 | 12/2018 |
| WO | 2020132275 A1 | 6/2020 |

OTHER PUBLICATIONS

PCT International Search Report issued during the prosecution of PCT US2019-068854.
Russian Search Report issued during the prosecution of Russian Patent Application No. RU 2021122137.
L. Desallais et al., "Immunization against an IL-6 peptide induces anti-IL-6 antibodies and modulates the Delayed-Type Hypersensitivity reaction in cynomolgus monkeys", Scientific Reports {6: 19549} DOI: 10.1038/srep19549.
Extended European Search Report dated Nov. 15, 2022, issued during the prosecution of European Patent Application No. EP 19905715.9.
Japanese Office Action drafted Dec. 28, 2023, issued during the prosecution of Japanese Patent Application No. 2021-537984.
Singapore Written Opinion dated Feb. 24, 2023, issued during the prosecution of 11202107042W.
L. Zhang et al., "Effect of inserted spacer in hepatic cell-penetrating multifunctional peptide component on the DNA intracellular delivery of quaternary complexes based on modular design", Intl Jnl of Nanomedicine, 2016:11 pp. 6283-6295.
S. W. Polyak et al., "Introduction of spacer peptides N-terminal to a cleavage recognition motif in recombinant fusion proteins can improve site-specific cleavage", Protein Engineering, vol. 10, No. 6, pp. 615-619, 1997.
Chinese Office Action dated Nov. 20, 2023, issued during the prosecution of CN 2019800869766.

(Continued)

*Primary Examiner* — Prema M Mertz
(74) *Attorney, Agent, or Firm* — Troutman Pepper Locke LLP; Peter N. Fill; Nicholas J. DiCeglie, Jr.

(57) ABSTRACT

The present disclosure is directed to individual peptide immunogen constructs targeting portions of the Interleukin-6 (IL-6) protein, compositions containing the constructs, antibodies elicited by the constructs, and methods for making and using the constructs and compositions thereof. The disclosed IL-6 peptide immunogen constructs contain a B cell epitope from IL-6 linked to a heterologous T helper cell (Th) epitope directly or through an optional heterologous spacer. The IL-6 peptide immunogen constructs stimulate the generation of highly specific antibodies directed to the IL-6 receptor (IL-6R) binding site for the prevention and/or treatment of diseases impacted by IL-6 dysregulation.

8 Claims, 32 Drawing Sheets
Specification includes a Sequence Listing.

(56) References Cited

OTHER PUBLICATIONS

Chinese Office Action dated Jul. 30, 2024, issued during the prosecution of CN 2019800869766.
Indonesia Office Action dated Mar. 2, 2023, issued during the prosecution of P00202105575.

Figure 1
Alignment of IL6 sequences from human, macaque, mouse and rat species (SEQ ID NOs: 227-230).

```
                    -20              -10               1                10                20
Human       MNSFSTSAFGPVAFSIGLLLVLPAAFPAPVPPGEDSKDVAAPHRQPLTSSERIDKQ
Macaque     MNSFSTSAFGPVAFSIGLLLVLPAAFPAPVLPGEDSKNVAAPHSQPLTSSERIDKH
Mouse       MKFLSARDFHPVAF-LGLMLVTTTAFPTSQVRRGDFTEDTTPNR-PVYTTSQVGGL
Rat         MKFLSARDFQPVAF-LGLMLLTATAFPTSQVRRGDFTEDTTHNR-PVYTTSQVGGL 30            40            50            60            70            80
Human       IRYILDGISALRKETCNKSNMCESSKEALAENNLNLPKMAEKDGCFQSGFNEETCL
Macaque     IRYILDGISALRKETCNRSNMCESSKEALAENNLNLPKMAEKDGCFQSGFNEDTCL
Mouse       ITHVLWEIVEMRKELCNGNSDCMNNDDALAENNLKLPEIQRNDGCYQTGYNQEICL
Rat         ITYVLREILEMRKELCNGNSDCMNSDDALSENNLKLPEIQRNDGCFQTGYNQEICL 90           100           110           120           130
Human       VKIITGLLEFEVYLEYLQNRFESS--EEQARAVQMSTKVLIQFLQKKAKNLDAITTP
Macaque     VKIITGLLEFEVYLEYLQNRFESS--EEQARAVQMSTKVLIQFLQKKAKNLDAITTP
Mouse       LKISSGLLEYHSYLEYMKNNLKDNKKDKARVLQRDTETLIHIFNQEVKDLHKIVLP
Rat         LKICSGLLEFRFYLEFYKNNLQDNKKDKARVIQSNTETLVHIFKQEIKDSYKIVLP 140           150           160           170           180
Human       DPTTNASLLTKLQAQ-NQWLQDMTTHLILRSFKEFLQSSLRALRQM  (SEQ ID NO. 227)
Macaque     EPTTNASLLTKLQAQ-NQWLQDMTTHLILRSFKEFLQSNLRALRQM  (SEQ ID NO. 228)
Mouse       TPISNALLTDKLESQ-KEWLRTKTIQFILKSLEEFLKVTLRSTRQT  (SEQ ID NO. 229)
Rat         TPTSNALLMEKLESQ-KEWLRTKTIQLILKALEEFLKVTMRSTRQT  (SEQ ID NO. 230)
```

High immunogenicity of IL-6 immunogens in guinea pig

IgGs raised by IL-6 peptide immunogens are crossreactive with recombinant human, monkey and rodent IL-6 proteins

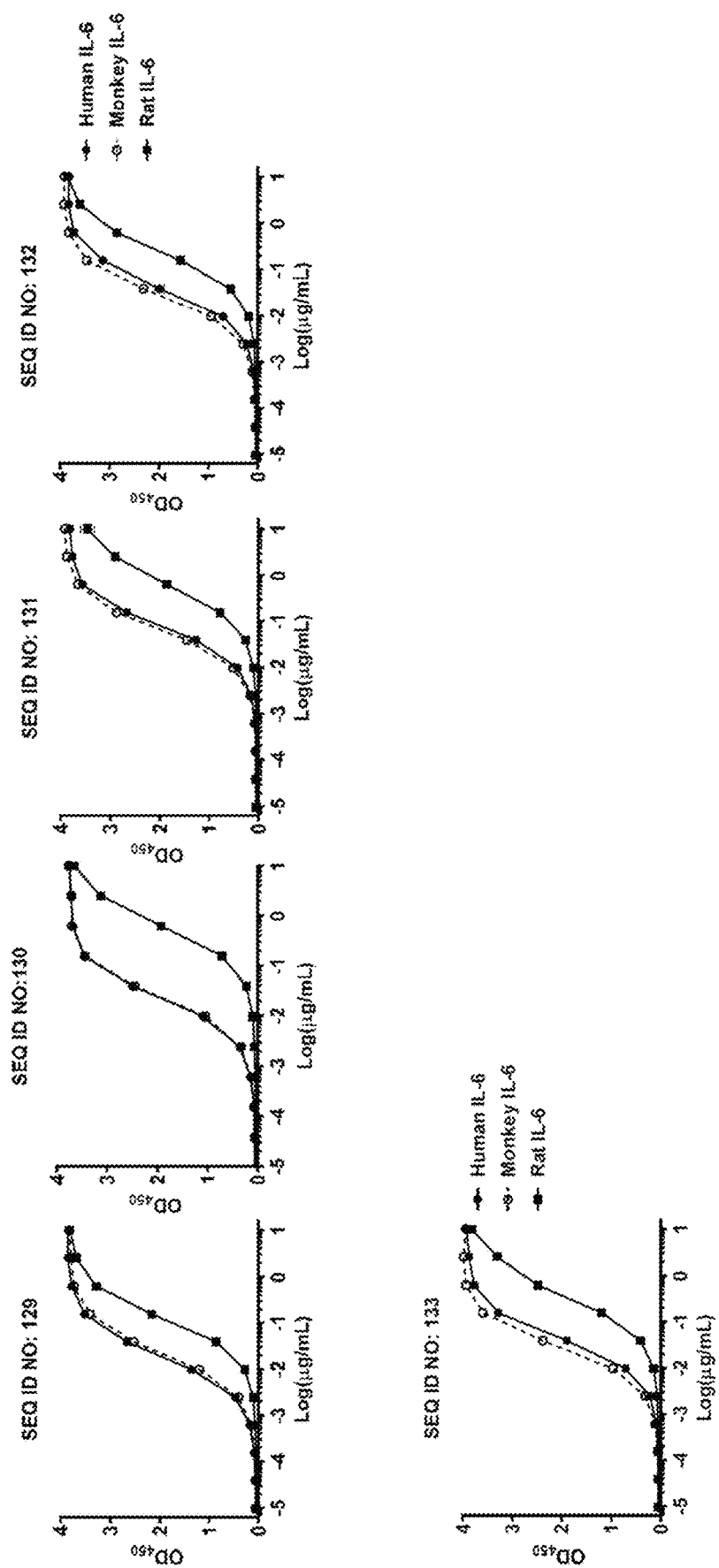

IgGs elicited by IL-6 peptide immunogens were able to inhibit IL-6 and IL-6R interaction via cis-signaling mode IgGs elicited by IL-6 peptide immunogens were able to inhibit IL-6 and IL-6R interaction via trans-signaling mode IgGs elicited by IL-6 peptide immunogens were able to suppress IL-6-induced STAT3 phosphorylation

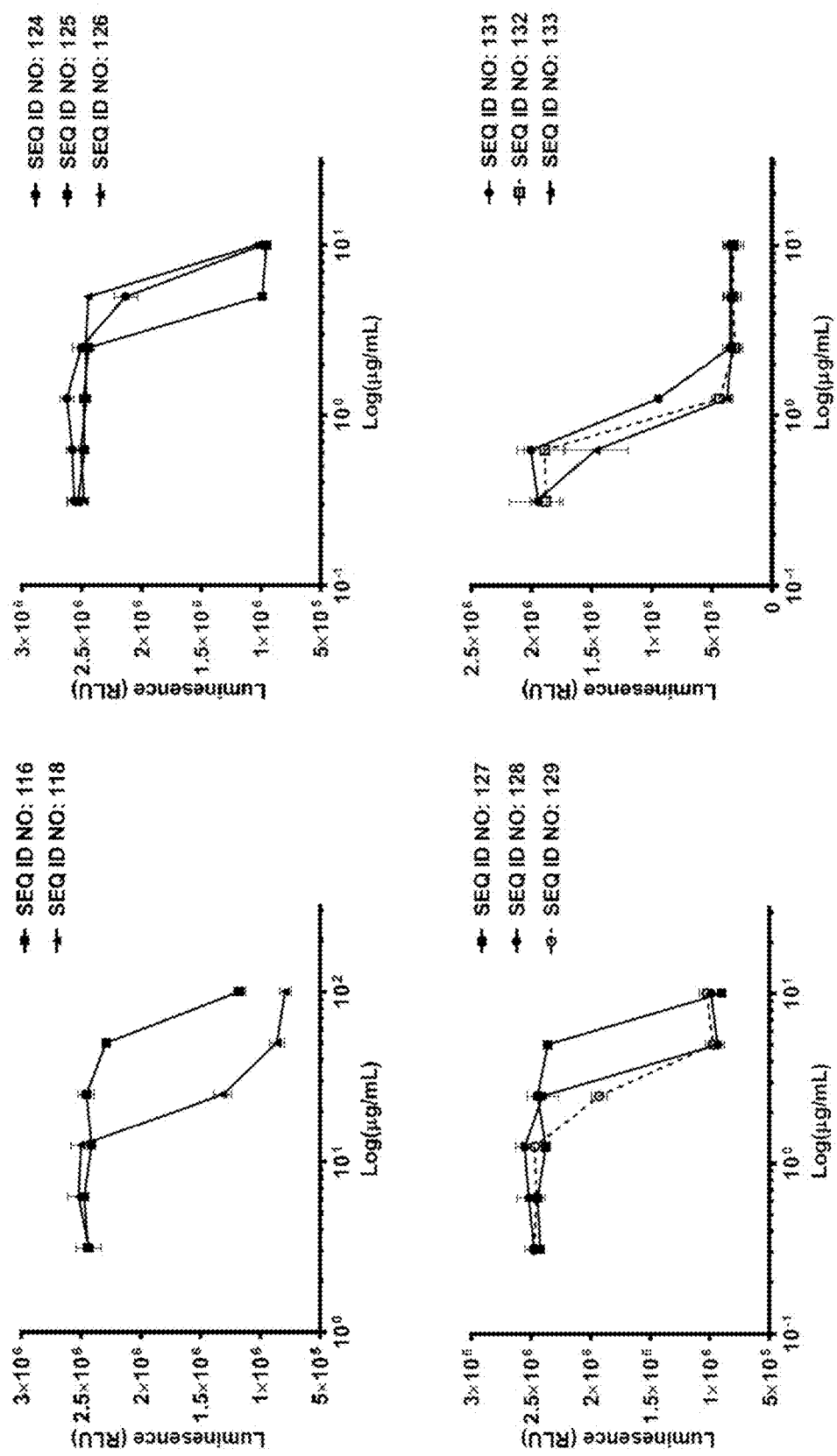

IgGs elicited by IL-6 peptide immunogens were able to suppress IL-6-dependent cell growth of human TF-1 cells IgGs elicited by IL-6 peptide immunogens were able to suppress IL-6-induced MCP-1 production of human U937 cells IgGs elicited by IL-6 peptide immunogens were able to suppress IL-6-induced MCP-1 production of human U937 cells

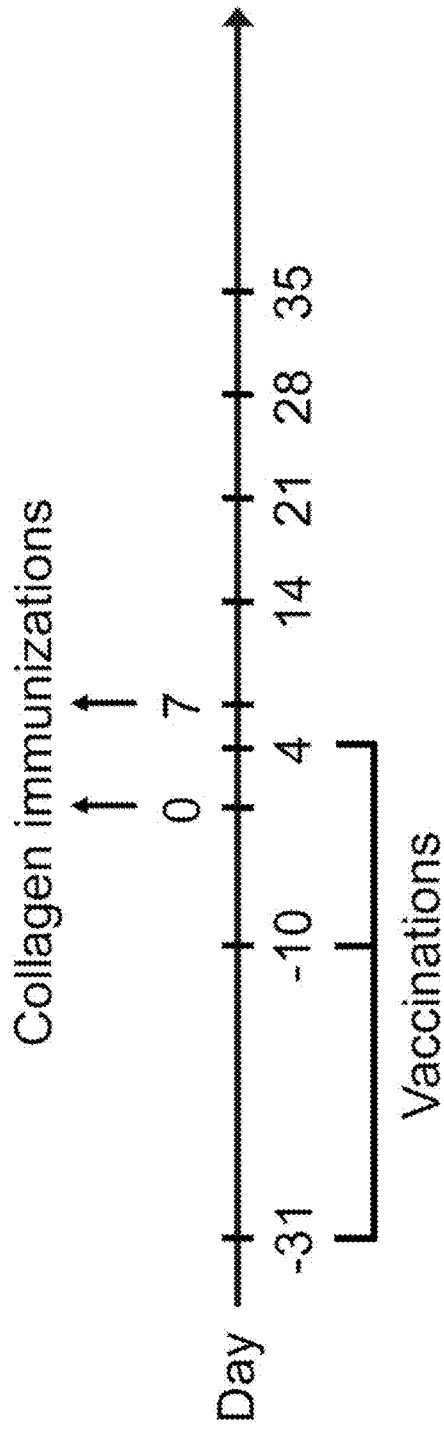

Figure 9
Experimental protocol for efficacy evaluation of rat IL-6 peptide constructs in rat collagen-induced arthritis (CIA) model

- *Animals:* Lewis rat
- *Groups:* Placebo and 2 vaccination groups
- *Adjuvant:* ISA 51 and CpG
- *Vaccine dose:* Immunize rats on day -31, -10 and 4 with 45 μg in 0.5 ml vaccine or adjuvant placebo by *i.m.* route.
- *Collagen:* Inject at the base of the tail (100 μg in 100 μL) on day 0 and 7 with bovine type II collagen/IFA emulsion by *i.d.* route.

Rat IL-6 peptide constructs (SEQ ID NOs: 148 and 157) elicited anti-IL-6 Ab titers in Lewis rats Rat vaccinated with rat IL-6 immunogens (SEQ ID NOs: 148 & 157) showed low arthritis score in a CIA model Rat vaccinated with rat IL-6 immunogens (SEQ ID NOs: 148 and 157) showed mild-to-moderate paw swelling in a CIA model Rat IL-6 immunogens (SEQ ID NOs: 148 and 157) attenuated the release of neutrophils from bone marrow into circulation

POC study protocol in a rat CIA model

- *Animals*: Lewis rat (female).
- *Groups*: Group 1 (placebo), Group 2 (SEQ NO: 148/ISA 51) and Group 3 (SEQ NO: 148/ISA 51/CpG).
- *Vaccine dose*: Immunize rats on day -7, 7, 14, 21 and 28 with 45 µg in 0.5 ml vaccine or adjuvant placebo by *i.m.* route.
- *Collagen*: Inject at the base of the tail (100 µg/100 µL) on day 0 and 7 with bovine type II collagen/IFA emulsion by *i.d.* route.

High immunogenicity of rat IL-6 peptide construct (SEQ ID NO: 148) in rats

Arthritis symptoms were reduced significantly throughout the study

Figure 18
Ankle joint disruption was alleviated
H&E stain (20X)
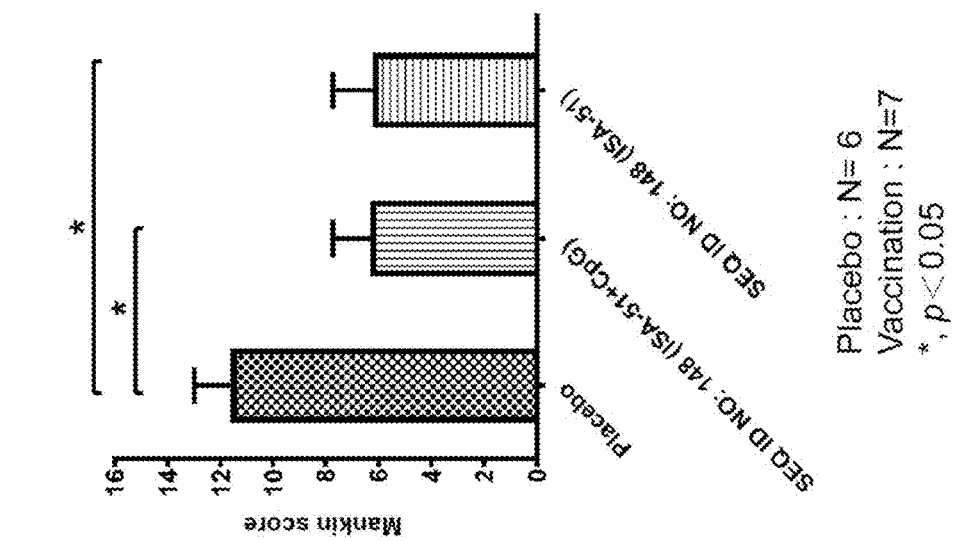
Pathological scoring
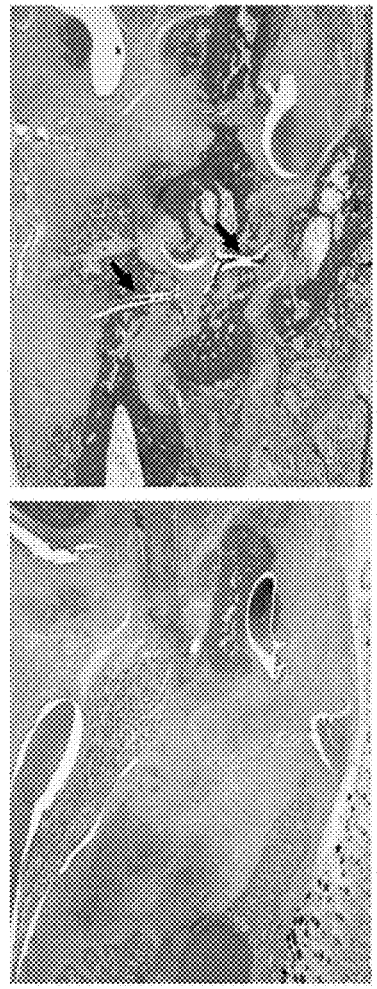
Arrows indicate joint space.

Production of tissue TNF-α, IL-17 and MCP-1 was significantly suppressed

MONTANIDE ISA 51 elicited greater anti-IL-6 IgG titer than ADJU-PHOS

IL-6 vaccination at the dose of 150 µg/dose partially reversed body weight loss

IL-6 vaccination at the doses of 45 and 150 µg/dose significantly reduce hind paw swelling The macroscopic observation of hind paw on day 24

IL-6 vaccination at the doses of 45 and 150 µg/dose significantly reduce arthritis symptoms IL-6 vaccination at the doses of 45 and 150 µg/shot significantly attenuated neutrophilia IL-6 vaccination at the doses of 45 and 150 μg/shot significantly attenuated platelet release AST (liver function) in rat CIA model Effects of UBITh®, peptide linker and adjuvant on immunogenicity 006# PEPTIDE IMMUNOGENS TARGETING INTERLEUKIN 6 (IL-6) AND FORMULATIONS THEREOF FOR IMMUNOTHERAPY OF DISEASES IMPACTED BY IL-6 DYSREGULATION This application is a national phase entry under 35 U.S.C. § 371 of International Application Number PCT/US2019/068854, filed Dec. 28, 2019, entitled "PEPTIDE IMMUNOGENS TARGETING INTERLEUKIN 6 (IL-6) AND FORMULATIONS THEREOF FOR IMMUNOTHERAPY OF DISEASES IMPACTED BY IL-6 DYSREGULATION", which claims the benefit of U.S. Provisional Application Ser. No. 62/786,192, filed Dec. 28, 2018, the entire contents of these prior applications are hereby incorporated by reference in their entireties as if fully set forth herein.

FIELD OF THE INVENTION

This disclosure relates to peptide immunogen constructs targeting interleukin 6 (IL-6) and formulations thereof for immunotherapy of diseases impacted by IL-6 dysregulation.

BACKGROUND OF THE INVENTION

IL-6 is a small (~25 kD) secreted glycoprotein composed of 184 amino acids (Table 1) characterized by a four-helix bundle structure. It is produced by several cell types, including leukocytes (T- and B-lymphocytes, monocytes, macrophages), fibroblasts, osteoblasts, keratinocytes, endothelial cells, mesangial cells, adipocytes, skeletal myocytes, cardiomyocytes, brain cells (astroglia, microglia, neurons), and some tumor cells in response to various stimuli, such as lipopolysaccharide and other bacterial products, viruses, cytokines (TNF-α, IL-1, transforming growth factor (TGF)-β), adenosine triphosphate, parathormone, vitamin D3, homocysteine, and angiotensin II (Sebba, 2008).

Circulating IL-6 is found in the blood of healthy humans at low concentration (≤1 pg/mL), and significantly increases during inflammatory responses, reaching concentrations in the range of ng/mL during sepsis. IL-6 contributes critically to host defense against infections and tissue injuries by stimulating acute-phase immune response and hematopoiesis. In addition, it also regulates metabolic, regenerative, and neural processes under physiological conditions. Once released, IL-6 exerts its pleiotropic biological effects by activating a unique IL-6 receptor (IL-6 R) signaling system, including the IL-6R and downstream signaling molecules.

The IL-6R is constituted by two chains: (1) an IL-6 binding chain or IL-6Rα, which exists in two forms, i.e., (a) an 80 kD transmembrane IL-6Rα (mIL-6Rα), and (b) a 50-55 kD soluble IL-6Rα (sIL-6Rα) and (2) a 130 kD signal-transducing chain, named IL-6Rβ (or gp130).

The membrane IL-6Rα (or mIL-6Rα) is expressed on the surface of a limited number of cell types, i.e., hepatocytes, megakaryocytes, and leukocytes, including monocytes, macrophages, neutrophils, and T- and B-lymphocytes. The soluble IL-6Rα (or sIL-6Rα) is present in human plasma (25-75 ng/mL) and tissue fluids and can be generated by proteolytic cleavage (shedding) of the mIL-6Rα by metalloproteases (A Disintegrin And Metalloproteinases (i.e., ADAM)), or, in minor part, via alternative splicing by omission of the transmembrane domain. The membrane IL-6Rβ is ubiquitously expressed on all human cells (Sebba, 2008).

Upon biding to IL-6Rα (either mIL-6Rα or sIL-6Rα), IL-6 induces the homodimerization of the IL-6Rα/IL-6Rβ chains, resulting in the formation of a hexamer (comprising two IL-6, two IL-6Rα, and two IL-6Rβ proteins), which in turn triggers the downstream signaling cascade (Rose-John, et al., 2017).

Cellular activation via IL-6 binding to mIL-6Rα is named "classic signaling". All other cells not expressing mIL-6Rα obtain their IL-6 signals by "trans-signaling": where IL-6 binds to the circulating sIL-6Rα, and this complex forms the signaling complex with IL-6Rβ on the cell surface. Trans-signaling can occur in a broad range of human cells, thus contributing to explain the pleiotropic activities of IL-6. It is currently understood that homeostatic and regenerative activities of IL-6 are mediated by classical signaling, while proinflammatory effects mainly result from trans-signaling pathway activation. Increasing evidence indicates that IL-6 trans-signaling is particularly involved in disease development. A soluble form of the sIL-6Rβ (or sgp130) was also detected in the circulation at relatively high concentrations, mainly produced by alternative splicing. Since sIL-6Rβ can bind to the IL-6/sIL-6Rα complex, it acts as a natural and specific inhibitor of IL-6 mediated trans-signaling while classic signaling is not affected by sIL-6Rβ.

While IL-6Rα is a unique binding receptor for IL-6, the or IL-6Rβ (or gp130) signal-transducing chain is shared by members of the IL-6 family, comprising leukemia inhibitory factor, oncostatin M, ciliary neurotrophic factor, IL-11, cardiotrophin-1, neuropoietin-1, IL-27, and IL-35.

After IL-6 binding, receptor homodimerization promotes the interaction between the IL-6Rβ (or gp130) chain with the tyrosine kinase JAK (Janus kinase), resulting in their mutual transactivation. In turn, JAK activation triggers three main intracellular signaling pathways, via phosphorylation of two key proteins, i.e., 1) the Src Homology domain-containing protein tyrosine Phospatase-2 (SHP-2), and 2) the signal transducer and activator of transcription proteins (STAT1-STAT3). Once phosphorylated, SHP-2 can interact with Grb2 (growth factor receptor bound protein 2) leading to the activation of the Ras/ERK/MAPK (rat sarcoma protein/extracellular signal-regulated kinase/mitogen-activated protein kinase) cascade; and/or activate the PI3K/Akt (phosphoinositol-3 kinase/protein kinase B) pathway. On the contrary, phosphorylation of STATs proteins induces the formation of heterodimers (STAT1/STAT3) or homodimers (STAT1/STAT1 and/or STAT3/STAT3), which subsequently translocate into the nucleus. In all cases, the activation of these intracellular pathways leads to the induction of the transcription of multiple target genes accounting for the pleiotropic biological activities of IL-6 (Lazzerini, et al., 2016).

IL-6 exerts a wide range of biological activities, crucially implicated in the activation of the acute inflammatory response, as well as in the transition from innate to acquired immunity. IL-6 has several additional roles in a variety of other processes, including metabolism, cognitive function, and embryonic development.

IL-6 effects on the activation of the acute inflammatory response has been studied. When infections or tissue injuries of various origins occur, a systemic acute-phase response is rapidly induced to neutralize pathogens and prevent their further invasion, minimize tissue damage, and promote wound healing. This acute-phase response, consisting of fever and production of acute-phase proteins by hepatocytes, is mainly driven by IL-6.

To that fact, IL-6 increases body temperature by acting on the neurons of the preoptic hypothalamic region involved in thermoregulation and stimulates the liver to synthesize acute-phase proteins, such as C-reactive protein (CRP), fibrinogen, complement component C3, serum amyloid A, hepcidin, haptoglobin, α1-acid glycoprotein, α1-antitrypsin, α1-antichymotrypsin, and ceruloplasmin, while albumin, transferrin, fibronectin, transthyretin, and retinol-binding protein ("negative" acute-phase proteins) production is inhibited.

In addition, IL-6 promotes monocyte-to-macrophage differentiation, stimulates the maturation of myeloid precursors and megakaryocytes leading to neutrophilia and thrombocytosis, induces angiogenesis via vascular endothelial growth factor production, enhances lymphocyte and neutrophil trafficking by upregulating adhesion molecule expression on endothelial cells (particularly, the intracellular adhesion molecule-1 (ICAM-1) and the vascular cell adhesion molecule (VCAM-1)), increases antibody production by B lymphocytes, and potentiates the proliferation of T helper (TH) lymphocytes promoting their differentiation toward TH2 or TH17 cells. In all cases, these changes contribute, via different but synergistic mechanisms, to realize an integrated response finalized to host defense.

Besides its key involvement in the immunoinflammatory response, IL-6 also plays an important role under physiological conditions by modulating a number of multisystemic functions such as embryogenesis, glucose and lipid metabolism, bone remodeling, liver regeneration, neural tissue homeostasis, cognitive function, sleep, memory, pain, and emotional behavior.

The knowledge of these extra-immunoinflammatory effects may help explain the pathogenesis of some systemic manifestations observed in Rheumatoid Arthritis (RA) and other chronic inflammatory diseases characterized by persistently elevated IL-6 levels.

In RA patients, the impact of this cytokine on metabolism and bone homeostasis is of particular pathophysiological and clinical interest.

Adipose tissue considerably contributes to IL-6 production under physiological conditions, accounting for ~35% of circulating IL-6 levels. During prolonged exercise, contracting skeletal muscle becomes a major source of IL-6, increasing its plasma levels up to 100-fold. IL-6 stimulates lipolysis (and inhibits lipogenesis) in adipocytes, and increases cholesterol and triglyceride uptake by peripheral tissues via enhancement of the very low-density lipoprotein receptor expression, promoting body weight loss and serum lipid level reduction. In addition, IL-6 enhances insulin sensitivity in hepatocytes and muscle cells, improving glucose utilization and tolerance. Although these effects suggest that this cytokine may be part of a physiological mechanism underlying the exercise-induced increase of insulin activity that enhances endurance. However, chronic elevation of IL-6, due in part for example to long term excessive exercise, could lead to insulin resistance in liver and adipose cells.

With regard to the impact on bone tissue, IL-6 affects bone resorption and bone formation that are required for skeletal development, growth and maintenance by regulating differentiation and activity of osteoblasts, osteoclasts, and chondrocytes. The role of IL-6 in enhancing the expression of receptor activator of nuclear factor-kB ligand (RANKL) on the surface of stromal/osteoblastic cells, which in turn stimulates osteoclast differentiation and bone resorption, can promote bone remodeling with potential positive effects for bone homeostasis under physiological conditions. In RA, it's exaggerated and long-lasting activation induces abnormal osteoclastogenesis, leading to osteoporosis and bone destruction.

An updated review on IL-6, IL-6 receptor, IL-6 signal transduction, pleotropic biological effects of IL-6, effects on the immune-inflammatory response, extra-immunoinflammatory effects, and the role of IL-6 in various pathological states including rheumatoid arthritis, autoimmune process development, articular damage, extra-articular manifestations is included here by reference (Lazzerini, P., et al., 2016) where supporting documents can be found for statements made in the above background section.

Since IL-6 is a pleiotropic cytokine that is involved in the physiology of virtually every organ system and plays a major role in response to injury or infection, aberrant expression of IL-6 has been implicated in diverse human illnesses, most notably inflammatory and autoimmune disorders, coronary artery and neurologic disease, gestational problems, and neoplasms.

There is an interest in developing antibodies to inhibit the IL-6 binding to IL6R (i.e. IL-6Rα and IL-6Rβ/or gp130) complex as therapy against many of these diseases. The first such antibody that was developed is Tocilizumab, followed by Sarilumab, both of which target IL-6R and have been approved for treatment of rheumatoid arthritis, Castleman's disease and systemic juvenile idiopathic arthritis. Siltuximab, a monoclonal antibody that targets IL-6, is currently the only US FDA approved therapy for idiopathic Multicentric Castleman's disease (MCD). Sirukumab, another high affinity anti-IL-6 monoclonal antibody designed to block the IL-6 pathway for adults with moderate-to-severe rheumatoid arthritis, was not recommended by the FDA's Arthritis Advisory Committee for approval due to increased mortality in patients who took the drug. Many other anti-IL-6 or anti-IL-6R monoclonal antibodies (discussed in Rose-John, et al., 2017) have been actively explored for such purpose. Although many monoclonal anti-IL-6 or anti-IL-6 receptor antibodies may prove efficacious in immunotherapy of certain diseases, they are expensive and must be frequently and chronically administered in order to maintain sufficient suppression of serum IL-6 and the clinical benefits derived therefrom.

Several vaccination methods for combating IL-6-related immune disorders have also been described. One approach uses a human IL-6 variant with seven amino acid substitutions, Sant1 (De Benedetti, et al., 2001; U.S. Pat. No. 6,706,261), as the immunogen. However, this work has not resulted in any clinical development since its initial disclosure nearly two decades ago. Another group (Desallais, L., et al., 2014) reported the use of five randomly selected IL-6 peptides covering over 40% of the IL-6 protein of 184 residues in length, that were attached through the use of a complicated chemical coupling procedure to a large carrier protein KLH to enhance the respective peptides' immunogenicity. The vaccine prepared under this method generated antibodies that were mostly directed to the unwanted carrier protein KLH and only a small portion to the targeted IL-6. In addition, this vaccine required Complete Freund's Adjuvant (CFA) and Incomplete Freund's Adjuvant (ICFA) in the formulation that are far from optimal for clinical and industrial applications.

As described above, there are a number of limitations and problems with current IL-6 vaccine designs (e.g. complicated chemical coupling procedures for immunogen preparation, use of KLH as the carrier protein where most of the elicited antibodies are directed to the carrier protein, use of clinically disallowed Complete Freund's Adjuvant to enhance the immunogenicity in vaccination, weak immunogenicity against target IL-6 in vaccinated animals despite use of most aggressive immunization protocol, unclear mechanism of action, etc.). Therefore, there is clearly an unmet need to develop an efficacious immunotherapeutic vaccine that is capable of eliciting highly specific immune responses against IL-6, easily administered to patients, able to be manufactured under stringent good manufacturing practices (GMP), and cost effective for worldwide application to treat patients suffering from diseases impacted by IL-6 dysregulation.

It is the main goal of the present disclosure is to create/develop IL-6 peptide immunogen constructs and vaccine formulations thereof wherein the B epitope of the designed peptide immunogen constructs mimic closely the IL-6R binding sites on IL-6; with such peptide immunogen constructs and formulations thereof capable of generating strong immune responses in the vaccinated hosts to allow for breakout of immune tolerance to a self-protein IL-6, and generation of efficacious antibodies targeting IL-6R binding site for treatment of diseases impacted by IL-6 dysregulation.

SUMMARY OF THE INVENTION

The present disclosure is directed to individual peptide immunogen constructs targeting Interleukin 6 (IL-6) and formulations thereof for immunotherapy of diseases impacted by IL-6 dysregulation.

These individual IL-6 peptide immunogen constructs have 30 or more amino acids in length comprising functional B cell epitopes derived from the IL-6 Receptor binding regions E42-C83 (SEQ ID NO: 16) or N144-I166 (SEQ ID NO: 19) or fragments thereof, which are linked through spacer residue(s) to heterologous T helper cell (Th) epitopes derived from pathogen proteins. These IL-6 peptide constructs, containing both designed B cell- and Th cell epitopes act together to stimulate the generation of highly specific antibodies directed against IL-6R binding region, offering therapeutic immune responses to subjects predisposed to, or suffering from, a disease impacted by IL-6 dysregulation.

In some embodiments, the disclosed IL-6 peptide immunogen constructs comprise a hybrid peptide having a B cell antigenic site (SEQ ID NOs: 5-20; 72-74, shown in Table 1) derived from the IL-6R binding region or fragments thereof, that is linked to a heterologous Th epitope derived from pathogenic proteins (SEQ ID NOs: 78-106 and 216-226, shown in Table 2) that act together to stimulate the generation of highly specific antibodies that are cross-reactive with the recombinant human IL-6 (SEQ ID NO: 1), or IL-6 of other species such as macaque (SEQ ID NO: 2), mouse (SEQ ID NO: 3), and rat IL-6 (SEQ ID NO: 4).

REFERENCES

1. CHANG, J. C. C., et al., "Adjuvant activity of incomplete Freund's adjuvant," *Advanced Drug Delivery Reviews*, 32(3):173-186 (1998)
2. CILIBERTO, G., et al., "Compositions and methods comprising immunogenic muteins of interleukin-6", U.S. Pat. No. 6,706,261 (2004)
3. DE BENEDETTI, F., et al., "In Vivo Neutralization of Human IL-6 (hIL-6) Achieved by Immunization of hIL-6-Transgenic Mice with a hIL-6 Receptor Antagonist", *J. Immunol.* 166:4334-4340 (2001)
4. DESALLAIS, L., et al., "Method for treating chronic colitis and systemic sclerosis for eliciting protective immune reaction against human IL-6", U.S. Pat. No. 9,669,077 (2017)
5. DESALLAIS, L., et al., "Immunization against an IL-6 peptide induces anti-IL-6 antibodies and modulates the Delayed-Type-Hypersensitivity reaction in cynomolgus monkeys", *Scientific Reports.* 6:19549; doi:10.1038/srep19549 (2016)
6. DESALLAIS, L., et al., "Targeting IL-6 by both passive and active immunization strategies prevents bleomycin-induced skin fibrosis", *Arthritis Research and Therapy.* 16:R157 (2014)
7. FIELDS, G. B., et al., Chapter 3 in *Synthetic Peptides: A User's Guide*, ed. Grant, W.H. Freeman & Co., New York, N.Y., p. 77 (1992)
8. LAZZERINI, P., et al., "Spotlight on sirukumab for the treatment of rheumatoid arthritis: the evidence to date", *Drug Design, Development and Therapy*, 10:3083-3098; website: doi.org/10.2147/DDDT.S99898) (2016)
9. MIHARA, M., et al., "IL-6/IL-6 receptor system and its role in physiological and pathological conditions", *Clinical Science*, 122(4):143-159 (2012)
10. ROSE-JOHN, S., et al., "The role of IL-6 in host defense against infections: immunobiology and clinical implications", *Nature Reviews Rheumatology*, 13:399-409 (2017)
11. SEBBA, A., "Tocilizumab: The first interleukin-6-receptor inhibitor", *American Journal of Health-System Pharmacy*, 65(15):1413-1418 (2008)
12. TRAGGIAI, E., et al., "An efficient method to make human monoclonal antibodies from memory B cells: potent neutralization of SARS coronavirus", *Nature Medicine*, 10(8):871-875 (2004)

BRIEF DESCRIPTION OF THE DRAWINGS

FIG. 1 presents sequence alignment of IL-6 sequences from human (SEQ ID NO: 227), macaque (SEQ ID NO: 228), mouse (SEQ ID NO: 229) and rat (SEQ ID NO: 230) species. Intramolecular loop structures that occur from amino acid positions 44-50 and 73-83 are shown with shaded cysteines and brackets.

FIGS. 4A-4B show the cross-reactivity of various purified polyclonal anti-IL-6 antibodies directed against different IL-6 peptide immunogen constructs. Specifically, the results for SEQ ID NOs: 107, 116, 118, 124-128 are shown in FIG.

4A and SEQ ID NOs: 129-133 are shown in FIG. 4B. ELISA plates were coated with recombinant human, monkey, mouse or rat IL-6 proteins. Polyclonal anti-IL-6 IgG antibodies purified from guinea pig sera by protein A chromatography were diluted from 10 μg/mL to 0.00238 ng/mL by a 4-fold serial dilution. The $EC_{50}$ was calculated by nonlinear regression with four-parameter logistic curve-fit.

Figure 5A:
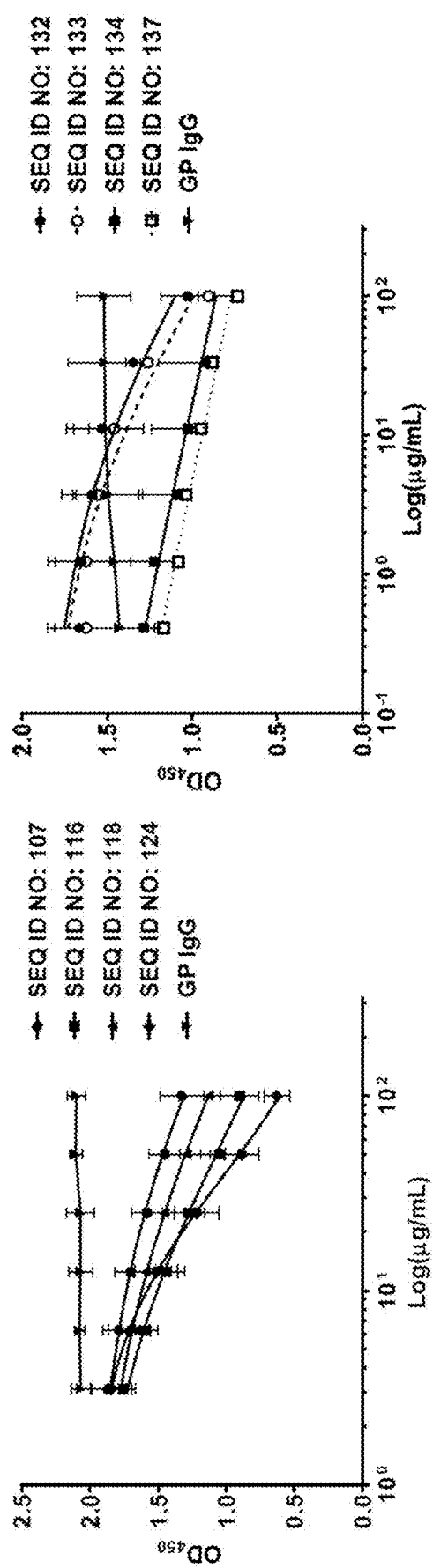

FIG. 5A illustrates the neutralizing activity of various purified polyclonal anti-IL-6 antibodies raised by different IL-6 peptide immunogen constructs (SEQ ID NOs: 107, 116, 118, 124, 132, 133, 124, and 137 as well as GP IgG) on the interaction of IL-6 and IL-6R in an ELISA-based assay. ELISA plates were coated with a recombinant human IL-6R protein. Human IL-6 at 10 ng/ml and various polyclonal anti-IL-6 IgG antibodies at descending concentrations from 100 to 0.412 μg/mL by a 3-fold serial dilution were premixed and then added to IL-6R-coated wells. Captured IL-6 was detected by biotin-labeled rabbit anti-IL-6 antibody, followed by streptavidin poly-HRP. The $IC_{50}$ was calculated by nonlinear regression with four-parameter logistic curve-fit.

Figure 5B:
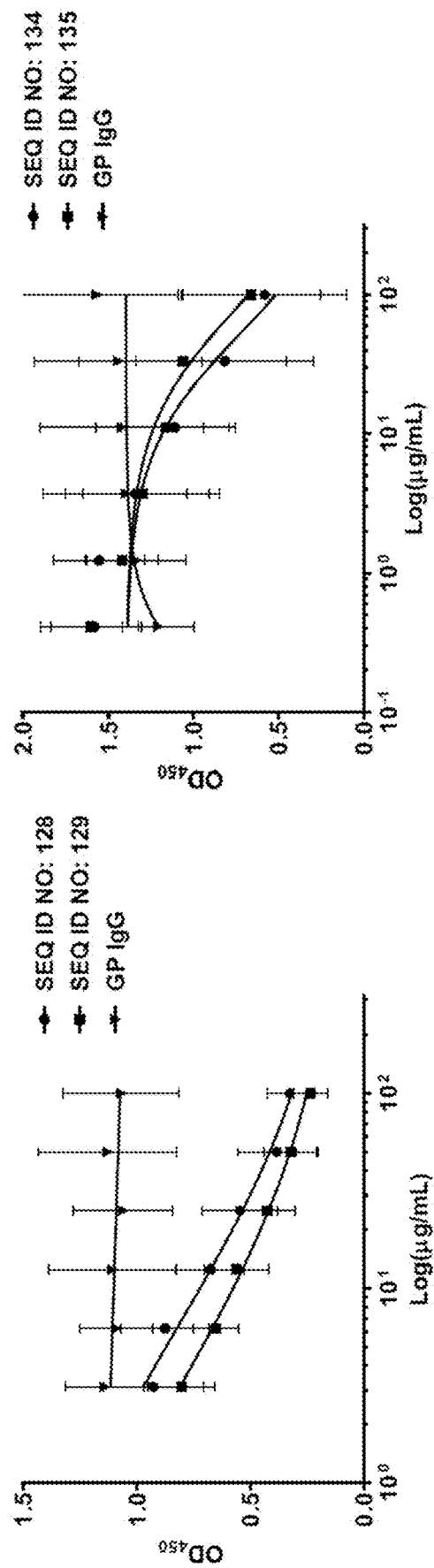

FIG. 5B illustrates the neutralizing activity of various purified polyclonal anti-IL-6 antibodies raised by different IL-6 peptide immunogen constructs (SEQ ID NOs: 128, 129, 134, and 135 as well as GP IgG) on the interaction of IL-6/IL-6R and gp130 in an ELISA-based assay. ELISA plates were coated with a recombinant gp130-Fc fusion protein. Preformed IL-6/IL-6R complex at a predefined ratio and various polyclonal anti-IL-6 IgG antibodies at descending concentrations from 100 to 0.412 μg/mL by a 3-fold serial dilution were premixed and then added to gp130-Fc-coated wells. Captured IL-6/IL-6R complex was detected by biotin-labeled rabbit anti-IL-6 antibody, followed by streptavidin poly-HRP. The $IC_{50}$ was calculated by nonlinear regression with four-parameter logistic curve-fit.

Figure 6:
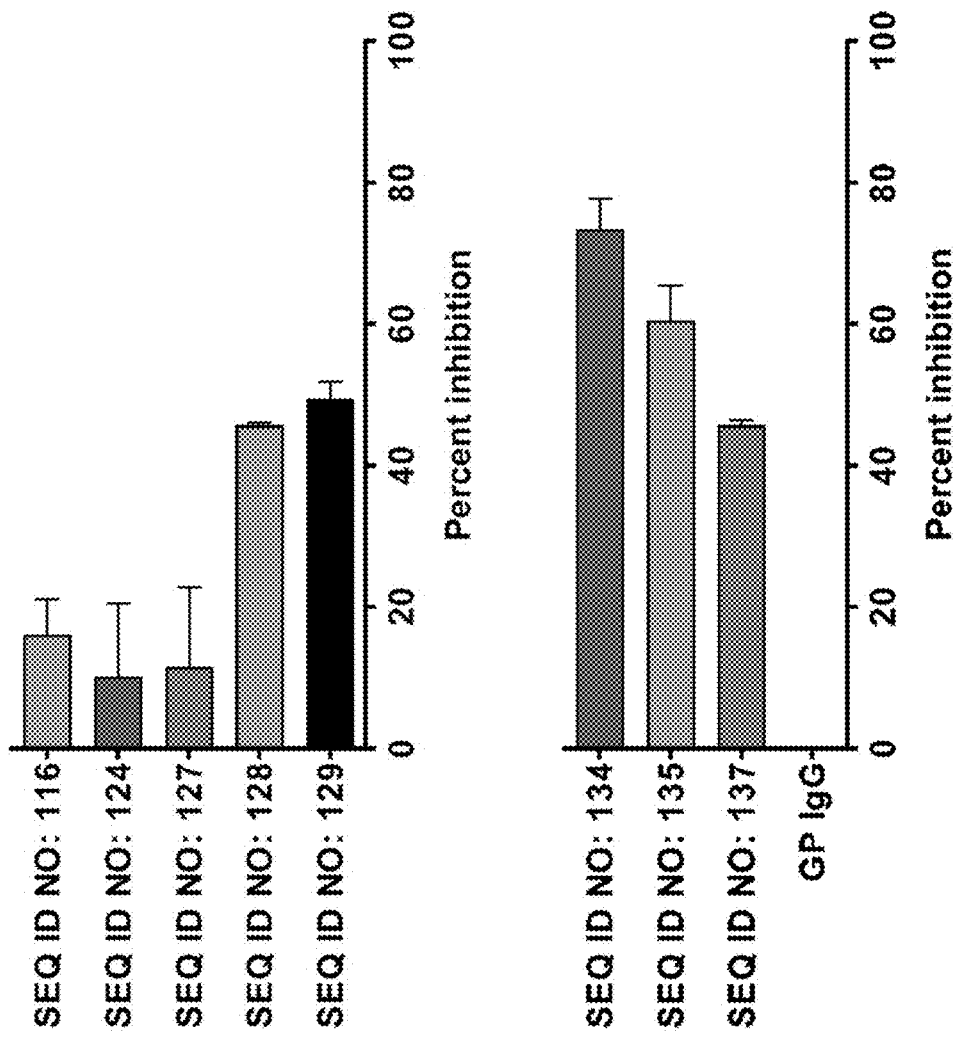

FIG. 6 illustrates the neutralizing activity of various purified polyclonal anti-IL-6 antibodies raised by different IL-6 peptide immunogen constructs (SEQ ID NOs: 116, 124, 127, 128, 129, 134, 135, and 137 as well as GP IgG) on IL-6-dependent STAT3 phosphorylation in an ELISA-based assay. RMPI 8226 cells were incubated with human IL-6 at 10 ng/mL and various polyclonal anti-IL-6 IgG antibodies at the concentration of 100 μg/mL at 37° C., 5% $CO_2$ for 30 min and then lysed to determine phosphorylated STAT3 level in an ELISA-based assay.

Figure 7B:
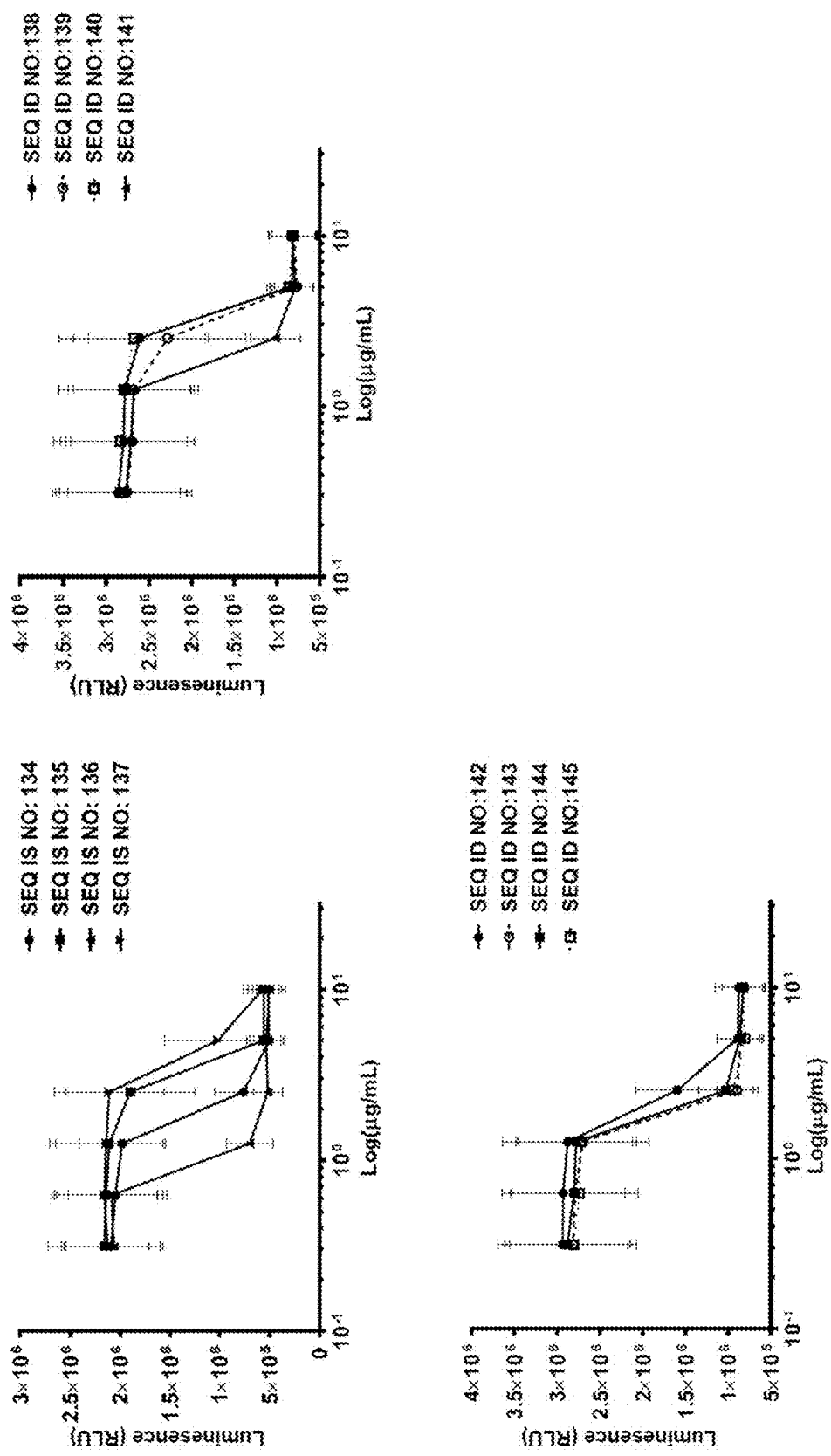

FIGS. 7A-7B illustrate the neutralizing activity of various purified polyclonal anti-IL-6 antibodies raised by different IL-6 peptide immunogen constructs on IL-6-dependent cell proliferation. The neutralizing activity of SEQ ID NOs: 116, 118, 124-129, 131, 132, and 133 are shown in FIG. 7A while the neutralizing activity of SEQ ID NOs: 134-145 are shown in FIG. 7B. TF-1 cells were incubated with human IL-6 at 10 ng/mL and various polyclonal anti-IL-6 IgG antibodies at indicated concentrations at 37° C., 5% $CO_2$ for 72 hours. The cell viability was monitored by measuring the amount of ATP in metabolically active cells.

Figure 8A:
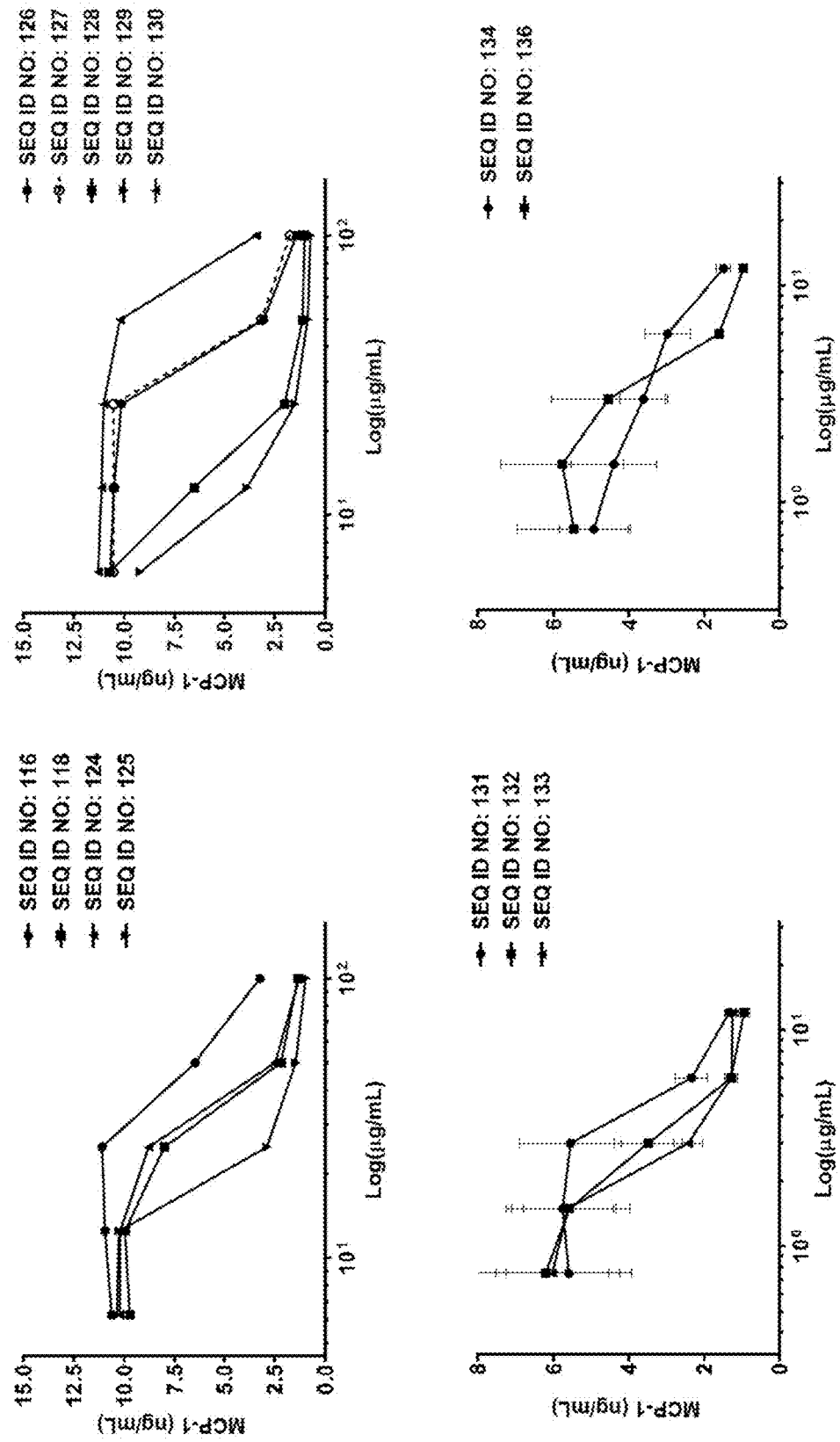
Figure 8B:
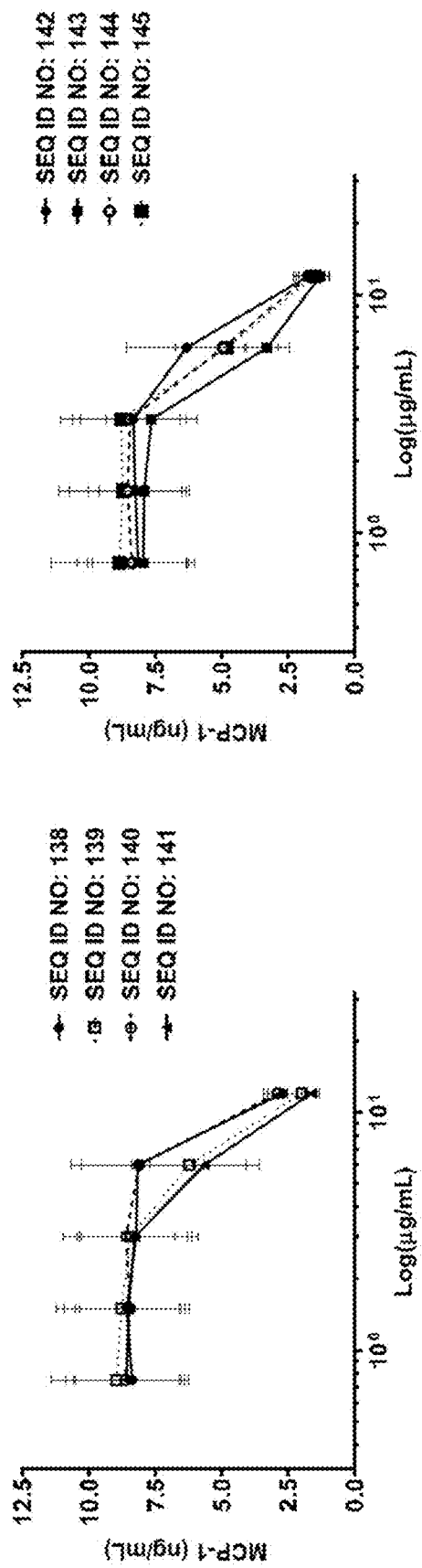

FIGS. 8A-8B illustrate the neutralizing activity of various purified polyclonal anti-IL-6 antibodies raised by different IL-6 peptide immunogen constructs on IL-6-induced MCP-1 secretion. The neutralizing activity of SEQ ID NOs: 116, 118, 124-134 and 136 are shown in FIG. 8A while the neutralizing activity of SEQ ID NOs: 138-145 are shown in FIG. 8B. U937 cells were incubated with human IL-6 at 10 ng/mL and various polyclonal anti-IL-6 IgG antibodies at indicated concentrations at 37° C., 5% $CO_2$ for 24 hours. The culture supernatants were collected to determine MCP-1 level.

FIG. 9 illustrates experimental design for efficacy evaluation of rat IL-6 peptide constructs in rat collagen-induced arthritis (CIA) with a preventive model. Female Lewis rats (n=7 per group) were intramuscularly immunized with peptide immunogen constructs of SEQ ID NOs: 148 or 157 at the dose of 45 μg on days −31, −10 and 4. To induce arthritis, animals were intradermally challenged with bovine type II collagen/IFA emulsion on days 0 and 7.

Figure 10:
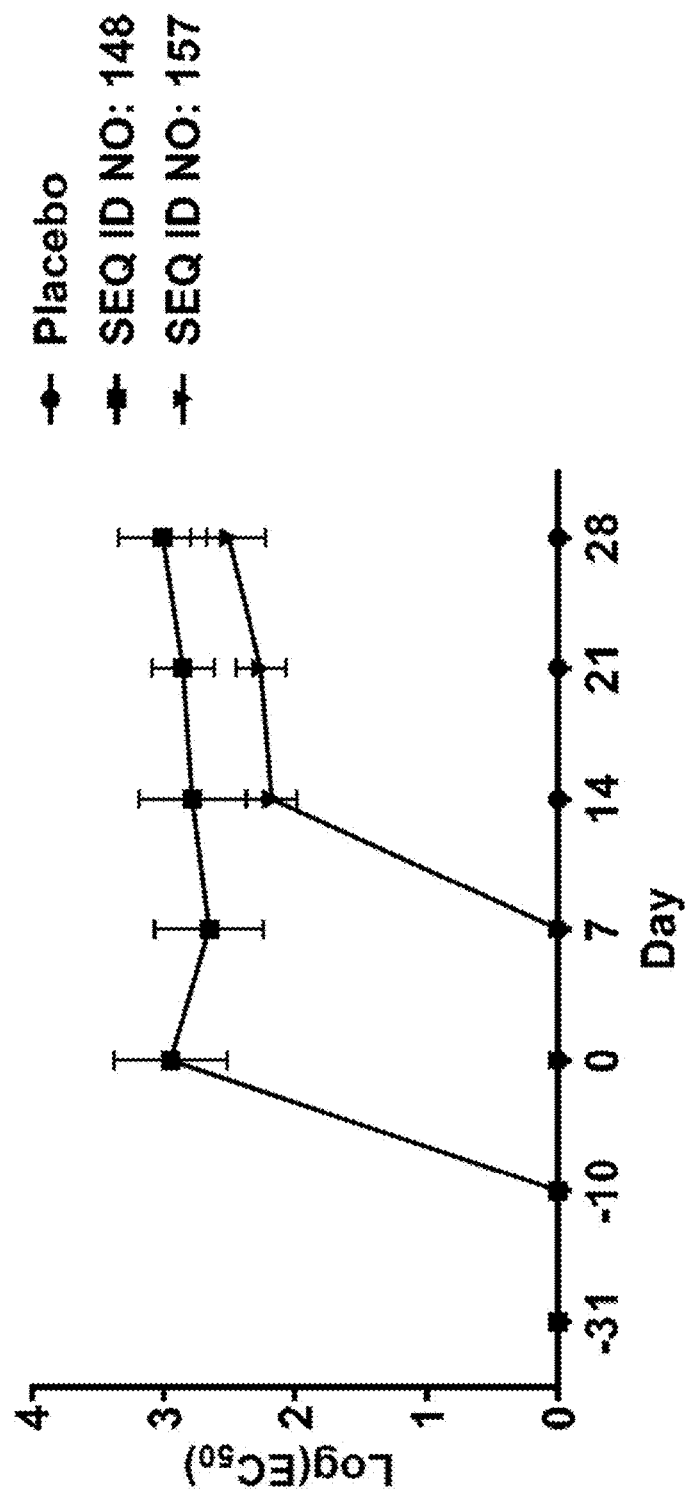

FIG. 10 illustrates the kinetics of antibody response over a 28-day period in rats immunized with different IL-6 peptide immunogen constructs (SEQ ID NOs: 148 and 157). ELISA plates were coated with recombinant rat IL-6. Serum was diluted from 1:100 to 1:4.19×10$^8$ by a 4-fold serial dilution. The titer of a tested serum, expressed as $Log_{10}$ ($EC_{50}$), was calculated by nonlinear regression with four-parameter logistic curve-fit.

Figure 11:
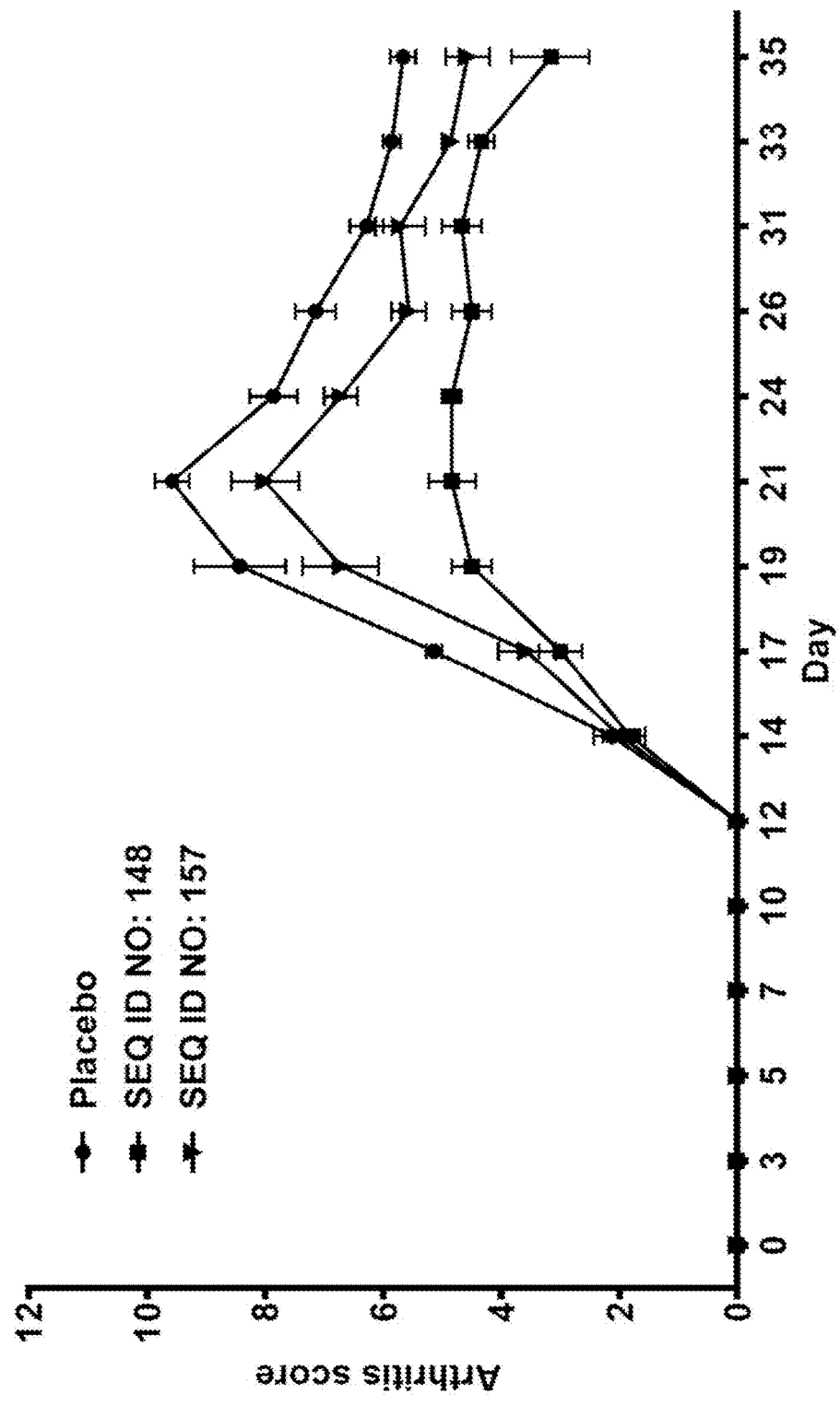

FIG. 11 illustrates the reduction of arthritis score in collagen-challenged rats which were previously immunized with different IL-6 peptide immunogen constructs (SEQ ID NOs: 148 and 157).

Figure 12:
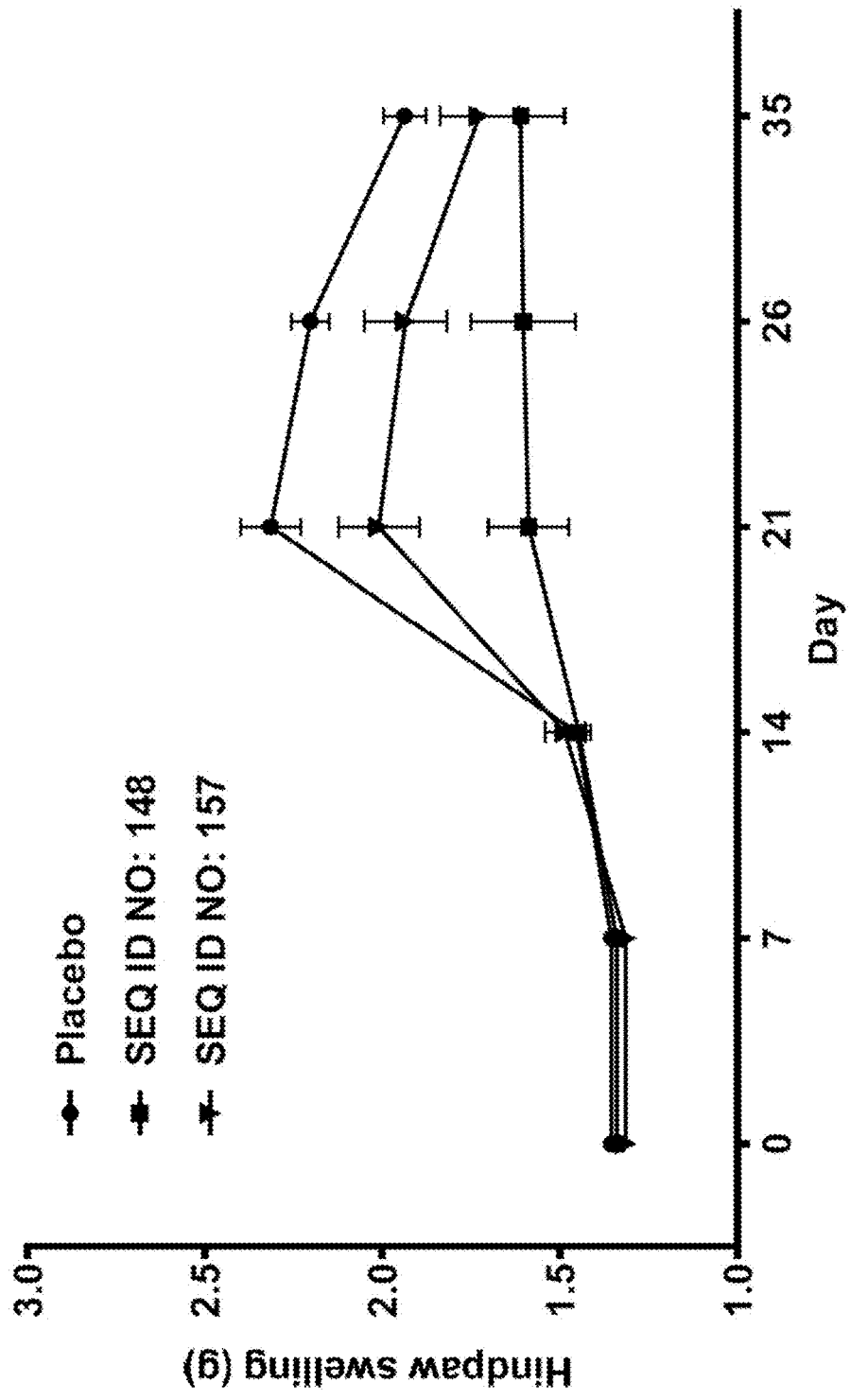

FIG. 12 illustrates the reduction of hind paw swelling in collagen-challenged rats which were previously immunized with different IL-6 peptide immunogen constructs (SEQ ID NOs: 148 and 157).

Figure 13:
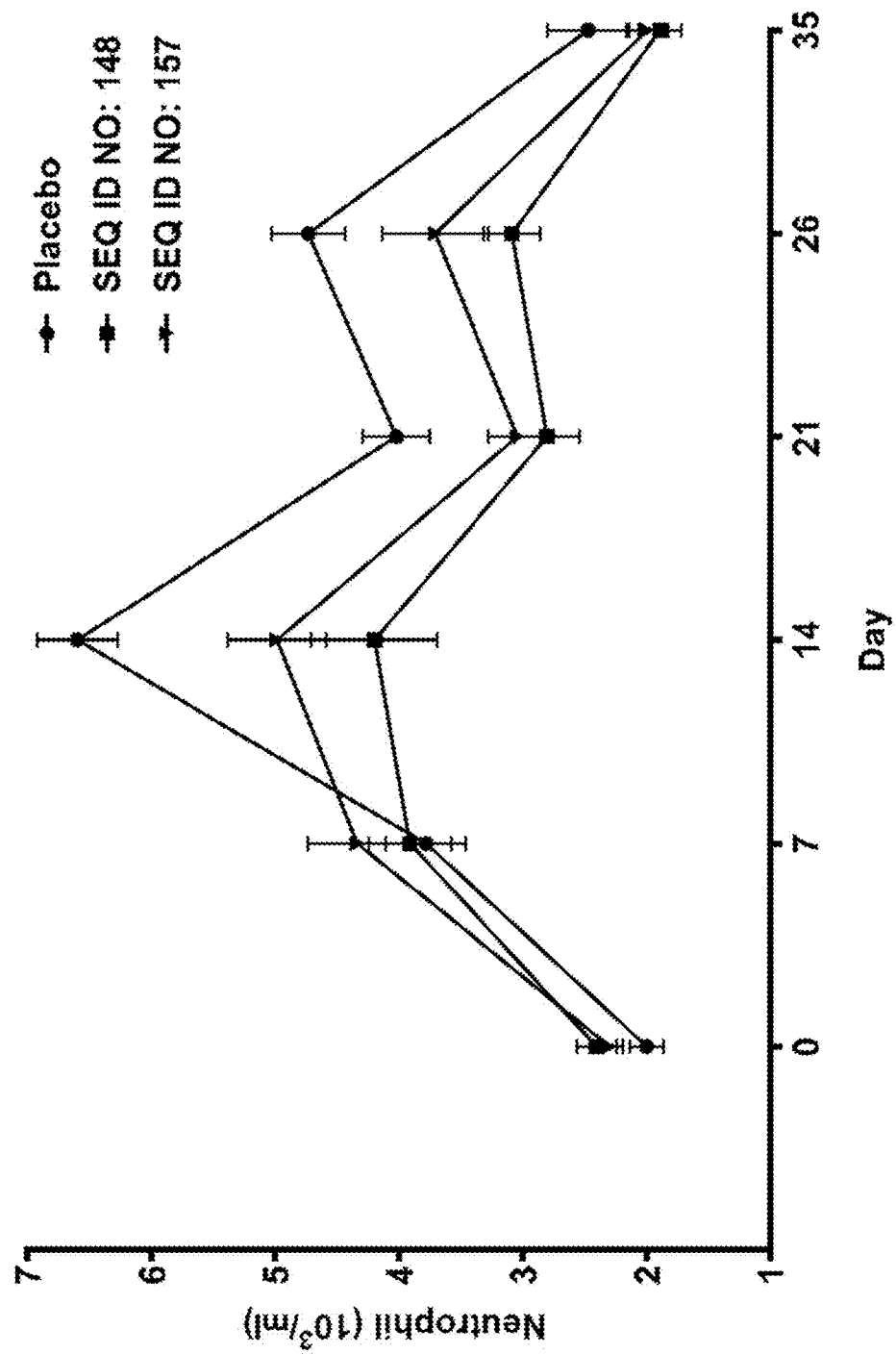

FIG. 13 illustrates the attenuation of blood neutrophilia in collagen-challenged rats which were previously immunized with different IL-6 peptide immunogen constructs (SEQ ID NOs: 148 and 157).

Figure 14:
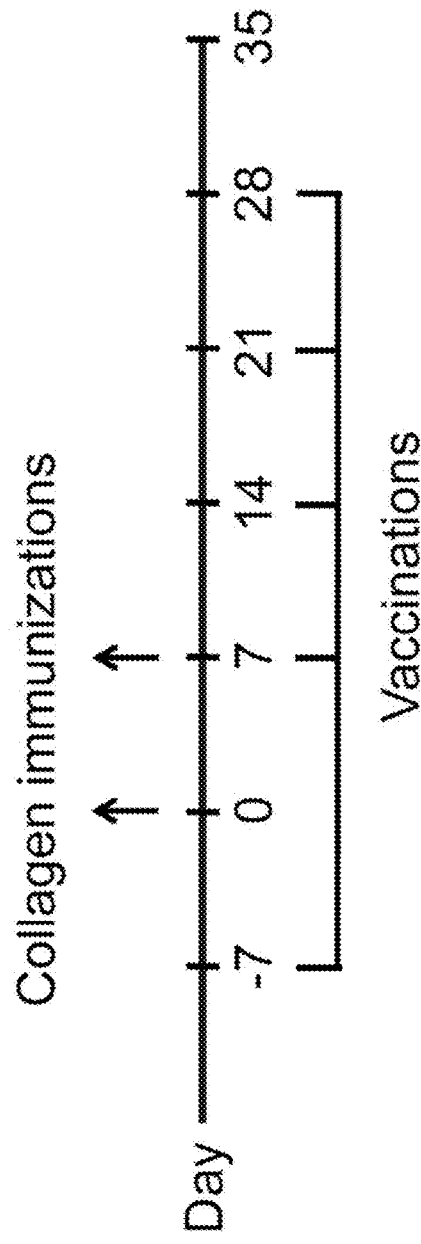

FIG. 14 illustrates experimental design for efficacy evaluation of rat IL-6 peptide immunogen constructs in rat collagen-induced arthritis (CIA) with a therapeutic model. Female Lewis rats (n=6 or 7 per group) were intramuscularly immunized with SEQ ID NO: 148 at the dose of 45 μg on days −7, 7, 14, 21 and 28. To induce arthritis, animals were intradermally challenged with bovine type H collagen/IFA emulsion on days 0 and 7.

Figure 15:
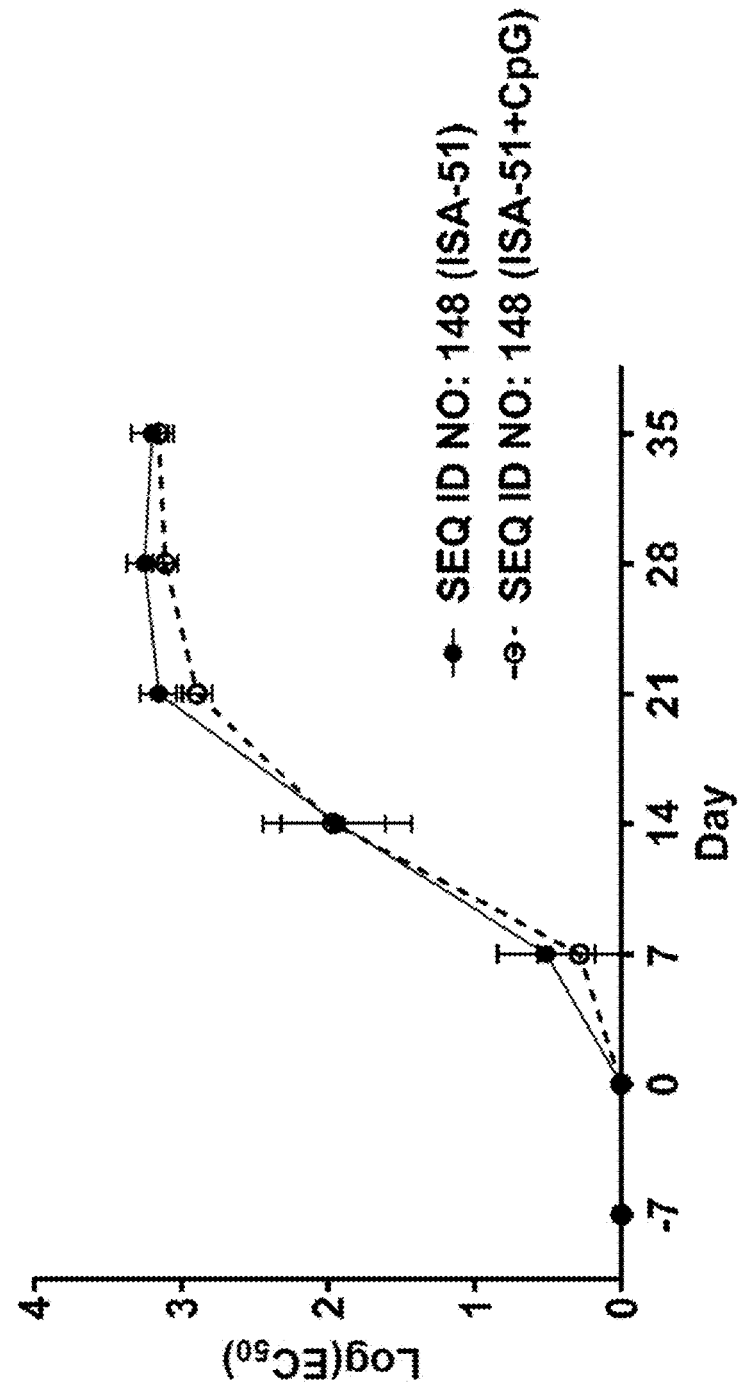

FIG. 15 illustrates the kinetics of antibody response over a 43-day period in rats immunized with SEQ ID NO: 148 formulated with either ISA 51 or ISA 51/CpG. ELISA plates were coated with recombinant rat IL-6. Serum was diluted from 1:100 to 1:4.19×10$^8$ by a 4-fold serial dilution. The titer of a tested serum, expressed as $Log_{10}(EC_{50})$, was calculated by nonlinear regression with four-parameter logistic curve-fit.

Figure 16:
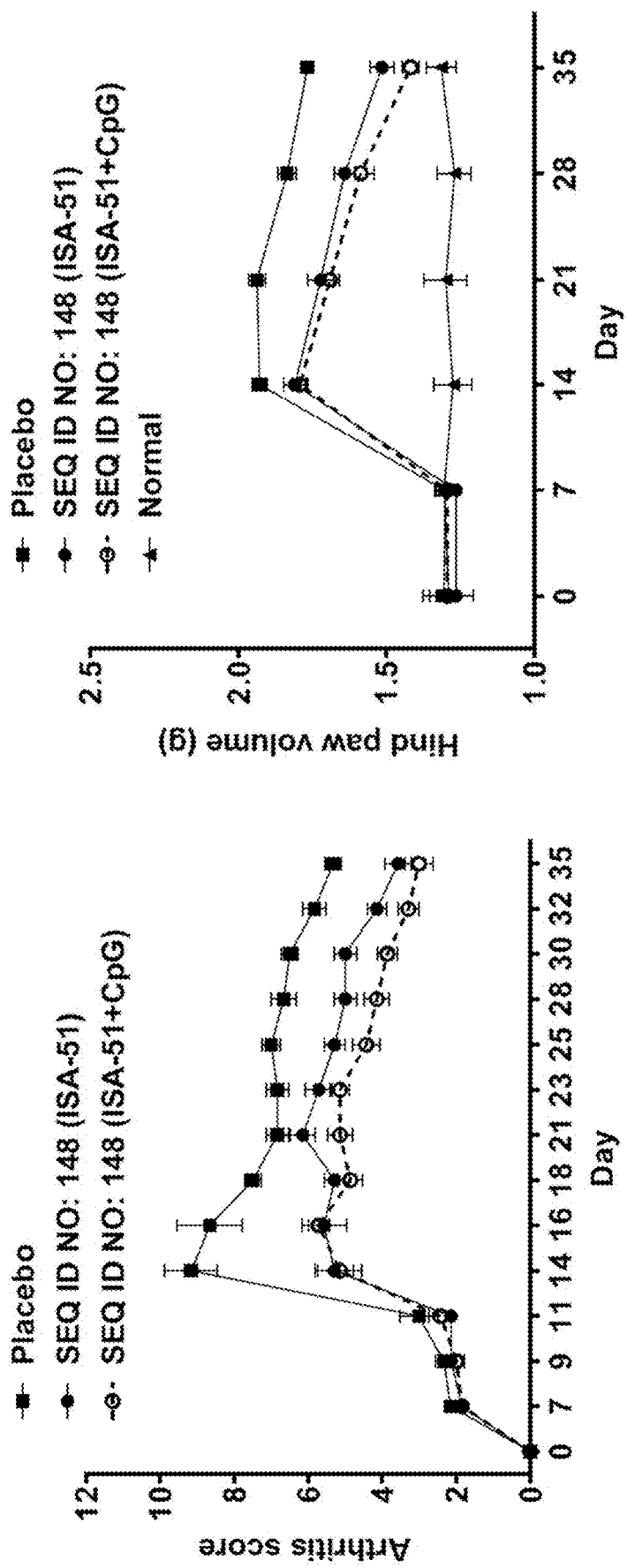

FIG. 16 illustrates the reduction of arthritis score and hind paw swelling in collagen-challenged rats that were previously immunized with SEQ ID NO: 148 formulated with either ISA 51 or ISA 51/CpG.

Figure 17:
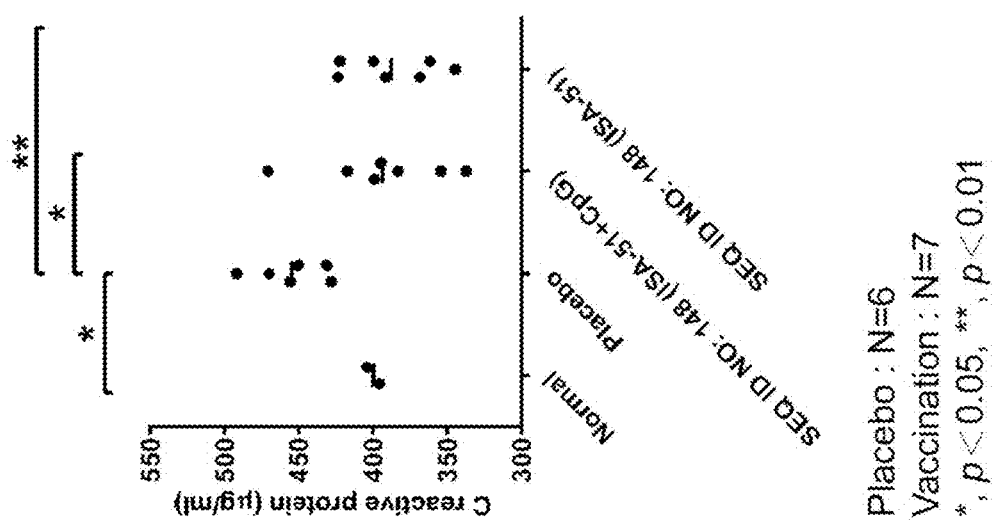

FIG. 17 illustrates the reduction of liver C-reactive protein (CRP) in collagen-challenged rats that were previously immunized with SEQ ID NO: 148 formulated with either ISA 51 or ISA 51/CpG.

FIG. 18 illustrates the alleviation of ankle joint disruption in collagen-challenged rats that were previously immunized with SEQ ID NO: 148 formulated with either ISA 51 or ISA 51/CpG.

Figure 19:
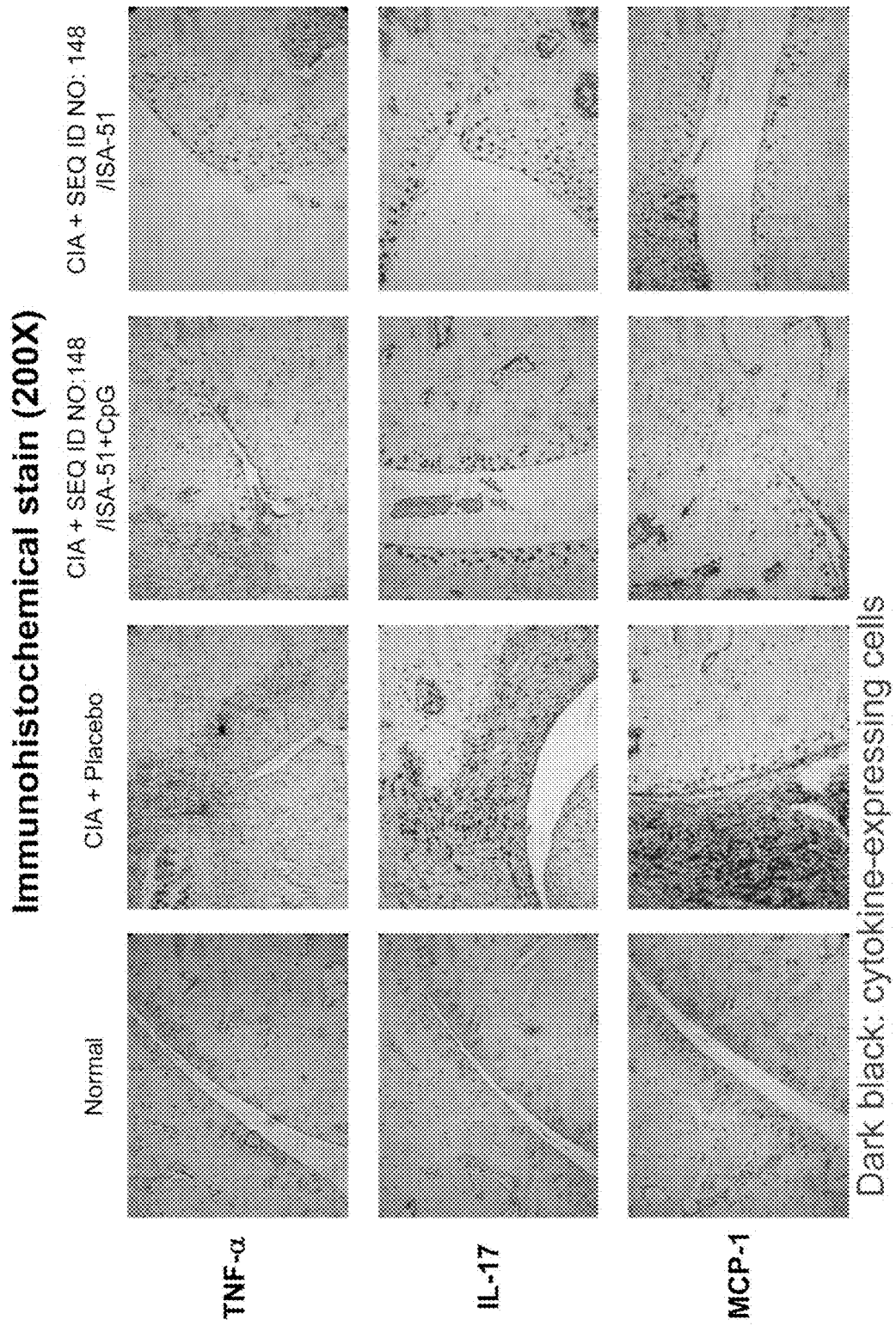

FIG. 19 illustrates the reduction of tissue inflammatory cytokine (TNF-α, IL-17 and MCP-1) production in collagen-challenged rats that were previously immunized with SEQ ID NO: 148 formulated with either ISA 51 or ISA 51/CpG.

Figure 20:
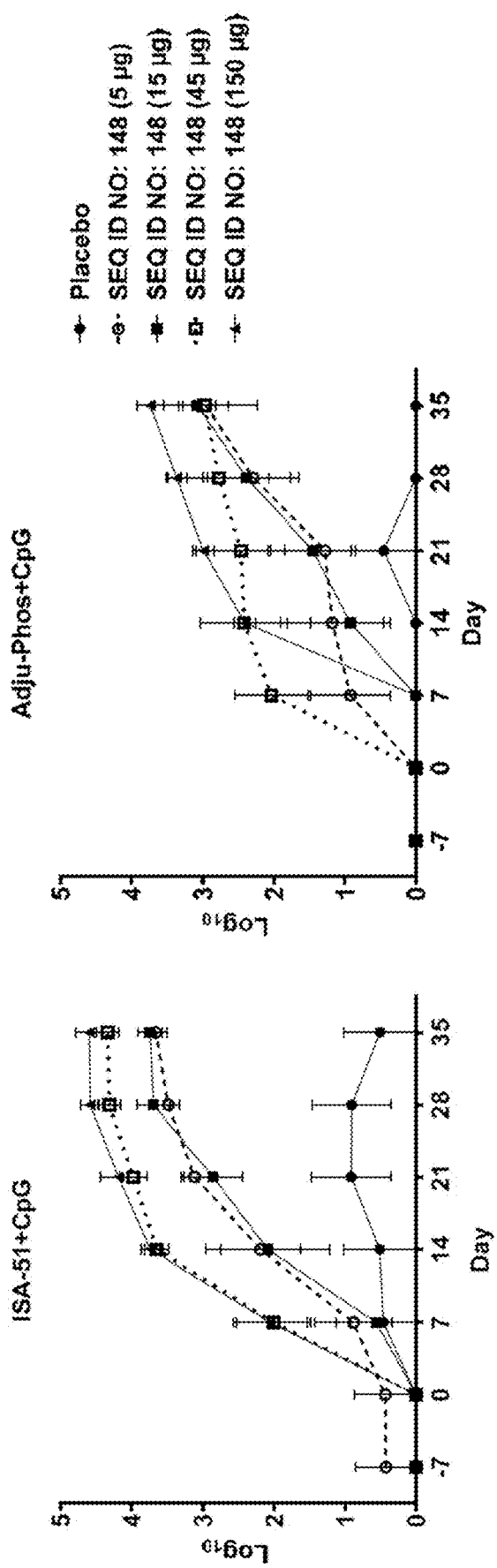

FIG. 20 illustrates the kinetics of antibody response over a 43-day period in rats immunized with different doses of SEQ ID NO: 148 formulated with either ISA 51/CpG or ADJU-PHOS/CpG. The study was conducted, following the same experimental design as FIG. 17. ELISA plates were coated with recombinant rat IL-6. Serum was diluted from 1:100 to 1:4.19×10⁸ by a 4-fold serial dilution. The titer of a tested serum, expressed as $Log_{10}$, was calculated by incorporating a cutoff of 0.45 into a four-parameter logistic curve of each serum sample with nonlinear regression.

Figure 21:
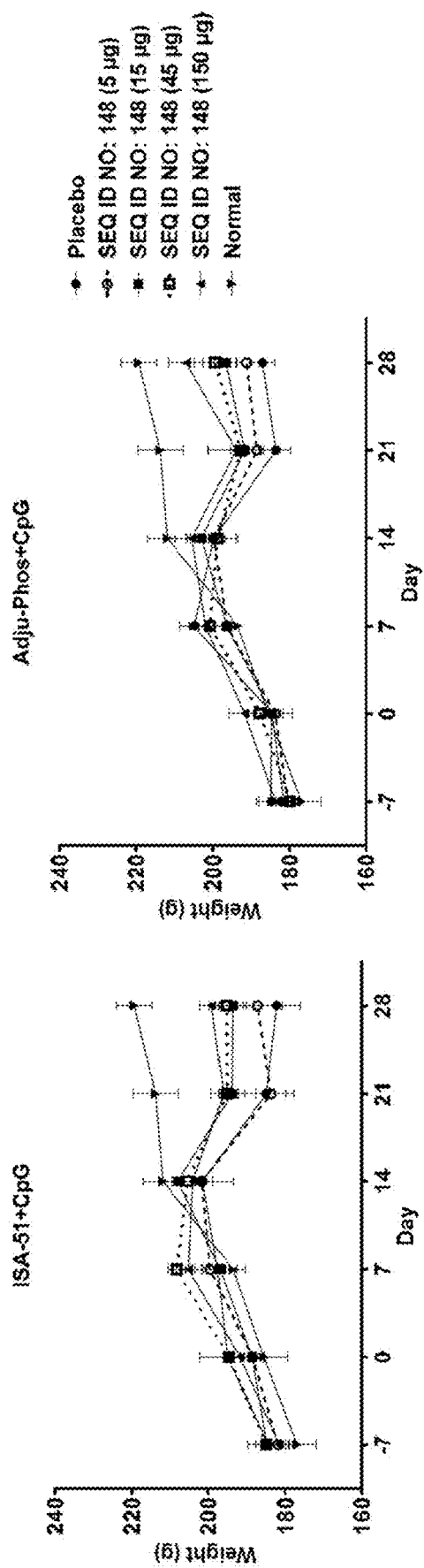

FIG. 21 illustrates the alleviation of weight loss in collagen-challenged rats that were immunized with ascending doses of SEQ ID NO: 148 formulated with either ISA 51/CpG or ADJU-PHOS/CpG.

Figure 22:
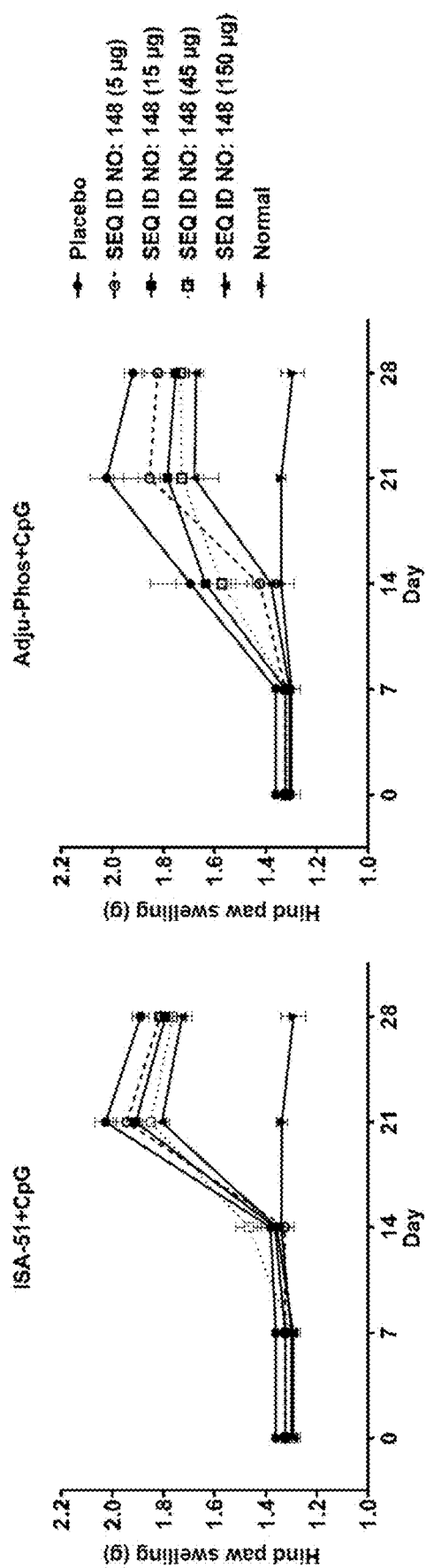

FIG. 22 illustrates the reduction of hind paw swelling in collagen-challenged rats that were immunized with ascending doses of SEQ ID NO: 148 formulated with either ISA 51/CpG or ADJU-PHOS/CpG.

Figure 23:
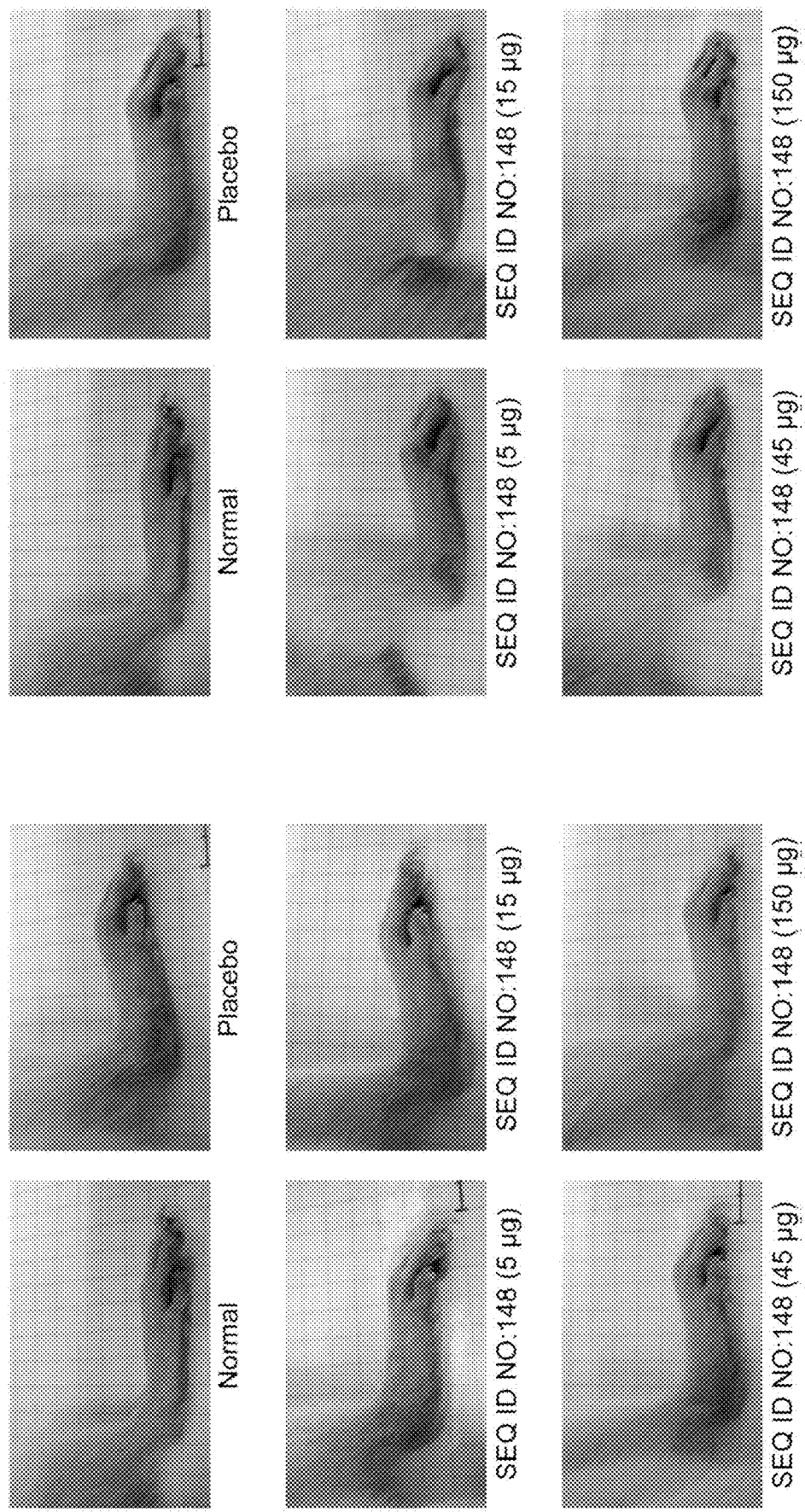

FIG. 23 shows the macroscopic observation of hind paw on day 24 of collagen-challenged rats that were immunized with ascending doses of SEQ ID NO: 148 formulated with either ISA 51/CpG or ADJU-PHOS/CpG.

Figure 24:
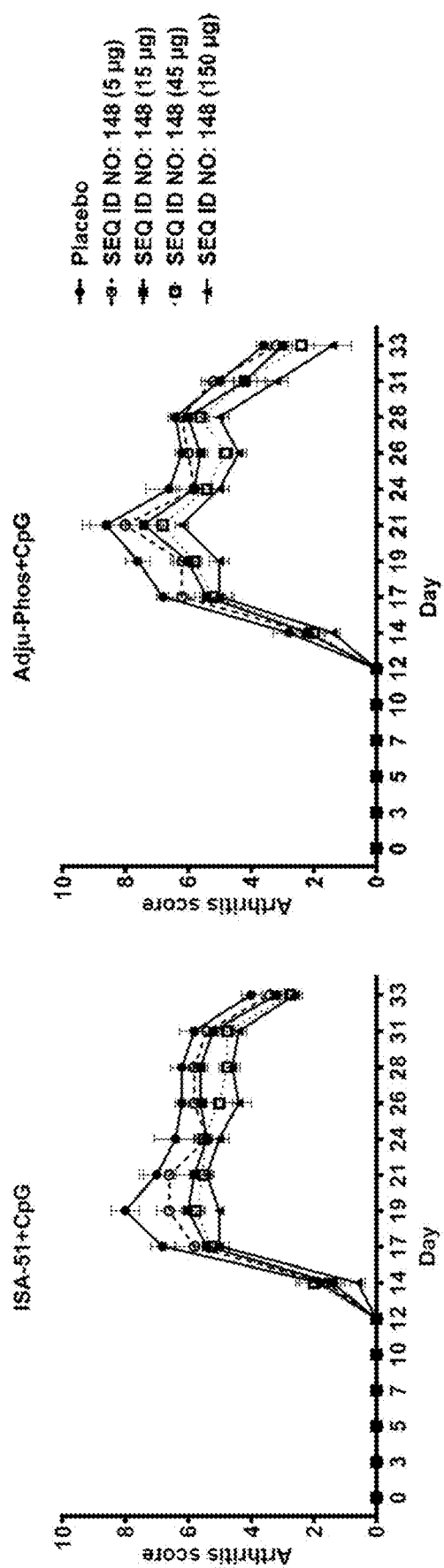

FIG. 24 illustrates the reduction of arthritis score in collagen-challenged rats that were immunized with ascending doses of SEQ ID NO: 148 formulated with either ISA 51/CpG or ADJU-PHOS/CpG.

Figure 25:
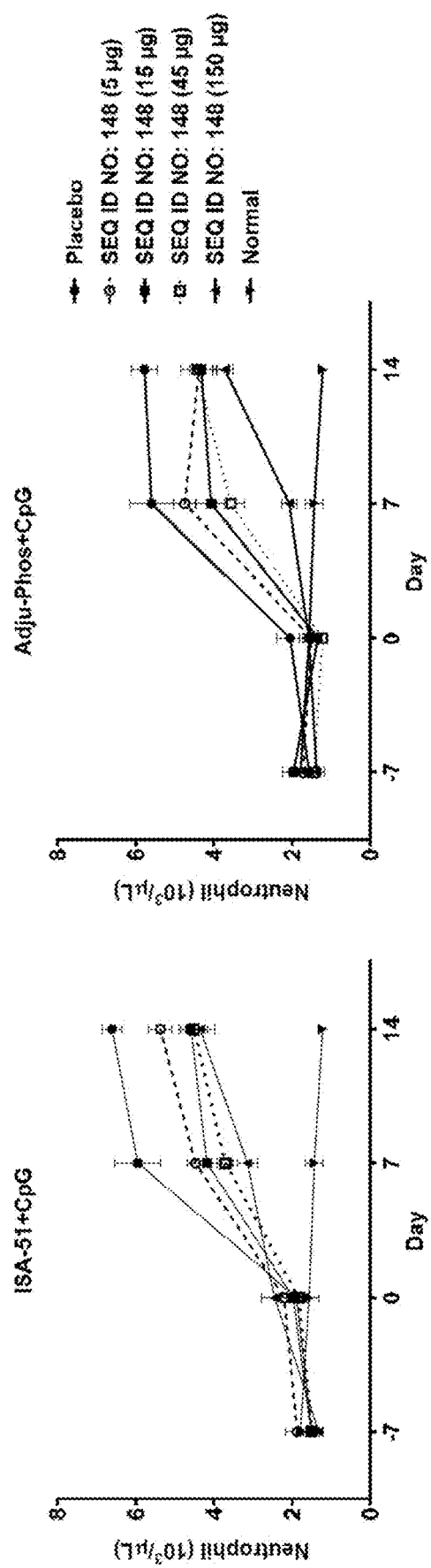

FIG. 25 illustrates the attenuation of blood neutrophilia in collagen-challenged rats that were immunized with ascending doses of SEQ ID NO: 148 formulated with either ISA 51/CpG or ADJU-PHOS/CpG.

Figure 26:
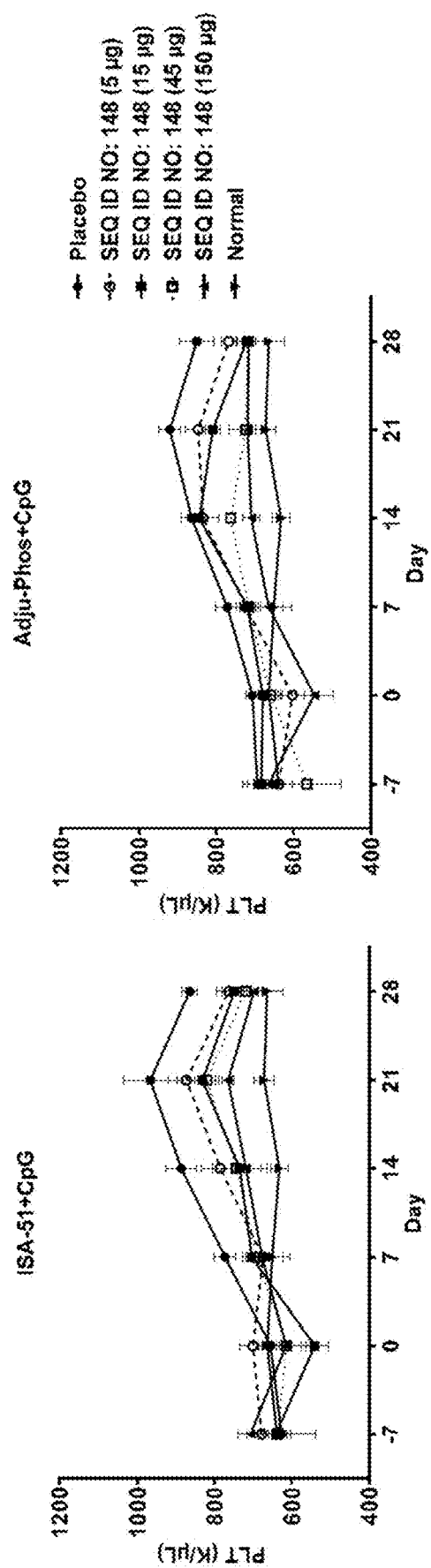

FIG. 26 illustrates the attenuation of platelet release in collagen-challenged rats that were immunized with ascending doses of SEQ ID NO: 148 formulated with either ISA 51/CpG or ADJU-PHOS/CpG.

Figure 27:
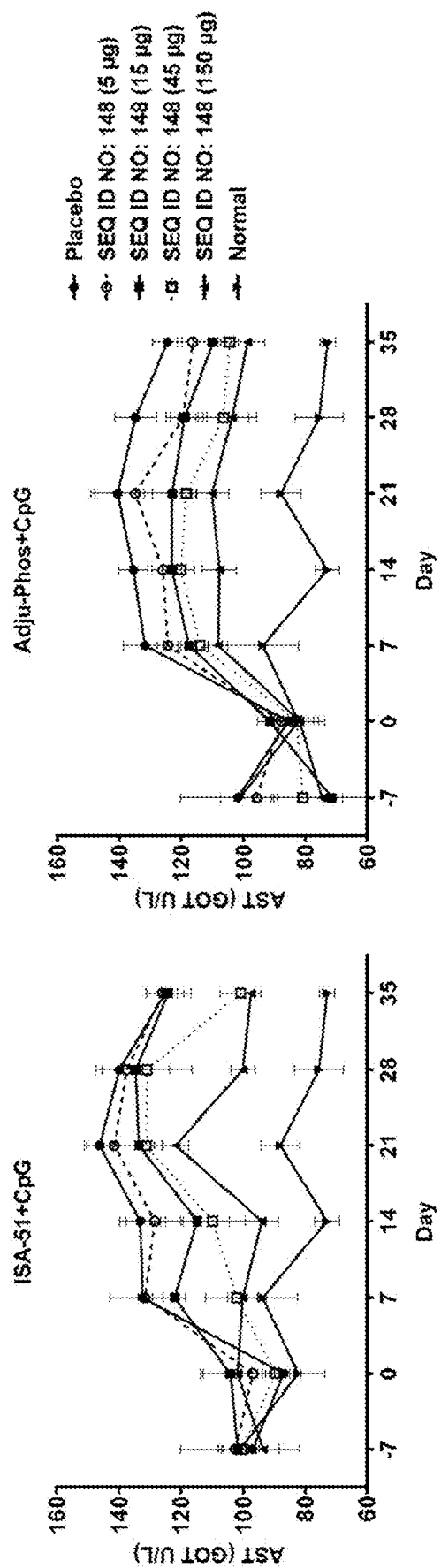

FIG. 27 illustrates the reduction of blood AST increase in collagen-challenged rats that were immunized with ascending doses of SEQ ID NO: 148 formulated with either ISA 51/CpG or ADJU-PHOS/CpG.

Figure 28:
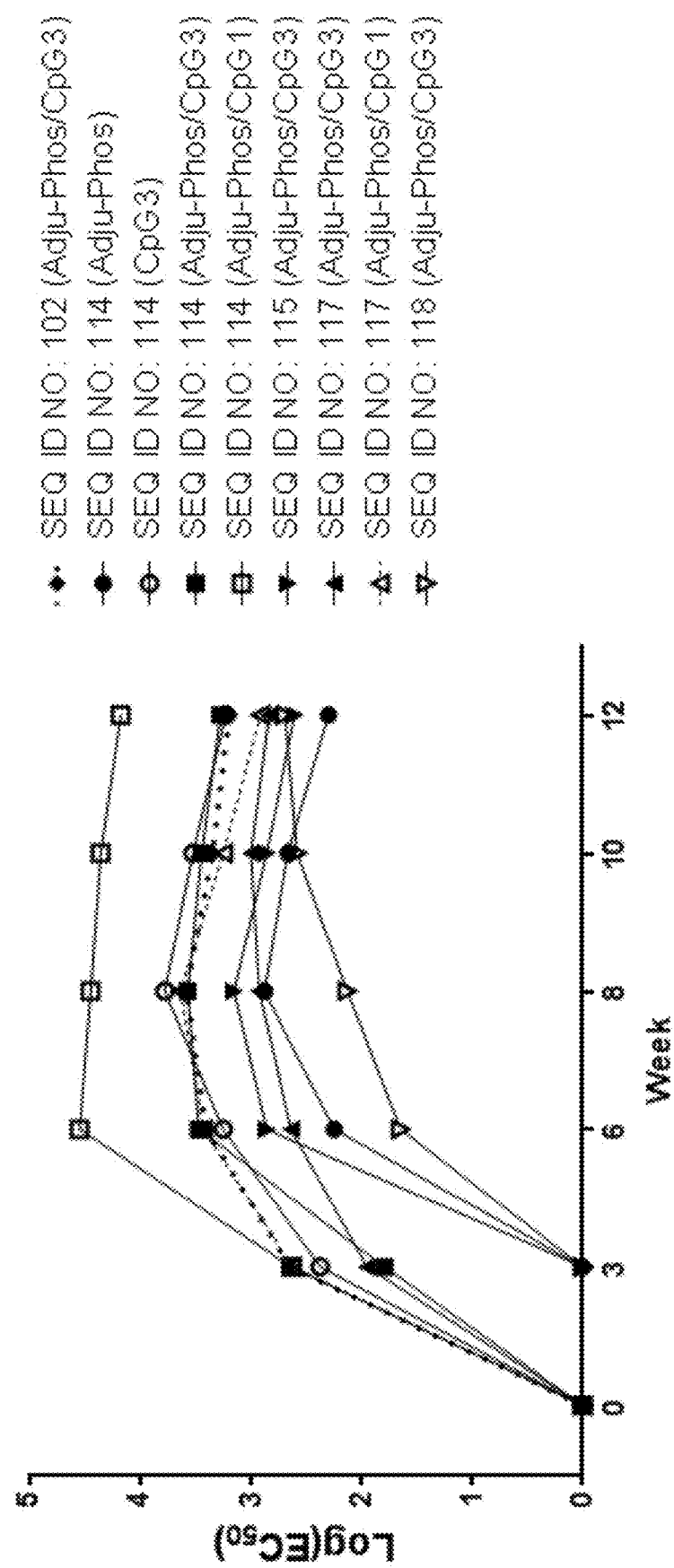

FIG. 28 illustrates the kinetics of antibody response over a 12-week period in guinea pigs immunized with different IL-6 peptide immunogen constructs (SEQ ID NOs: 102, 114, 115, 117, and 118) formulated with indicated adjuvants. ELISA plates were coated with recombinant human IL-6. Serum was diluted from 1:100 to 1:4.19×10⁸ by a 4-fold serial dilution. The titer of a tested serum, expressed as $Log_{10}(EC_{50})$, was calculated by nonlinear regression with four-parameter logistic curve-fit.

DETAILED DESCRIPTION OF THE INVENTION

The present disclosure is directed to individual peptide immunogen constructs targeting Interleukin 6 (IL-6) and formulations thereof for immunotherapy of diseases impacted by IL-6 dysregulation.

The disclosed IL-6 peptide immunogen constructs have 30 or more amino acids comprising functional B cell epitopes derived from the IL-6 receptor (IL-6R) binding regions E42-C83 (SEQ ID NO: 16) or N144-I166 (SEQ ID NO: 19) or fragments thereof (SEQ ID NOs: 5-19), which are linked through an optional heterologous spacer to a heterologous T helper cell (Th) epitopes derived from pathogen proteins (SEQ ID NOs: 78-106 and 216-226). These IL-6 peptide constructs, containing both designed B cell- and Th cell epitopes act together to stimulate the generation of highly specific antibodies directed against IL-6R binding region, offering preventative and/or therapeutic immune responses to patients suffering from, or predisposed to, diseases impacted by IL-6 dysregulation. The disclosed, IL-6 peptide immunogen constructs can comprise a hybrid peptide having a B cell antigenic site (SEQ ID NOs: 5-20; 72-75) derived from the IL-6R binding region, or fragments thereof, linked to a heterologous Th epitope derived from a pathogenic protein (e.g., SEQ ID NOs: 78-106 and 216-226 of Table 2) that act together to stimulate the generation of highly specific antibodies that are cross-reactive with the recombinant human IL-6 (SEQ ID NO: 1), or IL-6 of other species, such as macaque (SEQ ID NO: 2), mouse (SEQ ID NO: 3), and rat IL-6 (SEQ ID NO: 4).

In some embodiments, IL-6 peptide immunogen constructs (e.g., SEQ ID NOs: 107-186 of Table 3) contain hybrid peptides having a B cell antigenic site, for example C73-C83 (SEQ ID NO: 5), linked to heterologous Th epitopes derived from various pathogenic proteins (SEQ ID NOs: 78-106 and 216-226) capable of eliciting antibodies cross-reactive with the recombinant human IL-6 (SEQ ID NO: 1), and having cross-reactivities to IL-6 of other species (SEQ ID NOs: 2, 3, 4). Of the heterologous Th epitopes employed to enhance the B cell antigenic site, Th epitopes derived from natural pathogens EBV BPLF1 (SEQ ID NO: 105), EBV CP (SEQ ID NO: 102), *Clostridium Tetani* 1,2,4 (SEQ ID NOs: 78, 99-101), Cholera Toxin (SEQ ID NO: 85), *Schistosoma mansoni* (SEQ ID NO: 84) and those idealized artificial Th epitopes derived from Measles Virus Fusion protein (MVF 1 to 5) and Hepatitis B Surface Antigen (HBsAg 1 to 3) in the form of either single sequence or combinatorial sequences (e.g. SEQ ID NOs: 79, 86-92) are found of particular use in such B cell antigenicity enhancement through immunogenicity screening testing.

The present disclosure is also directed to peptide compositions comprising a mixture of IL-6 peptide immunogen constructs with heterologous Th epitopes derived from different pathogens. Compositions comprising a mixture of IL-6 peptide immunogen constructs can be used to allow coverage of as broad a genetic background in patients leading to a higher percentage in responder rate upon immunization for the prevention and/or treatment of diseases impacted by IL-6 dysregulation. Synergistic enhancement of an immune response can be observed when using peptide compositions containing more than one IL-6 peptide immunogen construct.

The antibody response derived from such peptide immunogen constructs was mostly (>90%) focused on the desired cross-reactivity against the IL-6R binding region peptides (SEQ ID NOs: 5-19) without much, if any, directed to the heterologous Th epitopes employed for immunogenicity enhancement. This is in sharp contrast to standard methods that use a conventional carrier protein, such as KLH, toxoid, or other biological carriers used for such peptide antigenicity enhancement.

The present disclosure is also directed to pharmaceutical compositions including formulations for the prevention and/or treatment of diseases impacted by IL-6 dysregulation. In some embodiments, pharmaceutical compositions comprising a stabilized immunostimulatory complex, which is formed by mixing a CpG oligomer with a peptide composition containing a mixture of the IL-6 peptide immunogen constructs through electrostatic association, to further enhance the IL-6 peptide immunogenicity towards the desired cross-reactivity with the full length human IL-6 (SEQ ID NO: 1) or with IL-6 of other species such as macaque (SEQ ID NO: 2), mouse (SEQ ID NO. 3), and rat (SEQ ID NO: 4).

In other embodiments, pharmaceutical compositions comprising a peptide composition of a mixture of the IL-6 peptide immunogen constructs in contact with mineral salts including Alum gel (ALHYDROGEL) or Aluminum phosphate (ADJU-PHOS) to form a suspension, or with MONTANIDE ISA 51 or 720 as adjuvant to form water-in-oil emulsions, was used for administration to patients for the prevention and/or treatment of diseases impacted by IL-6 dysregulation.

Furthermore, the present disclosure also provides a method for the low cost manufacture and quality control of IL-6 peptide immunogen constructs and formulations thereof, for the use of preventing and/or treating animals and patients with diseases impacted by IL-6 dysregulation.

The present disclosure is also directed to antibodies directed against the disclosed IL-6 peptide immunogen constructs. In particular, the IL-6 peptide immunogen constructs of the present disclosure are able to stimulate the generation of highly specific antibodies that are cross-reactive with the IL-6R binding sites on the IL-6 molecule. The disclosed antibodies bind with high specificity to IL-6R binding sites without much, if any, directed to the heterologous Th epitopes employed for immunogenicity enhancement, which is in sharp contrast to antibodies produced using conventional proteins or other biological carriers used for such peptide immunogenicity enhancement. Thus, the disclosed IL-6 peptide immunogen constructs are capable of breaking the immune tolerance against self-IL-6 protein, with a high responder rate, compared to other peptide or protein immunogens.

In certain embodiments, antibodies are directed against and specifically bind to the IL-6R binding sites on the human IL-6 molecule (SEQ ID NO: 1). The highly specific antibodies elicited by the IL-6 peptide immunogen constructs can inhibit IL-6 and IL-6R binding, and the downstream events such as IL-6-induced STAT3 phosphorylation, IL-6 dependent cell proliferation, IL-6 induced MCP production, and other IL-6 related pathological conditions; leading to effective treatment of patients suffering from diseases impacted by IL-6 dysregulation.

In a further aspect, the present disclosure provides human antibodies (polyclonal and monoclonal) against IL-6 induced in patients receiving compositions containing the disclosed IL-6 peptide immunogen constructs. An efficient method to make human monoclonal antibodies from B cells isolated from the blood of a human patient is described by Traggiai, et al. (2004), the disclosure of which is herein incorporated by reference in its entirety.

Based on their unique characteristics and properties, the disclosed antibodies elicited by the IL-6 peptide immunogen constructs are capable of providing an immunotherapeutic approach to treating patients suffering from diseases impacted by IL-6 dysregulation.

The present disclosure is also directed to methods of making the disclosed IL-6 peptide immunogen constructs, compositions, and antibodies. The disclosed methods provide for the low cost manufacture and quality control of IL-6 peptide immunogen constructs and compositions containing the constructs, which can be used in methods for treating patients suffering from diseases impacted by IL-6 dysregulation.

The present disclosure also includes methods for preventing and/or treating diseases impacted by IL-6 dysregulation in a subject using the disclosed IL-6 peptide immunogen constructs and/or antibodies directed against the IL-6 peptide immunogen constructs. The disclosed methods include a step of administering a composition containing a disclosed IL-6 peptide immunogen construct to a subject. In some embodiments, the composition utilized in the methods contain a disclosed IL-6 peptide immunogen construct in the form of a stable immunostimulatory complex with negatively charged oligonucleotides, such as a CpG oligomer, through electrostatic association, which can be further supplemented with an adjuvant, for administration to a subject predisposed to, or suffering from, a disease impacted by IL-6 dysregulation.

The disclosed methods also include dosing regimens, dosage forms, and routes for administering the peptide immunogen constructs to prevent and/or treat diseases impacted by IL-6 dysregulation.

General

The section headings used herein are for organizational purposes only and are not to be construed as limiting the subject matter described. All references or portions of references cited in this application are expressly incorporated by reference herein in their entirety for any purpose.

Unless otherwise explained, all technical and scientific terms used herein have the same meaning as commonly understood by one of ordinary skill in the art to which this invention belongs. The singular terms "a," "an," and "the" include plural referents unless context clearly indicates otherwise. Similarly, the word "or" is intended to include "and" unless the context clearly indicates otherwise. Hence, the phrase "comprising A or B" means including A, or B, or A and B. It is further to be understood that all amino acid sizes, and all molecular weight or molecular mass values, given for polypeptides are approximate, and are provided for description. Although methods and materials similar or equivalent to those described herein can be used in the practice or testing of the disclosed method, suitable methods and materials are described below. All publications, patent applications, patents, and other references mentioned herein are incorporated by reference in their entirety. In case of conflict, the present specification, including explanations of terms, will control. In addition, the materials, methods, and examples disclosed herein are illustrative only and not intended to be limiting.

IL-6 Peptide Immunogen Construct

The present disclosure provides peptide immunogen constructs containing a B cell epitope with an amino acid sequence from IL-6 Receptor (IL-6R) binding region E42-C83 (SEQ ID NO: 16) or N144-I166 (SEQ ID NO: 19), or fragments thereof (e.g. SEQ ID NOs: 5-19). The B cell epitope is covalently linked to a heterologous T helper cell (Th) epitope derived from a pathogen protein directly or through an optional heterologous spacer. These constructs, containing both designed B cell- and Th cell epitopes act together to stimulate the generation of highly specific antibodies directed against the IL-6R binding region on IL-6, offering therapeutic immune responses to patients predisposed to, or suffering from, a disease impacted by IL-6 dysregulation.

The phrase "IL-6 peptide immunogen construct" or "peptide immunogen construct", as used herein, refers to a peptide with more than 30 amino acids in length containing (a) a B cell epitope having about more than 10 contiguous amino acid residues from the IL-6R binding region represented by a peptide E42-C83 (SEQ ID NO: 16) or N144-I166 (SEQ ID NO: 19), or fragments thereof (e.g. SEQ ID NOs: 5-19), of the full-length human IL-6 (SEQ ID NO. 1); (b) a heterologous Th epitope; and (c) an optional heterologous spacer.

In certain embodiments, the IL-6 peptide immunogen construct can be represented by the formulae:

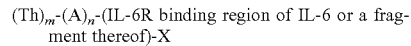

or

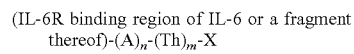

or (Th)$_m$-(A)$_n$-(IL-6R binding region of IL-6 or a fragment thereof)-(A)$_n$-(Th)$_m$-X wherein Th is a heterologous T helper epitope;

A is a heterologous spacer;

(IL-6R binding region of IL-6 or a fragment thereof) is a B cell epitope peptide having from 7 to 42 amino acid residues from IL-6R binding region of IL-6 (SEQ ID NO: 1);

X is an α-COOH or α-CONH$_2$ of an amino acid;

m is from 1 to about 4; and n is from 0 to about 10.

The IL-6 peptide immunogen constructs of the present disclosure were designed and selected based on a number of rationales, including:

i. the IL-6 B cell epitope peptide is non-immunogenic on its own to avoid autologous T cell activation;

ii. the IL-6 B cell epitope peptide can be rendered immunogenic by using a protein carrier or a potent T helper epitope(s);

iii. when the IL-6 B cell epitope peptide rendered immunogenic and administered to a host, the peptide immunogen construct:

a. elicits high titer antibodies preferentially directed against the IL-6 peptide sequence (B cell epitope) and not the protein carrier or T helper epitope(s);

b. breaks immune tolerance in the immunized host and generates highly specific antibodies having cross-reactivity with the IL-6 (SEQ ID NO: 1);

c. generates highly specific antibodies capable of inhibiting IL-6 and IL-6R binding, and the downstream events such as IL-6-induced STAT3 phosphorylation, IL-6 dependent cell proliferation, IL-6 induced MCP production; and d. generates highly specific antibodies capable of leading to the in vivo reduction of other IL-6 related pathological conditions.

The disclosed IL-6 peptide immunogen constructs and formulations thereof can effectively function as a pharmaceutical composition to prevent and/or treat subjects predisposed to, or suffering from, a disease impacted by IL-6 dysregulation.

The various components of the disclosed IL-6 peptide immunogen construct are described in further detail below.

a. B Cell Epitope Peptide from the IL-6R Binding Region

The present disclosure is directed to a novel peptide composition for the generation of high titer antibodies with specificity for the human recombinant IL-6 protein and cross-reactivities to the IL-6 proteins from macaque, mouse, and rat species. The site-specificity of the peptide composition minimizes the generation of antibodies that are directed to irrelevant sites on other regions on IL-6 or irrelevant sites on carrier proteins, thus providing high safety factor.

The term "IL-6", as used herein, refers to the full-length IL-6 protein from human (UniProtKB P05231; GenBank Accession No. NP_000591.1) and other species with cross-reactivities, including macaque (UniProtKB A0A1D5QM02-1; GenBank Accession No. NP_001274245.1), mouse (UniProtKB P08505; GenBank Accession No. NP_112445.1), and rat (UniProtKB P20607, GenBank Accession No. NP_036721.1). The amino acid sequence alignments of the full-length IL-6 sequences for human (SEQ ID NO: 227), macaque (SEQ ID NO: 228), mouse (SEQ ID NO: 229), and rat (SEQ ID NO: 230) are shown in FIG. 1.

More specifically, the term "IL-6", as used herein, refers to the amino acid sequence of the full-length, mature IL-6 protein with the N-terminal signal peptide (containing about 24 to 28 amino acids, depending on the species) cleaved. The amino acid sequence of the full-length mature IL-6 protein from human (SEQ ID NO: 1), macaque (SEQ ID NO: 2), mouse (SEQ ID NO: 3), and rat (SEQ ID NO: 4) are shown in Table 1. Throughout the present application, the numbering of the amino acid positions within the IL-6 protein are based on the full-length, mature sequences of IL-6, where the N-terminal signal sequence is cleaved, represented by SEQ ID NOs: 1-4, as shown in Table 1.

The IL-6R is constituted by two chains: (1) an IL-6 binding chain or IL-6Rα, which exists in two forms, i.e., (a) a 80 kD transmembrane IL-6Rα (mIL-6Rα)(UniProtKB: P08887; GenBank Accession No. NP_000556.1), and (b) a 50-55 kD soluble IL-6Rα (sIL-6Rα) (UniProtKB: P08887 or P08887-2) and, (2) a 130 kD signal-transducing chain, named IL-6Rβ or gp130 (UniProtKB: P40189; GenBank Accession No. NP_002175.2).

The membrane IL-6Rα (or mIL-6Rα) is expressed on the surface of a limited number of cell types, i.e., hepatocytes, megakaryocytes, and leukocytes, including monocytes, macrophages, neutrophils, and T- and B-lymphocytes. The soluble IL-6Rα (or sIL-6Rα) is present in human plasma (25-75 ng/mL) and tissue fluids and can be generated by proteolytic cleavage (shedding) of the mIL-6Rα by metalloproteases (A Disintegrin And Metalloproteinases (i.e. ADAM)), or, in minor part, via alternative splicing by omission of the transmembrane domain.

The membrane IL-6Rβ or gp130 is ubiquitously expressed on all human cells (Sabba, 2008).

In classic signaling, IL-6 binds to the membrane bound IL-6 receptor (mIL-6Rα) and the IL-6-mIL-6Rα complex associates with the IL-6Rβ-subunit (gp130), inducing gp130 dimerization and intracellular signaling. Alternatively, IL-6 can bind to soluble IL-6Rα (sIL-6Rα), which is generated by cleavage of mIL-6Rα by a disintegrin and metalloproteinase domain-containing protein 17 (ADAM17). The IL-6-sIL-6Rα complex then binds to membrane-bound IL-6Rβ3-subunit (gp130), even on cells that do not express IL-6R, and induces trans-signaling. Thus, upon biding to either mIL-6Rα (or sIL-6Rα), IL-6 induces the formation of a hexamer (comprising two IL-6, two IL-6Rα, and two IL-6Rβ (gp130)) proteins, which in turn triggers the downstream signaling cascade (Rose-John, et al., 2017).

Cellular activation via IL-6 binding to mIL-6Rα is named "classic signaling". All other cells not expressing mIL-6Rα obtain their IL-6 signals by "trans-signaling": IL-6 binds to the circulating sIL-6Rα, and this complex forms the signaling complex with IL-6Rβ or gp130 on the cell surface. Trans-signaling can occur in a broad range of human cells, thus contributing to the pleiotropic activities of IL-6. It is currently understood that homeostatic and regenerative activities of IL-6 are mediated by classical signaling, while proinflammatory effects mainly result from trans-signaling pathway activation. Increasing evidence indicates that IL-6 trans-signaling is particularly involved in disease development. A soluble form of the IL-6Rβ (sIL-6Rβ) or gp130 (sgp130) was also detected in the circulation at relatively high concentrations, mainly produced by alternative splicing. Since sgp130 can bind to the IL-6/sIL-6Rα complex, it acts as a natural and specific inhibitor of IL-6 mediated trans-signaling while classic signaling is not affected by sgp130.

While IL-6Rα is a unique binding receptor for IL-6, the IL-6Rβ (or gp130) signal-transducing chain is shared by members of the IL-6 family, comprising leukemia inhibitory factor, oncostatin M, ciliary neurotrophic factor, IL-11, cardiotrophin-1, neuropoietin-1, IL-27, and IL-35.

The IL-6 B cell epitope portion of the IL-6 peptide immunogen constructs targets the IL-6R binding regions on the IL-6 molecule. The B cell epitope peptides contain about 7 to about 42 amino acid residues derived from either E42-C83 (SEQ ID NO: 16) or N144-I166 (SEQ ID NO: 19) of the full-length, mature IL-6 protein (SEQ ID NOs: 1-4). The IL-6 B cell epitopes were selected after extensive serological screening using fragments of the IL-6 protein, some of which contained a naturally existing intramolecular loop within the protein, as shown by the shaded cysteine residues in FIG. 1.

In certain embodiments, the B cell epitope peptide, screened and selected based on design rationales, contains an amino acid sequence from the internal intra-molecular loop of IL-6 formed by endogenous cysteines (e.g., C73-C83 (SEQ ID NO: 5) or C44-C50 (SEQ ID NO: 15)) according to the numbering of the full-length, mature IL-6 protein sequence (SEQ ID NO: 1) or from C-terminus of the IL-6 molecule including amino acid sequence from N144-I166 (SEQ ID NO: 19). In some embodiments, the B cell epitope has an amino acid sequence of SEQ ID NOs: 5-19, as shown in Table 1.

The IL-6 B cell epitope peptide of the present disclosure also includes immunologically functional analogues or homologues of the IL-6 peptides (SEQ ID NOs: 5-19). Functional immunological analogues or homologues of IL-6 B cell epitope peptide include variants that retain substantially the same immunogenicity as the original peptide. Immunologically functional analogues can have a conservative substitution in an amino acid position: a change in overall charge, a covalent attachment to another moiety; or amino acid additions, insertions, or deletions; and/or any combination thereof (e.g., 11-6 peptides of SEQ ID NOs: 72-76).

b. Heterologous T Helper Cell Epitopes (Th Epitopes)

The present disclosure provides peptide immunogen constructs containing a B cell epitope from IL-6 covalently linked to a heterologous T helper cell (Th) epitope directly or through an optional heterologous spacer.

The heterologous Th epitope in the IL-6 peptide immunogen construct enhances the immunogenicity of the IL-6 fragment, which facilitates the production of specific high titer antibodies directed against the optimized target B cell epitope peptide (i.e., the IL-6 fragment) screened and selected based on design rationales.

The term "heterologous", as used herein, refers to an amino acid sequence that is derived from an amino acid sequence that is not part of, or homologous with, the wild-type sequence of IL-6. Thus, a heterologous Th epitope is a Th epitope derived from an amino acid sequence that is not naturally found in IL-6 (i.e., the Th epitope is not autologous to IL-6). Since the Th epitope is heterologous to IL-6, the natural amino acid sequence of IL-6 is not extended in either the N-terminal or C-terminal directions when the heterologous Th epitope is covalently linked to the IL-6 fragment.

The heterologous Th epitope of the present disclosure can be any Th epitope that does not have an amino acid sequence naturally found in IL-6. The Th epitope can also have promiscuous binding motifs to MHC class I molecules of multiple species. In certain embodiments, the Th epitope comprises multiple promiscuous MHC class II binding motifs to allow maximal activation of T helper cells leading to initiation and regulation of immune responses. The Th epitope is preferably immunosilent on its own, i.e. little, if any, of the antibodies generated by the IL-6 peptide immunogen constructs will be directed towards the Th epitope, thus allowing a very focused immune response directed to the targeted B cell epitope peptide of the IL-6.

Th epitopes of the present disclosure include, but are not limited to, amino acid sequences derived from foreign pathogens, as exemplified in Table 2 (SEQ ID NOs: 78-106 and 216-226). Further, Th epitopes include idealized artificial Th epitopes and combinatorial idealized artificial Th epitopes (e.g., SEQ ID NOs: 79, 86, 91, 92 and 79, 86-92). The heterologous Th epitope peptides presented as a combinatorial sequence (e.g., SEQ ID NOs: 87-90), contain a mixture of amino acid residues represented at specific positions within the peptide framework based on the variable residues of homologues for that particular peptide. An assembly of combinatorial peptides can be synthesized in one process by adding a mixture of the designated protected amino acids, instead of one particular amino acid, at a specified position during the synthesis process. Such combinatorial heterologous Th epitope peptides assemblies can allow broad Th epitope coverage for animals having a diverse genetic background. Representative combinatorial sequences of heterologous Th epitope peptides include SEQ ID NOs: 87-90 which are shown in Table 2. Th epitope peptides of the present disclosure provide broad reactivity and immunogenicity to animals and patients from genetically diverse populations.

c. Heterologous Spacer

The disclosed IL-6 peptide immunogen constructs optionally contain a heterologous spacer that covalently links the IL-6 B cell epitope peptide to the heterologous T helper cell (Th) epitope.

As discussed above, the term "heterologous", refers to an amino acid sequence that is derived from an amino acid sequence that is not part of, or homologous with, the natural type sequence of IL-6. Thus, the natural amino acid sequence of IL-6 is not extended in either the N-terminal or C-terminal directions when the heterologous spacer is covalently linked to the IL-6 B cell epitope peptide because the spacer is heterologous to the IL-6 sequence.

The spacer is any molecule or chemical structure capable of linking two amino acids and/or peptides together. The spacer can vary in length or polarity depending on the application. The spacer attachment can be through an amide- or carboxyl-linkage but other functionalities are possible as well. The spacer can include a chemical compound, a naturally occurring amino acid, or a non-naturally occurring amino acid.

The spacer can provide structural features to the IL-6 peptide immunogen construct. Structurally, the spacer provides a physical separation of the Th epitope from the B cell epitope of the IL-6 fragment. The physical separation by the spacer can disrupt any artificial secondary structures created by joining the Th epitope to the B cell epitope. Additionally, the physical separation of the epitopes by the spacer can eliminate interference between the Th cell and/or B cell responses. Furthermore, the spacer can be designed to create or modify a secondary structure of the peptide immunogen construct. For example, a spacer can be designed to act as a flexible hinge to enhance the separation of the Th epitope and B cell epitope. A flexible hinge spacer can also permit more efficient interactions between the presented peptide immunogen and the appropriate Th cells and B cells to enhance the immune responses to the Th epitope and B cell epitope. Examples of sequences encoding flexible hinges are found in the immunoglobulin heavy chain hinge region, which are often proline rich. One particularly useful flexible hinge that can be used as a spacer is provided by the sequence Pro-Pro-Xaa-Pro-Xaa-Pro (SEQ ID NO: 76), where Xaa is any amino acid, and preferably aspartic acid.

The spacer can also provide functional features to the IL-6 peptide immunogen construct. For example, the spacer can be designed to change the overall charge of the IL-6 peptide immunogen construct, which can affect the solubility of the peptide immunogen construct. Additionally, changing the overall charge of the IL-6 peptide immunogen construct can affect the ability of the peptide immunogen construct to associate with other compounds and reagents. As discussed in further detail below, the IL-6 peptide immunogen construct can be formed into a stable immunostimulatory complex with a highly charged oligonucleotide, such as CpG oligomers, through electrostatic association. The overall charge of the IL-6 peptide immunogen construct is important for the formation of these stable immunostimulatory complexes.

Chemical compounds that can be used as a spacer include, but are not limited to, (2-aminoethoxy) acetic acid (AEA), 5-aminovaleric acid (AVA), 6-aminocaproic acid (Ahx), 8-amino-3,6-dioxaoctanoic acid (AEEA, mini-PEG1), 12-amino-4,7,10-trioxadodecanoic acid (mini-PEG2), 15-amino-4,7,10,13-tetraoxapenta-decanoic acid (mini-PEG3), trioxatridecan-succinamic acid (Ttds), 12-amino-dodecanoic acid, Fmoc-5-amino-3-oxapentanoic acid (O1Pen), and the like.

Naturally-occurring amino acids include alanine, arginine, asparagine, aspartic acid, cysteine, glutamic acid, glutamine, glycine, histidine, isoleucine, leucine, lysine, methionine, phenylalanine, proline, serine, threonine, tryptophan, tyrosine and valine.

Non-naturally occurring amino acids include, but are not limited to, ε-N Lysine, β-alanine, ornithine, norleucine, norvaline, hydroxyproline, thyroxine, γ-amino butyric acid, homoserine, citrulline, aminobenzoic acid, 6-aminocaproic acid (Aca; 6-Aminohexanoic acid), hydroxyproline, mercaptopropionic acid (MPA), 3-nitro-tyrosine, pyroglutamic acid, and the like.

The spacer in the IL-6 peptide immunogen construct can be covalently linked at either N- or C-terminal end of the Th epitope and the IL-6 B cell epitope peptide. In some embodiments, the spacer is covalently linked to the C-terminal end of the Th epitope and to the N-terminal end of the IL-6 B cell epitope peptide. In other embodiments, the spacer is covalently linked to the C-terminal end of the IL-6 B cell epitope peptide and to the N-terminal end of the Th epitope. In certain embodiments, more than one spacer can be used, for example, when more than one Th epitope is present in the IL-6 peptide immunogen construct. When more than one spacer is used, each spacer can be the same as each other or different. Additionally, when more than one Th epitope is present in the IL-6 peptide immunogen construct, the Th epitopes can be separated with a spacer, which can be the same as, or different from, the spacer used to separate the Th epitope from the IL-6 B cell epitope peptide. There is no limitation in the arrangement of the spacer in relation to the Th epitope or the IL-6 B cell epitope peptide.

In certain embodiments, the heterologous spacer is a naturally occurring amino acid or a non-naturally occurring amino acid. In other embodiments, the spacer contains more than one naturally occurring or non-naturally occurring amino acid. In specific embodiments, the spacer is Lys-, Gly-, Lys-Lys-Lys-, (α, ε-N)Lys, ε-N-Lys-Lys-Lys-Lys (SEQ ID NO: 77), or Lys-Lys-Lys-ε-N-Lys (SEQ ID NO: 231).

d. Specific Embodiments of the IL-6 Peptide Immunogen Constructs

In certain embodiments, the IL-6 peptide immunogen constructs can be represented by the following formulae:

An IL-6 peptide immunogen construct having about more than 30 amino acids in length, represented by the formulae:

(Th)$_m$-(A)$_n$-(IL-6R binding region of IL-6 or a fragment thereof)-X or (IL-6R binding region of IL-6 or a fragment thereof-(A)-(Th)$_m$-X or (Th)$_m$-(A)$_n$-(IL-6R binding region of IL-6 or a fragment thereof)-(A)$_n$-(Th)$_m$-X wherein
Th is a heterologous T helper epitope;
A is a heterologous spacer;
(IL-6R binding region of IL-6 or a fragment thereof) is a B cell epitope peptide having about 7 to about 42 amino acid residues from IL-6R binding region of IL-6 (SEQ ID NO: 1);
X is an α-COOH or α-CONH$_2$ of an amino acid;
m is from 1 to about 4; and
n is from 0 to about 10.

In some embodiments, the (IL-6R binding region of IL-6 or a fragment thereof) is a B cell epitope peptide having an amino acid sequence selected from any of SEQ ID NOs: 5-19. In certain embodiments, the B cell epitope has an amino acid sequence from E42-C83 (SEQ ID NO: 16) or N144-I166 (SEQ ID NO: 19) of IL-6 (SEQ ID NOs: 1-4), or fragments thereof. In specific embodiments, the (IL-6R binding region of IL-6 or a fragment thereof) is a B cell epitope containing at least one naturally existing intramolecular loop from C73-C83 (SEQ ID NO: 5) and/or C44-C50 (SEQ ID NO: 15), as shown in FIG. 1.

In certain embodiments, the heterologous Th epitope in the IL-6 peptide immunogen construct has an amino acid sequence selected from any of SEQ ID NOs: 78-106, 216-226 or combinations thereof, as shown in Table 2. In some embodiments, the IL-6 peptide immunogen construct contains more than one Th epitope.

In certain embodiments, the optional heterologous spacer is selected from any of Lys-, Gly-, Lys-Lys-Lys-, (α, ε-N) Lys, Pro-Pro-Xaa-Pro-Xaa-Pro (SEQ ID NO: 76), ε-N-Lys-Lys-Lys-Lys (SEQ ID NO: 77), Lys-Lys-Lys-ε-N-Lys (SEQ ID NO: 231), and any combination thereof, where Xaa is any amino acid, but preferably aspartic acid. In specific embodiments, the heterologous spacer is ε-N-Lys-Lys-Lys-Lys (SEQ ID NO: 77) or Lys-Lys-Lys-ε-N-Lys (SEQ ID NO: 231).

In certain embodiments, the IL-6 B cell epitope peptide has about 7 to about 42 amino acid residues from the full-length, mature IL-6 protein of SEQ ID NO: 1. In specific embodiments, the IL-6 B cell epitope peptide contains an amino acid sequence from an intramolecular loop of IL-6 contained within (E42-C83, SEQ ID NO: 16). In specific embodiments, the IL-6 B cell epitope peptide contain an internal loop of IL-6 from amino acids C73-C83 (SEQ ID NO: 5) or IL-6 C44-C50 (SEQ ID NO: 15) (e.g., SEQ ID NOs: 5-8, 10, 12, 15-17), as shown in Table 1.

In certain embodiments, the IL-6 peptide immunogen construct has an amino acid sequence selected from any of SEQ ID NOs: 107-215 as shown in Table 3. In specific embodiments, the IL-6 peptide immunogen construct has an amino acid sequence selected from any of SEQ ID NOs: 107-160.

IL-6 peptide immunogen constructs comprising Th epitopes can be produced simultaneously in a single solid-phase peptide synthesis in tandem with the IL-6 fragment. Th epitopes also include immunological analogues of Th epitopes. Immunological Th analogues include immune-enhancing analogs, cross-reactive analogues and segments of any of these Th epitopes that are sufficient to enhance or stimulate an immune response to the IL-6 B cell epitope peptide.

The Th epitope in the IL-6 peptide immunogen construct can be covalently linked at either N- or C-terminal end of the IL-6 B cell epitope peptide. In some embodiments, the Th epitope is covalently linked to the N-terminal end of the IL-6 B cell epitope peptide. In other embodiments, the Th epitope is covalently linked to the C-terminal end of the IL-6 B cell epitope peptide. In certain embodiments, more than one Th epitope is covalently linked to the IL-6 B cell epitope peptide. When more than one Th epitope is linked to the IL-6 B cell epitope peptide, each Th epitope can have the same amino acid sequence or different amino acid sequences. In addition, when more than one Th epitope is linked to the IL-6 B cell epitope peptide, the Th epitopes can be arranged in any order. For example, the Th epitopes can be consecutively linked to the N-terminal end of the IL-6 B cell epitope peptide, or consecutively linked to the C-terminal end of the IL-6 B cell epitope peptide, or a Th epitope can be covalently linked to the N-terminal end of the IL-6 B cell epitope peptide while a separate Th epitope is covalently linked to the C-terminal end of the IL-6 B cell epitope peptide. There is no limitation in the arrangement of the Th epitopes in relation to the IL-6 B cell epitope peptide.

In some embodiments, the Th epitope is covalently linked to the IL-6 B cell epitope peptide directly. In other embodiments, the Th epitope is covalently linked to the IL-6 fragment through a heterologous spacer.

e. Variants, Homologues, and Functional Analogues

Variants and analogs of the above immunogenic peptide constructs that induce and/or cross-react with antibodies to the preferred IL-6 B cell epitope peptides can also be used. Analogs, including allelic, species, and induced variants, typically differ from naturally occurring peptides at one, two, or a few positions, often by virtue of conservative substitutions. Analogs typically exhibit at least 80 or 90% sequence identity with natural peptides. Some analogs also include unnatural amino acids or modifications of N- or C-terminal amino acids at one, two, or a few positions.

Variants that are functional analogues can have a conservative substitution in an amino acid position; a change in overall charge; a covalent attachment to another moiety; or amino acid additions, insertions, or deletions; and/or any combination thereof.

Conservative substitutions are when one amino acid residue is substituted for another amino acid residue with similar chemical properties. For example, the nonpolar (hydrophobic) amino acids include alanine, leucine, isoleucine, valine, proline, phenylalanine, tryptophan and methionine; the polar neutral amino acids include glycine, serine, threonine, cysteine, tyrosine, asparagine, and glutamine; the positively charged (basic) amino acids include arginine, lysine and histidine; and the negatively charged (acidic) amino acids include aspartic acid and glutamic acid.

In a particular embodiment, the functional analogue has at least 50% identity to the original amino acid sequence. In another embodiment, the functional analogue has at least 80/6 identity to the original amino acid sequence. In yet another embodiment, the functional analogue has at least 85% identity to the original amino acid sequence. In still another embodiment, the functional analogue has at least 90% identity to the original amino acid sequence.

Variants also include variations to the phosphorylated residues. For example, variants can include different residues within the peptides that are phosphorylated. Variant immunogenic IL-6 peptides can also include pseudo-phosphorylated peptides. The pseudo-phosphorylated peptides are generated by substituting one or more of the phosphorylated serine, threonine, and tyrosine residues of the IL-6 peptides with acidic amino acid residues such as glutamic acid and aspartic acid.

Functional immunological analogues of the Th epitope peptides are also effective and included as part of the present disclosure. Functional immunological Th analogues can include conservative substitutions, additions, deletions and insertions of from one to about five amino acid residues in the Th epitope which do not essentially modify the Th-stimulating function of the Th epitope. The conservative substitutions, additions, and insertions can be accomplished with natural or non-natural amino acids, as described above for the IL-6 B cell epitope peptide. Table 2 identifies another variation of a functional analogue for Th epitope peptide. In particular, SEQ ID NOs: 79 and 86 of MvF1 and MvF2 Th are functional analogues of SEQ ID NOs: 89 and 91 of MvF4 and MvF5 in that they differ in the amino acid frame by the deletion (SEQ ID NOs: 79 and 86) or the inclusion (SEQ ID NOs: 89 and 91) of two amino acids each at the N- and C-termini. The differences between these two series of analogous sequences would not affect the function of the Th epitopes contained within these sequences. Therefore, functional immunological Th analogues include several versions of the Th epitope derived from Measles Virus Fusion protein MvF1-4 Ths (SEQ ID NOs: 79, 86, 87 and 89) and from Hepatitis Surface protein HBsAg 1-3 Ths (SEQ ID NOs: 88, 90, and 92).

Compositions

The present disclosure also provides compositions comprising the disclosed IL-6 immunogen peptide constructs.

a. Peptide Compositions

Compositions containing the disclosed IL-6 peptide immunogen constructs can be in liquid or solid/lyophilized form. Liquid compositions can include water, buffers, solvents, salts, and/or any other acceptable reagent that does not alter the structural or functional properties of the IL-6 peptide immunogen constructs. Peptide compositions can contain one or more of the disclosed IL-6 peptide immunogen constructs.

b. Pharmaceutical Compositions

The present disclosure is also directed to pharmaceutical compositions containing the disclosed IL-6 peptide immunogen constructs.

Pharmaceutical compositions can contain carriers and/or other additives in a pharmaceutically acceptable delivery system. Accordingly, pharmaceutical compositions can contain a pharmaceutically effective amount of an IL-6 peptide immunogen construct together with pharmaceutically-acceptable carrier, adjuvant, and/or other excipients such as diluents, additives, stabilizing agents, preservatives, solubilizing agents, buffers, and the like.

Pharmaceutical compositions can contain one or more adjuvant that act(s) to accelerate, prolong, or enhance the immune response to the IL-6 peptide immunogen constructs without having any specific antigenic effect itself. Adjuvants used in the pharmaceutical composition can include oils, oil emulsions, aluminum salts, calcium salts, immune stimulating complexes, bacterial and viral derivatives, virosomes, carbohydrates, cytokines, polymeric microparticles. In certain embodiments, the adjuvant can be selected from alum (potassium aluminum phosphate), aluminum phosphate (e.g. ADJU-PHOS®), aluminum hydroxide (e.g. ALHYDROGEL®), calcium phosphate, incomplete Freund's adjuvant (IFA), Freund's complete adjuvant, MF59, adjuvant 65, Lipovant, ISCOM, liposyn, saponin, squalene, L121, EmulsIL-6n®, monophosphoryl lipid A (MPL), Quil A, QS21, MONTANIDE® ISA 35, ISA 50V, ISA 50V2, ISA 51, ISA 206, ISA 720, liposomes, phospholipids, peptidoglycan, lipopolysaccahrides (LPS), ASO1, ASO2, ASO3, ASO4, AF03, lipophilic phospholipid (lipid A), gamma inulin, algammulin, glucans, dextrans, glucomannans, galactomannans, levans, xylans, dimethyldioctadecylammonium bromide (DDA), as well as the other adjuvants and emulsifiers.

In some embodiments, the pharmaceutical composition contains MONTANIDE™ ISA 51 (an oil adjuvant composition comprised of vegetable oil and mannide oleate for production of water-in-oil emulsions), TWEEN® 80 (also known as: Polysorbate 80 or Polyoxyethylene (20) sorbitan monooleate), a CpG oligonucleotide, and/or any combination thereof. In other embodiments, the pharmaceutical composition is a water-in-oil-in-water (i.e. w/o/w) emulsion with EmulsIL-6n or EmulsIL-6n D as the adjuvant.

Pharmaceutical compositions can also include pharmaceutically acceptable additives or excipients. For example, pharmaceutical compositions can contain antioxidants, binders, buffers, bulking agents, carriers, chelating agents, coloring agents, diluents, disintegrants, emulsifying agents, fillers, gelling agents, pH buffering agents, preservatives, solubilizing agents, stabilizers, and the like.

Pharmaceutical compositions can be formulated as immediate release or for sustained release formulations. Additionally the pharmaceutical compositions can be formulated for induction of systemic, or localized mucosal, immunity through immunogen entrapment and co-administration with microparticles. Such delivery systems are readily determined by one of ordinary skill in the art.

Pharmaceutical compositions can be prepared as injectables, either as liquid solutions or suspensions. Liquid vehicles containing the IL-6 peptide immunogen construct can also be prepared prior to injection. The pharmaceutical composition can be administered by any suitable mode of application, for example, i.d., i.v., i.p., i.m., intranasally, orally, subcutaneously, etc. and in any suitable delivery device. In certain embodiments, the pharmaceutical composition is formulated for intravenous, subcutaneous, intradermal, or intramuscular administration. Pharmaceutical compositions suitable for other modes of administration can also be prepared, including oral and intranasal applications.

Pharmaceutical compositions can also be formulated in a suitable dosage unit form. In some embodiments, the pharmaceutical composition contains from about 0.1 μg to about 1 mg of the IL-6 peptide immunogen construct per kg body weight. Effective doses of the pharmaceutical compositions vary depending upon many different factors, including means of administration, target site, physiological state of the patient, whether the patient is human or an animal, other medications administered, and whether treatment is prophylactic or therapeutic. Usually, the patient is a human but nonhuman mammals including transgenic mammals can also be treated. When delivered in multiple doses, the pharmaceutical compositions may be conveniently divided into an appropriate amount per dosage unit form. The administered dosage will depend on the age, weight and general health of the subject as is well known in the therapeutic arts.

In some embodiments, the pharmaceutical composition contains more than one IL-6 peptide immunogen construct. A pharmaceutical composition containing a mixture of more than one IL-6 peptide immunogen construct to allow for synergistic enhancement of the immunoefficacy of the constructs. Pharmaceutical compositions containing more than one IL-6 peptide immunogen construct can be more effective in a larger genetic population due to a broad MHC class II coverage thus provide an improved immune response to the IL-6 peptide immunogen constructs.

In some embodiments, the pharmaceutical composition contains an IL-6 peptide immunogen construct selected from SEQ ID NOs: 107-215 (Table 3), as well as homologues, analogues and/or combinations thereof.

In certain embodiments, IL-6 peptide immunogen constructs (SEQ ID NOs: 170-172) with heterologous Th epitopes derived from MVF and HBsAg in a combinatorial form (SEQ ID NOs: 87-90) were mixed in an equimolar ratio for use in a formulation to allow for maximal coverage of a host population having a diverse genetic background. Synergistic enhancement in IL-6 73-83 immunogen constructs (SEQ ID NOs: 170, 172) was observed in the peptide compositions of this disclosure.

Furthermore, the antibody response elicited by IL-6 peptide immunogen construct (e.g. UBITh® 1 with SEQ ID NO: 91) was mostly (>90%) focused on the desired cross-reactivity against the B cell epitope peptide of IL-6 (SEQ ID NO: 5) without much, if any, directed to the heterologous Th epitopes employed for immunogenicity enhancement (Example 6, Table 8). This is in sharp contrast to the conventional protein such as KLH or other biological protein carriers used for such IL-6 peptide immunogenicity enhancement.

In other embodiments, pharmaceutical compositions comprising a peptide composition of for example a mixture of the IL-6 peptide immunogen constructs in contact with mineral salts including Alum gel (ALHYDROGEL) or Aluminum phosphate (ADJUPHOS) as adjuvant to form a suspension formulation was used for administration to hosts.

Pharmaceutical compositions containing an IL-6 peptide immunogen construct can be used to elicit an immune response and produce antibodies in a host upon administration.

c. Immunostimulatory Complexes

The present disclosure is also directed to pharmaceutical compositions containing an IL-6 peptide immunogen construct in the form of an immunostimulatory complex with a CpG oligonucleotide. Such immunostimulatory complexes are specifically adapted to act as an adjuvant and as a peptide immunogen stabilizer. The immunostimulatory complexes are in the form of a particulate, which can efficiently present the IL-6 peptide immunogen to the cells of the immune system to produce an immune response. The immunostimulatory complexes may be formulated as a suspension for parenteral administration. The immunostimulatory complexes may also be formulated in the form of water in oil (w/o) emulsions, as a suspension in combination with a mineral salt or with an in-situ gelling polymer for the efficient delivery of the IL-6 peptide immunogen construct to the cells of the immune system of a host following parenteral administration.

The stabilized immunostimulatory complex can be formed by complexing an IL-6 peptide immunogen construct with an anionic molecule, oligonucleotide, polynucleotide, or combinations thereof via electrostatic association. The stabilized immunostimulatory complex may be incorporated into a pharmaceutical composition as an immunogen delivery system.

In certain embodiments, the IL-6 peptide immunogen construct is designed to contain a cationic portion that is positively charged at a pH in the range of 5.0 to 8.0. The net charge on the cationic portion of the IL-6 peptide immunogen construct, or mixture of constructs, is calculated by assigning a +1 charge for each lysine (K), arginine (R) or histidine (H), a −1 charge for each aspartic acid (D) or glutamic acid (E) and a charge of 0 for the other amino acid within the sequence. The charges are summed within the cationic portion of the IL-6 peptide immunogen construct and expressed as the net average charge. A suitable peptide immunogen has a cationic portion with a net average positive charge of +1. Preferably, the peptide immunogen has a net positive charge in the range that is larger than +2. In some embodiments, the cationic portion of the IL-6 peptide immunogen construct is the heterologous spacer. In certain embodiments, the cationic portion of the IL-6 peptide immunogen construct has a charge of +4 when the spacer sequence is (α, ε-N)Lys, ε-N-Lys-Lys-Lys-Lys (SEQ ID NO: 77).

An "anionic molecule" as described herein refers to any molecule that is negatively charged at a pH in the range of 5.0-8.0. In certain embodiments, the anionic molecule is an oligomer or polymer. The net negative charge on the oligomer or polymer is calculated by assigning a −1 charge for each phosphodiester or phosphorothioate group in the oligomer. A suitable anionic oligonucleotide is a single-stranded DNA molecule with 8 to 64 nucleotide bases, with the number of repeats of the CpG motif in the range of 1 to 10. Preferably, the CpG immunostimulatory single-stranded DNA molecules contain 18-48 nucleotide bases, with the number of repeats of CpG motif in the range of 3 to 8.

More preferably the anionic oligonucleotide is represented by the formula: 5' $X^1CGX^2$ 3' wherein C and G are unmethylated; and $X^1$ is selected from the group consisting of A (adenine), G (guanine) and T (thymine); and $X^2$ is C (cytosine) or T (thymine). Or, the anionic oligonucleotide is represented by the formula: 5' $(X^3)_2CG(X^4)_2$ 3' wherein C and G are unmethylated; and $X^3$ is selected from the group consisting of A, T or G; and $X^4$ is C or T. In specific embodiments, the CpG oligonucleotide has the sequence of CpG1: 5' TCg TCg TTT TgT CgT TTT gTC gTT TTg TCg TT 3' (fully phosphorothioated) (SEQ ID NO: 232), CpG2: 5' Phosphate TCg TCg TTT TgT CgT TTT gTC gTT 3'(fully phosphorothioated)(SEQ ID NO: 233), or CpG3 5' TCg TCg TTT TgT CgT TTT gTC gTT 3' (fully phosphorothioated) (SEQ ID NO: 234).

The resulting immunostimulatory complex is in the form of particles with a size typically in the range from 1-50 microns and is a function of many factors including the relative charge stoichiometry and molecular weight of the interacting species. The particulated immunostimulatory complex has the advantage of providing adjuvantation and upregulation of specific immune responses in vivo. Additionally, the stabilized immunostimulatory complex is suitable for preparing pharmaceutical compositions by various processes including water-in-oil emulsions, mineral salt suspensions and polymeric gels.

The present disclosure is also directed to pharmaceutical compositions, including formulations, for prevention and/or treatment of diseases impacted by IL-6 dysregulation. In some embodiments, pharmaceutical compositions comprising a stabilized immunostimulatory complex, which is formed through mixing a CpG oligomer with a peptide composition containing a mixture of the IL-6 peptide immunogen constructs (e.g., SEQ ID NOs: 107-215) through electrostatic association, to further enhance the immunogenicity of the IL-6 peptide immunogen constructs and elicit antibodies that are cross-reactive with the IL-6 proteins of SEQ ID NOs: 1-4 that are directed at the IL-6R binding regions (Example 6).

In yet other embodiments, pharmaceutical compositions contain a mixture of the IL-6 peptide immunogen constructs (e.g., any combination of SEQ ID NOs: 107-215) in the form of a stabilized immunostimulatory complex with CpG oligomers that are, optionally, mixed with mineral salts, including Alum gel (ALHYDROGEL) or Aluminum phosphate (ADJUPHOS) as an adjuvant with high safety factor, to form a suspension formulation for administration to hosts.

Antibodies

The present disclosure also provides antibodies elicited by the disclosed IL-6 peptide immunogen constructs.

The present disclosure provides IL-6 peptide immunogen constructs and formulations thereof, cost effective in manufacturing, optimal in their design that are capable of eliciting high titer antibodies targeting the IL-6R binding region of the IL-6 molecule that is capable of breaking the immune tolerance against self-protein IL-6 with a high responder rate in immunized hosts. The antibodies generated by the IL-6 peptide immunogen constructs have high affinity towards the IL-6R binding region.

In some embodiments, IL-6 peptide immunogen constructs for eliciting antibodies comprise a hybrid of an IL-6 peptide having a B cell epitope containing about 7 to about 42 amino acids covering the IL-6Rα and IL-6Rβ binding regions with an option to comprise an intramolecular loop structure derived from the IL-6 peptide C73-C83 (SEQ ID NO: 5) or C44-C50 (SEQ ID NO: 15) within IL-6 (see Table 1, FIG. 1, and SEQ ID NOs: 1 and 227) linked to a heterologous Th epitope derived from pathogenic proteins such as Measles Virus Fusion (MVF) protein and others (SEQ ID NOs: 78-106 and 216-226) through an optional spacer. The B cell epitope and Th epitope of the IL-6 peptide immunogen constructs act together to stimulate the generation of highly specific antibodies cross-reactive with the IL-6R binding region of the IL-6 protein (SEQ ID NO: 1).

Traditional methods for immunopotentiating a peptide, such as through chemical coupling to a carrier protein, for example, Keyhole Limpet Hemocyanin (KLH) or other carrier proteins such as Diphtheria toxoid (DT) and Tetanus Toxoid (TT) proteins, typically result in the generation of a large amount of antibodies directed against the carrier protein. Thus, a major deficiency of such peptide-carrier protein compositions is that most (>90%) of antibodies generated by the immunogen are the non-functional antibodies directed against the carrier protein KLH, DT or TT, which can lead to epitopic suppression.

Unlike the traditional method for immunopotentiating a peptide, the antibodies generated by the disclosed IL-6 peptide immunogen constructs (e.g. SEQ ID NO: 142) bind with high specificity to the IL-6 B cell epitope peptide (e.g., SEQ ID NOs: 5-19) with little, if any, antibodies directed against the heterologous Th epitope (e.g. SEQ ID NO: 91 of Table 8) or optional heterologous spacer. In particular, the polyclonal antibodies elicited in immunized animals bind, with high specificity, to the central IL-6R binding region (SEQ ID NO: 107), which results in the inhibition of IL-6 and IL-6R interaction via cis-signaling, as shown in FIG. 5A.

Methods

The present disclosure is also directed to methods for making and using the IL-6 peptide immunogen constructs, compositions, and pharmaceutical compositions.

a. Methods for Manufacturing the IL-6 Peptide Immunogen Construct

The IL-6 peptide immunogen constructs of this disclosure can be made by chemical synthesis methods well known to the ordinarily skilled artisan (see, e.g., Fields et al., Chapter 3 in Synthetic Peptides: A User's Guide, ed. Grant, W.H. Freeman & Co., New York, N.Y., 1992, p. 77). The IL-6 peptide immunogen constructs can be synthesized using the automated Merrifield techniques of solid phase synthesis with the α-NH2 protected by either t-Boc or F-moc chemistry using side chain protected amino acids on, for example, an Applied Biosystems Peptide Synthesizer Model 430A or 431. Preparation of IL-6 peptide immunogen constructs comprising combinatorial library peptides for Th epitopes can be accomplished by providing a mixture of alternative amino acids for coupling at a given variable position.

After complete assembly of the desired I1-6 peptide immunogen construct, the resin can be treated according to standard procedures to cleave the peptide from the resin and the functional groups on the amino acid side chains can be deblocked. The free peptide can be purified by HPLC and characterized biochemically, for example, by amino acid analysis or by sequencing. Purification and characterization methods for peptides are well known to one of ordinary skill in the art.

The quality of peptides produced by this chemical process can be controlled and defined and, as a result, reproducibility of IL-6 peptide immunogen constructs, immunogenicity, and yield can be assured. Detailed description of the manufacturing of the IL-6 peptide immunogen construct through solid phase peptide synthesis is shown in Example 1.

The range in structural variability that allows for retention of an intended immunological activity has been found to be far more accommodating than the range in structural variability allowed for retention of a specific drug activity by a small molecule drug or the desired activities and undesired toxicities found in large molecules that are co-produced with biologically-derived drugs.

Thus, peptide analogues, either intentionally designed or inevitably produced by errors of the synthetic process as a mixture of deletion sequence byproducts that have chromatographic and immunologic properties similar to the intended peptide, are frequently as effective as a purified preparation of the desired peptide. Designed analogues and unintended analogue mixtures are effective as long as a discerning QC procedure is developed to monitor both the manufacturing process and the product evaluation process so as to guarantee the reproducibility and efficacy of the final product employing these peptides.

The I1-6 peptide immunogen constructs can also be made using recombinant DNA technology including nucleic acid molecules, vectors, and/or host cells. As such, nucleic acid molecules encoding the IL-6 peptide immunogen construct and immunologically functional analogues thereof are also encompassed by the present disclosure as part of the present disclosure. Similarly, vectors, including expression vectors, comprising nucleic acid molecules as well as host cells containing the vectors are also encompassed by the present disclosure as part of the present disclosure.

Various exemplary embodiments also encompass methods of producing the IL-6 peptide immunogen construct and immunologically functional analogues thereof. For example, methods can include a step of incubating a host cell containing an expression vector containing a nucleic acid molecule encoding an IL-6 peptide immunogen construct and/or immunologically functional analogue thereof under such conditions where the peptide and/or analogue is expressed. The longer synthetic peptide immunogens can be synthesized by well-known recombinant DNA techniques. Such techniques are provided in well-known standard manuals with detailed protocols. To construct a gene encoding a peptide of this disclosure, the amino acid sequence is reverse translated to obtain a nucleic acid sequence encoding the amino acid sequence, preferably with codons that are optimum for the organism in which the gene is to be expressed. Next, a synthetic gene is made typically by synthesizing oligonucleotides which encode the peptide and any regulatory elements, if necessary. The synthetic gene is inserted in a suitable cloning vector and transfected into a host cell. The peptide is then expressed under suitable conditions appropriate for the selected expression system and host. The peptide is purified and characterized by standard methods.

b. Methods for the Manufacturing of Immunostimulatory Complexes

Various exemplary embodiments also encompass methods of producing the Immunostimulatory complexes comprising IL-6 peptide immunogen constructs and CpG oligodeoxynucleotide (ODN) molecule. Stabilized immunostimulatory complexes (ISC) are derived from a cationic portion of the IL-6 peptide immunogen construct and a polyanionic CpG ODN molecule. The self-assembling system is driven by electrostatic neutralization of charge. Stoichiometry of the molar charge ratio of cationic portion of the IL-6 peptide immunogen construct to anionic oligomer determines extent of association. The non-covalent electrostatic association of IL-6 peptide immunogen construct and CpG ODN is a completely reproducible process. The peptide/CpG ODN immunostimulatory complex aggregates, which facilitate presentation to the "professional" antigen presenting cells (APC) of the immune system thus further enhancing the immunogenicity of the complexes. These complexes are easily characterized for quality control during manufacturing. The peptide/CpG ISC are well tolerated in vivo. This novel particulate system comprising CpG ODN and IL-6 peptide immunogen constructs was designed to take advantage of the generalized B cell mitogenicity associated with CpG ODN use, yet promote balanced Th-1/Th-2 type responses.

The CpG ODN in the disclosed pharmaceutical compositions is 100% bound to immunogen in a process mediated by electrostatic neutralization of opposing charge, resulting in the formation of micron-sized particulates. The particulate form allows for a significantly reduced dosage of CpG from the conventional use of CpG adjuvants, less potential for adverse innate immune responses, and facilitates alternative immunogen processing pathways including antigen presenting cells (APC). Consequently, such formulations are novel conceptually and offer potential advantages by promoting the stimulation of immune responses by alternative mechanisms.

c. Methods for the Manufacturing of Pharmaceutical Compositions

Various exemplary embodiments also encompass pharmaceutical compositions containing IL-6 peptide immunogen constructs. In certain embodiments, the pharmaceutical compositions employ water in oil emulsions and in suspension with mineral salts.

In order for a pharmaceutical composition to be used by a large population, safety becomes another important factor for consideration. Despite there has been use of water-in-oil emulsions in many clinical trials, Alum remains the major adjuvant for use in formulations due to its safety. Alum or its mineral salts Aluminum phosphate (ADJUPHOS) are, therefore, frequently used as adjuvants in preparation for clinical applications.

Other adjuvants and immunostimulating agents include 3 De-O-acylated monophosphoryl lipid A (MPL) or 3-DMP, polymeric or monomeric amino acids, such as polyglutamic acid or polylysine. Such adjuvants can be used with or without other specific immunostimulating agents, such as muramyl peptides (e.g., N-acetylmuramyl-L-threonyl-D-isoglutamine (thr-MDP), N-acetyl-normuramyl-L-alanyl-D-isoglutamine (nor-MDP), N-acetylmuramyl-L-alanyl-D-isoglutaminyl-L-alanine-2-(1'-2' dipalmitoyl-sn-glycero-3-hydroxyphosphoryloxy)-ethylamine (MTP-PE), N-acetylglucsaminyl-N-acetylmuramyl-L-Al-D-isoglu-L-Ala-dipalmitoxy propylamide (DTP-DPP) THERAMIDE™), or other bacterial cell wall components. Oil-in-water emulsions include MF59 (see WO 90/14837 to Van Nest et al., which is hereby incorporated by reference in its entirety), containing 5% Squalene, 0.5% TWEEN 80, and 0.5% Span 85 (optionally containing various amounts of MTP-PE) formulated into submicron particles using a microfluidizer; SAF, containing 10% Squalene, 0.4% TWEEN 80, 5% pluronic-blocked polymer L121, and thr-MDP, either microfluidized into a submicron emulsion or vortexed to generate a larger particle size emulsion; and the RIBI™ adjuvant system (RAS) (Ribi ImmunoChem, Hamilton, Mont.) containing 2% squalene, 0.2% TWEEN 80, and one or more bacterial cell wall components selected from the group consisting of monophosphoryllipid A (MPL), trehalose dimycolate (TDM), and cell wall skeleton (CWS), preferably MPL+CWS (Detox™). Other adjuvants include Complete Freund's Adjuvant (CFA), Incomplete Freund's Adjuvant (IFA), and cytokines, such as interleukins (IL-1, IL-2, and IL-12), macrophage colony stimulating factor (M-CSF), and tumor necrosis factor (TNF-α).

The choice of an adjuvant depends on the stability of the immunogenic formulation containing the adjuvant, the route of administration, the dosing schedule, the efficacy of the adjuvant for the species being immunized, and, in humans, a pharmaceutically acceptable adjuvant is one that has been approved or is approvable for human administration by pertinent regulatory bodies. For example, alum, MPL or Incomplete Freund's adjuvant (Chang, et al., 1998), which is hereby incorporated by reference in its entirety) alone or optionally all combinations thereof are suitable for human administration.

The compositions can include pharmaceutically-acceptable, non-toxic carriers or diluents, which are defined as vehicles commonly used to formulate pharmaceutical compositions for animal or human administration. The diluent is selected so as not to affect the biological activity of the combination. Examples of such diluents are distilled water, physiological phosphate-buffered saline, Ringer's solutions, dextrose solution, and Hank's solution. In addition, the pharmaceutical composition or formulation may also include other carriers, adjuvants, or nontoxic, nontherapeutic, non-immunogenic stabilizers, and the like.

Pharmaceutical compositions can also include large, slowly metabolized macromolecules, such as proteins, polysaccharides like chitosan, polylactic acids, polyglycolic acids and copolymers (e.g., latex functionalized sepharose, agarose, cellulose, and the like), polymeric amino acids, amino acid copolymers, and lipid aggregates (e.g., oil droplets or liposomes). Additionally, these carriers can function as immunostimulating agents (i.e., adjuvants).

The pharmaceutical compositions of the present disclosure can further include a suitable delivery vehicle. Suitable delivery vehicles include, but are not limited to viruses, bacteria, biodegradable microspheres, microparticles, nanoparticles, liposomes, collagen minipellets, and cochleates.

d. Methods of Using Pharmaceutical Compositions

The present disclosure also includes methods of using pharmaceutical compositions containing IL-6 peptide immunogen constructs.

In certain embodiments, the pharmaceutical compositions containing IL-6 peptide immunogen constructs can be used for the treatment of diseases impacted by dysregulation of IL-6.

In some embodiments, the methods comprise administering a pharmaceutical composition comprising a pharmacologically effective amount of an IL-6 peptide immunogen construct to a host in need thereof. In certain embodiments, the methods comprise administering a pharmaceutical composition comprising a pharmacologically effective amount of an IL-6 peptide immunogen construct to a warm-blooded animal (e.g., humans, Cynomolgus macaques, mice) to elicit highly specific antibodies cross-reactive with the human IL-6 protein (SEQ ID NO: 1), or IL-6 proteins from other species (SEQ ID NOs: 2-4).

In certain embodiments, the pharmaceutical compositions containing IL-6 peptide immunogen constructs can be used to treat diseases impacted by dysfunction of IL-6 regulation as shown in both in vitro assays and in vivo disease models.

e. In Vitro Functional Assays and In Vivo Proof of Concept Studies

Antibodies elicited in immunize hosts by the IL-6 peptide immunogen constructs can be used in in vitro functional assays. These functional assays include, but are not limited to:

(1) in vitro binding to IL-6 protein (SEQ ID NO: 1) as a recombinant protein;
(2) inhibition in vitro of IL-6 to IL-6Rα cis-binding;
(3) inhibition in vitro of IL-6/IL-6Rα to IL-6Rβ trans-binding (Example 3);
(4) inhibition in vitro of IL-6 induced TF-1 proliferation (Examples 3 and 7);
(5) inhibition in vitro of IL-6 induced STAT3 phosphorylation (Examples 3 and 7);
(6) inhibition in vitro of IL-6 induced MCP-1 production by human U937 cells (Examples 3 and 7);
(7) inhibition in vivo of collagen-induced arthritis (CIA) model in rats;
(8) inhibition/attenuation in vivo of the release of neutrophils from bone marrow into circulation in rats;
(9) inhibition in vivo of arthritis symptoms as indicated in rats by arthritis scores measured by
   (i) inflammation induced liver secretory proteins;
   (ii) ankle join disruption;
   (iii) production of tissue TNF-α, IL-17 and MCP;
   (iv) reversed body weight loss;
   (v) hind paw swelling;
   (vi) attenuated neutrophilia;
   (vii) attenuated platelet release.

SPECIFIC EMBODIMENTS (1) An IL-6 peptide immunogen construct having about 30 or more amino acids, represented by the formulae:

(Th)$_m$-(A)$_n$-(IL-6R binding region of IL-6 or a fragment thereof)-X or (IL-6R binding region of IL-6 or a fragment thereof)-(A)$_n$-(Th)$_m$-X or (Th)$_m$-(A)$_n$-(IL-6R binding region of IL-6 or a fragment thereof)-(A)$_n$-(Th)$_m$-X wherein
Th is a heterologous T helper epitope;
A is a heterologous spacer;
(IL-6R binding region of IL-6 or a fragment thereof) is a B cell epitope peptide having about 7 to about 42 amino acid residues from IL-6R binding region of IL-6 (SEQ ID NO: 1);
X is an α-COOH or α-CONH$_2$ of an amino acid;
m is from 1 to about 4; and
n is from 0 to about 10.

(2) The IL-6 peptide immunogen construct according to (1), wherein the IL-6R binding region or fragment thereof is selected from the group consisting of SEQ ID NOs: 5-19.

(3) The IL-6 peptide immunogen construct according to any of (1) or (2), wherein the Th epitope is selected from the group consisting of SEQ ID NOs: 78-106 and 216-226.

(4) The IL-6 peptide immunogen construct according to (1), wherein the peptide immunogen construct is selected from the group consisting of SEQ ID NOs: 107-215.

(5) An IL-6 peptide immunogen construct comprising:
   a. a B cell epitope comprising from about 7 to about 42 amino acid residues from the IL-6 sequence of SEQ ID NOs: 1 to 4;
   b. a T helper epitope comprising an amino acid sequence selected from the group consisting of SEQ ID NOs: 78-106, 216-226, and any combination thereof; and
   c. an optional heterologous spacer selected from the group consisting of an amino acid, Lys-, Gly-, Lys-Lys-Lys-, (α, ε-N)Lys, ε-N-Lys-Lys-Lys-Lys (SEQ ID NO: 77), Lys-Lys-Lys-ε-N-Lys (SEQ ID NO: 231), and Pro-Pro-Xaa-Pro-Xaa-Pro (SEQ ID NO: 76), and any combination thereof,
   wherein the B cell epitope is covalently linked to the T helper epitope directly or through the optional heterologous spacer.

(6) The IL-6 peptide immunogen construct of (5), wherein the B cell epitope is selected from the group consisting of SEQ ID NOs: 5 to 19.

(7) The IL-6 peptide immunogen construct of (5), wherein the T helper epitope is selected from the group consisting of SEQ ID NOs: 78-106.

(8) The IL-6 peptide immunogen construct of (5), wherein the optional heterologous spacer is (α, ε-N)Lys, ε-N-Lys-Lys-Lys-Lys (SEQ ID NO: 77), Lys-Lys-Lys-ε-N-Lys (SEQ ID NO: 231), or Pro-Pro-Xaa-Pro-Xaa-Pro (SEQ ID NO: 76), where Xaa is any amino acid, and preferably aspartic acid.

(9) The IL-6 peptide immunogen construct of (5), wherein the T helper epitope is covalently linked to the amino terminus of the B cell epitope.

(10) The IL-6 peptide immunogen construct of (5), wherein the T helper epitope is covalently linked to the amino terminus of the B cell epitope through the optional heterologous spacer.

(11) A composition comprising an IL-6 peptide immunogen construct according to (1).

(12) A pharmaceutical composition comprising:
   a. a peptide immunogen construct according to (1); and
   b. a pharmaceutically acceptable delivery vehicle and/or adjuvant.

(13) The pharmaceutical composition of (12), wherein
   a. the IL-6R binding region or fragment thereof is selected from the group consisting of SEQ ID NOs: 5-19;
   b. the Th epitope is selected from the group consisting of SEQ ID NOs: 78-106 and 216-226; and
   c. the heterologous spacer is selected from the group consisting of an amino acid, Lys-, Gly-, Lys-Lys-Lys-, (α, ε-N)Lys, ε-N-Lys-Lys-Lys-Lys (SEQ ID NO: 77), Lys-Lys-Lys-ε-N-Lys (SEQ ID NO: 231), and Pro-Pro-Xaa-Pro-Xaa-Pro (SEQ ID NO: 76), and any combination thereof; and
   wherein the IL-6 peptide immunogen construct is mixed with an CpG oligodeoxynucleotide (ODN) to form a stabilized immunostimulatory complex.

(14) The pharmaceutical composition of (12), wherein
   a. the IL-6 peptide immunogen construct is selected from the group consisting of SEQ ID NOs: 107-215; and
   wherein the IL-6 peptide immunogen construct is mixed with an CpG oligodeoxynucleotide (ODN) to form a stabilized immunostimulatory complex.

(15) A method for generating antibodies against IL-6 in an animal comprising administering the pharmaceutical composition according to (12) to the animal.

(16) An isolated antibody or epitope-binding fragment thereof that specifically binds to the IL-6R binding region of IL-6 or a fragment thereof in the IL-6 peptide immunogen construct according to (1).

(17) The isolated antibody or epitope-binding fragment thereof according to (16) bound to the IL-6 peptide immunogen construct.

An isolated antibody or epitope-biding fragment thereof that specifically binds to the B cell epitope peptide of the IL-6 peptide immunogen construct according to any of (1) to (10).

(18) A composition comprising the isolated antibody or epitope-binding fragment thereof according to (16).

(19) A method of preventing and/or treating a disease impacted by IL-6 dysregulation in an animal comprising administering the pharmaceutical composition of (12) to the animal.

Example 1

Synthesis of IL-6 Related Peptides and Preparation of Formulations Thereof a. Synthesis of IL-6 Related Peptides Methods for synthesizing IL-6 related peptides that were included in the development effort of IL-6 peptide immunogen constructs are described. The peptides were synthesized in small-scale amounts that are useful for serological assays, laboratory pilot and field studies, as well as large-scale (kilogram) amounts, which are useful for industrial/commercial production of pharmaceutical compositions. A large repertoire of IL-6 related antigenic peptides having sequences with lengths from approximately 7 to 70 amino acids were designed for epitope mapping and for the screening and selection of the most optimal peptide immunogen constructs for use in an efficacious IL-6 targeted therapeutic composition.

Representative full length IL-6 of human, mouse, rat and macaque species (SEQ ID NOs: 1-4), IL-6 peptide fragments, and 10-mer peptide employed for epitope mapping in various serological assays are listed in Table 1 (SEQ ID NOs: 5-75).

Selected IL-6 B cell epitope peptides were made into IL-6 peptide immunogen constructs by synthetically linking to a carefully designed helper T cell (Th) epitope peptide which was derived from pathogen proteins including Measles Virus Fusion protein (MVF), Hepatitis B Surface Antigen protein (HBsAg), peptide influenza, *Clostridium tetani*, and Epstein-Barr virus (EBV) identified in Table 2 (SEQ ID NOs: 78-106 and 216-226). The Th epitope peptides were used either in a single sequence (SEQ ID NOs: 78-86 and 91-106) or a combinatorial library (SEQ ID NOs: 87-90) to enhance the immunogenicity of their respective IL-6 peptide immunogen constructs.

Representative IL-6 peptide immunogen constructs selected from hundreds of peptide constructs are identified in Table 3 (SEQ ID NOs: 107-215).

All peptides used for immunogenicity studies or related serological tests for detection and/or measurement of anti-IL-6 antibodies were synthesized on a small scale using F-moc chemistry by peptide synthesizers of Applied Bio-Systems Models 430A, 431 and/or 433. Each peptide was produced by an independent synthesis on a solid-phase support, with F-moc protection at the N-terminus and side chain protecting groups of trifunctional amino acids. Completed peptides were cleaved from the solid support and side chain protecting groups were removed by 90% Trifluoroacetic acid (TFA). Synthetic peptide preparations were evaluated by Matrix-Assisted Laser Desorption/Ionization-Time-Of-Flight (MALDI-TOF) Mass Spectrometry to ensure correct amino acid content. Each synthetic peptide was also evaluated by Reverse Phase HPLC (RP-HPLC) to confirm the synthesis profile and concentration of the preparation. Despite rigorous control of the synthesis process (including stepwise monitoring the coupling efficiency), peptide analogues were also produced due to unintended events during elongation cycles, including amino acid insertion, deletion, substitution, and premature termination. Thus, synthesized preparations typically included multiple peptide analogues along with the targeted peptide.

Despite the inclusion of such unintended peptide analogues, the resulting synthesized peptide preparations were nevertheless suitable for use in immunological applications including immunodiagnosis (as antibody capture antigens) and pharmaceutical compositions (as peptide immunogens). Typically, such peptide analogues, either intentionally designed or generated through synthetic process as a mixture of byproducts, are frequently as effective as a purified preparation of the desired peptide, as long as a discerning QC procedure is developed to monitor both the manufacturing process and the product evaluation process to guarantee the reproducibility and efficacy of the final product employing these peptides. Large scale peptide syntheses in the multi-hundred to kilo gram quantities were conducted on a customized automated peptide synthesizer UB12003 or the like at 15 mmole to 150 mmole scale.

For active ingredients used in the final pharmaceutical composition for clinical trials, IL-6 related peptide immunogen constructs were purified by preparative RP-HPLC under a shallow elution gradient and characterized by MALDI-TOF mass spectrometry, amino acid analysis and RP-HPLC for purity and identity.

b. Preparation of Compositions Containing IL-6 Peptide Immunogen Constructs

Formulations employing water in oil emulsions and in suspension with mineral salts were prepared. In order for a pharmaceutical composition designed to be used by a large population, safety becomes another important factor for consideration. Despite the fact that water-in-oil emulsions have been used in humans as pharmaceutical compositions in many clinical trials, Alum remains the major adjuvant for use in pharmaceutical composition due to its safety. Alum or its mineral salts ADJUPHOS (Aluminum phosphate) are therefore frequently used as adjuvants in preparation for clinical applications.

Briefly, the formulations specified in each of the study groups described below generally contained all types of IL-6 designer peptide immunogen constructs. Over 200 designer IL-6 peptide immunogen constructs were carefully evaluated in guinea pigs for their relative immunogenicity with the corresponding IL-6 peptide representative of the immunogen's B epitope peptides. Epitope mapping and serological cross-reactivities were analyzed amongst the varying homologous peptides by ELISA assays using plates coated with peptides selected from the list with SEQ ID NOs: 1-75.

The IL-6 peptide immunogen constructs at varying amounts were prepared in a water-in-oil emulsion with Seppic MONTANIDE™ ISA 51 as the approved oil for human use, or mixed with mineral salts ADJUPHOS (Aluminum phosphate) or ALHYDROGEL (Alum) as specified. Compositions were typically prepared by dissolving the IL-6 peptide immunogen constructs in water at about 20 to 800 µg/mL and formulated with MONTANIDE™ ISA 51 into water-in-oil emulsions (1:1 in volume) or with mineral salts ADJUPHOS or ALHYDROGEL (Alum) (1:1 in volume). The compositions were kept at room temperature for about 30 min and mixed by vortex for about 10 to 15 seconds prior to immunization. Animals were immunized with 2 to 3 doses of a specific composition, which were administered at time 0 (prime) and 3 week post initial immunization (wpi)(boost), optionally 5 or 6 wpi for a second boost, by intramuscular route. Sera from the immunized animals were then tested with selected B epitope peptide(s) to evaluate the immunogenicity of the various IL-6 peptide immunogen constructs present in the formulation and for the corresponding sera's cross-reactivity with IL-6 proteins. Those IL-6 peptide immunogen constructs with potent immunogenicity found in the initial screening in guinea pigs were further tested in in vitro assays for their corresponding sera's functional properties. The selected candidate IL-6 peptide immunogen constructs were then prepared in water-in-oil emulsion, mineral salts, and alum-based formulations for dosing regimens over a specified period as dictated by the immunization protocols.

Only the most promising IL-6 peptide immunogen constructs were further assessed extensively prior to being incorporated into final formulations for immunogenicity, duration, toxicity and efficacy studies in GLP guided pre-clinical studies in preparation for submission of an Investigational New Drug application followed by clinical trials in patients impacted by IL-6 dysregulation.

The following examples serve to illustrate the present disclosure and are not to be used to limit the scope of the disclosure.

Example 2

Serological Assays and Reagents

Serological assays and reagents for evaluating functional immunogenicity of the IL-6 peptide immunogen constructs and formulations thereof are described in details below.

a. IL-6 or IL-6 Peptide Fragment Based ELISA Tests for Antibody Specificity Analysis ELISA assays for evaluating immune serum samples described in the following Examples were developed and described below. The wells of 96-well plates were coated individually for 1 hour at 37° C. with 100 µL of IL-6 or IL-6 fragment peptides (SEQ ID NOs: 1 to 20, 72 to 75), at 2 µg/mL (unless noted otherwise), in 10 mM $NaHCO_3$ buffer, pH 9.5 (unless noted otherwise).

The IL-6 or IL-6 fragment peptide-coated wells were incubated with 250 µL of 3% by weight gelatin in PBS at 37° C. for 1 hour to block non-specific protein binding sites, followed by three washes with PBS containing 0.05% by volume TWEEN® 20 and dried. Sera to be analyzed were diluted 1:20 (unless noted otherwise) with PBS containing 20% by volume normal goat serum, 1% by weight gelatin and 0.05% by volume TWEEN® 20. One hundred microliters (100 µL) of the diluted specimens (e.g., serum, plasma) were added to each of the wells and allowed to react for 60 minutes at 37° C. The wells were then washed six times with 0.05% by volume TWEEN® 20 in PBS in order to remove unbound antibodies. Horseradish peroxidase (HRP)-conjugated species (e.g., guinea pig or rat) specific goat polyclonal anti-IgG antibody or Protein A/G were used as a labeled tracer to bind with the antibody/peptide antigen complex formed in positive wells. One hundred microliters of the HRP-labeled detection reagent, at a pre-titered optimal dilution and in 1% by volume normal goat serum with 0.05% by volume TWEEN® 20 in PBS, was added to each well and incubated at 37° C. for another 30 minutes. The wells were washed six times with 0.05% by volume TWEEN® 20 in PBS to remove unbound antibody and reacted with 100 µL of the substrate mixture containing 0.04% by weight 3', 3', 5', 5'-Tetramethylbenzidine (TMB) and 0.12% by volume hydrogen peroxide in sodium citrate buffer for another 15 minutes. This substrate mixture was used to detect the peroxidase label by forming a colored product. Reactions were stopped by the addition of 100 µL of 1.0M $H_2SO_4$ and absorbance at 450 nm ($A_{450}$) determined. For the determination of antibody titers of the immunized animals that received the various peptide formulations, a 10-fold serial dilutions of sera from 1:100 to 1:10,000 or a 4-fold serial dilutions of sera from 1:100 to $1:4.19 \times 10^8$ were tested, and the titer of a tested serum, expressed as $Log_{10}$, was calculated by linear regression analysis of the $A_{450}$ with the cutoff $A_{450}$ set at 0.5.

b. Assessment of Antibody Reactivity Towards Th Peptide by Th Peptide Based ELISA Tests The wells of 96-well ELISA plates were coated individually for 1 hour at 37° C. with 100 µL of Th peptide at 2 µg/mL (unless noted otherwise), in 10 mM $NaHCO_3$ buffer, pH 9.5 (unless noted otherwise) in similar ELISA method and performed as described above. For the determination of antibody titers of the immunized animals that received the various IL-6 peptide formulations, 10-fold serial dilutions of sera from 1:100 to 1:10,000 were tested, and the titer of a tested serum, expressed as $Log_{10}$, was calculated by linear regression analysis of the $A_{450}$ with the cutoff $A_{450}$ set at 0.5.

c. Fine Specificity Analyses of a Target IL-6 B Cell Epitope Peptide Determined by Epitope Mapping Through B Cell Epitope Cluster 10-Mer Peptide-Based ELISA Tests Fine specificity analyses of anti-IL-6 antibodies from hosts immunized with IL-6 peptide immunogen constructs were determined by epitope mapping using B cell epitope cluster 10mer peptide-based ELISA tests. Briefly, the wells of 96-well plates were coated with individual IL-6 10-mer peptides (SEQ ID NOs: 21-71) at 0.5 µg per 0.1 mL per well and then 100 µL serum samples (1:100 dilution in PBS) were incubated in 10-mer plate wells in duplicate following the steps of the antibody ELISA method described above. The target B cell epitope related fine specificity analyses of anti-IL-6 antibodies from immunized hosts were tested with corresponding IL-6 peptide, or with non-relevant control peptide for specificity confirmation.

d. Immunogenicity Evaluation

Preimmune and immune serum samples from animal or human subjects were collected according to experimental protocols and heated at 56° C. for 30 minutes to inactivate serum complement factors. Following the administration of the formulations, blood samples were obtained according to protocols and their immunogenicity against specific target site(s) were evaluated by corresponding IL-6 B cell epitope peptide-based ELISA tests. Serially diluted sera were tested and positive titers were expressed as $Log_{10}$ of the reciprocal dilution. Immunogenicity of a particular formulation is assessed for its ability to elicit high titer antibody response directed against the desired epitope specificity within the target antigen and high cross-reactivities with IL-6 proteins, while maintaining a low to negligible antibody reactivity towards the "Helper T cell epitopes" employed to provide enhancement of the desired B cell responses.

e. Immunoassay for Assessment of C-Reactive Protein (CRP) Level in Rat Sera

Rat C-reactive protein (CRP) levels were measured by a sandwich ELISA using polyclonal rabbit anti-rat CRP antibody (Sino Biological), as capture antibody and biotin-labeled rabbit anti-rat CRP antibody (Assaypro LLC), as detection antibody. Briefly, the polyclonal rabbit anti-rat CRP antibody was immobilized on 96-well plates at 50 ng/well in coating buffer (15 mM $Na_2CO_3$, 35 mM $NaHCO_3$, pH 9.6) and incubated at 4° C. overnight. Coated wells were blocked by 200 µL/well of assay diluents (1% BSA, 0.05% TWEEN-20 and 0.01% ProClin 300 in PBS) at room temperature for 1 hour. Plates were washed 3 times with 200 µL/well of wash buffer (PBS with 0.05% TWEEN-20 and 0.01% ProClin 300). Recombinant rat CRP (Sino Biological) was used to generate a standard curve (range 450 to 1.84 ng/mL by 2.5-fold serial dilution) in assay diluent. 100 µL of the diluted sera (1:30,000) and standards were added to coated wells. The incubation was carried out at room temperature for 2 hours. All wells were aspirated and washed 5 times with 200 µL/well of wash buffer. The captured CRP was incubated with 100 µL of detection antibody solution (100 ng/ml biotin-labeled rabbit anti-rat CRP antibody in assay diluent) at room temperature for 1 hour. Then, the bound biotin-labeled antibodies were detected using streptavidin poly-HRP (1:10,000 dilution, Thermo Fisher Scientific) for 1 hour (100 µL/well). All wells were aspirated and washed 6 times with 200 µL/well of wash buffer. Finally, wells were developed by 100 µL/well of NeA-Blue TMB substrate (Clinical Science Products) and the reaction was stopped by addition of 100 µL/well of 1M $H_2SO_4$. The colorimetric absorbance was measured by a VersaMax ELISA Microplate Reader (Molecular Devices) and the standard curve was created by using the SoftMax Pro software (Molecular Devices) to generate a four parameter logistic curve-fit and used to calculate the concentrations of CRP in all tested samples. Student t tests were used to compare data by using the Prism software (GraphPad Software).

Example 3

Assessment of Functional Properties of Antibodies Elicited by the IL-6 Peptide Immunogen Constructs and Formulations Thereof in Animals Immune sera or purified anti-IL-6 antibodies in immunized animals were further tested for their ability to (1) block the interaction between IL-6 and its receptor IL-6R (IL-6α and IL-6Rβ/gp130) and (2) suppress the IL-6-induced STAT3 phosphorylation in RPMI 8226 cells and (3) suppress IL-6-dependent TF-1 cell proliferation, as well as (4) inhibit monocyte chemotractant protein-1 (MCP-1) production in U937 cell line.

a. Cells (1) RPMI 8226 cell line was purchased from the American Type Culture Collection (Manassas, VA) and maintained in RPMI1640 medium supplemented with 10% Fetal Bovine Serum (FBS), 4.5 g/L L-glutamine, sodium pyruvate, and 1% penicillin/streptomycin in a humidified 37° C. incubator with 5% $CO_2$.

(2) TF-1 cell line was maintained in RPMI 1640 medium supplemented with 2 mM Glutamine, 1% Sodium Pyruvate (NaP), with 2 ng/ml Human Granulocyte Macrophage Colony Stimulating Factor (Human GM-CSF) and 10% FBS and 1% penicillin/streptomycin in a humidified 37° C. incubator with 5% $CO_2$.

(3) U937 cell line was maintained in RPMI 1640 medium supplemented with 2 mM Glutamine, 1% NaP and 10% FBS and 1% penicillin/streptomycin in a humidified 37° C. incubator with 5% $CO_2$.

b. Binding of IL-6 to IL-6Rα Chain (Cis-Binding)

The purified IgG polyclonal antibodies from pooled immune sera of guinea pigs previously immunized with different IL-6 peptide immunogen constructs were examined for their relative ability to inhibit the binding of IL-6 to IL-6Rα by ELISA. The wells of 96-well plates were coated individually with 50 μL of recombinant His-tagged human IL-6Rα (GenScript), at 4 μg/mL, in coating buffer (15 mM $Na_2CO_3$, 35 mM $NaHCO_3$, pH 9.6) and incubated at 4° C. overnight. Coated wells were blocked by 200 μL/well of assay diluents (1% BSA, 0.05% TWEEN-20 and 0.01% ProClin 300 in PBS) at room temperature for 1 hour. Plates were washed 3 times with 200 μL/well of wash buffer (PBS with 0.05% TWEEN-20 and 0.01% ProClin 300). 100 μL mixture of human IL-6 (GenScript) at 10 ng/mL and purified guinea pig IgG polyclonal antibodies at different concentrations was pre-incubated for 1 hour at room temperature and then added to coated wells. The incubation was carried out at room temperature for 1 hour. All wells were aspirated and washed 3 times with 200 μL/well of wash buffer. The captured IL-6 was detected by 100 μL/well of biotin-labeled rabbit anti-IL-6 antibody (1:1,000 dilution, R&D Systems) at room temperature for 1 hour. Then, the bound biotin-labeled antibodies were detected using streptavidin poly-HRP (1:40,000 dilution, Thermo Fisher Scientific) for 1 hour (100 μL/well). All wells were aspirated and washed 3 times with 200 μL/well of wash buffer. Finally, wells were developed by 100 μL/well of OptEIA TMB substrate (BD Biosciences) and the reaction was stopped by addition of 100 μL/well of 1M $H_2SO_4$. The colorimetric absorbance was measured by a VersaMax ELISA Microplate Reader (Molecular Devices) and the reactivity curve was generated by using four parameter logistic curve-fitting for calculation of the half of maximal inhibitory concentration ($IC_{50}$) in Prism 6 software (GraphPad Software).

c. Binding of IL-6/IL-6Rα Chain Complex to IL-6Rβ Chain/Gp130 (Trans-Binding)

The wells of 96-well plates were coated individually with 50 μL of recombinant human gp130-Fc chimera protein (R&D systems), at 300 ng/mL, in coating buffer (15 mM $Na_2CO_3$, 35 mM $NaHCO_3$, pH 9.6) and incubated at 4° C. overnight. Coated wells were blocked by 200 μL/well of assay diluents (1% BSA, 0.05% TWEEN-20 and 0.01% ProClin 300 in PBS) at room temperature for 1 hour. Plates were washed 3 times with 200 μL/well of wash buffer (PBS with 0.05% TWEEN-20 and 0.01% ProClin 300). Before assaying, the sIL-6Rα/IL-6 complexes were formed in a 1:20 molar ratio of IL-6 to sIL-6Rα by incubating His-tagged human IL-6Rα 4 μg/mL, GenScript) and IL-6 (100 ng/mL, GenScript) at room temperature for 1 hour. Ten L of pre-formed complex solution were incubated with purified guinea pig IgG polyclonal antibodies at different concentrations in a total volume of 100 μL at room temperature for 1 hour and then the mixture was added to gp130-Fc-coated wells. The incubation was carried out at room temperature for 1 hour. All wells were aspirated and washed 3 times with 200 μL/well of wash buffer. The captured IL-6 was detected by 100 μL/well of biotin-labeled rabbit anti-IL-6 antibody (1:1,000 dilution, R&D Systems) at room temperature for 1 hour. Then, the bound biotin-labeled antibodies were detected using streptavidin poly-HRP (1:40,000 dilution, Thermo Fisher Scientific) for 1 hour (100 μL/well). All wells were aspirated and washed 3 times with 200 μL/well of wash buffer. Finally, wells were developed by 100 μL/well of OptEIA TMB substrate (BD Biosciences) and the reaction was stopped by addition of 100 μL/well of 1M $H_2SO_4$. The colorimetric absorbance was measured by a VersaMax ELISA Microplate Reader (Molecular Devices) and the reactivity curve was generated by using four parameter logistic curve-fitting for calculation of the half of maximal inhibitory concentration ($IC_{50}$) in Prism 6 software (GraphPad Software).

d. IL-6-Dependent TF-1 Cell Proliferation Assay

The human erythroleukemia TF-1 cells are able to proliferate in response to human IL-6. The assay were performed by simultaneously incubating $5 \times 10^3$ cells with human recombinant IL-6 at a final concentration of 10 ng/mL in the presence of purified guinea pig IgG polyclonal antibodies at different concentrations in a total volume of 100 μL of RPMI 1640 medium supplied with 2.5% FBS per well at 37° C., 5% $CO_2$ for 72 hours. Tocilizumab, an anti-IL-6 receptor antibody, was also included as a study control. Cell growth and viability was determined by adding 40 μL of CellTiterGlo reagent (Promega) per well and then incubating the reaction at room temperature for 10 min. The resulting luminescence was measured by a SpectraMax i3x Multi-Mode microplate reader (Molecular Devices) and the reactivity curve was generated by using four parameter logistic curve-fitting for calculation of the half of maximal inhibitory concentration ($IC_{50}$) in Prism 6 software (GraphPad Software).

e. IL-6-Induced STAT3 Phosphorylation Assay

The human myeloma cell line RPMI 8226 without constitutively active STAT3 phosphorylation requires IL-6 exposure for activation of STAT3. To investigate whether the purified IgG could inhibit IL-6-induced STAT3 phosphorylation in RPMI 8226 cells, $8 \times 10^5$ cells were simultaneously incubated with IL-6 at a final concentration of 10 ng/mL in the presence of guinea pig polyclonal antibodies at the concentration of 100 μg/mL in a total volume of 500 μL of RMPI 8226 culture medium at 37° C., 5% $CO_2$ for 30 min. Tocilizumab, an anti-IL-6 receptor antibody, was included as a study control. The phosphorylated STAT3 level was measured by PathScan p-Stat3 ELISA kit (Cell Signaling). Briefly, the cell lysate was prepared by suspending cells in 30 μL of cell lysis buffer (Cell Signaling) supplied with 1% Phosphatase Inhibitor Cocktail 3 (Sigma-Aldrich) with cell debris removed by centrifugation at 12,000×g at 4° C. for 10 min. Ten μg of clear cell lysate was used to measure the content of phosphorylated STAT3 according to vendor's instructions brochure. The colorimetric absorbance was measured by a VersaMax ELISA Microplate Reader (Molecular Devices).

f. IL-6-Induced MCP-1 Production

U937 is promonocytic cell line that can be induced to differentiate into mature macrophages by several agents. IL-6 can promote MCP-1 production in monocytic cells. Anti-IL-6 antibodies elicited by the IL-6 peptide construct immunogens could modulate IL-6-dependent MCP-1 secretion in U937 cell line. The assay were performed by incubating $8 \times 10^3$ cells, human recombinant IL-6 at a final concentration of 10 ng/mL and purified guinea pig IgG polyclonal antibodies at different concentrations in a total volume of 100 μL of U937 culture medium per well at 37° C., 5% $CO_2$ for 24 hours. Tocilizumab as an anti-IL-6 receptor antibody was also included as study control. The clear supernatant was prepared by centrifuging the culture medium at 300×g for 10 min and stored at −30° C. 100 μL of diluted supernatant (1:100 dilution) was applied to human MCP-1 quantitation ELISA kit (Thermo Fisher) according to vendor's instructions. The colorimetric absorbance was measured by a VersaMax ELISA Microplate Reader (Molecular Devices) and the standard curve was created by using the SoftMax Pro software (Molecular Devices) to generate a four parameter logistic curve-fit and used to calculate the concentrations of MCP-1 in all tested samples. The reactivity curve was generated by using four parameter logistic curve-fitting for calculation of the half of maximal inhibitory concentration ($IC_{50}$) in Prism 6 software (GraphPad Software).

Example 4

Animals Used in Safety, Immunogenicity, Toxicity and Efficacy Studies

Guinea Pigs:

Immunogenicity studies were conducted in mature, naïve, adult male and female Duncan-Hartley guinea pigs (300-350 g/BW). The experiments utilized at least 3 Guinea pigs per group. Protocols involving Duncan-Hartley guinea pigs (8-12 weeks of age; Covance Research Laboratories, Denver, PA, USA) were performed under approved IACUC applications at a contracted animal facility under UBI sponsorship.

Rat:

The Lewis rats were employed for the induction of collagen-induced arthritis (CIA). Female Lewis rats, ages 8-12 weeks, were purchased from Biolasco and weight-matched to approximately 180 g. Animals were housed at UBI Asia Laboratory Animal Facility and acclimatized for 1 week under constant temperature (22° C.), humidity (72%), 12-h light/12-h dark cycle. Rats had free access to rat chow and water. All protocols followed the Principles of Laboratory Animal Care. Collagen challenge injection was administered at the base of the tail on day 0 and 7 by intradermal route. Blood collection was carried out as indicated in the protocol. Clinical observation was made 3 times a week using a scoring system for evaluating arthritis severity in CIA Rodent Models until day 35. Antibody titers were tested for anti-IL-6 (rat) by ELISA assay. The relevant inflammation biomarkers, such as CRP, and hematology assays for blood WBC counts were assessed.

Example 5

Formulations for Immunogenicity Assessment of IL-6 Peptide Constructs in Guinea Pigs Pharmaceutical compositions and formulations used in each experiment are described in greater detail as shown below. Briefly, the formulations specified in each of the study groups generally contained all types of designer IL-6 peptide immunogen constructs with a segment of the IL-6 B cell epitope peptide linked via different type of spacers (e.g., εLys (εK) or lysine-lysine-lysine (KKK) to enhance the peptide construct's solubility) and promiscuous helper T cell epitopes including two sets of artificial T helper epitopes derived from Measles virus fusion protein and Hepatitis B surface antigen. The IL-6 B cell epitope peptides are linked at the N- or C-terminus of the designer peptide constructs. Hundreds of designer IL-6 peptide immunogen constructs were initially evaluated in guinea pigs for their relative immunogenicity with the corresponding IL-6 B cell epitope peptides. The IL-6 peptide immunogen constructs were either prepared under varying amounts in a water-in-oil emulsion with Seppic MONTANIDE ISA 51 as the approved oil for human vaccine use, or with mineral salts (ADJUPHOS) or ALHYDROGEL (Alum) as a suspension, as specified. Formulations were usually prepared by dissolving the IL-6 peptide constructs in water at about 20 to 800 μg/mL and formulated either with MONTANIDE ISA 51 into water-in-oil emulsions (1:1 in volume) or with mineral salts (ADJUPHOS) or ALHYDROGEL (Alum) (1:1 in volume). The formulations were kept at room temperature for about 30 min and mixed by vortex for about 10 to 15 seconds prior to immunization.

Some animals were immunized with 2 to 3 doses of a specific formulation, which were administered at time 0 (prime) and 3 week post initial immunization (wpi) (boost), optionally 5 or 6 wpi for a second boost, by intramuscular route. These immunized animals were then evaluated for the immunogenicity of the corresponding IL-6 peptide immunogen constructs used in the respective formulations for their cross-reactivity with the recombinant IL-6. Those IL-6 peptide immunogen constructs with potent immunogenicity in the initial screening in guinea pigs were further tested in both water-in-oil emulsion, mineral salts, and alum-based formulations in macaques for dosing regimens over a specified period as dictated by the immunizations protocols.

Only the most promising IL-6 peptide immunogen construct candidates were further assessed extensively to evaluate for their ability to breakout immune tolerancein mice or rats using corresponding mouse or rat IL-6 peptide immunogen constructs. The IL-6 peptide immunogen constructs with best immunogenicity in rats, which elicited anti-IL-6 antibody titers against endogenous IL-6; especially for the capability of suppressing blood inflammatory factors and alleviate rheumatoid arthritis clinical symptoms of the CIA induced Lewis rat models or in cynomolgus macaques for the capability of suppressing blood neutrophilia, triggered by subcutaneous administration of exogenous IL-6. The optimized IL-6 peptide immunogen constructs were incorporated into final formulations for GLP guided immunogenicity, duration, toxicity and proof of efficacy studies in preparation for submission of an Investigational New Drug application and clinical trials in patients with autoimmune rheumatoid arthritis.

Example 6

Figure 2:
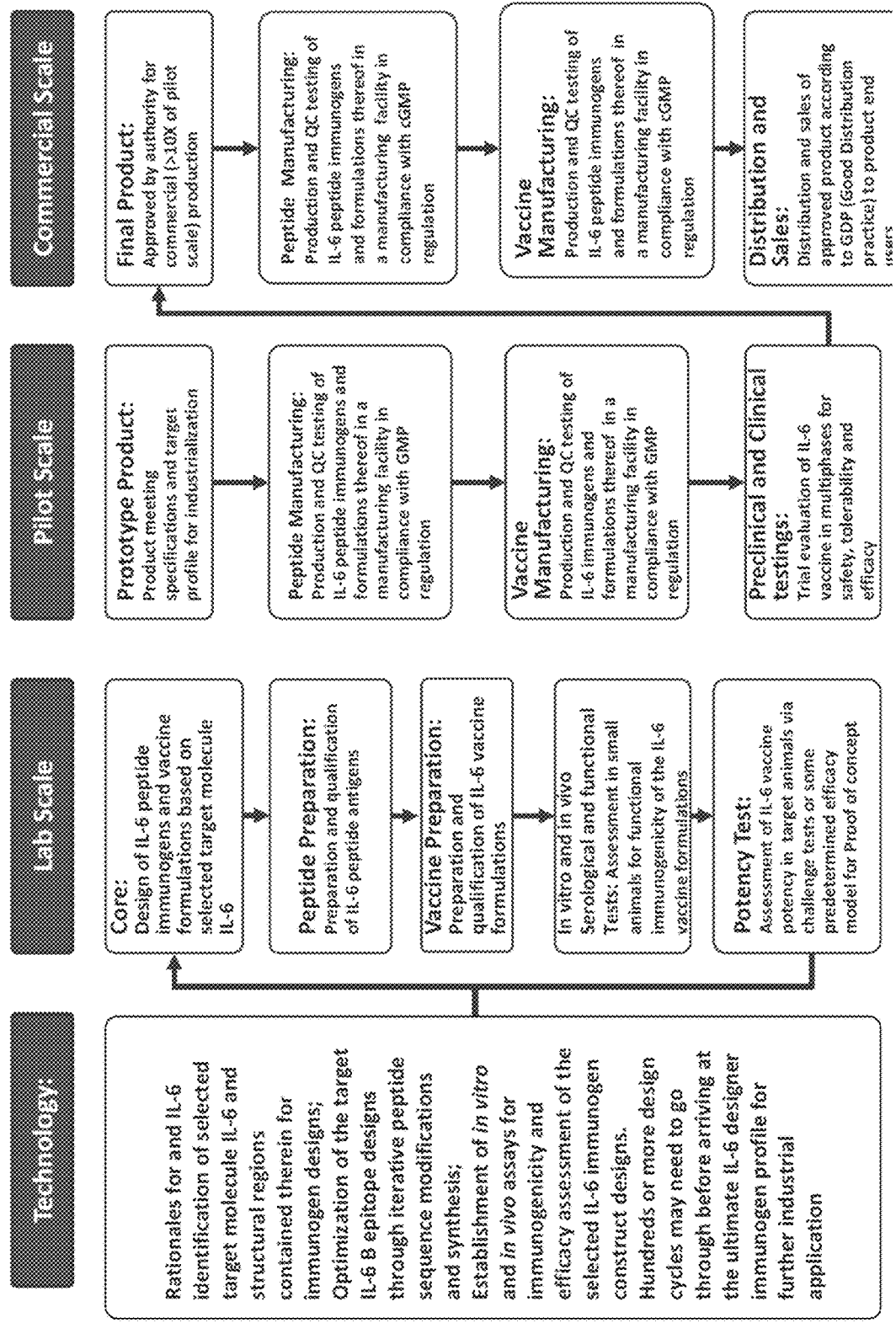
FIG. 2 is a flow chart identifying the development process leading to commercialization (industrialization) of a pharmaceutical composition directed against a selected target according to a particular embodiment disclosed herein. The present disclosure includes IL-6 peptide immunogen design, IL-6 peptide composition design, IL-6 pharmaceutical formulation design, in vitro IL-6 functional antigenicity study design, in vivo IL-6 immunogenicity and efficacy study design, and IL-6 treatment clinical protocol design. Detailed evaluation and analysis of each of the steps had led to a series of experiments which would ultimately lead to the commercialization of a safe and efficacious IL-6 pharmaceutical composition.

Design Rationale. Screening, Identification, Assessment of Functional Properties and Optimization of Multi-Component Formulations Incorporating IL-6 Peptide Immunogen Constructs for Treatment of Autoimmune Rheumatoid Arthritis IL-6, a cytokine, is selected as the target molecule for design and as the content of the present disclosure. FIG. 1 presents alignment of IL-6 sequences from human (SEQ ID NO: 227), macaque (SEQ ID NO: 228), mouse (SEQ ID NO: 229) and rat (SEQ ID NO: 230) species. A general summary of the inventive and development steps is described in FIG. 2 with a flow chart identifying the development process leading to commercialization (industrialization) of an IL-6 formulation. Detailed evaluation and analyses of each of the steps, with pleasant and unpleasant surprises, had led to a myriad of experiments in the past which would ultimately result in commercialization of a safe and efficacious IL-6 formulation.

a. Design History

Each peptide immunogen construct or immunotherapeutic product requires its own design focus and approach based on its specific disease mechanism and the target protein(s) required for intervention. The target IL-6 molecule which designs are modeled after is a cytokine. The process from research to commercialization typically requires one or more decades to accomplish. Identification of the IL-6 B cell epitope peptides correlating to the functional site(s) for intervention is key to the immunogen construct design. Consecutive pilot immunogenicity studies in guinea pigs incorporating various T helper support (carrier proteins or suitable T helper peptides) in various formulations are conducted to evaluate the functional properties of the elicited antibodies. Upon extensive serological validation, candidate IL-6 B cell epitope peptide immunogen constructs are then further tested in the target species or in non-human primate to further validate the immunogenicity and direction of the IL-6 peptide immunogen design. Selected IL-6 peptide immunogen constructs are then prepared in varying mixtures to evaluate subtle differences in functional property related to the respective interactions amongst peptide constructs when used in combinations. Upon additional evaluation, the final peptide constructs, peptide compositions and formulations thereof, along with the respective physical parameters of the formulations are established leading to the final product development process.

b. Design and Validation of IL-6 Derived Peptide Immunogen Constructs for Pharmaceutical Compositions with Potential to Treat Patients Suffering from Diseases Impacted by IL-6 Dysregulation Including Autoimmune Rheumatoid Arthritis.

In order to generate the most potent peptide constructs for incorporation into the pharmaceutical compositions, a repertoire of human IL-6 B cell epitope peptides (SEQ ID NOs: 5-19) and promiscuous T helper epitopes derived from various pathogens or artificially T helper epitopes (SEQ ID NOs: 78-106 and 216-226) were further designed and made into IL-6 peptide immunogen constructs (SEQ ID NOs: 107-215) for immunogenicity studies initially in guinea pigs.

i) Selection of IL-6 B Cell Epitope Peptide Sequences from the Region Comprising Two Intramolecular Loops for Design The region located in between and comprising the two intramolecular loops are selected, amongst many other regions tested, for further B cell epitope peptide design. This region is found to be nearby the α and β or gp130 chains of the IL-6R. Upon binding of IL-6 to IL-6R, IL-6R will transmit the activation signals intracellularly leading to major cellular events thereafter. The two loops are C73-C83 (SEQ ID NO: 5) and C44-C50 (SEQ ID NO: 15) as shown within SEQ ID NO: 1 of Table 1, or SEQ ID NO: 227 of FIG. 1, between the two loops are located 3 to 4 alpha-helical bundles.

Initially, the mouse and rat counterpart loop structure (e.g. SEQ ID NOs: 20 and 74) for IL-6 C73-C83 (SEQ ID NO: 5) were selected as B epitope to design IL-6 peptide immunogen construct linked with UBITh® 3 T helper peptide (SEQ ID NO: 89) and linker (SEQ ID NO: 77). The two IL-6 peptide immunogen constructs were formulated with ISA 51 and CpG for prime immunization in guinea pigs at 400 µg/1 mL and boosts (3, 6 and 9 wpi) at 100 µg/0.25 mL. To test the immunogenicity in guinea pigs, ELISA assay were used with guinea pig immune sera diluted at a 10-fold serial dilution from 1:100 to 1:10000. ELISA plates were coated with human IL-6 peptide (SEQ ID NO: 5), mouse or rat peptide (SEQ ID NOs: 20 and 74) at 0.5 µg peptide per well. The titer of a tested serum, expressed as $Log_{10}$, was calculated by linear regression analysis of the A450 nm with the cutoff $A_{450}$ set at 0.5. The ELISA results showed that the two peptide immunogen constructs from human IL-6 73-83 (SEQ ID NO: 107) and mouse IL-6 72-82 (SEQ ID NO: 146) not only induced high immunogenicity titers against their own B epitope peptide human IL-6 C73-C83 (SEQ ID NO: 5) and mouse B epitope peptide (SEQ ID NO: 20), the two antisera were also found to have moderate cross-reactivity against their homologous B epitope peptides from human and mouse IL-6 as shown in Table 4. The study indicated that the designed two peptide immunogens are able to induce specific antibodies with cross-reactivity against human IL-6 C73-C83 peptide and its mouse counterpart peptide. In addition, IL-6 peptide immunogen constructs 124, 125, 126 and 132 (cyclic) and 133 (noncyclic) with sequences extended beyond the IL-6 73-83 to the N-terminal portion of the loop were also tested for immunogenicity as well as their cross-reactivities with human IL-6 protein as shown in Table 5A indicative of both high immunogenicity and moderate cross-reactivities.

Subsequently, the other looped structure from IL-6 C44 to C50 was subject to design. Varying sizes of B cell epitope peptides covering the C44-C50 loop were selected to construct IL-6 peptide immunogens. UBITh®1 T helper epitope peptide (SEQ ID NO: 91) and short linker εK or longer linker KKK-εK (SEQ ID NO: 77) were used to build the new human IL-6 immunogen constructs. UBITh® 1 T helper epitope peptide along with linker sequence were placed either at the N or C terminus or at both ends of the construct to the target B cell epitope peptide. Seven human IL-6 immunogen constructs (SEQ ID NO: 128, 129, 131, and 134-137) from three different sizes of B epitopes IL-6 44-50 (SEQ ID NO. 15), IL-6 42-57 (SEQ ID NO: 12), IL-6 42-72 (SEQ ID NO: 10), were designed and employed for immunogenicity study. Each peptide immunogen was formulated ISA51 and CpG to immunize guinea pigs at dose at 400 µg/ml as prime immunization and 100 µg/ml as boost dose at 3, 6, 9 wpi, 3 guinea pigs per group. ELISA assay was conducted to evaluate the immunogenicity of the designed IL-6 peptide immunogens. IL-6 B epitope peptides and human IL-6 protein (SEQ ID NO: 1) were used to coat the plate wells served as targeting peptides. Guinea pig immune serum was diluted from 1:100 to 1:100000 by a 10-fold serial dilution. The titer of a tested serum, expressed as $Log_{10}$, was calculated by linear regression analysis of the A450 nm with the cut off $A_{450}$ set at 0.5. All eight peptide immunogens induced strong immunogenicity titers against the B epitope peptides coated in the plate wells. The ELISA results showed that these seven peptide immunogen constructs not only induced high immunogenicity titers against the corresponding IL-6 B epitope peptide, but also the these antisera were with moderate cross-reactivity against human IL-6 protein (SEQ ID NO: 1) shown in Table 5B.

Furthermore, two other B cell epitope peptides with sequences taken from between the two loops of SEQ ID NO: 13 and SEQ ID NO: 9 (i.e. IL-6 61-75 and IL-6 52-72) were subject to design. UBITh® 1 T helper epitope peptide (SEQ ID NO: 91) and short linker εK or longer linker KKK-εK (SEQ ID NO: 77) were used to build the new human IL-6 immunogen constructs (SEQ ID NOs: 127, 138-145). UBITh® 1 T helper epitope peptide along with linker sequence were placed either at the N or C terminus of the construct to the target B cell epitope peptide. Nine human IL-6 immunogen constructs (SEQ ID NO: 127, 138-145) from three different sizes of B epitopes IL-6 52-72 (SEQ ID NO: 9), IL-6 61-75 (SEQ ID NO: 13), IL-6 61-72 (SEQ ID NO: 14) were designed and employed for immunogenicity study. Each peptide immunogen was formulated ISA51 and CpG to immunize guinea pigs at dose at 400 μg/ml as prime immunization and 100 μg/ml as boost dose at 3, 6, 9 wpi, 3 guinea pigs per group. ELISA assay was conducted to evaluate the immunogenicity of the designed IL-6 peptide immunogens. IL-6 B epitope peptides and human IL-6 protein (SEQ ID NO: 1) were used to coat the plate wells served as targeting peptides. Guinea pig immune serum was diluted from 1:100 to 1:100000 by a 10-fold serial dilution. The titer of a tested serum, expressed as $Log_{10}$, was calculated by linear regression analysis of the A450 nm with the cut off $A_{450}$ set at 0.5. All nine peptide immunogens induced strong immunogenicity titers against the B epitope peptides coated in the plate wells. The ELISA results showed that these eight peptide immunogen constructs not only induced high immunogenicity titers against the corresponding IL-6 B epitope peptide, but also the these antisera were with moderate cross-reactivity against human IL-6 protein (SEQ ID NO: 1) shown in Table 5C.

In addition to peptide constructs comprising endogenous internal loops as described above, IL-6 B cell epitope peptide design was also directed at an epitope related to monoclonal antibody Olokizumab on human IL-6. Olokizumab is known to inhibit IL-6/sIL-6R binding to gp130. Two different sequence size peptides covering part of Olokizumab related conformational epitope were designed to build IL-6 peptide immunogen constructs. UBITh® 1 T helper epitope peptide (SEQ ID NO: 91) and longer linker εK-KKK (SEQ ID NO: 77) were selected to build the new human IL-6 immunogen constructs. UBITh® 1 T helper epitope and linker sequence were placed at either the N terminus or the C terminus, or both, of B epitope peptide. Five human IL-6 immunogen constructs (SEQ ID NOs: 112-117) from two different sizes of B epitopes (SEQ ID NO: 18 and 19) were designed and employed for immunogenicity study. One more IL-6 73-83 construct (SEQ ID NO: 118) with UBITh® 1 on both of N and C terminus (group 6) was served as a control for immunogenicity and immune specificity comparison. Each peptide immunogen was formulated ISA51 and CpG to immunize guinea pigs at dose at 400 μg/ml as prime immunization and 100 μg/ml as boost dose at 3, 6, 9 wpi, 3 guinea pigs per group. ELISA assay was conducted to evaluate the immunogenicity of these designed peptide immunogens. Three B epitope peptides of IL-6 C73-C83 (SEQ ID NO: 5), IL-6 150-162 (SEQ ID NO: 18) and IL-6 144-166 (SEQ ID NO: 19) were used to coat the plate wells served as targeting peptides. Guinea pig immune serum was diluted from 1:100 to 1:100000 by a 10-fold serial dilution. The titer of a tested serum, expressed as $Log_{10}$, was calculated by linear regression analysis of the A450 nm with the cut off $A_{450}$ set at 0.5. All six peptide immunogens induced strong immunogenicity titers against their own B epitope peptides coated in the plate wells. The ELISA data showed that there were cross-reactivity among the five immunogen constructs (SEQ ID NOs: 112-117), because they share the same helix-turn-helix structures from aa sequence 144 to 166 as shown in Table 5D. The cross-reactivities of the immune sera from these constructs to human IL-6 protein was shown in Table 5E indicative of the potential of this site for IL-6 binding intervention which would be tested in other IL-6 induced functional assays.

ii) Rankine of Heterologous T Helper Epitopes Derived from Pathogens and their Inclusion in the IL-6 Peptide Immunogen Constructs Design to Enhance the Immunogenicity of the Selected IL-6 B Epitope Peptide.

Table 2 lists a total of 29 heterologous Th epitopes (SEQ ID NOs: 78-106 and 216-226) that have been tested for their relative potency in multispecies, from mice, rats, guinea pigs, baboons, and macaques etc., to enhance B cell epitope immunogenicity.

A representative study of IL-6 peptide immunogen constructs containing the IL-6 C73-C83 B cell epitope peptide (SEQ ID NO: 5) linked through an εK spacer with individual promiscuous T helper epitopes was conducted for immunogenicity study in guinea pigs to rank the relative effectiveness of the respective heterologous T helper epitopes as shown in Table 6. Results obtained at 6 weeks post initial immunization (6wpi) were used to rank the different IL-6 peptide immunogen constructs. Although all selected Th epitopes had the capability of enhancing the immunogenicity of the IL-6 B-epitope peptide, the most potent construct was found to be the construct of SEQ ID NO: 119.

Careful calibration of immunogenicity for each and all IL-6 peptide immunogen constructs in different species including primates would assure ultimate Th peptide selection and success in the development of a final formulation.

iii) Assessment of Immunogenicity of IL-6 Peptide Immunogen Constructs for their Antibody Reactivities with Recombinant IL-6.

FIG. 3 further illustrates the kinetics of antisera over a 12-week period in guinea pigs immunized with 25 different IL-6 peptide immunogen constructs (SEQ ID NOs: 107, 112-114, 116-118 and 124-145). The guinea pig antisera from 0, 3, 6, 8/9 and 12 wpi were diluted from 1:100 to $1:4.19\times10^{1}$ by a 4-fold serial dilution. ELISA plates were coated with human IL-6 (GenScript) at 50 ng per well. The titer, expressed as Log ($EC_{50}$), of a tested serum was calculated by using four parameter logistic curve-fitting to obtain the half of maximal effect concentration ($EC_{50}$) in Log. All of 25 immunogen constructs were able to elicit a certain extent of cross-reactivity to native human IL-6, suggesting their raised anti-IL-6 antibodies may be potential to neutralize IL-6 activity.

To investigate whether the designed human IL-6 peptide immunogens will elicit antibodies with cross-reactivity from different animal species, which the data could provide useful information in further animal study. The 8- or 9-wpi sera induced by 29 different immunogen constructs (SEQ ID NOs: 107, 112-114, 116-118 and 124-145) were selected for IgG purification by protein A affinity chromatography. FIG. 4 illustrated the purified polyclonal guinea pig IgGs induced by SEQ ID NOs: 107, 116, 118 and 124-133 will cross-reacted with human, monkey and rat recombinant IL-6 proteins (all purchased from GenScript). Among these, the peptides of (SEQ ID NOs: 107, 118 and 124-126) contain IL-6 73-83 loop with different peptide construction, the peptides (SEQ ID NOs: 128, 129 and 131) contains IL-6 44-50 loop, and SEQ ID NO: 132 contains both loops.

iv) Identification of Endogenous/Autologous Th Epitopes for Exclusion in IL-6 B Epitope Peptide Design.

Identification of potential endogenous/autologous Th epitopes present in a target protein would provide benefit in the design of a composition for immunotherapeutic intervention as the presence of helper T cell epitope(s) structure feature in a peptide immunogen construct could potentially cause undesired inflammation upon booster immunization due to activation of autologous T cells, as in the previous of AN1792 for Alzheimer's disease vaccine. As shown in Table 7, despite formulation in potent water in oil emulsion formulation, free IL-6 B cell epitope peptides IL-6 62-83 (SEQ ID NO: 6), IL-6 58-83 (SEQ ID NO: 7); IL-6 52-83 (SEQ ID NO: 8), IL-6 52-72 (SEQ ID NO: 9); and IL-6 42-72 (SEQ ID NO: 10) gave clean background in the immunogenicity testing indicative of their qualification as candidate for IL-6 B cell epitope peptides used for the building of IL-6 peptide immunogen constructs for use in IL-6 formulation.

v) Focused Antibody Response Elicited by IL-6 Peptide Immunogen Constructs is Targeted at the IL-6 B Cell Epitope Only It is well known that all carrier proteins (e.g. Keyhole Limpet Hemocyanin (KLH) or other carrier proteins such as Diphtheria toxoid (DT) and Tetanus Toxoid (TT) proteins) used to potentiate an immune response directed against the targeted B cell epitope peptide by chemical conjugation of such B cell epitope peptide to the respective carrier protein will elicit more than 90% of the antibodies directed against the potentiating carrier protein and less than 10% of the antibodies directed against the targeted B cell epitope in immunized hosts. It is therefore of interest to assess the specificity of the IL-6 peptide immunogen constructs of the present disclosure. A series of eight IL-6 peptide immunogen constructs (SEQ ID NOs: 138-145 from Table 3) with B cell epitopes of varying lengths that are linked through a spacer sequence to the heterologous T cell epitope UBITh® 1 (SEQ ID NO: 91) were prepared for immunogenicity assessment. The UBITh® 1 (T helper peptide used for B epitope immunopotentiation) was coated to the plates and the guinea pig immune sera were employed to test for cross-reactivities with the UBITh® 1 peptide used for immunopotentiation. In contrast to the high immunogenicity of these constructs towards the corresponding targeted IL-6 B cell epitope peptides as illustrated by the high titers of antibodies generated towards the IL-6 B epitope(s) while as most, if not all, of the immune sera were found non-reactive to the UBITh®1 peptide as shown in Table 8.

In summary, simple immunogen design incorporating target IL-6 B cell epitope peptide linked to carefully selected T helper epitope allows the generation of a focused and clean immune response targeted only to the corresponding IL-6 B cell epitope peptide. For pharmaceutical composition design, the more specific the immune response it generates, the higher safety profile it provides for the composition. The IL-6 peptide immunogen constructs of this disclosure is thus highly specific yet highly potent against its target.

vi) Assessment of Immunogenicity of IL-6 Peptide Immunogen Constructs for their Antibodies to Inhibit IL-6 and IL-6R Interaction IL-6 signals via a heterotrimeric IL-6R/gp130 complex, whose engagement triggers activation of downstream signaling. Neither IL-6 nor IL-6R alone can activate the downstream signaling. A further study was conducted to investigate whether the candidate IL-6 peptide immunogen constructs could elicit antibodies in guinea pigs and that the elicited antibodies could neutralize IL-6 so as to block the interaction between IL-6 and IL-6 receptor (LL-6R) (Rose-John, et al., 2017).

Purified guinea pig IgGs from immune sera of guinea pigs immunized by 25 respective candidate IL-6 peptide immunogen constructs (SEQ ID NOs: 107, 116, 118, 124-145) were employed in an ELISA assay to assess their (a) relative immunogenicity by ELISA using the corresponding IL-6 B cell epitope peptide as the solid phase antigen coating as described in EXAMPLE 3; (b) relative ability to cross-react with IL-6 proteins from human, monkey and rodent species; and if yes to both (a) and (b), can these purified antibodies neutralize IL-6 protein and therefore would inhibit the interactions between IL-6 and IL-6Rα (i.e. cis-signaling) or IL-6/LL-6Rα and IL-6Rb/or gp130 (i.e. trans-signaling).

Figure 3:
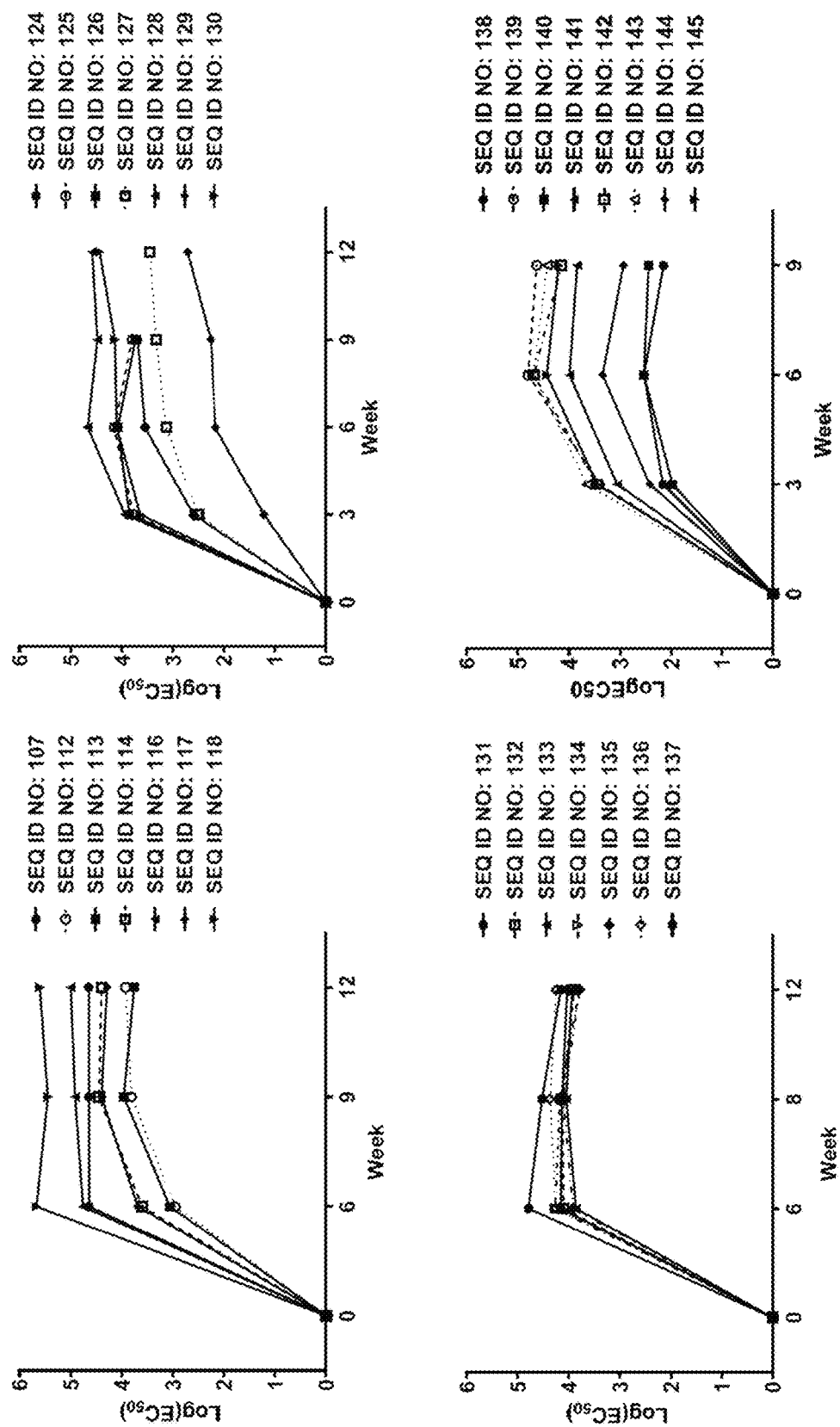
FIG. 3 shows four graphs that illustrate the kinetics of antibody response over a 12-week period in guinea pigs immunized with different IL-6 peptide immunogen constructs. Specifically, the antibody response to peptide immunogen constructs of SEQ ID NOs: 107, 112-114, and 116-118 is shown in the graph in the upper left; SEQ ID NOs: 124-130 is shown in the graph in the upper right; SEQ ID NOs: 131-137 is shown in the graph in the lower left; and SEQ ID NOs: 138-145 are shown in the graph in the lower right. ELISA plates were coated with recombinant human IL-6. Serum was diluted from 1:100 to $1:4.19 \times 10^8$ by a 4-fold serial dilution. The titer of a tested serum, expressed as $Log_{10}(EC_{50})$, was calculated by nonlinear regression with four-parameter logistic curve-fit.
Figure 4A:
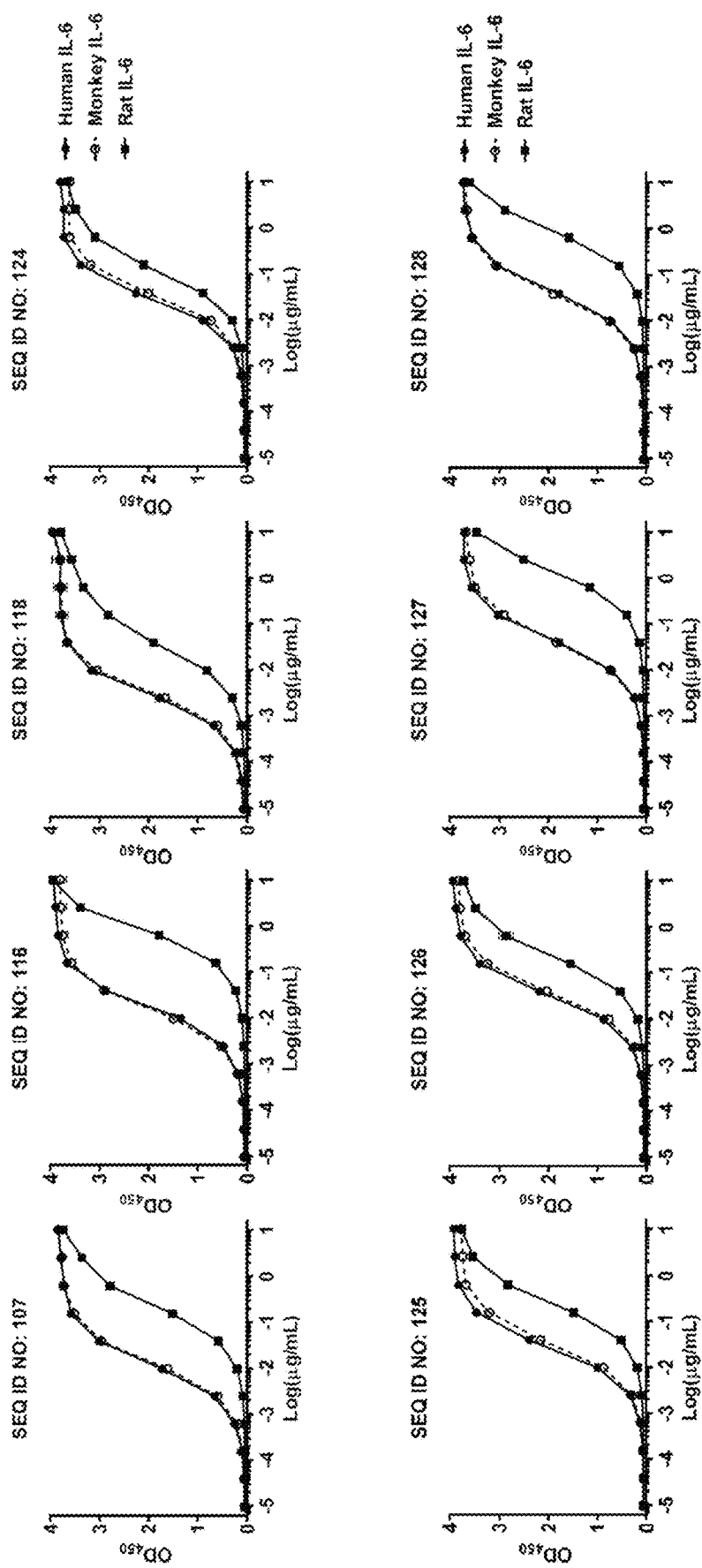

As shown in FIG. 3, all purified antibodies of guinea pigs immunized with carefully designed respective candidate IL-6 peptide immunogen constructs demonstrated significant antibody titers in a time course matching with the immunization schedule. Furthermore, all purified antibodies from the immune sera derived from immunization with these IL-6 peptide immunogen constructs demonstrated high reactivities with human IL-6 protein and also moderate cross-reactivities with monkey (macaque) and rodent IL-6 proteins as shown in FIGS. 4A and 4B.

Furthermore, as shown in FIG. 5A, representative antibodies purified from immune sera of guinea pigs immunized with respective candidate IL-6 peptide immunogen constructs (e.g. those with SEQ ID NOs: 107, 116, 118, 124, 132-134 and 137) inhibited competitively in a dose dependent manner the IL-6 and IL-6Rα interaction via the cis-signaling mode.

As shown in FIG. 5B, representative antibodies purified from immune sera of guinea pigs immunized with respective candidate IL-6 peptide immunogen constructs (e.g. those with SEQ ID NOs: 128, 129, 134 and 135) inhibited competitively in a dose dependent manner the IL-6-IL-6Rα complex with IL-6Rb/gp130 interaction via the trans-signaling mode.

On the contrary, the antibodies purified from immune sera derived from a peptide immunogen construct (SEQ ID NO: 130) comprising a prior art B cell epitope peptide sequence (SEQ ID NO: 11) could suppress neither the cis- not the trans-pathway.

vii) Epitope Mapping for Fine Specificity Analysis by Immune Sera (9 wpi) Elicited by Various IL-6 Peptide Immunogen Constructs The design of an IL-6 composition containing an I1-6 peptide immunogen construct was focused on the region comprising the two intramolecular loops C44-C50 (SEQ ID NO: 15) and C73-C83 (SEQ ID NO: 5) nearby the IL-6R binding site. This structure-based design aims to retain at least one of the native intramolecular loops as an immunogenic target.

Eight representative IL-6 B cell epitope peptides of 62-83 (SEQ ID NO: 124), 58-83 (SEQ ID NO: 125), 52-83 (SEQ ID NO: 126), 52-72 (SEQ ID NO: 127), 42-72 (SEQ ID NO: 128) with Th located at the N-terminal to the B cell epitope), 42-72 (SEQ ID NO: 129 with the Th located at the C terminal of the B cell epitope), 50-67 (SEQ ID NO: 130), and 73-83 (SEQ ID NO: 107).

IL-6 62-83 (SEQ ID NO: 6), 58-83 (SEQ ID NO: 7), 52-83 (SEQ ID NO: 8), 52-72 (SEQ ID NO: 9), 42-72 (SEQ ID NO: 10), 50-67 (SEQ ID NO: 11) and 73-83 (SEQ ID NO: 5) were used for designing the B cell epitope peptides that were linked with UBITh® 1 (SEQ ID NO: 91) in N- or C-terminus of the B cell epitope peptides to form the prototype peptide immunogens. The εK linker or εK-KKK (SEQ ID NO: 77) spacer was used between the B cell and Th epitopes to form the peptide immunogen constructs shown in Table 3 (SEQ ID NOs: 124-130,107). All B cell epitope peptides within amino acids (aa) 42-83, 42-72, and 73-83 were designed with a C44-C50 or C73-C83 constrained loop structure by cyclization.

ELISA tests using individual IL-6 B cell epitope peptides of C73-C83 (SEQ ID NO: 5) and E42-G72 (SEQ ID NO: 10) for plate coating were evaluated for antibody reactivities of the hyperimmune sera obtained from guinea pigs immunized with IL-6 peptide immunogen constructs (SEQ ID NOs: 124-130, 107). The results showed that constructs SEQ ID NOs: 124, 125, 126, and 107 comprising the C73-C83 loop structure induced high titer antibodies against IL-6 B cell epitope peptide C73-C83 (SEQ ID NO: 5) while the guinea pig antisera induced by IL-6 peptide immunogen constructs SEQ ID NOs: 127-130 comprising C44-C50 loop structure had antibody reactivity with B cell epitope peptide E42-C72 (SEQ ID NO: 10) while having little or no cross-reactivity to the C73-C83 loop (SEQ ID NO: 5), indicative of the high specificity of the immunogenicity, i.e. the designed immunogen constructs are able to evoke specific antibodies to react with the IL-6 corresponding B cell epitope domains (Table 9).

In a fine epitope mapping study (Table 9) to localize the antibody binding site(s) to specific residues within the target region, 51 overlapping 10-mer peptides (SEQ ID NOs: 21 to 71) were synthesized that cover from amino acid 32 to amino acid 91 sequence region of IL-6. These 10-mer peptides were individually coated onto 96-well microtiter plate wells as solid-phase immunoabsorbents. The pooled guinea pig antisera were added at a 1:100 dilution in specimen diluent buffer to the plate wells coated with 10-mer peptide at 2.0 μg/mL followed by incubation for one hour at 37° C. After washing the plate wells with wash buffer, the horseradish peroxidase-conjugated rProtein A/G was added and incubated for 30 min. After washing with PBS again, the substrate was added to the wells for measurement of absorbance at 450 nm by ELISA plate reader, when the samples were analyzed in duplicate. The binding of IL-6 peptide immunogen elicited immune sera to the corresponding IL-6 B cell epitope peptide coated wells represent the maximal antibody binding signal.

The fine epitope mapping results showed that the pooled guinea pig sera from IL-6 peptide immunogen constructs of SEQ ID NOs: 124, 125, 126, and 107 comprising the C73-C83 loop structure induced high titer antibodies mainly against a cluster of 10mer peptides from amino acid 69-78 (SEQ ID NO: 58) to amino acid 76-85 (SEQ ID NO: 65) with high cross-reactivities to peptides with amino acids 35-44 (SEQ ID NO: 24) and some occasional moderate activities to slight extension beyond N-terminus of the loop.

Surprisingly, the pooled guinea pig sera from IL-6 peptide immunogen constructs of SEQ ID NOs: 127-129 comprising the C44-C50 loop structure induced high titer antibodies mainly against a cluster of 10mer peptides from amino acid 61-70 (SEQ ID NO: 50) to amino acid 67-76 (SEQ ID NO: 56) outside the C44-C50 loop with IL-6 peptide construct 129 having broader scattered antibody reactivities extended to the N-terminal portion of the B epitope peptide 41-50 (SEQ ID NO: 30), 45-54 (SEQ ID NO: 34), 57-66 (SEQ ID NO: 46), 58-67 (SEQ ID NO: 47). It is of interest to note that immune sera generated by IL-6 peptide immunogen constructs 128 and 129 showed preferential Trans-inhibition in competitive IL-6/IL-6Rα cis- and (IL-6/IL-6Rα complex)/IL-6Rβ trans-competitive binding inhibition studies by respective ELISAs.

In summary, the designed synthetic IL-6 peptide immunogen constructs represented by looped structures C44-C50 and C73-C83 within IL-6 that is linked to UBITh® 1 epitope peptide which induced a robust immune response generating polyclonal antibodies targeted at distinct clusters of 10mer peptides which have close proximity to the IL-6R binding region allowing for binding inhibition of either IL-6/IL-6Rα mediated CIS- or (IL-6/IL-6Rα complex)/IL-6Rβ (or Gp130) mediated-TRANS-competitive binding inhibition (See FIGS. 5A and 5B) which should have important medical implications.

Example 7

Assessment of Functional Properties of Antibodies Elicited by the IL-6 Peptide Immunogen Constructs and Formulations Thereof in an Ex-Vivo Mode After demonstration of the high immunogenicity and cross-reactivities of the antibodies purified from immune sera of guinea pigs immunized with carefully selected respective candidate IL-6 immunogen constructs, the following studies were designed to assess whether the representative purified IgG from these immune sera could (a) suppress IL-6-induced STAT3 phosphorylation; (b) inhibit cell proliferation in TF-1 cell line; and (c) suppress IL-6-induced MCP-1 production in U937 cells, all in an ex vivo mode.

Suppression of IL-6-Induced STAT3 Phosphorylation by Anti-IL-6 Antibodies

IL-6 signaling pathway is involved in the complex formation of IL-6/IL-6Rα/IL6Rb (or Gp130) initially on cell membrane followed by the downstream protein STAT3 phosphorylation in cytoplasm. The RPMI 8226 cell line was used to assess the ability of those purified anti-IL-6 antibodies derived from immune sera of guinea pigs immunized with carefully selected candidate IL-6 peptide immunogen constructs for their ability to suppress IL-6 induced STAT3 phosphorylation because this 8226 cell line does not express constitutively phosphorylated STAT3.

Firstly, cultured cells were treated with IL-6 (10 ng/ml) and the purified IgGs at different concentrations simultaneously. The anti-IL-6R monoclonal antibody, As seen in FIG. 6, the anti-IL-6 IgGs elicited by representative immunogens (SEQ ID NOs: 128, 129, 134, 135 and 137) could reduce STAT3 phosphorylation at the IgG concentration of 100 μg/mL. The IgG from immune sera elicited by a peptide construct (SEQ ID NO: 130) comprising a prior art B epitope sequence (SEQ ID NO: 11) could not inhibit STAT3 phosphorylation.

Suppression of IL-6-Dependent Cell Proliferation in TF-1 Cell

The human erythroleukemia TF-1 cells are able to proliferate in response to human IL-6. To investigate whether the purified IgGs from immune sera of guinea pigs immunized with carefully selected candidate IL-6 peptide constructs (SEQ ID NOs: 116, 118, 124-129, 131-145) are able to suppress IL-6 dependent cell proliferation in TF-1 cell line, all TF-1 cell cultures were treated with IL-6 (10 ng/ml) and purified guinea pig IgGs simultaneously. TF-1 cells without IL-6 treatment, as well as TF-1 cells with only IL-6 but without antibodies, were set up as controls. As shown in FIGS. 7A and 7B, the TF-1 cells were more proliferative in the presence of IL-6 only than all other groups and that their cell proliferated as much as double to the cells without IL-6. The growth of the TF-1 cells in the presence of anti-IL-6 IgG antibodies elicited by representative candidate IL-6 peptide immunogen constructs (SEQ ID NOs: 116, 118, 124-245, 127-129, 131-145) could be suppressed to a certain extent (FIGS. 7A and 7B). The IgG from immune sera elicited by a peptide construct (SEQ ID NO: 130) comprising a prior art B epitope sequence (SEQ ID NO: 11) could not inhibit IL-6 induced cell proliferation.

Suppression of IL-6 Induced MCP-1 Production

MCP-1 plays a central role in both acute and chronic inflammatory processes. MCP-1 is a chemotactic factor that attracts monocytes and basophils in the pathogenesis of diseases. IL-6 can induce MCP-1 expression in the promonocytic cell line U937. To investigate whether anti-IL-6 antibodies elicited in guinea pigs by the IL-6 peptide immunogen constructs could suppress IL-6-dependent MCP-1 secretion in U937 cell line, all cell culture groups were treated with IL-6 cytokine at a concentration of 10 ng/ml for the induction of the MCP-1 production. Representative preparations of purified IgGs from immune sera of guinea pigs elicited by candidate IL-6 peptide immunogen constructs (SEQ ID NOs: 116, 118, 124-134, 136 138-145) were added in the test groups at different concentrations and Tocilizumab was also included as a positive control. The U937 cell culture in the presence of IL-6 only without adding antibody was set up as a negative control. An antibody concentration-dependent suppression of MCP-1 production was observed in the treatment groups with purified IgG antibodies elicited by representative candidate peptide constructs in a dose dependent manner as shown in FIGS. 8A and 8B to a varying degree with the exception of IgG from immune sera elicited by a peptide construct (SEQ ID NO: 130) comprising a prior art B epitope sequence (SEQ ID NO: 11) (See FIG. 8A).

The above ex-vivo functional studies indicate that these representative IL-6 peptide immunogen constructs demonstrated the suppression of IL-6 induced inflammatory processes and pathogenesis, indicative of their potential for treatment of diseases impacted by IL-6 dysregulation including autoimmune rheumatoid disease.

Example 8

Assessment of Rat IL-6 Peptide Immunogen Construct Candidates in a Preventive Mode on a Collagen Induced Arthritis (CIA) Model in Lewis Rats The effect of IL-6 peptide immunogen constructs on a rat Collagen-Induced Arthritis (CIA) model for rheumatoid arthritis was assessed in a prevention study as described below.

Human IL-6 shares about 40% amino acid sequence identity with rat IL-6. Based on rat IL-6 protein sequence, rat peptide immunogen constructs (SEQ ID NOs: 148 and 157) were designed as homologues of human IL-6 B cell epitope peptides of IL-6 73-83 and IL-6 144-166 with UBITh®3 as a B cell epitope peptide enhancing T helper epitope (SEQ ID NO: 89) and εK-KKK as a linker (SEQ ID NO: 77) linked at either the N or the C terminus of the IL-6 B epitope peptide, respectively.

The Lewis rats were used for this study with the protocol briefly shown in FIG. 9. A total of 21 rats were assigned into 3 groups with the placebo group injected with the adjuvant only.

Rats in the experimental groups were injected with the IL-6 peptide immunogen constructs formulated with ISA 51 and CpG at 45 μg/0.5 mL dose for prime and boost immunizations. A total of three doses were administered on day −31, −10 and 4. All rats were injected at the base of the tail with bovine type H collagen/IFA emulsion (100 μg in 100 μL per rat) by intradermal route 4 days before the third administration (day 0) and boosted 3 days after the third administration (day 7). The rats were bled at days on day −31, −10, 0, 7, 14, 21, 26, 28 and 35. ELISA assay was employed to measure immunogenicity titers against rat recombinant IL-6 protein.

The ELISA results showed no detectable antibody titer was observed in each group prior to immunization at day −31. After three immunizations, none of the placebo-treated rats showed detectable antibody titers against anti-rat recombinant IL-6. The peptide immunogen (SEQ ID NO: 148) targeting IL-6 73-83 B cell epitope could elicit more potent anti-IL-6 antibody titers than those in the other group (SEQ ID NO: 157) at around 3.0 of Log($EC_{50}$) during the period of CIA (FIG. 10).

Effect of IL-6 Immunotherapy Evaluated in a Preventative Mode on Rat CIA Model

Rats with rat IL-6 peptide construct (with SEQ ID NOs 148 or 157) immunization followed by CIA arthritis elicitation were carefully examined for clinical signs and symptoms of arthritis. CIA induced arthritis rapidly developed in the rats with collagen (bovine type II collagen, Chondrex Inc.) injections. Clinical inflammatory signs of acute arthritis, including erythema and joint swelling, graded on a scale of 0-4 each paw (total score ranging from 0 to 16) were found in the hind paws around 2 weeks after collagen challenges. The maximum arthritis severity score and most severe paw swelling were found around 3 week post-challenge of CIA in each group (FIGS. 11 and 12). The treatment efficacy in different IL-6 immunogen constructs were evaluated by arthritis severity score. The group immunized by (SEQ ID NOs: 148) exhibited lower alleviated arthritis severity score and less paw swelling than the other tested immunogen construct (SEQ ID NO: 157) and statistically significant difference compared with the placebo group during this in vivo immunotherapeutic study (FIGS. 11 and 12 and Tables 10 and 11).

To observe if the IL-6 immunogen is able to attenuate release of neutrophils from bone marrow into circulation during the rat CIA challenged study, the results showed that the numbers of neutrophils released from bone marrow gradually increased from day 0 and reached its peak at day 14. Rat IL-6 immunogens (SEQ ID NO: 148) effectively attenuated the release of neutrophils from bone marrow into circulation (FIG. 13 and Table 12). It indicated that both of the designed IL-6 immunogen constructs played an important role in reducing the inflammatory processes.

This study results indicated that the IL-6 rat B cell epitope peptide IL-6 72-82 represent a good candidate for human IL-6 peptide immunogen construct incorporating IL-6 73-83 as the B cell epitope peptide for treatment of diseases impacted by IL-6 dysregulation in a prevention mode where the induced polyclonal antibodies to the IL-6 molecule would neutralize blood circulating cytokine IL-6 to block/suppress its signal transduction thus reducing the clinical inflammatory pathological processes.

The CIA rats were injected 3 times by intramuscular route with the rat IL-6 peptide immunogen constructs or adjuvant only. The animals had good overall tolerability to the candidate rat IL-6 formulations at 45 µg/0.5 mL dose. Candidate rat IL-6 peptide immunogen with SEQ ID NO: 148 displayed higher efficacy in antibody response and attenuation of arthritis severity than that one with SEQ ID NO: 157.

Example 9

Effect of IL-6 Peptide Immunogen Constructs and Formulations Thereof for Treatment of Rheumatoid Arthritis as Demonstrated in a Therapeutic Mode in a Cia Model in Lewis Rats Proof of Concept (POC) Study for IL-6 Peptide Immunogen Constructs in Lewis Rat Collagen Induced Arthritis (CIA) Model In order to confirm efficacy of the IL-6 immunogen construct (SEQ ID NO: 148), a POC study was conducted in the Lewis rat CIA model, in which two different adjuvant formulations were evaluated in this efficacy study as shown in FIG. 14. Seven animals were assigned to each of the two treatment groups and six animals for the placebo group. Animals in two treatment groups were injected with peptide immunogen construct (SEQ ID NO: 148) formulated either with ISA 51 only or with ISA51/CpG in 45 µg/0.5 mL/dose for both prime and boosts at days −7, 7, 14, 21 and 28. The placebo group was injected with only adjuvant vehicle without peptide immunogen construct at the same injection time points as the treatment groups. All groups were injected with bovine type II collagen/IFA emulsion (100 µg in 100 µL per rat) at the base of the tail by intradermal route on days 0 and 7 to induce arthritis. The study was terminated on day 35.

The immunogenicity titer against rat IL-6 recombinant protein from the immunized rat serum was assessed by ELISA. The results showed that both treatment groups with same IL-6 peptide immunogen construct formulated by different adjuvants generated high antibody titers against rat IL-6 with steady increase after immunization. The titer peaked in both treatment groups on day 21 at the level of 3 Log ($EC_{50}$) and remained in plateau till study termination at day 35 (FIG. 15). This result further confirmed that this peptide immunogen construct (SEQ ID NO: 148) is rather immunogenic and able to break out immune tolerance to induce specific polyclonal antibodies against rat IL-6 with both adjuvant formulations effectively enhanced the antibody production.

The clinical assessment of CIA induced arthritis in Lewis rats were evaluated between treatment group and placebo group before and after the immunization by the IL-6 immunogen constructs, as well as by CIA arthritis induction. The arthritis severity was graded on a scale of 0-4 each paw (total score ranging from 0 to 16) based on the clinical signs of arthritis severity during the study. Results showed that CIA induced arthritis developed rapidly in the rats after being challenged with collagen. The adjuvant placebo group reached maximum arthritis score of 9 at day 14. In contrast, both two treatment groups showed much milder severity of arthritis that both scores are less than 6 at the same time point of day 14 with a statistical significance (p<0.01). Since then the decreased arthritis scores were observed in all groups monitored in every 2 to 3 day from days 14 to 35, with a total of 9 assessments made till the end of study. Results from each assessment showed that the two treatment groups had much lower scores of arthritis severity than the placebo group with statistical significances (mostly with p<0.01 or P<0.001) from days 14 to 35. By end of the study on day 35, the placebo group was with a score around 6, while both of the treatment groups were with scores around 3 as shown in FIG. 16. The clinical signs of CIA in the hind paws were also evaluated, results showed an increase in hind paw volume in all arthritic rats from day 14 due to the consequence of inflammation in the joints. But a similar result was observed that the two treatment groups were with much less hind paw volumes than the placebo group on days 14, 21, 28 and 35 respectively with statistical significances (p<0.01 to P<0.001 mostly). By the end of study on day 35, the hind paw volumes in these two treatment groups were close to the normal volume, while placebo group remained in higher volume as shown in FIG. 16. All these findings indicated that the two adjuvants displayed similar clinical efficacy in the present study, but ISA51+CpG combo is slightly better than ISA51.

Serum IL-6 levels positively correlated with the extent and severity of joint involvement; while some other downstream serum inflammatory biomarkers, such as C-reactive protein (CRP) is also an indicator to evaluate the inflammation severity. ELISAs were used to determine the serum levels of CRP. Rats from the placebo group (adjuvant vehicle-treated CIA) had significantly higher serum CRP levels (p<0.05) when compared to the two treatment groups (FIG. 17). The mean values of serum CRP in immunogen (SEQ ID NO: 148) treated CIA rats were close to the normal values, significantly lower than those of the placebo group on day 21.

The histopathological examination study was conducted to assess the effect of IL-6 peptide immunogen on histological disruption changes in ankle joints. The CIArats (7/pertreatment group, 6/placebo group) were sacrificed on day 35, and ankle joint tissues were removed for fixation, decalcification and paraffin embedding of tissue sections. Tissue sections were prepared and stained with H&E. The histopathological examination are shown in FIG. 18 where the normal control group displayed healthy articular space and normal tissues. In contrast, the placebo group demonstrated typical features of arthritis, which was characterized by marked synovial and periarticular inflammation, synovial hyperplasia, and bone erosion. The joint pathology of the CIA rats immunized with (SEQ ID NO: 148) revealed much milder inflammation with milder cell infiltration, lighter synovial hyperplasia and bone erosion, indicating ankle join disruption was alleviated by peptide immunogen construct (SEQ ID NO: 148). FIG. 18 also presented the comparison of the pathological scores in three different groups, which a modified Mankin Scoring system was adapted to evaluate articular cartilage by grading 0 to 6 in cartilage structure, 0-3 in cell morphology, 0-4 Safranin O staining and 0-4 in Synovial inflammation and hyperplasia (Clin Immunol. 124: 244-257). Peptide immunogen construct (SEQ ID NO: 148) treatment groups significantly reduced the pathological score to 6 when compared with score of 11 in the placebo group.

Inflammatory cytokines are suggested to have an important role in the RA pathogenesis. Immunohistochemical staining method was applied to assess the inflamed ankle tissues. Briefly, the formalin-fixed paraffin embedded tissue sections were deparaffinized in xylene, immersed in decreasing concentrations of ethanol, and rehydrated in water. All sections were processed for microwave-enhanced antigen retrieval. Slide-mounted sections immersed in Antigen Retrieval Citrate Solution (Scytek) were heated until boiling in a microwave oven at maximum power and cooled down to room temperature for 30 min. Endogenous peroxidase activity was blocked with 3% hydrogen peroxide/PBS for 10 min. Sections were preincubated with Ultravision Protein Block (ThermoFisher) at room temperature for 1 h. Then the sections were incubated with primary rabbit anti-rat IL-17 (Abbiotec, 1:100 diluted in PBST), anti-rat TNF-α (Abcam, 1:100 diluted in PBST) or anti-rat MCP-1 (Abcam, 1:200 diluted in PBST) at 4° C. overnight, washed with TBST (Scytek), and developed by Polink-2 Plus HRP Rabbit with DAB Kit (GBI Labs). The sections were counterstained with hematoxylin (Leica Biosystems), dehydrated and mounted in Surgipath Micromount mounting medium (Leica Biosystems). FIG. 19 showed the substantial increase of tissue TNF-α, IL-17 and MCP-1 in the placebo group. However, production of these cytokines was greatly suppressed in IL-6 immunogen-treated CIA rats.

This study indicated that IL-6 peptide immunogen construct immunization dramatically reduced the incidence of inflammatory arthritis and protected the bone and cartilage from destruction. These findings strongly support the clinical application of IL-6 peptide immunogen immunization in vivo for treatment or prevention of the rheumatoid arthritis and other autoimmune diseases.

Evaluation of Effects of Dosing and Adjuvants on Immune Response Elicited by IL-6 Peptide Immunogen Constructs in CIA Models The POC study in CIA rats demonstrated that the designed peptide immunogen constructs with high immunogenicity and therapeutic efficacy against IL-6 induced pathogenesis that implicates a potential immunotherapeutic application in rheumatoid arthritis and other autoimmune diseases. The following studies will focus on the optimization of the peptide immunogen constructs and selection of adjuvants as well as the dose determination in CIA Lewis rats.

MONTANIDE ISA 51 and ADJU-PHOS as different adjuvants formulated with same peptide immunogen (SEQ ID NO: 148) plus CpG respectively were evaluated in rat CIA immunization study. Five rats assigned into each of 5 groups were received one of two adjuvant formulations, total 10 groups for these two different adjuvants. All animals in the treatment groups were injected by different doses at 5, 15, 45, 150 µg in 0.5 ml through i.m. route in prime and boosts at day −7, 7, 14, 21 and 28 with clinical observation till to day 35. Two different adjuvant placebo groups without peptide immunogen received injection with only adjuvant vehicles in the formulation. In the following studies the anti-IL-6 titers, body weight, hind paw swelling examination, arthritis severity score, blood neutrophil, platelet counts and liver function were all assessed.

Anti-IL-6 titer was measured by ELISA against rat IL-6 recombinant protein coated in the plate wells. Results showed none of the two placebo groups injected with two different adjuvant vehicles was found detectable anti-IL-6 antibody titers, while all treatment groups immunized with IL-6 immunogen construct (SEQ ID NO: 148) with both adjuvant formulations generated antibody against rat IL-6 by ELISA. Generally speaking, the result showed that a dose dependent manner was observed, especially for the groups with ISA 51 formulation (FIG. 20). The ISA 51 formulation induced higher immune response than ADJUPHOS formulation in immunized rats, with immunogenicity $Log_{10}$ values over 3 from all doses respectively.

Body weights were monitored every seven days during the study process of 35 days. In FIG. 21, the body weight change pattern of the immunized rats is depicted, compared to the normal rats, the loss of body weight in the experimental CIA rats started on day 14, reaching the lowest point on day 21, and then gradually increased the body weight in each group. At the end of study (day 35) all CIA rats still showed around 10% loss in body weight, compared to normal control. The data also indicted a dose-dependent manner in body weight changes, the lower body weight loss was observed in higher dose group. The dose groups at 150 µg gained more body weight than other dose groups no matter what adjuvant used. Comparatively, the dose group at 150 µg with ADJUPHOS gained more body weight than any other groups on day 28 and 35, beyond 200 g level (Table 13).

Clinical severity of the CIA induced inflammation and destruction in rat was also assessed by the quantification of the paw volume changes. Macroscopic observation indicated that IL-6 immunogen construct (SEQ ID NO: 148) formulated with either ISA 51 or ADJUPHOS can protect against CIA development in rat model. The acute clinical signs of swelling and redness in paw were recorded in the rats during the study after collagen challenges. All immunized rats showed an increase of paw swelling from day 7 to 21, and then gradually recovered along with the inflammation reduction, as shown FIG. 22 and Table 14. The placebo group displayed the significant swelling and redness changes in macroscopic observation when compared to the normal group on day 24 (FIG. 23). Peptide immunogen construct (SEQ ID NO: 148) reduced paw redness and swelling in a dose-dependent manner. The maximum inflammation reduction by quantitative analysis was found in 150 µg dose group on day 24. ADJU-PHOS performed slightly better than MONTANIDE ISA 51.

The clinical severity of arthritis was graded on a scale of (0-4) for each paw, according to inflammatory changes in erythema and swelling signs (score criteria). Animals were examined every two or three days and measured as mean±S.D. to evaluate the arthritis severity (FIG. 24 and Table 15). The initial signs of arthritis development induced by collagen challenges were visible on day 14. The arthritis scores of the CIA groups increased rapidly, reaching a maximum score of 5-9 around day 20, and then the inflammatory manifestation gradually became weaker from day 21 to day 35 in both treatment and placebo groups. However, all treatment groups with immunogen construct (SEQ ID NO. 148) resulted in greater attenuation of arthritis by the clinical sign score than the placebo group during the study. The peptide immunogen dose dependent manner was also observed that the higher dose groups received the lower arthritis score in all treatment groups either with adjuvant ISA51 or ADJUPHOS. The two placebo groups with two different adjuvant vehicles were found with more severity in clinical arthritis signs by having higher clinical sign scores than those in all of the treatment groups. The best dose level was found at 45 and 150 µg, which significantly reduced arthritis signs and symptoms when compared to the doses at 5 and 15 µg with both ISA 51 and ADJUPHOS formulations. On day 33 and 35, at 150 µg dose level of ADJUPHOS formulation groups presented more significant reduction of arthritis scores with 61% and 63% than those in the ISA 51 groups with 31% and 45% reduction, respectively.

The neutrophil counts increased rapidly from day 0 to 7 after the first collagen injection, and then gradually rose after the second challenge until day 14. The elevated neutrophil counts were rapidly decreased by immunization in a dose-dependent manner (FIG. 25 and Table 16).

All immunogen treatment groups were found with more neutrophil count reduction than the placebo groups at each time point. In the IL-6 immunogen treatment groups, two higher doses significantly reduced neutrophilia, however at 45 and 150 μg doses from ADJUPHOS formulation significantly reduced neutrophil counts ($p<0.001$) to $1.55\pm0.23\times10^3$ per μL and $1.36\pm0.25\times10^3$ per μL, respectively, which was better than the formulation with ISA 51 at the same dose levels.

Collagen induced arthritis is also associated with a significant increase in platelet count. In the tested CIA rats, the mean platelet count exhibits a steady increase after the first collagen injection in all groups, then gradually decreased (FIG. 26 and Table 17). The dose-dependence was also observed, showing lower platelet count for higher dose. Especially, IL-6 composition formulated with ADJUPHOS at 45 and 150 μg doses significantly reduced the platelet level close to the normal value whereas the placebo groups were with higher blood platelet counts in each time points.

Liver damage was quantified by measuring serum aspartate aminotransferase (AST) level (FIG. 27 and Table 18) using a routine human AST test on a Hitachi 7080 chemistry analyzer (Hitachi). Treatment of the rats with an IL-6 peptide immunogen construct formulation and collagen led to moderately increase in serum AST levels between days 0 and 7 as compared to normal rat group. AST concentrations were steady till day 21, then slowly decreased to the end of study. The dose dependency was also observed for AST level. The rats with 150 μg dose displayed significant lower AST level in both formulations. At the 45 μg dose, significant lower AST level was only shown in ADJUPHOS formulation, not in ISA 51.

In summary, Il-6 peptide immunogen construct (SEQ ID NO: 148) formulated with adjuvants are able to induce IL-6 antibodies to neutralize excessive IL-6 resulting in attenuation of arthritis severity and suppression of inflammatory factors such as blood neutrophil and platelet counts, as well as protection of liver functions. A similar dose-dependent pattern of response to the composition was observed in each of the IL-6 peptide immunogen constructs treatment groups. The results revealed that the animals receiving 150 μg per dose gave the highest immune response followed by those receiving 45 μg. Furthermore, both adjuvant delivery systems, ISA 51 and ADJUPHOS, showed the capacity of attenuation of arthritis symptoms when used in combination with the IL-6 peptide immunogen constructs. However, adjuvant ADJU-PHOS performed slightly better than MONTANIDE ISA 51 in all arthritis-related pathological parameters. The highest dose at 150 μg per 0.5 mL ADJUPHOS is therefore considered an optimal dosage for immunization in rats and will be used as a guide to explore immunogenicity in different species.

Example 10

Treatment of Chronic Inflammatory Diseases by Immunization with IL-6 Peptide Immunogen Constructs and Formulations Thereof IL-6 participates in a broad spectrum of biological events, such as immune responses, haemopoiesis and acute-phase reactions. However, overproduction of IL-6 has been implicated in the pathogenesis of a variety of diseases, including several chronic inflammatory diseases and cancer. The use of inhibitors towards IL-6 signaling should provide critical information for better understanding of the molecular mechanisms of diseases impacted by IL-6 dysregulation which would facilitate the development of new therapeutic intervention for these diseases. Clinical applications of IL-6 peptide immunogen constructs and formulations thereof of the present disclosure as pharmaceutical compositions for disease prevention and/or treatment are described in EXAMPLES 11 to 15. A review article on potential clinical applications of IL-6 inhibitors towards IL-6 signaling in diseases in hereby provided as a reference (Mihara, et al., 2012).

Anemia of Chronic Inflammatory Diseases (ACD)

Anemia is often observed in patients with chronic inflammatory diseases, such as RA, inflammatory bowel disease and cancer, and is called ACD (anemia of chronic disease). ACD is characterized by hypoferremia in the presence of adequate iron stores. Inflammatory cytokines are thought to play important roles in ACD.

Anemia observed in monkey collagen-induced arthritis is characterized by decreased serum iron and transferrin saturation and by elevated serum ferritin. The severity of anemia is correlated with serum IL-6 levels. Hepcidin is a master regulator of iron homoeostasis in humans and other mammals. It inhibits the absorption of iron in the small intestine and the release of recycled iron from macrophages, effectively decreasing the delivery of iron to maturing erythrocytes in the bone marrow. Mice genetically engineered to overproduce hepcidin die of severe iron deficiency shortly after birth.

IL-6 induces hepcidin production in liver cells. Administration of TCZ, a monoclonal antibody directed at IL-6 receptor, to monkeys with collagen-induced arthritis rapidly improved anemia and induced a rapid, but transient, reduction in serum hepcidin. Hepcidin mRNA expression was more potently induced by serum from arthritic monkeys than from healthy animals which was inhibited by the administration of TCZ. These lines of evidence indicate that TCZ improves anemia in monkey arthritis through the inhibition of IL-6-induced hepcidin production.

In place of expensive antibody treatment, administration with IL-6 peptide immunogen constructs and formulations thereof of the present disclosure in patients for elicitation of IL-6R binding site antibodies to intervene at IL-6 and IL-6 R binding leading to disease treatment.

Example 11

Treatment of Cancer by Immunization with IL-6 Peptide Immunogen Constructs and Formulations Thereof Chronic Inflammation in Human Carcinogenesis Chronic inflammation plays an important role in human carcinogenesis. There are many reports describing elevated serum levels of IL-6 in cancer patients which are related to disease severity and outcome. IL-6 has been implicated in the modulation of growth and differentiation of many cancers. IL-6 elevation has also been found to be associated with poor prognosis in renal cell carcinoma, ovarian cancer, lymphoma, melanoma and prostate cancer. By activating ERK1/2, IL-6 stimulates tumor cell proliferation. IL-6 is an important regulator of cell survival, providing tumor cells with a mechanism to escape cell death induced by stress and cytotoxic drugs. Additionally, the physiological role of IL-6 has been shown to promote not only tumor proliferation but also metastasis and symptoms of cachexia.

Multiple Myeloma (MM)

MM is a malignancy of plasma cells and is the most common malignant lymphoma in adults. It is characterized by localization of tumor cells to the bone marrow where these cells disseminate and induce bone diseases. The interaction between MM cells and stromal cells in the bone marrow microenvironment stimulates the production of cytokines, growth factors and adhesion molecules. Together they play an important role in the proliferation and localization of MM cells in the bone marrow. MM cells cause osteolysis leading to bone pain and hypercalcemia. IL-6 is a major growth factor for MM cells. In approximately half of all MM patients, proliferation of cultured MM cells was observed to be mediated by an autocrine loop, and it is now well known that IL-6 produced by the bone marrow environment is the major cytokine involved in the growth and survival of MM cells. Moreover, IL-6 is well known to be an essential factor in the survival of MM cells, since it prevents apoptosis of MM cells induced by different stimuli such as dexamethasone, Fas and serum deprivation. The IL-6-sIL-6R complex is more potent than IL-6 alone in up-regulating both Bcl-xL and Mcl-1 in native MM cells, which do not express IL-6R on the cell surface. It is, therefore, important to have compositions containing IL-6 peptide immunogen constructs that can elicit antibodies directed at sites that would interfere with Trans-signaling, i.e. interfering at the level of IL-6/IL-6Rα complex with IL-6Rβ/i.e.gp130. The IL-6 composition of the present disclosure can, therefore, be applicable in treatment of MM.

Prostate Cancer

The expression of IL-6 and IL-6R and the role of IL-6 as a growth factor in prostate cancer are well documented. IL-6 is responsible for resistance to apoptosis and increased levels of an anti-apoptotic member of the Bcl-2 family in the advanced prostate cancer cell line LNCaP. Since the growth of prostate cancer cells depends on the presence of androgens, almost all patients with advanced prostate cancer respond initially to androgen deprivation and anti-androgen therapy. Because IL-6 stimulates androgen synthesis and expression of ARs (androgen receptors) on prostate cancer cells, it is possible that IL-6 diminishes the therapeutic effect of anti-androgen treatment in prostate cancer. On the other hand, in AR-negative prostate cancer cells, IL-6 is known as an inhibitor of apoptosis. IL-6 compositions of the present disclosure would allow generation of anti-IL-6 antibodies in immunized patients to neutralize the negative impact exerted by IL-6 in these cancer patients.

Cancer-Related Anorexia and Cachexia

Cancer-related anorexia and cachexia are serious complications associated with malignant diseases. The features of cachexia are anemia, abnormalities of liver function, fatigue and vomiting. Elevated serum IL-6 in patients with pancreatic cancer and correlation with cachexia has been observed. As described above, IL-6 is related to iron metabolism. In addition, IL-6 also has a regulatory role related to excessive glucose metabolism and muscle loss. IL-6 is also known to be essential for cancer cachexia in a syngeneic mouse model, in which treatment with an anti-IL-6 antibody prevented the induction of cancer cachexia. In addition, in syngeneic mice, injection of IL-6 cDNA-transfected Lewis lung carcinoma cells resulted in unaltered net tumor growth rate, but caused weight loss and shortened survival. An anti-human IL-6 antibody (ALD518) was reported to reverse fatigue and reduce loss of lean body mass (−0.19 kg in patients taking ALD518 compared with −1.50 kg in those taking placebo) in patients with advanced non-small cell lung cancer. In these patients, ALD518 increased hemoglobin, hematocrit, mean corpuscular hemoglobin and albumin, and raised hemoglobin levels to ≥12 g/dl in 58% of patients with hemoglobin levels of ≤11 g/dl at baseline. Therefore, anti-IL-6 antibodies, either as a monoclonal antibody or as antibodies elicited by immunizing patients with compositions containing IL-6 peptide immunogen constructs, could be a non-erythropoietic-stimulating agent for cancer-related anemia.

Patients with long-standing ulcerative colitis carry a much higher risk of developing colon cancer, suggesting a role of the immune system as a tumor promoter in the colon. A study has shown that IL-6, which is produced in innate immune cells within the lamina propria in response to intestinal injury, enhances proliferation of tumor-initiating cells and protects normal and pre-malignant intestinal epithelial cells from apoptosis during acute colonic inflammation and CAC (colitis-associated cancer) induction. Furthermore, in azoxymethane-induced colonic tumors in ulcerative colitis models, the appearance of tumors was accompanied by the co-appearance of an F4/80+CD11bhighGr1low (M2) macrophage subset, which is a source of tumor-promoting factors, including IL-6. These results suggest that IL-6 blockade could be an approach for the therapy of Colitis-associated cancer.

In place of expensive antibody treatment to intervene IL-6 and IL-6 Receptor interaction and reduction of IL-6 serum level leading to treatment and amelioration of cancer including multiple myeloma (MM), androgen dependent or androgen independent prostate cancer, non-small cell lung cancer, cancer-related anorexia and cachexia, cancer-related anemia, and colitis-associated cancer, immunization with IL-6 peptide immunogen constructs and formulations thereof would be suitable for treatment of these devastating diseases.

Example 12

Treatment of Rheumatoid Arthritis by Immunization with IL-6 Peptide Immunogen Construct and Formulations Thereof Rheumatoid Arthritis (RA)

Rheumatoid Arthritis (RA) is a chronic progressive autoimmune inflammatory disease with unknown etiology that particularly affects the joints of the hands and feet. The synovial tissue of affected joints is infiltrated by inflammatory cells, such as macrophages and lymphocytes, leading to hyperplasia with neovascularization which in turn causes joint swelling, stiffness and pain. This process ultimately leads to cartilage destruction and bone resorption in the joints with some patients suffering permanent disability. The biological activities of IL-6 and the elevation of IL-6 in the serum and the synovial fluids of RA patients indicate that IL-6 is one of the key cytokines involved in the development of RA. Seven Phase III clinical trials with anti-IL-6R monoclonal antibody TCZ (tocilizumab) carried out in Japan and worldwide have revealed its efficacy, either as a monotherapy or as a combo-therapy with DMARDs (disease-modifying anti-rheumatic drugs) in the treatment of adult patients with moderate-to-severe RA. Moreover, both SAMURAI (Study of Active Controlled Monotherapy Used for Rheumatoid Arthritis, an IL-6 Inhibitor) and LITHE (Tocilizumab safety and the prevention of structural joint damage trial) trials proved that radiological damage of joints was significantly inhibited by TCZ treatment. As a result, TCZ has now been approved for the treatment of RA in many countries.

Systemic Juvenile Idiopathic Arthritis (sJIA)

Systemic juvenile idiopathic arthritis (sJIA) is a subtype of chronic childhood arthritis that leads to joint destruction and functional disability accompanied by systemic inflammation. This long-lasting inflammation also causes spike fever, anemia and impairment of growth. The acute complication of sJIA known as macrophage activation syndrome is associated with serious morbidity. IL-6 has been reported to be markedly elevated in patient blood and synovial fluid, and the IL-6 level has been shown to correlate with disease activity. TCZ showed outstanding efficacy in a randomized double-blind placebo-controlled withdrawal Phase III trial for 56 patients with sJIA, who had been refractory to conventional treatment regimens. It was approved in 2008 in Japan as the first biological drug for sJIA.

In place of expensive antibody treatment as shown above to intervene at the level of IL-6 and IL-6 Receptor interaction for reduction of IL-6 serum level and amelioration of sJIA disease, immunization with IL-6 peptide immunogen constructs and formulations thereof of the present disclosure would be suitable for treatment of sJIA disease.

Example 13

Treatment of Castleman's Disease by Immunization with IL-6 Peptide Immunogen Constructs and Formulations Thereof Castleman's disease is a lymphoproliferative disease with benign hyperplastic lymph nodes characterized by follicular hyperplasia and capillary proliferation accompanied by endothelial hyperplasia. IL-6 is produced in high levels in the hyperplastic lymph nodes and IL-6 is the key element responsible for the various clinical symptoms. Two open-label clinical trials have shown that anti IL-6R antibody TCZ administered at 8 mg/kg of body weight every 2 weeks had a marked effect on clinical symptoms, laboratory findings, as well as histologically determined amelioration. Moreover, TCZ treatment resulted in a rapid reduction in serum hepcidin-25 in patients with Castleman's disease. Long-term reductions, accompanied by progressive normalization of iron-related parameters and improvement in symptoms, were observed after the start of TCZ treatment, indicative of IL-6 playing an essential role in the induction of hepcidin in Castleman's disease. TCZ was approved as an orphan drug for Castleman's disease in 2005 in Japan.

In place of expensive antibody treatment to intervene at the level of IL-6 and IL-6 Receptor interaction leading to reduction of IL-6 serum level and amelioration of Castleman's disease, immunization with IL-6 peptide immunogen constructs and formulations thereof would be suitable for treatment of Castleman's disease.

Example 14

Treatment of Depression by Immunization with IL-6 Peptide Immunogen Constructs and Formulations Thereof The association between the immune system and the brain may offer new mechanistic understanding and insights for treatment of depression. Cytokine-mediated communication between the immune system and the brain has been implicated in the pathogenesis of depression. Major depression is common (one in four) after interferon treatment, a potent inducer of cytokines, in patients affected by hepatitis C virus. Experimental immuno-activation in healthy volunteers leads to depressive symptoms and reduced cognitive performance. Meta-analyses of cross-sectional studies have confirmed elevated levels of circulating inflammatory cytokines in depressed patients. Longitudinal studies have demonstrated that elevated serum cytokine levels precede, so potentially cause depressive symptoms. Furthermore, activation of the inflammatory system is thought to underlie anti-depressant resistance, highlighting an involvement of inflammation in treatment response. Based on these findings, it would be most meaningful to target inflammatory cytokines especially IL-6 employing IL-6 peptide immunogen constructs and formulations thereof of the present disclosure to provide therapeutic benefit for patients with depression and pain, in particular for those with chronic inflammatory conditions.

TABLE 1

Amino Acid Sequences of IL-6 and Its Fragments Employed in Serological Assays

| Amino Acid positions within IL-6 | SEQ ID NO: | Sequence |
|---|---|---|
| Human IL-6$_{1-184}$ | 1 | PVPPG EDSKD VAAPH RQPLT SSERI DKQIR YILDG ISALR KETCN KSNMC ESSKE ALAEN NLNLP KMAEK DGCFQ SGFNE ETCLV KIITG LLEFE VYLEY LQNRF ESSEE QARAV QMSTK VLIQF LQKKA KNLDA ITTPD PTTNA SLLTK LQAQN QWLQD MTTHL ILRSF KEFLQ SSLRA LRQM |
| Macaque IL-6$_{1-184}$ | 2 | PVLPG EDSKD VAAPH SQPLT SSERI DKHIR YILDG ISALR KETCN RSNMC ESSKE AIAEN NLNLP KMAEK DGCFQ SGFNE DTCLV KIITG LLEFE VYLEY LQNRF ESSEE QARAV QMSTK VLIQF LQKKA KNLDA ITTPE PTTNA SLLTK LQAQN QWLQD MTTHL ILRSF KEFLQ SSLRA LRQM |
| Mouse IL-6$_{1-184}$ | 3 | SQVRR GDFTE DTTPN RPVYT TSQVG GLITH VLWEI VEMRK ELCNG NSDCM NNDDA LAENN LKLPE IQRND GCYQT GYNQE ICLLK ISSGL LEYHS YLEYM KNNLK DNKKD KARVL QRDTE TLIHI FNQEV KDLHK IVLPT PISNA LLTDK LESQK EWLRT KTIQF TLKSL EEFLK VTLRS TRQT |

TABLE 1-continued

Amino Acid Sequences of IL-6 and Its Fragments Employed in Serological Assays

| Amino Acid positions within IL-6 | SEQ ID NO: | Sequence |
|---|---|---|
| Rat IL-6$_{1-184}$ | 4 | SQVRR GDFTE DTTHN PPVYT TSQVG GLITY VLREI LEMRK ELCNG NSDCM NSDDA LSENN LKLPE IQRND GCFQT GYNQE ICLLK ICSGL LEFRF YLEFV KNNLQ DNKKD KARVI QSNTE TLVHI FKQEI KDSYK IVLPT PTSNA LLMEK LESQK EWLRT KTIQL ILKAL EEFLK VTMRS TRQT |
| IL-6$_{73-83}$ | 5 | CFQSG FNEET C |
| IL-6$_{52-83}$ | 6 | LNLPK MAEKD GCFQS GFNEE TC |
| IL-6$_{58-83}$ | 7 | AENNL NLPKM AEKDG CFQSG FNEET C |
| IL-6$_{52-83}$ | 8 | SSKEA LAENN LNLPK MAEKD GCFQS GFNEE TC |
| IL-6$_{52-72}$ | 9 | SSKEA LAENN LNLPK MAEKD G |
| IL-6$_{42-72}$ | 10 | ETCNK SNMCE SSKEA LAENN LNLPK MAEKD G |
| IL-6$_{50-67}$ | 11 | CESSK EALAE NNLNL PKC |
| IL-6$_{42-57}$ | 12 | ETCNK SNMCE SSKEA L |
| IL-6$_{81-75}$ | 13 | NLNLP KMAEK DGSFQ |
| IL-6$_{51-72}$ | 14 | NLNLP KMAEK DG |
| IL-6$_{44-50}$ | 15 | CNKSN MC |
| IL-6$_{42-83}$ | 16 | ETCNK SNMCE SSKEA LAENN LNLPK MAEKD GCFQS GFNEE TC |
| IL-6$_{44-83}$ | 17 | CNKSN MCESS KEALA ENNLN LPKMA EKDGC FQSGF NEETC |
| IL-6$_{150-162}$ | 18 | CLQAQ NQWLQ DMC |
| IL-6$_{144-166}$ | 19 | CASLL TKLQA QNQWL QDMTT HLC |
| Mouse IL-6$_{72-82}$ | 20 | CYQTG YNQEI C |
| IL-6$_{32-41}$ | 21 | ILDGI SALRK |
| IL-6$_{33-42}$ | 22 | LDGIS ALRKE |
| IL-6$_{34-43}$ | 23 | DGISA LRKET |
| IL-6$_{35-44}$ | 24 | GISAL RKETC |
| IL-6$_{36-45}$ | 25 | ISALP KETCN |
| IL-6$_{37-46}$ | 26 | SALRK ETCNK |
| IL-6$_{38-47}$ | 27 | ALRKE TCNKS |
| IL-6$_{39-48}$ | 28 | LRKET CNKSN |
| IL-6$_{40-49}$ | 29 | RKETC NKSNM |
| IL-6$_{41-50}$ | 30 | KETCN KSNMC |
| IL-6$_{42-51}$ | 31 | ETCNK SNMCE |
| IL-6$_{43-52}$ | 32 | TCNKS NMCES |
| IL-6$_{44-53}$ | 33 | CNKSN MCESS |
| IL-6$_{45-54}$ | 34 | NKSNM CESSK |
| IL-6$_{46-55}$ | 35 | KSNMC ESSKE |
| IL-6$_{47-56}$ | 36 | SNMCE SSKEA |
| IL-6$_{48-57}$ | 37 | NMCES SKEAL |

TABLE 1-continued

Amino Acid Sequences of IL-6 and Its Fragments Employed in Serological Assays

| Amino Acid positions within IL-6 | SEQ ID NO: | Sequence |
|---|---|---|
| IL-6$_{49-58}$ | 38 | MCESS KEALA |
| IL-6$_{50-59}$ | 39 | CESSK EALAE |
| IL-6$_{51-60}$ | 40 | ESSKE ALAEN |
| IL-6$_{52-61}$ | 41 | SSKEA LAENN |
| IL-6$_{53-62}$ | 42 | SKEAL AENNL |
| IL-6$_{54-63}$ | 43 | KEALA ENNLN |
| IL-6$_{55-64}$ | 44 | EALAE NNLNL |
| IL-6$_{56-65}$ | 45 | ALAEN NLNLP |
| IL-6$_{57-66}$ | 46 | LAENN LNLPK |
| IL-6$_{58-67}$ | 47 | AENNL NLPKM |
| IL-6$_{59-68}$ | 48 | ENNLN LPKMA |
| IL-6$_{60-69}$ | 49 | NNLNL PKMAE |
| IL-6$_{61-70}$ | 50 | NLNLP KMAEK |
| IL-6$_{62-71}$ | 51 | LNLPK MAEKD |
| IL-6$_{63-72}$ | 52 | NLPKM AEKDG |
| IL-6$_{64-73}$ | 53 | LPKMA EKDGC |
| IL-6$_{65-74}$ | 54 | PKMAE KDGCF |
| IL-6$_{66-75}$ | 55 | KMAEK DGCFQ |
| IL-6$_{67-76}$ | 56 | MAEKD GCFQS |
| IL-6$_{68-77}$ | 57 | AEKDG CFQSG |
| IL-6$_{69-78}$ | 58 | EKDGC FQSGF |
| IL-6$_{70-79}$ | 59 | KDGCF QSGFN |
| IL-6$_{71-80}$ | 60 | DGCFQ SGFNE |
| IL-6$_{72-81}$ | 61 | GCFQS GFNEE |
| IL-6$_{73-82}$ | 62 | CFQSG FNEET |
| IL-6$_{74-83}$ | 63 | FQSGF NEETC |
| IL-6$_{75-84}$ | 64 | QSGFN EETCL |
| IL-6$_{76-85}$ | 65 | SGFNE ETCLV |
| IL-6$_{77-86}$ | 66 | GFNEE TCLVK |
| IL-6$_{78-87}$ | 67 | FNEET CLVKI |
| IL-6$_{79-88}$ | 68 | NEETC LVKII |
| IL-6$_{80-89}$ | 69 | EETCL VKIIT |
| IL-6$_{81-90}$ | 70 | ETCLV KIITG |
| IL-6$_{82-91}$ | 71 | TCLVK IITGL |
| Mouse IL-6$_{154-184}$ | 236 | QKEWL RTKTI QFILK SLEEK LKVTL RSTRQ T |
| Rat IL-6$_{150-162}$ | 72 | <u>C</u>LESQK EWLRT KT<u>C</u> |
| Rat IL-6$_{144-166}$ | 73 | <u>C</u>ALLM EKLES QKEWL RTKTI QL<u>C</u> |

TABLE 1-continued

Amino Acid Sequences of IL-6 and Its Fragments Employed in Serological Assays

| Amino Acid positions within IL-6 | SEQ ID NO: | Sequence |
|---|---|---|
| Rat IL-6$_{72-82}$ | 74 | CFQTG YNQEI C |
| Macaque IL-6$_{73-83}$ | 75 | CFQSG FNEDT C |
| Spacer 1 | 76 | PPXPXP |
| Spacer 2 | 77 | εK-KKK |
| Spacer 3 | 231 | KKK-εK |

*The cysteines that substitute the amino acids at the N-terminal and/or C-terminal of the IL-6 fragments are underlined.

TABLE 2

Amino Acid Sequences of Pathogen Protein Derived Th Epitopes Including Idealized Artificial Th Epitopes for Employment in the Design of IL-6 Peptide Immunogen Constructs

| Description | SEQ ID NO: | Sequence |
|---|---|---|
| Clostridium tetani1 Th | 78 | KKQYIKANSKFIGITEL |
| MvF1 Th | 79 | LSEIKGVIVHRLEGV |
| Bordetella pertussis Th | 80 | GAYARCPNGTRALTVAELPGNAEL |
| Clostridium tetani2 Th | 81 | WVRDIIDDFTNESSQKT |
| Diphtheria Th | 82 | DSETADNLEKTVAALSILPGHGC |
| Plasmodium falciparum Th | 83 | DHEKKHAKMEKASSVFNVVNS |
| Schistosoma mansoni Th | 84 | KWFKTNAPNGVDEKHRH |
| Cholera Toxin Th | 85 | ALNIWDRFDVFCTLGATTGYLKGNS |
| MvF2 Th | 86 | ISEIKGVIVHKIEGI |
| KKKMvF3 Th | 87 | KKKISISEIKGVIVHKIEGILF<br>      T    RT     TR   T |
| HBsAg1 Th | 88 | KKKLFLLTKLLTLPQSLD<br>RRRIKII RII  I  L IR<br>VRVV  VV  V I V<br>F FF   FF F V F<br>                 F |
| MvF4 Th (UBITh® 3) | 89 | ISISEIKGVIVHKIETILF<br>   T    RT    TR |
| HBsAg2 Th | 90 | KKKIITITRIITIPQSLD<br>    FFLL   L   ITTI |
| MvF5 Th (UBITh® 1) | 91 | ISITEIKGVIVHRIETILF |
| HBsAg3 Th (UBITh® 2) | 92 | KKKIITITRIITTITTID |
| Influenza MP1_1 Th | 93 | FVFTLTVPSER |
| Influenza MP1_2 Th | 94 | SGPLKAEIAQRLEDV |
| Influenza NSP1 Th | 95 | DRLPPDQKS |
| EBV BHRF1 Th | 96 | AGLTLSLLVICSYLFISRG |
| Clostridium tetani TTI Th | 97 | QYIKANSKFIGITEL |
| EBV EBNA-1 Th | 98 | PGPLRESIVCYFMVFLQTHI |
| Clostridium tetani TT2 Th | 99 | FNNFTVSFWLRVPKVSASHLE |
| Clostridium tetani TT3 Th | 100 | KFIIKRYTPNNEIDSF |
| Clostridium tetani TT4 Th | 101 | VSIDKFRIFCKALNPK |
| EBV CP Th | 102 | VPGLYSPCRAFFNKEELL |
| HCMV IE1 Th | 103 | DKREMWMACIKELH |
| EBV GP340 Th | 104 | TGHGARTSTEPTTDY |
| EBV BPLF1 Th | 105 | KELKRQYEKKLRQ |
| EBV EBNA-2 Th | 106 | TVFYNIPPMPL |
| KKKMvF3 Th (individual) | 216 | KKKISISEIKGVIVHKIEGILF |
|  | 217 | KKKISITEIRTVIVTRIETILF |
| HBsAg1 Th (individual) | 218 | KKKLFLLTKLLILPQSLD |
|  | 219 | RRRIKIITRIITIPLSIR |
|  | 220 | KKKVRVVTKVVTVPISVD |
|  | 221 | KKKFFFFTKFFTKPVSFD |
|  | 222 | KKKLFLLTKLLTLPFSLD |

TABLE 2-continued

Amino Acid Sequences of Pathogen Protein Derived Th Epitopes Including Idealized Artificial Th Epitopes for Employment in the Design of IL-6 Peptide Immunogen Constructs

| Description | SEQ ID NO: | Sequence |
| --- | --- | --- |
| MvF4 Th (individual) | 223 | ISISEIKGVIVHKIETILF |
|  | 224 | ISITEIRTVIVTRIETILF |
| HBsAg2 Th (individual) | 225 | KKKIITITRIITIPQSLD |
|  | 226 | KKKFFLLTRILTIITTID |

TABLE 3

Amino Acid Sequences of IL-6 Peptide Immunogen Constructs

| Description | SEQ ID NO: | Sequence* |
| --- | --- | --- |
| UBITh® 3-εK-KKK-IL-6$_{73-83}$ | 107 | UBITh® 3-εK-KKK-$C$FQSGFNEET$C$ |
| IL-673-63-KKK-εK-UBITh® 3 | 108 | $C$FQSGFNEET$C$-KKK-εK-UBITh® 3 |
| UBITh® 3-εK-KKK-IL-6$_{154-184}$ | 109 | UBITh® 3-εK-KKK-QNWLQDMTTHLILRSFKEFLQSSLRALRQM |
| {[(IL-6$_{154-184}$)2α,εK-K]2α,εK-K}2α,εK-KKK-UBITh® 3 | 110 | {[(QNWLQDMTTHLILRSFKEFLQSSLRALRQM)2α,εK-K]2α,εK-K}2α,εK-KKK-UBITh3 |
| {[(KK-IL-6$_{154-184}$)2α,εK-K]2α,εK-K}2α,εK-KKK-UBITh® 3 | 111 | {[(KK-QNWLWMTTHLILRSIKEFLQSSLRALPQM)2α,εK-K]2α,εK-K}2α,εK-KKK-UBITh3 |
| UBITh® 1-εK-KKK-IL-6$_{150-162}$ | 112 | UBITh1-εK-KKK-$C$LQAQNWLQDM$C$ |
| IL-6150-132-KKK-εK-UBITh® 1 | 113 | $C$LQAQNWLQDM$C$-KKK-εK-UBITh1 |
| UBITh® 1-εK-KKK-IL-6$_{150-162}$-KKK-εK-UBITh® 1 | 114 | UBITh1-εK-KKK-$C$LQAQNWLQDM$C$-KKIK-εK-UBITh1 |
| UBITh® 1-εK-KKK-IL-6$_{144-166}$ | 115 | UBITh1-εK-KKK-$C$ASLLTKLQAQNWLQDMTTHL$C$ |
| IL-6$_{144-166}$-KKK-εK-UBITh® 1 | 116 | $C$ASLLTKLQAQNWMTTHL$C$-KKK-εK-UBITh1 |
| UBITh® 1-εK-KKK-IL-6$_{144-166}$-KKK-εK-UBITh® 1 | 117 | UBITh1-εK-KKK-$C$ASLLTKLQAQNWLQDMTTHL$C$-KKK-εK-UBITh1 |
| UBITh1-εK-KKK-IL-6$_{73-83}$-KKK-εK-UBITh® 1 | 118 | UBITh1-εK-KKK-$C$FQSGFNEET$C$-KKK-εK-UBITh1 |
| UBITh® 1-εK-KKK-IL-6$_{73-83}$ | 119 | UBITh1-εK-KKK-$C$FQSGFNEET$C$ |
| UBITh® 2-εK-KKK-IL-6$_{73-83}$ | 120 | UBITh2-εK-KKK-$C$FQSGFNEET$C$ |
| IL-6$_{144-163}$-KKK-εK-UBITh® 2 | 121 | $C$ASLLTKLQAQKWLQDMTTHL$C$-KKK-εK-UBITh2 |
| UBITh® 1-εK-IL-6$_{73-83}$ | 122 | UBITh1-εK-$C$FQSGFNEET$C$ |
| UBITh® 2-εK-IL-6$_{73-83}$ | 123 | UBITh2-εK-$C$FQSGFNEET$C$ |
| UBITh® 1-εK-IL-6$_{62-83}$ | 124 | UBITh1-εK-LNLPKMAEKDG$C$FQSGFNEET$C$ |
| UBITh® 1-εK-IL-6$_{58-83}$ | 125 | UBITh1-εK-AENNLNLPKMAEKDG$C$FQSGFNEET$C$ |
| UBITh® 1-εK-IL-6$_{52-83}$ | 126 | UBITh1-εK-SSKEALAENNLNLPKMAEKDG$C$FQSGFNEET$C$ |
| UBITh® 1-εK-IL-6$_{52-72}$ | 127 | UBITh1-εK-SSKEALAENNLNLPKMAEKDG |
| UBITh® 1-εK-IL-6$_{42-72}$ | 128 | UBITh1-εK-ET$C$KSNM$C$ESSKEALAENNLNLPKMAEKDG |
| IL-6$_{42-72}$-εK-UBITh® 1 | 129 | ET$C$WKSNM$C$ESSKEALAENNLNLPKMAEKDG-εK-UBITh1 |
| UBITh® 1-εK-IL-6$_{50-67}$ | 130 | UBITh1-εK-$C$ESSKEALAENNLNLPK$C$ |
| UBITh® 1-εK-IL-6$_{44-50}$ | 131 | UBITh1-εK-$C$NKSNM$C$ |
| UBITh® 1-εK-IL-6$_{44-83}$ | 132 | UBITh1-εK-$C$NKSNM$C$ESSKEALAENNLNLPKMAEKDG$C$FQSGFNEET$C$ |

TABLE 3-continued

Amino Acid Sequences of IL-6 Peptide Immunogen Constructs

| Description | SEQ ID NO: | Sequence* |
|---|---|---|
| UBITh® 1-εK-IL-6$_{44-83}$ | 133 | UBITh1-εK-CNKSNMCESSKEALAENNLNLPKMAEKDGCFQSGFNEETC |
| UBITh® 1-εK-KKK-IL-6$_{42-57}$ | 134 | UBITh1-εK-KKK-ETCNKSNMCESSKEAL |
| IL-6$_{42-57}$-KKK-εK-UBITh® 1 | 135 | ETCNKSNMCESSKEAL-KKK-εK-UBITh1 |
| UBITh® 1-εK-IL-6$_{42-57}$ | 136 | UBITh1-εK-ETCNKSNMCESSKEAL |
| IL-6$_{42-57}$-εK-UBITh® 1 | 137 | ETCNKSNMCESSKEAL-εK-UBITh1 |
| UBITh® 1-εK-KKK-IL-6$_{61-75}$ | 138 | UBITh1-εK-KKK-NLNLPKMAEKDGSFQ |
| IL-6$_{61-75}$-KKK-εK-UBITh® 1 | 139 | NLNLPKMAEKDGSFQ-KKK-εK-UBITh1 |
| UBITh® 1-εK-IL-6$_{61-75}$ | 140 | UBITh1-εK-NLNLPKMAEKDGSFQ |
| IL-6$_{61-75}$-εK-UBITh® 1 | 141 | NLNLPKMAEKDGSFQ-εK-UBITh1 |
| UBITh® 1-εK-KKK-IL-6$_{61-72}$ | 142 | UBITh1-εK-KKK-NLNLPKMAEKDG |
| IL-6$_{61-72}$-KKK-εK-UBITh® 1 | 143 | NLNLFKMAEKDG-KKK-εK-UBITh1 |
| UBITh® 1-εK-IL-6$_{61-72}$ | 144 | UBITh1-KKK-εK-NLNLFKMAEKDG |
| IL-6$_{61-72}$-εK-UBITh® 1 | 145 | NLNLFKMAEKDG-εK-UBITh1 |
| UBITh® 3-εK-KKK-mouse counterpart IL-6$_{72-82}$ | 146 | UBITh3-εK-KKK-CYQTGYNQEIC |
| UBITh® 3-εK-KKK-mouse counterpart IL-6$_{154-184}$ | 147 | UBITh3-εK-KKK-QKEWLRTKTIQFILKSLEEFLKVTLRSTRQT |
| UBITh® 3-εK-KKK-rat counterpart IL-6$_{72-82}$ | 148 | UBITh3-εK-KKK-CFQTGYNQEIC |
| UBITh® 3-εK-KKK-rat counterpart IL-6$_{72-82}$-KKK-εK-UBITh® 3 | 149 | UBITh3-εK-KKK-CFQTGYNQEIC-KKK-εK-UBITh3 |
| UBITh® 1-εK-KKK-rat counterpart IL-672-82 | 150 | UBITh1-εK-KKK-CFQTGYNQEIC |
| UBITh® 1-εK-KKK-rat counterpart IL-672-82-KKK-εK-UBITh® 1 | 151 | UBITh1-εK-KKK-CFQTGYNQEIC-KKK-εK-UBITh1 |
| rat counterpart L-6150-162-KKK-εK-UBITh® 1 | 152 | CLESQKEWLRTKC-KKK-εK-UBITh1 |
| UBITh® 1-εK-KKK-rat counterpart IL-6$_{150-182}$-KKK-εK-UBITh® 1 | 153 | UBITh1-εK-KKK-CLESQKEWLRTKC-KKK-εK-UBITh1 |
| rat counterpart IL-6$_{144-166}$-KKK-εK-UBITh® 1 | 154 | CALLMEKLESQKEWLRTKTIQLC-KKK-εK-UBITh1 |
| rat counterpart IL-6$_{150-162}$-KKK-εK-UBITh® 3 | 155 | CLESQKEWLRTKC-KKK-εK-UBITh3 |
| UBITh® 3-εK-KKK-rat counterpart IL-6$_{150-162}$-KKK-εK-UBITh® 3 | 156 | UBITh3-εK-KKK-CLESQKEWLRTKC-KKK-εK-UBITh3 |
| rat counterpart IL-6$_{144-166}$-KKK-εK-UBITh® 3 | 157 | CALLMEKLESQKEWLRTKTIQLC-KKK-εK-UBITh3 |
| UBITh® 3-εK-KKK-macaque counterpart IL-6$_{73-83}$ | 158 | UBITh3-εK-KKK-CFQSGFNEDTC |
| UBITh® 1-εK-KKK-macaque counterpart IL-6$_{73-83}$ | 159 | UBITh1-εK-KKK-CFQSGFNEDTC |
| UBITh® 2-εK-KKK-macaque counterpart IL-6$_{73-83}$ | 160 | UBITh2-εK-KKK-CFQSGFNEDTC |
| Clostridium tetani1 Th-KKK-εK-IL-6$_{73-83}$ | 161 | KKQYIKANSKFIGITEL-KKK-εK-CFQSGFNEETC |

TABLE 3-continued

Amino Acid Sequences of IL-6 Peptide Immunogen Constructs

| Description | SEQ ID NO: | Sequence* |
|---|---|---|
| MvF1 Th-KKK-εK-IL-6₇₃₋₈₃ | 162 | LSEIKGVIVHRLEGV-KKK-εK-CFQSGFNEETC |
| *Bordetella pertussis* Th-KKK-εK-IL-6₇₃₋₈₃ | 163 | GAYARCPNGTRALTVAELRGNAEL-KKK-εK-CFQSGFNEETC |
| *Clostridium tetani2* Th-KKK-εK-IL-6₇₃₋₈₃ | 164 | WVRDIIDDFTNESSQKT-KKK-εK-CFQSGFNEETC |
| *Diphtheria* Th-KKK-εK-IL-6₇₃₋₈₃ | 165 | DSETADNLEKTVAALSILPGHGC-KKK-εK-CFQSGFNEETC |
| *Plasmodium falciparum* Th-KKK-εK-IL-6₇₃₋₈₃ | 166 | DHEKKHAKMEKASSVFNVVNS-KKK-εK-CFQSGFNEETC |
| *Schistosoma mansoni* Th-KKK-εK-IL-6₇₃₋₈₃ | 167 | KWFKTNAPNGVDEKHRH-KKK-εK-CFQSGFNEETC |
| *Cholera Toxin* Th-KKK-εK-IL-6₇₃₋₈₃ | 168 | ALNIWDRFDVFCTLGATTGYLKGNS-KKK-εK-CFQSGFNEETC |
| MvF2 Th-KKK-εK-IL-6₇₃₋₈₃ | 169 | ISEIKGVIVHKIEGI-KKK-εK-CFQSGFNEETC |
| KKKMvF3 Th-KKK-εK-IL-6₇₃₋₈₃ | 170 | KKKISISEIKGVIVHKIEGILF-KKK-εK-CFQSGFNEETC<br>    T  RT    TR   T |
| HBsAg1 Th-KKK-εK-IL-6₇₃₋₈₃ | 171 | KKKLFLLTKLLTLPQSID-KKK-εK-CFQSGFNEETC<br>   RRRIKII RII I L IR<br>    VRVV   VV V  I V<br>    F FF    FF F  V F<br>                   F |
| HBsAg2 Th-KKK-εK-IL-6₇₃₋₈₃ | 172 | KKKIITITRIITIPQSLD-KKK-εK-CFQSGFNEETC<br>   FFLL   L    ITTI |
| Influenza MP1_1 Th-KKK-εK-IL-6₇₃₋₈₃ | 173 | FVFTLTVPSER-KKK-εK-CFQSGFNEETC |
| Influenza MP1_2 Th-KKK-εK-IL-6₇₃₋₈₃ | 174 | SGPLKAEIAQRLEDV-KKK-εK-CFQSGFNEETC |
| Influenza NSP1 Th-KKK-εK-IL-6₇₃₋₈₃ | 175 | DRLRRDQKS-KKK-εK-CFQSGFNEETC |
| EBV BHRF1 Th-KKK-εK-IL-6₇₃₋₈₃ | 176 | AGLTLSLLVICSYLFISRG-KKK-εK-CFQSGFNEETC |
| *Clostridium tetani* TTI Th-KKK-εK-IL-6₇₃₋₈₃ | 177 | QYIKANSKFIGITEL-KKK-εK-CFQSGFNEETC |
| EBV EBNA-1 Th-KKK-εK-IL-6₇₃₋₈₃ | 178 | PGPLRESIVCYFMVFLQTHI-KKK-εK-CFQSGFNEETC |
| *Clostridium tetani* TT2 Th-KKK-εK-IL-6₇₃₋₈₃ | 179 | FNNFTVSFWLRVPKVSASHLE-KKK-εK-CFQSGFNEETC |
| Clostridium tetani TT3 Th-KKK-εK-IL-6₇₃₋₈₃ | 180 | KFIIKRYTPNNEIDSF-KKK-εK-CFQSGFNEETC |
| *Clostridium tetani* TT4 Th-KKK-εK-IL-6₇₃₋₈₃ | 181 | VSIDKRIFCKALNPK-KKK-εK-CFQSGFNEETC |
| EBV CP Th-KKK-εK-IL-6₇₃₋₈₃ | 182 | VPGLYSPCRAFFNKEELL-KKK-εK-CFQSGFNEETC |
| HCMV IE1 Th-KKK-εK-IL-6₇₃₋₈₃ | 183 | DKREMWMACIKELH-KKK-εK-CFQSGFNEETC |
| EBV GP340 Th-KKK-εK-IL-6₇₃₋₈₃ | 184 | TGHGARTSTEPTTDY-KKK-εK-CFQSGFNEETC |
| EBV BPLF1 Th-KKK-εK-IL-6₇₃₋₈₃ | 185 | KELKRQYEKKLRQ-KKK-εK-CFQSGFNEETC |
| EBV EBNA-2 Th-KKK-εK-IL-6₇₃₋₈₃ | 186 | TVFYNIPPMPL-KKK-εK-CFCSGENEETC |
| IL-6₄₂₋₇₂-εK-*Clostridium tetani1* Th | 187 | ETCNKSNMCESSKEALAENNLNLPKMAEKDG-εK-KKQYIKANSKFIGITEL |
| IL-6₄₂₋₇₂-εK-MvF1 | 188 | ETCNKSNMCESSKEALAENNLNLPKMAEKDG-εK-LSEIHGVIVHRLEGV |
| IL-642-72-εK-*Bordetella pertussis* Th | 189 | ETCNKSNMCESSKEALAENNLNLPKMAEKDG-εK-GAYARCPNGTRALTVAELRGNAEL |
| IL-6₄₂₋₇₂-εK-*Clostridium tetani2* Th | 190 | ETCNKSNMCESSKEALAENNLNLPKMAEKDG-εK-WVRDIIDDFTNESSQKT |

TABLE 3-continued

Amino Acid Sequences of IL-6 Peptide Immunogen Constructs

| Description | SEQ ID NO: | Sequence* |
|---|---|---|
| IL-6$_{42-72}$-εK-Diphtheria Th | 191 | ETCNKSNMCESSHEALAENNLNLPKMAEKDG-εK-DSETADNLEKTVAALSILPGHGC |
| IL-6$_{42-72}$-εK-Plasmodium falciparum Th | 192 | ETCNKSNMCESSHEALAENNLNLPKMAEKDG-εK-DHEKKHAKMEKASSVFNVVNS |
| IL-6$_{42-72}$-εK-Schistosoma mansoni Th | 193 | ETCNKSNMCESSHEALAENNLNLPKMAEKDG-εK-KWFKTNAPNGVDEKHRH |
| IL-6$_{42-72}$-εK-Cholera Toxin Th | 194 | ETCNKSNMCESSKEALAENNLNLPKMAEKDG-εK-ALNIWDRFDVFCTLGATTGYLKGNS |
| IL-6$_{42-72}$-εK-MvF2 Th | 195 | ETCNKSNMCESSKEALAENNLNLPKMAEKDG-εK-ISEIKGVIVHKIEGI |
| IL-6$_{42-72}$-εK-KKKMvF3 Th | 196 | ETCNKSNMCESSKEALAENNLNLPKMAEKDG-εK-KKKISISEIKGVIVHKIEGILF<br>                                               T   RT    TR  T |
| IL-6$_{42-72}$-εK-HBSAg1 Th | 197 | ETCNKSNMCESSKEALAEHNLNLPKMAEKDG-εK-KKKLFLLTKLLTLPQSLD<br>                                             RRRIKII RII I L IR<br>                                             VRVV   VV V I  V<br>                                             F  FF    FF FF F V  F<br>                                                                      F |
| IL-6$_{42-72}$-εK-HBsAg2 Th | 198 | ETCNKSNMCESSKEALAENNLNLPKMAEKDG-εK-KKKIITITRIITIPQSLD<br>                                           FFLL   L   ITTI |
| IL-6$_{42-72}$-εK-HBsAg3 Th (UBITh® 2) | 199 | ETCNKSNMCESSKEALAENNLNLPKMAEKDG-εK-KKKIITITRIITIITTID |
| IL-6$_{42-72}$-εK-Influenza MP1_1 Th | 200 | ETCNKSNMCESSKEALAENNLNLPKMAEKDG-εK-FVFTLTVPSER |
| IL-6$_{42-72}$-εK-Influenza MP1_2 Th | 201 | ETCNKSNMCESSKEALAENNLNLPKMAEKDG-εK-SGPLKAEIAQRLEDV |
| IL-6$_{42-72}$-εK-Influenza NSP1 Th | 202 | ETCNKSNMCESSKEALAENNLNLPKMAEKDG-εK-DRLRRDQKS |
| IL-6$_{42-72}$-εK-EBV BHRF1 Th | 203 | ETCNKSNMCESSKEALAENNLNLPKMAEKDG-εK-AGLTLSLLVICSYLFISRG |
| Clostridium tetani TT1 Th | 204 | ETCNKSNMCESSKEALAENNLNLPKMAEKDG-εK-QYIKANSKFIGITEL |
| IL-6$_{42-72}$-εK-EBV EBNA-1 Th | 205 | ETCNKSNMCESSKEALAENNLNLPKMAEKDG-εK-PGPLRESIVCYFMVFLQTHI |
| IL-6$_{42-72}$-εK-Clostridium tetani TT2 Th | 206 | ETCNKSNMCESSKEALAENNLNLPKMAEKDG-εK-FNNFTVSFWLRVPKVSASHLE |
| IL-6$_{42-72}$-εK-Clostridium tetani TT3 Th | 207 | ETCNKSNMCESEKEALAENNLNLPKMAEKDG-εK-KFIIKRYTPNNEIDSF |
| IL-6$_{42-72}$-εK-Clostridium tetani TT4 Th | 208 | ETCNKSNMCESEKEALAENNLNLPKMAEKDG-εK-VSIDKFRIFCKALNPK |
| IL-6$_{42-72}$-εK-EBV CP Th | 209 | ETCNKSNMCESEKEALAENNLNLPKMAEKDG-εK-VPGLYSPCRAFFNKEELL |
| IL-6$_{42-72}$-εK-HCMV IE1 Th | 210 | ETCNKSNMCESEKEALAENNLNLPKMAEKDG-εK-DKREMWMACIKELH |
| IL-6$_{42-72}$-εK-EBV GP340 Th | 211 | ETCNKSNMCESSKEALAENNLNLPKMAEKDG-εK-TGHGARTSTEPTTDY |
| IL-6$_{42-72}$-εK-EBV BPLF1 Th | 212 | ETCNKSNMCESSKEALAENNLNLPKMAEKDG-εK-KELKRQYEKKLRQ |
| IL-6$_{42-72}$-εK-EBV EBNA-2 Th | 213 | ETCNKSNMCESSKEALAEHNLNLPKMAEKDG-εK-TVFYNIPPMPL |
| IL-6$_{42-72}$-εK-HBsAg4 Th (UBITh® 4) | 214 | ETCNKSNMCESSKEALAEHNLNLPKMAEKDG-εK-FFLLTRILTIPQSLD |
| IL-6$_{42-72}$-εK-Inv Th | 215 | ETCNKSNMCESSKEALAENNLNLPKMAEKDG-εK-TAKSKKFPSYTATYQF |

The polypeptide is cyclized by formation of an inter-cysteine disulfide bond, which are identified in bold italics. The cysteines that substitute the amino acids at the N-terminal and/or C-terminal of the IL-6 fragments are underlined.
UBITh® 1: SEQ ID NO: 91
UBITh® 2: SEQ ID NO: 92
UBITh® 3: SEQ ID NO: 89

TABLE 4

Immunogenicity Assessment of Vaccine Formulations Containing IL-6 Derived
Peptide Immunogen Constructs Targeting IL-6R Binding Sites in Guinea Pigs

| Group # | Peptide immunogen description | SEQ ID NO | Animal No | IL-$6_{73-83}$ (SEQ ID NO: 5) ELISA $Log_{10}$ Titer 0 wpi | 3 wpi | 6 wpi | 9 wpi | 12 wpi | 15 wpi | Mouse IL-$6_{72-82}$ (SEQ ID NO: 20) ELISA $Log_{10}$ Titer 0 wpi | 3 wpi | 6 wpi | 9 wpi | 12 wpi | 15 wpi |
|---|---|---|---|---|---|---|---|---|---|---|---|---|---|---|---|
| 1 | UBITh ®3-εK-KKK-IL-$6_{73-83}$ | 107 | 5856 | 0.075 | 3.269 | 4.757 | 5.046 | 5.026 | 5.095 | 0.072 | 0.000 | 0.000 | 0.000 | 0.000 | 0.248 |
| | | | 5857 | 0.069 | 3.084 | 4.607 | 5.083 | 5.107 | 5.303 | 0.073 | 0.000 | 3.009 | 4.572 | 4.647 | 4.937 |
| | | | 5858 | 0.068 | 3.508 | 4.868 | 6.138 | 6.600 | 7.270 | 0.071 | 0.000 | 3.590 | 4.225 | 4.497 | 4.718 |
| | | | Avg | 0.071 | 3.287 | 4.744 | 5.422 | 5.578 | 5.889 | 0.072 | 0.000 | 2.200 | 2.932 | 3.048 | 3.301 |
| 2 | UBITh ®3-εK-KKK-Mouse IL-$6_{72-82}$ | 146 | 5859 | 0.144 | 0.000 | 0.000 | 0.059 | 0.000 | 1.694 | 0.071 | 1.805 | 3.951 | 4.690 | 4.554 | 4.639 |
| | | | 5860 | 0.062 | 0.000 | 2.893 | 4.409 | 4.253 | 4.929 | 0.066 | 1.728 | 4.391 | 4.858 | 4.690 | 5.057 |
| | | | 5861 | 0.061 | 0.000 | 2.375 | 4.754 | 4.768 | 4.500 | 0.065 | 2.426 | 4.479 | 5.113 | 4.994 | 4.825 |
| | | | Avg | 0.089 | 0.000 | 1.756 | 3.074 | 3.007 | 3.708 | 0.067 | 1.986 | 4.274 | 4.887 | 4.746 | 4.840 |

Tables 5A-5E

Immunogenicity Assessment of Vaccine Formulations Containing IL-6 Derived Peptide Immunogen Constructs Targeting IL-6/IL-6Rα/IL-6R (or gp130) Binding Sites

TABLE 5A

| Peptide Immunogen Description | SEQ ID NO: | Animal ID | Anti-corresponding IL-6 B epitope ELISA $Log_{10}$ Titer 0 wpi | 3 wpi | 6 wpi | 9 wpi | Recombinant human IL-6 ELISA $Log_{10}$ Titer 0 wpi | 3 wpi | 6 wpi | 9 wpi |
|---|---|---|---|---|---|---|---|---|---|---|
| UBITh ®1-εK-IL-$6_{62-83}$ | 124 | 6468 | 0.095 | 6.029 | 5.994 | 6.286 | 0.091 | 3.637 | 4.720 | 5.009 |
| | | 6469 | 0.077 | 7.267 | 6.766 | 5.796 | 0.081 | 4.687 | 5.243 | 5.242 |
| | | 6470 | 0.068 | 5.101 | 5.341 | 5.267 | 0.072 | 2.881 | 3.947 | 3.872 |
| | | Avg. | 0.080 | 6.132 | 6.034 | 5.783 | 0.081 | 3.735 | 4.637 | 4.708 |
| UBITh ®1-εK-IL-$6_{58-83}$ | 125 | 6471 | 0.061 | 5.799 | 6.189 | 5.537 | 0.086 | 4.063 | 4.807 | 4.840 |
| | | 6472 | 0.055 | 5.320 | 6.160 | 5.636 | 0.073 | 3.695 | 4.683 | 4.709 |
| | | 6473 | 0.060 | 5.501 | 5.997 | 5.737 | 0.065 | 3.801 | 4.575 | 4.609 |
| | | Avg. | 0.059 | 5.540 | 6.115 | 5.637 | 0.075 | 3.853 | 4.688 | 4.719 |
| UBITh ®1-εK-IL-$6_{52-83}$ | 126 | 6474 | 0.066 | 5.581 | 5.817 | 5.706 | 0.079 | 3.320 | 3.450 | 3.354 |
| | | 6475 | 0.071 | 5.368 | 5.359 | 5.423 | 0.080 | 4.047 | 4.714 | 4.835 |
| | | 6476 | 0.117 | 6.325 | 5.947 | 6.074 | 0.093 | 4.517 | 4.759 | 4.899 |
| | | Avg. | 0.085 | 5.758 | 5.708 | 5.734 | 0.084 | 3.961 | 4.308 | 4.363 |
| UBITh ®1-εk-IL$6_{44-83}$ | 132 | 6781 | 0.108 | 9.831 | 6.452 | 6.037 | 0.099 | 4.089 | 4.348 | 4.077 |
| | | 6782 | 0.134 | >10 | >10 | 7.710 | 0.095 | 4.066 | 4.389 | 4.590 |
| | | 6783 | 0.124 | 6.444 | 7.188 | 6.200 | 0.092 | 3.367 | 4.321 | 4.581 |
| | | Avg. | 0.122 | 8.758 | 7.880 | 6.649 | 0.095 | 3.841 | 4.353 | 4.416 |
| UBITh ®1-εk-IL$6_{44-83}$ w/o cyclization | 133 | 6784 | 0.094 | >10 | 8.999 | 8.441 | 0.107 | 4.426 | 4.723 | 4.848 |
| | | 6785 | 0.112 | 8.580 | 5.873 | 5.320 | 0.109 | 3.737 | 4.491 | 4.450 |
| | | 6786 | 0.125 | 7.047 | 5.983 | 5.764 | 0.096 | 3.190 | 3.865 | 4.314 |
| | | Avg. | 0.110 | 8.542 | 6.952 | 6.508 | 0.104 | 3.784 | 4.360 | 4.537 |

TABLE 5B

| Peptide Immunogen Description | SEQ ID NO: | Animal ID | Anti-corresponding IL-6 B epitope ELISA $Log_{10}$ Titer 0 wpi | 3 wpi | 6 wpi | 9 wpi | Recombinant human IL-6 ELISA $Log_{10}$ Titer 0 wpi | 3 wpi | 6 wpi | 9 wpi |
|---|---|---|---|---|---|---|---|---|---|---|
| UBITh ®1-εk-IL$6_{44-50}$ | 131 | 6778 | 0.116 | 5.017 | 5.220 | 5.411 | 0.167 | 2.000 | 3.756 | 4.739 |
| | | 6779 | 0.106 | 5.242 | 5.834 | 5.740 | 0.082 | 3.273 | 4.510 | 4.710 |
| | | 6780 | 0.097 | 4.449 | 4.800 | 4.927 | 0.080 | 2.603 | 3.987 | 4.745 |
| | | Avg. | 0.106 | 4.903 | 5.285 | 5.359 | 0.110 | 2.625 | 4.084 | 4.731 |
| UBITh ®1-εK-KKK-IL-$6_{42-57}$ | 134 | 6907 | 0.069 | 5.182 | 5.903 | 9.445 | 0.084 | 0.000 | 0.286 | 1.666 |
| | | 6908 | 0.121 | 6.538 | >10 | >10 | 0.089 | 1.796 | 2.823 | 3.661 |
| | | 6909 | 0.117 | 5.459 | 6.729 | 8.381 | 0.123 | 2.603 | 3.575 | 3.675 |
| | | Avg. | 0.102 | 5.726 | 7.544 | 9.275 | 0.099 | 1.468 | 2.228 | 3.001 |
| IL-$6_{42-57}$-KKK-εK-UBITh ®1 | 135 | 6910 | 0.087 | 4.127 | 4.990 | 5.110 | 0.106 | 2.748 | 4.543 | 4.547 |
| | | 6911 | 0.132 | 4.593 | 5.098 | 5.124 | 0.096 | 3.356 | 4.865 | 4.942 |
| | | 6912 | 0.103 | 3.344 | 4.869 | 5.257 | 0.127 | 2.932 | 5.006 | 5.341 |
| | | Avg. | 0.108 | 4.021 | 4.986 | 5.164 | 0.110 | 3.012 | 4.805 | 4.943 |

TABLE 5B-continued

| Peptide Immunogen Description | SEQ ID NO: | Animal ID | Anti-corresponding IL-6 B epitope ELISA Log₁₀ Titer | | | | Recombinant human IL-6 ELISA Log₁₀ Titer | | | |
|---|---|---|---|---|---|---|---|---|---|---|
| | | | 0 wpi | 3 wpi | 6 wpi | 9 wpi | 0 wpi | 3 wpi | 6 wpi | 9 wpi |
| UBITh ®1-εK-IL-6$_{42-57}$ | 136 | 6913 | 0.164 | 4.939 | 5.877 | 6.791 | 0.092 | 0.000 | 1.276 | 1.993 |
| | | 6914 | 0.107 | 5.801 | >10 | >10 | 0.084 | 0.000 | 0.000 | 1.646 |
| | | 6915 | 0.163 | 5.198 | 8.628 | 9.684 | 0.160 | 0.000 | 0.199 | 0.789 |
| | | Avg. | 0.144 | 5.313 | 8.168 | 8.825 | 0.112 | 0.008 | 0.492 | 1.476 |
| IL-6$_{42-57}$-εK-UBITh ®1 | 137 | 6916 | 0.093 | 4.426 | 4.927 | 5.323 | 0.098 | 3.062 | 4.501 | 4.286 |
| | | 6917 | 0.185 | 3.588 | 4.955 | 5.234 | 0.095 | 2.703 | 4.511 | 4.482 |
| | | 6918 | 0.177 | 4.428 | 5.039 | 5.573 | 0.110 | 3.045 | 4.322 | 4.584 |
| | | Avg. | 0.151 | 4.147 | 4.974 | 5.377 | 0.101 | 2.937 | 4.445 | 4.451 |
| UBITh ®1-εK-IL-6$_{42-72}$ | 128 | 6480 | 0.053 | 5.120 | 6.071 | 5.758 | 0.075 | 2.900 | 3.763 | 4.094 |
| | | 6481 | 0.056 | 4.952 | 5.147 | 5.183 | 0.077 | 1.520 | 2.947 | 3.437 |
| | | 6482 | 0.070 | 5.631 | 6.368 | 5.876 | 0.093 | 3.306 | 4.838 | 4.921 |
| | | Avg. | 0.060 | 5.234 | 5.862 | 5.606 | 0.082 | 2.575 | 3.849 | 4.151 |
| IL-6$_{42-72}$-εK-UBITh ®1 | 129 | 6483 | 0.070 | 6.120 | 9.601 | 6.595 | 0.106 | 3.368 | 4.867 | 4.722 |
| | | 6484 | 0.101 | 5.227 | 5.748 | 5.616 | 0.126 | 2.962 | 4.727 | 4.833 |
| | | 6485 | 0.204 | 4.982 | 5.734 | 6.744 | 0.100 | 2.628 | 4.842 | 5.030 |
| | | Avg. | 0.125 | 5.443 | 7.028 | 6.318 | 0.111 | 2.986 | 4.812 | 4.862 |

TABLE 5C

| Peptide Immunogen Description | SEQ ID NO: | Animal ID | Anti-corresponding IL-6 B epitope ELISA Log₁₀ Titer | | | | | Recombinant human IL-6 ELISA Log₁₀ Titer | | | | |
|---|---|---|---|---|---|---|---|---|---|---|---|---|
| | | | 0 wpi | 3 wpi | 6 wpi | 9 wpi | 12 wpi | 0 wpi | 3 wpi | 6 wpi | 9 wpi | 12 wpi |
| UBITh ®1-εK-IL-6$_{52-72}$ | 127 | 6477 | 0.077 | 5.967 | >10 | >10 | 9.554 | 0.085 | 4.894 | 4.973 | 5.036 | 5.064 |
| | | 6478 | 0.069 | 4.872 | 5.631 | 5.606 | 5.620 | 0.087 | 2.524 | 3.745 | 4.504 | 4.543 |
| | | 6479 | 0.066 | 4.964 | 6.758 | 5.416 | 5.254 | 0.086 | 3.068 | 4.721 | 4.155 | 4.601 |
| | | Avg. | 0.071 | 5.268 | 7.463 | 7.007 | 6.809 | 0.086 | 3.495 | 4.480 | 4.565 | 4.736 |
| UBITh ®1-εK-KKK-IL-6$_{61-75}$ | 138 | 6931 | 0.080 | 7.800 | >10 | >10 | >10 | | | | | |
| | | 6932 | 0.081 | 4.743 | >10 | 7.720 | 6.116 | | | | | |
| | | 6933 | 0.086 | 5.025 | 7.309 | 5.600 | 5.618 | | | | | |
| | | Avg. | 0.082 | 5.856 | 9.103 | 7.773 | 7.245 | | | | | |
| IL-6$_{61-75}$-KKK-εK-UBITh ®1 | 139 | 6934 | 0.081 | 4.936 | >10 | >10 | >10 | 0.185 | 2.065 | 4.816 | 5.175 | 5.941 |
| | | 6935 | 0.067 | 4.338 | 6.256 | 6.198 | 6.391 | 0.056 | 0.000 | 4.649 | 4.469 | 4.121 |
| | | 6936 | 0.077 | 4.722 | 9.491 | >10 | >10 | 0.066 | 1.884 | 4.326 | 4.839 | 5.005 |
| | | Avg. | 0.075 | 4.665 | 8.582 | 8.733 | 8.797 | 0.102 | 1.316 | 4.597 | 4.828 | 5.022 |
| UBITh ®1-εK-IL-6$_{61-75}$ | 140 | 6937 | 0.074 | 9.149 | >10 | 5.812 | 5.329 | | | | | |
| | | 6938 | 0.077 | >10 | >10 | 6.699 | 6.271 | | | | | |
| | | 6939 | 0.078 | 4.875 | 5.538 | 5.222 | 5.228 | | | | | |
| | | Avg. | 0.077 | 8.008 | 8.513 | 5.911 | 5.609 | | | | | |
| LL-6$_{61-75}$-εK-UBITh ®1 | 141 | 6940 | 0.080 | 4.219 | 6.593 | 7.813 | 9.316 | 0.078 | 2.448 | 3.980 | 4.703 | 4.691 |
| | | 6941 | 0.102 | 4.428 | >10 | >10 | >10 | 0.072 | 0.000 | 3.740 | 3.741 | 4.425 |
| | | 6942 | 0.066 | 4.576 | 5.331 | 5.550 | 5.784 | 0.054 | 2.974 | 4.056 | 3.561 | 3.766 |
| | | Avg. | 0.083 | 4.408 | 7.308 | 7.788 | 8.367 | 0.068 | 1.807 | 3.925 | 4.002 | 4.294 |
| UBITh ®1-εK-KKK-IL-6$_{61-72}$ | 142 | 6943 | 0.058 | 4.419 | 5.181 | 5.260 | 5.183 | 0.063 | 2.018 | 3.609 | 4.149 | 3.721 |
| | | 6944 | 0.055 | 4.118 | 6.343 | 7.205 | 6.550 | 0.062 | 2.190 | 3.712 | 3.740 | 3.417 |
| | | 6945 | 0.080 | 3.196 | 9.163 | >10 | 7.040 | 0.088 | 0.000 | 4.629 | 4.111 | 4.247 |
| | | Avg. | 0.064 | 3.911 | 6.896 | 7.488 | 6.258 | 0.071 | 1.403 | 3.983 | 4.000 | 3.795 |
| IL-6$_{61-72}$-KKK-εK-UBITh ®1 | 143 | 6946 | 0.091 | 4.407 | 7.728 | 6.830 | 7.277 | 0.086 | 0.000 | 4.319 | 4.321 | 4.984 |
| | | 6947 | 0.075 | 4.035 | 5.149 | 5.892 | 6.936 | 0.098 | 2.474 | 3.701 | 4.567 | 5.023 |
| | | 6948 | 0.142 | 4.677 | >10 | >10 | 10.50 | 0.077 | 2.218 | 3.927 | 4.002 | 4.169 |
| | | Avg. | 0.102 | 4.373 | 7.626 | 7.574 | 8.238 | 0.087 | 1.564 | 3.982 | 4.297 | 4.725 |
| UBITh ®1-εK-IL-6$_{61-72}$ | 144 | 6949 | 0.061 | 4.448 | 5.640 | 6.093 | 5.669 | 0.077 | 0.000 | 2.462 | 2.469 | 2.303 |
| | | 6950 | 0.062 | 3.830 | 5.975 | 5.180 | 5.130 | 0.079 | 0.000 | 3.080 | 2.096 | 2.822 |
| | | 6951 | 0.053 | 3.075 | 4.982 | 5.152 | 5.135 | 0.069 | 0.000 | 0.504 | 2.424 | 3.019 |
| | | Avg. | 0.058 | 3.784 | 5.532 | 5.475 | 5.311 | 0.075 | 0.000 | 2.015 | 2.330 | 2.715 |
| IL-6$_{61-72}$-εK-UBITh ®1 | 145 | 6952 | 0.062 | 4.552 | >10 | 9.189 | >10 | 0.075 | 2.706 | 4.641 | 4.929 | 5.963 |
| | | 6953 | 0.077 | 4.925 | >10 | 9.487 | 8.383 | 0.089 | 1.434 | 3.581 | 3.394 | 3.819 |
| | | 6954 | 0.072 | 4.799 | >10 | >10 | >10 | 0.091 | 0.000 | 3.698 | 3.231 | 3.849 |
| | | Avg. | 0.070 | 4.759 | >10 | 9.559 | 9.461 | 0.085 | 1.380 | 3.973 | 3.851 | 4.544 |

TABLE 5D

| Peptide Immunogen Description | SEQ ID NO: | Animal ID | IL-6$_{150-162}$ (SEQ ID NO: 18) ELISA Log$_{10}$ Titer | | | | | IL-6$_{144-168}$ (SEQ ID NO: 19) ELISA Log$_{10}$ Titer | | | | |
|---|---|---|---|---|---|---|---|---|---|---|---|---|
| | | | 0 wpi | 3 wpi | 6 wpi | 9 wpi | 12 wpi | 0 wpi | 3 wpi | 6 wpi | 9 wpi | 12 wpi |
| UBITh ®1-εK-KKK-IL-6$_{150-162}$ | 112 | 5922 | 0.142 | 5.119 | 10.45 | 13.64 | 8.987 | 0.108 | 3.712 | 5.335 | 6.266 | 5.649 |
| | | 5923 | 0.165 | 5.903 | 11.60 | 10.03 | 9.642 | 0.107 | 4.957 | 7.377 | 6.371 | 6.709 |
| | | 5924 | 0.137 | 4.955 | 9.930 | 11.50 | 7.520 | 0.109 | 4.693 | 9.363 | 10.05 | 7.225 |
| | | Avg. | 0.148 | 5.326 | 10.659 | 11.723 | 8.716 | 0.108 | 4.454 | 7.358 | 7.563 | 6.528 |
| IL-6$_{150-162}$-KKK-εK-UBITh ®1 | 113 | 5925 | 0.144 | 5.021 | 12.87 | 10.76 | 8.075 | 0.105 | 4.074 | 5.682 | 5.826 | 5.538 |
| | | 5926 | 0.134 | 4.896 | 10.00 | 10.40 | 6.590 | 0.106 | 3.460 | 4.988 | 5.529 | 5.050 |
| | | 5927 | 0.130 | 4.775 | 8.258 | 6.923 | 5.503 | 0.118 | 3.488 | 5.571 | 6.004 | 5.353 |
| | | Avg. | 0.136 | 4.897 | 10.376 | 9.360 | 6.723 | 0.110 | 3.674 | 5.414 | 5.786 | 5.314 |
| UBITh ®1-εK-KKK-IL-6$_{150-162}$-KKK-εK-UBITh ®1 | 114 | 5928 | 0.131 | 3.918 | 8.087 | 7.117 | 5.708 | 0.135 | 5.102 | 5.540 | 5.249 | 5.080 |
| | | 5929 | 0.132 | 4.523 | 9.677 | 10.82 | 9.332 | 0.128 | 4.884 | 7.679 | 6.790 | 6.691 |
| | | 5930 | 0.105 | 4.907 | 7.852 | 10.21 | 8.091 | 0.106 | 4.913 | 6.390 | 8.374 | 7.352 |
| | | Avg. | 0.122 | 4.449 | 8.539 | 9.384 | 7.710 | 0.123 | 4.966 | 6.536 | 6.804 | 6.374 |
| IL-6$_{144-166}$-KKK-εK-UBITh ®1 | 116 | 5931 | 0.117 | 4.167 | 5.297 | 5.149 | 5.288 | 0.086 | 5.085 | 8.697 | 7.119 | 6.063 |
| | | 5932 | 0.115 | 4.530 | 8.601 | 6.292 | 5.623 | 0.087 | 4.841 | 7.173 | 6.104 | 5.559 |
| | | 5933 | 0.102 | 4.762 | 11.53 | 9.904 | 7.665 | 0.085 | 4.912 | 9.426 | 8.211 | 6.798 |
| | | Avg. | 0.111 | 4.486 | 8.476 | 7.115 | 6.192 | 0.086 | 4.946 | 8.432 | 7.145 | 6.140 |
| UBITh ®1-εK-KKK-IL-6$_{144-166}$-KKK-εK-UBITh ®1 | 117 | 5934 | 0.096 | 4.342 | 7.321 | 6.628 | 5.458 | 0.088 | 4.348 | 6.672 | 6.485 | 5.391 |
| | | 5935 | 0.115 | 4.511 | 7.652 | 6.771 | 8.311 | 0.088 | 4.603 | 7.851 | 7.369 | 7.400 |
| | | 5936 | 0.098 | 3.824 | 6.401 | 5.810 | 5.148 | 0.105 | 3.865 | 5.352 | 5.301 | 5.027 |
| | | Avg. | 0.103 | 4.226 | 7.125 | 6.403 | 6.306 | 0.094 | 4.272 | 6.625 | 6.385 | 5.939 |

TABLE 5E

| Peptide Immunogen Description | SEQ ID NO: | Animal No | Antibody titer (Log EC$_{50}$) to recombinant human IL-6 | | | |
|---|---|---|---|---|---|---|
| | | | 3 wpi | 6 wpi | 9 wpi | 12 wpi |
| UBITh ®1-εK-KKK-IL-6$_{150-162}$ | 112 | 5922-5924 | <1 | 2.958 | 3.809 | 3.926 |
| IL-6$_{150-162}$-KKK-εK-UBITh ®1 | 113 | 5925-5927 | <1 | 3.602 | 3.96 | 3.757 |
| UBITh ®1-εK-KKK-IL-6$_{150-162}$-KKK-εK-UBITh ®1 | 114 | 5928-5930 | <1 | 3.602 | 4.444 | 4.394 |
| IL-6$_{144-166}$-KKK-εK-UBITh ®1 | 116 | 5931-5933 | <1 | 4.755 | 4.908 | 4.998 |
| UBITh ®1-εK-KKK-IL-6$_{144-166}$-KKK-εK-UBITh ®1 | 117 | 5934-5936 | <1 | 3.687 | 4.393 | 4.287 |
| UBITh ®3-εK-KKK-IL-6$_{73-83}$-KKK-εK-UBITh ®3 | 118 | 5937-5939 | 4.569 | 5.663 | 5.443 | 5.598 |

TABLE 6

Immunogenicity Enhancement of IL-6 B Epitope Peptide (C73-C83) with Ranking Heterologous Th Epitope Peptides from Pathogenic Proteins

| Group No. | IL-6 peptide immunogen construct | SEQ ID NO: | Animal ID | Recombinant human IL-6 ELISA Log$_{10}$ Titer | | |
|---|---|---|---|---|---|---|
| | | | | 0 wpi | 6 wpi | 8 wpi |
| 1 | UBITh ®1-εK-KKK-IL-6 (C73-C83) | 119 | 6381 | 0.142 | 5.360 | 5.367 |
| | | | 6382 | 0.091 | 7.456 | 9.026 |
| | | | 6383 | 0.098 | 5.459 | 6.674 |
| | | | Avg | 0.110 | 6.082 | 7.022 |
| 18 | Clostridium tetani TT1 Th-KKK-εK-IL-6 (C73-C83) | 177 | 6432 | 0.064 | 5.135 | NS |
| | | | 6433 | 0.061 | 5.174 | 4.894 |
| | | | 6434 | 0.068 | 5.193 | 4.939 |
| | | | Avg | 0.864 | 5.167 | 4.917 |
| 29 | UBITh ®3-εK-KKK-IL-6 (C73-C83) | 107 | 6465 | 0.082 | 7.387 | 5.788 |
| | | | 6466 | 0.096 | 5.458 | 5.214 |
| | | | 6467 | 0.111 | 6.062 | 5.385 |
| | | | Avg | 0.096 | 6.302 | 5.462 |
| 22 | Clostridium tetani TT4 Th-KKK-εK-IL-6 (C73-C83) | 181 | 6444 | 0.115 | 5.395 | 5.292 |
| | | | 6445 | 0.167 | 4.896 | 4.967 |
| | | | 6446 | 0.086 | 3.644 | 3.395 |
| | | | Avg | 0.123 | 4.645 | 4.551 |
| 28 | UBITh ®2-εK-KKK-IL-6 (C73-C83) | 120 | 6462 | 0.094 | 11.29 | >10 |
| | | | 6463 | 0.143 | 4.215 | 4.754 |
| | | | 6464 | 0.095 | 4.553 | 4.984 |
| | | | Avg | 0.111 | 6.685 | 7.246 |
| 26 | EBV BPLF1 Th-KKK-εK-IL-6 (C73-C83) | 185 | 6456 | 0.083 | 2.948 | 3.035 |
| | | | 6457 | 0.084 | 3.552 | 4.506 |
| | | | 6458 | 0.078 | 2.525 | 2.397 |
| | | | Avg | 0.882 | 3.008 | 3.313 |

TABLE 6-continued

Immunogenicity Enhancement of IL-6 B Epitope Peptide (C73-C83) with Ranking Heterologous Th Epitope Peptides from Pathogenic Proteins

| Group No. | IL-6 peptide immunogen construct | SEQ ID NO: | Animal ID | Recombinant human IL-6 ELISA $Log_{10}$ Titer | | |
|---|---|---|---|---|---|---|
| | | | | 0 wpi | 6 wpi | 8 wpi |
| 20 | Clostridium tetani TT2 Th-KKK-εK-IL-6 (C73-C83) | 179 | 6438 | 0.084 | 4.796 | 4.936 |
| | | | 6439 | 0.091 | 4.120 | 3.696 |
| | | | 6440 | 0.074 | 3.163 | 2.925 |
| | | | Avg | 0.083 | 4.026 | 3.852 |
| 2 | Clostridium tetani1 Th-KKK-εK-IL-6 (C73-C83) | 161 | 6384 | 0.083 | 2.505 | 2.834 |
| | | | 6385 | 0.080 | 5.337 | 5.201 |
| | | | 6386 | 0.084 | 3.830 | 4.881 |
| | | | Avg | 0.082 | 3.891 | 4.305 |
| 11 | KKKMvF3 Th-KKK-εK-IL-6 (C73-C83) | 170 | 6411 | 0.077 | 0.807 | 1.987 |
| | | | 6412 | 0.095 | 4.880 | 4.837 |
| | | | 6413 | 0.186 | 3.963 | 4.471 |
| | | | Avg | 0.119 | 3.217 | 3.765 |
| 23 | EBV CP Th-KKK-εK-IL-6 (C73-C83) | 182 | 6447 | 0.088 | 2.120 | 2.810 |
| | | | 6448 | 0.068 | 1.101 | 2.177 |
| | | | 6449 | 0.074 | 3.623 | 3.975 |
| | | | Avg | 0.077 | 2.281 | 2.987 |
| 9 | Cholera Toxin Th-KKK-εK-IL-6 (C73-C83) | 168 | 6405 | 0.143 | 0.000 | 0.000 |
| | | | 6406 | 0.084 | 2.360 | 3.649 |
| | | | 6407 | 0.083 | 4.848 | 4.840 |
| | | | Avg | 0.103 | 2.403 | 2.830 |
| 8 | Schistosoma mansoni Th-KKK-εK-IL-6 (C73-C83) | 167 | 6402 | 0.070 | 2.533 | 3.341 |
| | | | 6403 | 0.084 | 3.444 | 3.452 |
| | | | 6404 | 0.087 | 0.000 | 0.374 |
| | | | Avg | 0.081 | 1.992 | 2.389 |

TABLE 7

Lack of Endogenous IL-6 Th Epitopes within the Selected IL6R Binding Site B Epitope Sequences

| Group No. | peptide immunogen description | SEQ ID NO: | Animal ID | IL-6$_{52-83}$ (SEQ ID NO: 8) ELISA $Log_{10}$ Titer | | | IL-6$_{42-72}$ (SEQ ID NO: 10) ELISA $Log_{10}$ Titer | | | Recombinant human IL-6 ELISA $Log_{10}$ Titer | | |
|---|---|---|---|---|---|---|---|---|---|---|---|---|
| | | | | 0 wpi | 3 wpi | 6 wpi | 0 wpi | 3 wpi | 6 wpi | 0 wpi | 3 wpi | 6 wpi |
| 1 | IL-6$_{62-83}$ | 6 | 6489 | 0.071 | 0.000 | 2.603 | 0.089 | 0.000 | 2.746 | 0.143 | 0.000 | 0.000 |
| | | | 6490 | 0.097 | 0.000 | 0.000 | 0.119 | 0.000 | 0.000 | 0.130 | 0.000 | 0.000 |
| | | | 6491 | 0.143 | 0.000 | 0.000 | 0.127 | 0.000 | 0.000 | 0.159 | 0.272 | 0.000 |
| 2 | IL-6$_{58-83}$ | 7 | 6492 | 0.075 | 0.000 | 0.000 | 0.080 | 0.000 | 0.000 | 0.093 | 0.000 | 0.000 |
| | | | 6493 | 0.081 | 0.000 | 0.000 | 0.085 | 0.000 | 0.000 | 0.085 | 0.000 | 0.000 |
| | | | 6494 | 0.058 | 0.000 | 0.000 | 0.065 | 0.000 | 0.000 | 0.102 | 0.000 | 0.000 |
| 3 | IL-6$_{52-83}$ | 8 | 6495 | 0.078 | 0.000 | 0.000 | 0.062 | 0.000 | 0.000 | 0.085 | 0.000 | 0.000 |
| | | | 6496 | 0.061 | 0.000 | 0.000 | 0.062 | 0.000 | 0.000 | 0.092 | 0.000 | 0.000 |
| | | | 6497 | 0.099 | 0.000 | 0.000 | 0.098 | 0.000 | 0.000 | 0.135 | 0.000 | 0.000 |
| 4 | IL-6$_{52-72}$ | 9 | 6498 | 0.094 | 0.000 | 0.000 | 0.112 | 0.00 | 0.000 | 0.130 | 0.000 | 0.000 |
| | | | 6499 | 0.117 | 0.000 | 0.000 | 0.093 | 0.000 | 0.000 | 0.097 | 0.000 | 0.000 |
| | | | 6500 | 0.062 | 0.000 | 0.000 | 0.073 | 0.000 | 0.000 | 0.086 | 0.000 | 0.000 |
| 5 | IL-6$_{42-72}$ | 10 | 6501 | 0.076 | 0.000 | 0.000 | 0.056 | 0.000 | 2.650 | 0.076 | 0.000 | 0.000 |
| | | | 6502 | 0.059 | 0.000 | 0.000 | 0.069 | 0.000 | 0.000 | 0.095 | 0.000 | 0.000 |
| | | | 6503 | 0.062 | 0.000 | 0.000 | 0.059 | 0.000 | 0.000 | 0.072 | 0.000 | 0.000 |

TABLE 8

Immunogenicity Assessment in Guinea Pigs against the Th Epitope Portion of the IL-6 Peptide Immunogen Constructs

| Peptide Immunogen Description | SEQ ID NO: | Animal ID | Anti-corresponding IL-6 B epitope ELISA $Log_{10}$ Titer | | | UBITh ®1 (SEQ ID NO: 91) ELISA $Log_{10}$ Titer | | |
|---|---|---|---|---|---|---|---|---|
| | | | 0 wpi | 3 wpi | 6 wpi | 0 wpi | 3 wpi | 6 wpi |
| UBITh ®1-εK-KKK-IL-6$_{61-75}$ | 138 | 6931 | 0.080 | 7.800 | >10 | 0.073 | 0.000 | 0.923 |
| | | 6932 | 0.081 | 4.743 | >10 | 0.065 | 0.000 | 0.000 |
| | | 6933 | 0.086 | 5.025 | 7.309 | 0.063 | 0.000 | 0.000 |
| | | Avg. | 0.082 | 5.856 | 9.103 | 0.067 | 0.800 | 8.308 |

TABLE 8-continued

Immunogenicity Assessment in Guinea Pigs against the Th Epitope Portion of the IL-6 Peptide Immunogen Constructs

| Peptide Immunogen Description | SEQ ID NO: | Animal ID | Anti-corresponding IL-6 B epitope ELISA $\log_{10}$ Titer | | | UBITh ®1 (SEQ ID NO: 91) ELISA $\log_{10}$ Titer | | |
|---|---|---|---|---|---|---|---|---|
| | | | 0 wpi | 3 wpi | 6 wpi | 0 wpi | 3 wpi | 6 wpi |
| IL-$6_{61-75}$-KKK-εK-UBITh ®1 | 139 | 6934 | 0.081 | 4.936 | >10 | 0.085 | 0.000 | 1.091 |
| | | 6935 | 0.067 | 4.338 | 6.256 | 0.055 | 0.000 | 1.272 |
| | | 6936 | 0.077 | 4.722 | 9.491 | 0.070 | 0.000 | 1.307 |
| | | Avg. | 0.075 | 4.665 | 3.582 | 0.070 | 0.000 | 1.223 |
| UBITh ®1-εK-IL-$6_{61-75}$ | 140 | 6937 | 0.074 | 9.149 | >10 | 0.056 | 0.484 | 1.845 |
| | | 6938 | 0.077 | >10 | >10 | 0.082 | 0.792 | 1.446 |
| | | 6939 | 0.078 | 4.875 | 5.538 | 0.076 | 0.000 | 0.750 |
| | | Avg. | 0.077 | 8.008 | 3.513 | 0.071 | 0.425 | 1.347 |
| IL-$6_{61-75}$-εK-UBITh ®1 | 141 | 6940 | 0.080 | 4.219 | 6.593 | 0.063 | 0.198 | 1.550 |
| | | 6941 | 0.102 | 4.428 | >10 | 0.064 | 0.000 | 0.896 |
| | | 6942 | 0.066 | 4.576 | 5.331 | 0.055 | 0.000 | 1.244 |
| | | Avg. | 0.083 | 4.408 | 7.308 | 0.061 | 0.066 | 1.230 |
| UBITh ®1-εK-KKK-IL-$6_{61-72}$ | 142 | 6943 | 0.058 | 4.419 | 5.181 | 0.058 | 0.000 | 0.544 |
| | | 6944 | 0.055 | 4.118 | 6.343 | 0.057 | 0.000 | 0.000 |
| | | 6945 | 0.080 | 3.196 | 9.163 | 0.062 | 0.000 | 0.000 |
| | | Avg. | 0.064 | 3.911 | 6.896 | 0.059 | 0.000 | 0.181 |
| IL-$6_{61-72}$-KKK-εK-UBITh ®1 | 143 | 6946 | 0.091 | 4.407 | 7.728 | 0.083 | 0.000 | 1.344 |
| | | 6947 | 0.075 | 4.035 | 5.149 | 0.077 | 0.000 | 0.510 |
| | | 6948 | 0.142 | 4.677 | >10 | 0.066 | 0.000 | 0.770 |
| | | Avg. | 0.102 | 4.373 | 7.626 | 0.076 | 0.000 | 0.875 |
| UBITh ®1-εK-IL-$6_{61-72}$ | 144 | 6949 | 0.061 | 4.448 | 5.640 | 0.056 | 0.000 | 0.000 |
| | | 6950 | 0.062 | 3.830 | 5.975 | 0.062 | 0.000 | 0.000 |
| | | 6951 | 0.053 | 3.075 | 4.982 | 0.066 | 0.000 | 0.000 |
| | | Avg. | 0.058 | 3.784 | 5.532 | 0.062 | 0.800 | 8.800 |
| IL-$6_{61-72}$-εK-UBITh ®1 | 145 | 6952 | 0.062 | 4.552 | >10 | 0.061 | 0.119 | 1.046 |
| | | 6953 | 0.077 | 4.925 | >10 | 0.063 | 0.371 | 1.618 |
| | | 6954 | 0.072 | 4.799 | >10 | 0.077 | 0.084 | 1.622 |
| | | Avg. | 0.070 | 4.759 | >10 | 0.067 | 0.191 | 1.429 |

TABLE 9

Mapping of IL6R Binding B Epitopes with Immune Sera from IL-6 Peptide Immunogen Constructs 10 mer peptide design for epitope mapping from TABLE 9-continued Mapping of IL6R Binding B Epitopes with Immune Sera from IL-6 Peptide Immunogen Constructs 10 mer peptide design for epitope mapping from 32 to 91 of IL-6
ILDGISALRKETCNKSNMCSSSKEALAENNLNLPKMAEKDGCFQSGFNEETCLVKIITGL

| | SEQ ID NO 236 | Amino Acids | 124 IL6$_{62-83}$ | 125 IL6$_{58-83}$ | 126 IL6$_{52-63}$ | 127 IL6$_{52-72}$ | 128 IL6$_{42-72}$ | 129 IL6$_{42-72}$ | 130 IL6$_{50-87}$ | 107 IL6$_{73-87}$ |
|---|---|---|---|---|---|---|---|---|---|---|
| SKEALAENNL | 42 | 53-82 | 0.142 | 0.110 | 0.113 | 0.119 | 0.259 | 0.106 | 0.885 | 0.176 |
| KEALAENNLN | 43 | 54-83 | 0.160 | 0.116 | 0.100 | 0.209 | 0.296 | 0.126 | 0.696 | 0.196 |
| EALAENNLNL | 44 | 55-64 | 0.140 | 0.148 | 0.123 | 0.146 | 0.152 | 0.198 | 0.289 | 0.219 |
| ALAENNLNLP | 45 | 56-65 | 0.140 | 0.305 | 3.206 | 0.165 | 0.296 | 0.553 | 3.379 | 0.212 |
| LAENNLNLPK | 46 | 57-66 | 0.146 | 0.192 | 0.323 | 0.294 | 0.403 | 1.916 | 4.000 | 0.230 |
| AENNLNLPKM | 47 | 58-67 | 0.138 | 0.121 | 0.131 | 0.106 | 0.116 | 1.025 | 4.000 | 0.188 |
| ENNLNLPKMA | 48 | 59-68 | 0.136 | 0.146 | 0.112 | 0.112 | 0.108 | 0.486 | 1.615 | 0.198 |
| NNLNLPKMAE | 49 | 60-69 | 0.137 | 0.109 | 0.099 | 0.096 | 0.108 | 0.111 | 0.111 | 0.189 |
| NLNLPKMAEK | 50 | 61-70 | 0.186 | 0.378 | 0.356 | 4.000 | 3.881 | 2.363 | 0.348 | 0.180 |
| LNLPKMAEKD | 51 | 62-71 | 0.142 | 0.195 | 0.176 | 4.000 | 2.654 | 1.040 | 0.120 | 0.181 |
| NLPKMAEKDG | 52 | 63-72 | 0.131 | 0.118 | 0.107 | 4.000 | 4.000 | 0.426 | 0.890 | 0.162 |
| LPKMAEKDGC | 53 | 64-73 | 0.969 | 1.986 | 1.778 | 4.000 | 4.000 | 4.000 | 4.000 | 0.168 |
| PKMAEKDGCF | 54 | 65-74 | 0.396 | 0.332 | 0.196 | 1.161 | 2.952 | 0.824 | 0.164 | 0.200 |
| KMAEKDGCFQ | 55 | 65-75 | 0.721 | 0.450 | 0.293 | 3.430 | 3.929 | 0.640 | 0.196 | 0.204 |
| MAEKDGCFQS | 56 | 67-76 | 1.319 | 2.215 | 0.771 | 0.106 | 0.666 | 4.000 | 0.139 | 0.177 |
| AEKDGCFQSG | 57 | 68-77 | 0.350 | 0.136 | 0.098 | 0.114 | 0.106 | 0.101 | 0.144 | 0.199 |
| EKDGCFQSGF | 58 | 60-78 | 1.274 | 0.497 | 0.261 | 0.124 | 0.103 | 0.117 | 0.152 | 3.661 |
| KDGCFQSGFN | 59 | 70-79 | 3.756 | 3.695 | 3.681 | 0.109 | 0.114 | 0.118 | 0.158 | 3.937 |
| DGCFQSGFNE | 60 | 71-80 | 3.600 | 2.264 | 1.172 | 0.117 | 0.104 | 0.121 | 0.148 | 3.893 |
| GCFQSGFNEE | 61 | 72-81 | 3.758 | 3.495 | 3.133 | 0.100 | 0.108 | 0.115 | 0.144 | 3.935 |
| CFQSGFNEET | 62 | 73-82 | 3.732 | 2.260 | 3.057 | 0.106 | 0.100 | 0.102 | 0.159 | 3.839 |
| FQSGFNEETC | 63 | 74-83 | 3.785 | 3.800 | 3.867 | 0.106 | 0.107 | 0.118 | 3.992 | 4.000 |

TABLE 9-continued

Mapping of IL6R Binding B Epitopes with Immune Sera from IL-

TABLE 10

Arthritis Score of CIA Rats Immunized with Vaccines Containing IL-6R Binding Site Peptide Constructs

| Group | 17 day | 19 day | 21 day | 24 day | 26 day | 31 day | 33 day | 35 day |
|---|---|---|---|---|---|---|---|---|
| Placebo | 5.1 ± 0.4 | 8.4 ± 2.1 | 9.6 ± 0.8 | 7.9 ± 1.1 | 7.1 ± 0.9 | 6.3 ± 0.8 | 6.1 ± 0.6 | 5.7 ± 0.5 |
| SEQ ID NO: 148 (Rat IL-6$_{72-82}$) | 3.0 ± 0.9*** | 4.5 ± 0.8** | 4.8 ± 1.0**** | 4.8 ± 0.4**** | 4.5 ± 0.8*** | 4.5 ± 0.8** | 4.4 ± 0.7**** | 3.2 ± 1.6** |
| SEQ ID NO: 157 (Rat IL-6$_{144-166}$) | 3.6 ± 1.3** | 6.7 ± 1.7 | 8.0 ± 1.5* | 6.0 ± 0.8* | 5.6 ± 0.8** | 5.4 ± 0.8 | 5.1 ± 0.7*** | 4.6 ± 1.0* |

*$p < 0.05$
**$p < 0.01$
***$p < 0.001$
****$p < 0.0001$

TABLE 11

Hind Paw Swelling of CIA Rats Immunized with Vaccines Containing IL-6R Binding Site Peptide Constructs

| Group | 14 day | 21 day | 26 day | 35 day |
|---|---|---|---|---|
| Placebo | 1.5 ± 0.1 | 2.3 ± 0.2 | 2.2 ± 0.1 | 1.9 ± 0.1 |
| SEQ ID NO: 148 | 1.4 ± 0.1 | 1.6 ± 0.3*** | 1.6 ± 0.4** | 1.6 ± 0.3* |
| SEQ ID NO: 157 | 1.5 ± 0.1 | 2.0 ± 0.3* | 1.9 ± 0.3 | 1.6 ± 0.3 |

*$p < 0.05$
**$p < 0.01$
***$p < 0.001$

TABLE 12

Neutrophil Levels of CIA Rats Immunized with Vaccines Containing IL-6R Binding Site Peptide Constructs

| Group | 0 day | 7 day | 14 day | 21 day | 26 day |
|---|---|---|---|---|---|
| Placebo | 2.0 ± 0.4 | 3.8 ± 0.9 | 6.6 ± 0.8 | 4.0 ± 0.7 | 4.7 ± 0.8 |
| SEQ ID NO: 148 | 2.4 ± 0.4 | 3.9 ± 0.8 | 4.2 ± 1.2** | 2.8 ± 0.6** | 3.1 ± 0.6** |
| SEQ ID NO: 157 | 2.3 ± 0.3 | 4.3 ± 1.0 | 5.0 ± 1.1** | 3.0 ± 0.6* | 3.7 ± 1.1 |

*, $p<0.05$ **, $p<0.01$

TABLE 13

Body Weight of CIA Rats Immunized with Vaccine Formulations Containing IL-6R Binding Site Derived Peptide Construct (SEQ ID NO: 148) at Different Dose Levels

| Group | ISA 51/CpG formulation | | | ADJU-PHOS/CpG formulation | | |
|---|---|---|---|---|---|---|
| | 21 day | 28 day | 35 day | 21 day | 28 day | 35 day |
| Placebo | 184.9 ± 16.3 | 182.2 ± 13.7 | 182.9 ± 13.0 | 183.6 ± 8.7 | 187.1 ± 7.3 | 190.0 ± 8.1 |
| 5 µg/dose | 183.7 ± 8.8 | 187.2 ± 14.4 | 189.1 ± 11.6 | 188.6 ± 11.5 | 191.2 ± 9.6 | 191.8 ± 10.0 |
| 15 µg/dose | 193.8 ± 7.4 | 193.7 ± 7.8 | 196.8 ± 14.5 | 191.7 ± 8.2 | 196.6 ± 6.4 | 198.3 ± 7.1 |
| 45 µg/dose | 195.2 ± 3.1 | 195.3 ± 8.7 | 198.3 ± 4.2 | 192.7 ± 18.9 | 199.4 ± 12.0 | 198.0 ± 12.5 |
| 150 µg/dose | 196.0 ± 7.2 | 199.2 ± 6.8* (+9.3%) | 197.9 ± 2.4* (+8.2%) | 194.0 ± 16.5 | 206.9 ± 10.0** (+10.6%) | 206.4 ± 6.9** (+8.6%) |

*$p < 0.05$
**$p < 0.01$

TABLE 14

Hind Paw Swelling of CIA Rats Immunized with Vaccine Formulations Containing IL-6R Binding Site Peptide Construct (SEQ ID NO: 148) at Different Dose Levels

| Group | ISA 51/CpG formulation | | | ADJU-PHOS/CpG formulation | | |
|---|---|---|---|---|---|---|
| | 14 day | 21 day | 28 day | 14 day | 21 day | 28 day |
| Placebo | 1.38 ± 0.11 | 2.02 ± 0.09 | 1.89 ± 0.07 | 1.69 ± 0.35 | 2.02 ± 0.14 | 1.92 ± 0.08 |
| 5 µg/dose | 1.33 ± 0.03 | 1.94 ± 0.12 | 1.81 ± 0.04 | 1.42 ± 0.11 | 1.85 ± 0.31 | 1.82 ± 0.12 |
| 15 µg/dose | 1.36 ± 0.05 | 1.91 ± 0.06* (−5.4%) | 1.79 ± 0.10 | 1.63 ± 0.26 | 1.78 ± 0.26 | 1.75 ± 0.18 |
| 45 µg/dose | 1.47 ± 0.10 | 1.85 ± 0.10* (−8.4%) | 1.75 ± 0.08* (−7.4%) | 1.57 ± 0.26 | 1.73 ± 0.19* (−11.9%) | 1.73 ± 0.07** (−10%) |
| 150 µg/dose | 1.36 ± 0.06 | 1.81 ± 0.07** (−10.4%) | 1.70 ± 0.06** (−10%) | 1.38 ± 0.06 | 1.68 ± 0.21* (−16.8%) | 1.67 ± 0.06*** (−13.1%) |

*$p < 0.05$
**$p < 0.01$
***$p < 0.001$

Tables 15A-15B

Arthritis Score of CIA Rats Immunized with Vaccine Formulations Containing IL-6R Binding Site Peptide Construct (SEQ ID NO: 148) at Different Dose Levels

TABLE 15A

Formulation with ISA 51/CpG

| Group | 17 day | 19 day | 21 day | 24 day | 26 day |
|---|---|---|---|---|---|
| Placebo | 6.8 ± 0.8 | 8 ± 1 | 7.2 ± 1.1 | 6.8 ± 1.1 | 6.2 ± 0.4 |
| 5 µg/dose | 5.8 ± 1.3 | 6.6 ± 0.9* (−18%) | 6.8 ± 1.5 | 5.4 ± 0.9 | 5.8 ± 0.8 |
| 15 µg/dose | 5.4 ± 0.9* (−22%) | 6 ± 1.2* (−25%) | 5.8 ± 1.3 | 5.4 ± 0.9 | 5.6 ± 1.1 |
| 45 µg/dose | 5.3 ± 0.5* (−24%) | 5.8 ± 0.5** (−28%) | 5.5 ± 0.6* (−24%) | 5.0 ± 0.8* (−28%) | 5.0 ± 0.8* (−19%) |
| 150 µg/dose | 5.0 ± 0.7** (−26%) | 5.0 ± 0.0*** (−38%) | 5.4 ± 0.5 (−25%) | 4.8 ± 0.4** (−32%) | 4.4 ± 0.9** (−29%) |

| Group | 28 day | 31 day | 33 day | 35 day |
|---|---|---|---|---|
| Placebo | 6.2 ± 0.8 | 5.8 ± 1.1 | 4.0 ± 0.7 | 4.0 ± 0.7 |
| 5 µg/dose | 5.8 ± 0.4 | 5.4 ± 0.9 | 3.4 ± 0.5 | 3.2 ± 0.4 |
| 15 µg/dose | 5.6 ± 0.5 | 5.2 ± 1.3 | 3.2 ± 0.4 | 3.0 ± 0.7 |
| 45 µg/dose | 4.8 ± 0.5* (−23%) | 4.8 ± 0.5 | 2.8 ± 0.5* (−30%) | 2.5 ± 0.6* (−38%) |
| 150 µg/dose | 4.6 ± 0.5** (−26%) | 4.4 ± 0.5* (−24%) | 2.6 ± 0.5** (−35%) | 2.2 ± 0.4** (−45%) |

*$p < 0.05$
**$p < 0.01$
***$p < 0.001$

TABLE 15B

Formulation with ADJU-PHOS/CpG

| Group | 17 day | 19 day | 21 day | 24 day | 26 day |
|---|---|---|---|---|---|
| Placebo | 6.8 ± 0.4 | 7.6 ± 0.9 | 8.6 ± 1.7 | 7.0 ± 1.0 | 6.2 ± 0.4 |
| 5 µg/dose | 6.2 ± 1.3 | 6.2 ± 0.8* (−18%) | 8.0 ± 2.6 | 5.8 ± 1.1 | 6.0 ± 0.7 |
| 15 µg/dose | 5.4 ± 1.3 | 6.0 ± 1.0* (−21%) | 7.4 ± 1.3 | 5.8 ± 1.3 | 5.6 ± 0.5 |

TABLE 15B-continued

| | Formulation with ADJU-PHOS/CpG | | | | |
|---|---|---|---|---|---|
| 45 µg/dose | 5.2 ± 1.3* (−24%) | 5.8 ± 0.4** (−22%) | 6.8 ± 0.4* (−21%) | 5.4 ± 1.1* (−23%) | 4.8 ± 0.4** (−23%) |
| 150 µg/dose | 5.0 ± 1.0** (−26%) | 5.0 ± 0.7*** (−34%) | 6.2 ± 0.4* (−28%) | 5.0 ± 0.7** (−29%) | 4.4 ± 0.5*** (−29%) |

| Group | 28 day | 31 day | 33 day | 35 day |
|---|---|---|---|---|
| Placebo | 6.4 ± 0.5 | 5.0 ± 1.0 | 3.6 ± 0.5 | 3.8 ± 0.8 |
| 5 µg/dose | 6.2 ± 0.8 | 5.2 ± 0.8 | 3.2 ± 1.1 | 3.2 ± 0.4 |
| 15 µg/dose | 6.0 ± 1.0 | 4.2 ± 1.6 | 3.0 ± 1.0 | 3.0 ± 0.7 |
| 45 µg/dose | 5.6 ± 0.5* (−13%) | 4.2 ± 0.8* (−16%) | 2.4 ± 0.9* (−33%) | 2.8 ± 0.4* (−26%) |
| 150 µg/dose | 5.0 ± 0.7** (−22%) | 3.2 ± 0.8** (−36%) | 1.4 ± 1.3** (−61%) | 1.4 ± 1.3** (−63%) |

*p < 0.05
**p < 0.01
***p < 0.001

Tables 16A-16B

Neutrophil Level of CIA Rats Immunized with Vaccine Formulations Containing IL-6R Binding Site Peptide Construct (SEQ ID NO: 148) at Different Dose Levels

TABLE 16A

| | Formulation with ISA 51/CpG | | | | |
|---|---|---|---|---|---|
| Group | 7 day | 14 day | 21 day | 28 day | 35 day |
| Placebo | 5.94 ± 1.32 | 6.60 ± 0.58 | 4.22 ± 0.47 | 4.19 ± 0.75 | 2.29 ± 0.50 |
| 5 µg/dose | 4.47 ± 0.46* | 5.37 ± 0.68* | 4.23 ± 0.22 | 3.76 ± 0.36 | 2.12 ± 0.43 |
| 15 µg/dose | 4.17 ± 0.86* | 4.57 ± 0.69** | 4.03 ± 0.54 | 3.75 ± 0.39 | 2.09 ± 0.25 |
| 45 µg/dose | 3.70 ± 0.45** (−38%) | 4.50 ± 0.68** (−32%) | 3.72 ± 0.35 (−12%) | 3.56 ± 0.40 (−15%) | 1.89 ± 0.36 (−17%) |
| 150 µg/dose | 3.15 ± 0.56** (−47%) | 4.34 ± 0.85** (−34%) | 3.61 ± 0.35* (−14%) | 3.12 ± 0.36* (−26%) | 1.66 ± 0.35 (−27%) |

*p < 0.05
**p < 0.01

TABLE 16B

| | Formulation with ADJU-PHOS/CpG | | | | |
|---|---|---|---|---|---|
| Group | 7 day | 14 day | 21 day | 28 day | 35 day |
| Placebo | 5.99 ± 0.85 | 5.77 ± 0.75 | 4.08 ± 0.22 | 4.05 ± 0.33 | 2.32 ± 0.25 |
| 5 µg/dose | 4.74 ± 0.67* | 4.38 ± 1.06* | 3.83 ± 0.89 | 3.65 ± 0.41 | 2.08 ± 0.55 |
| 15 µg/dose | 4.06 ± 0.91** | 4.32 ± 0.65* | 3.56 ± 0.60 | 3.55 ± 0.33* | 2.05 ± 0.45 |
| 45 µg/dose | 3.58 ± 0.79** (−40%) | 4.43 ± 0.93* (−18%) | 3.46 ± 0.25** (−15%) | 3.43 ± 0.37* (−15%) | 1.55 ± 0.23*** (−33%) |
| 150 µg/dose | 2.07 ± 0.45**** (−65%) | 3.72 ± 0.47*** (−36%) | 2.44 ± 0.31**** (−40%) | 2.53 ± 0.47*** (−38%) | 1.36 ± 0.25*** (−41%) |

*p < 0.05
**p < 0.01
***p < 0.001
****p < 0.0001

Tables 17A-17B

Platelet Release of CIA Rats Immunized with Vaccine Formulations Containing IL-6R Binding Site Peptide Construct (SEQ ID NO: 148) at Different Dose Levels

TABLE 17A

| | Formulation with ISA 51/CpG | | | |
|---|---|---|---|---|
| Group | 7 day | 14 day | 21 day | 28 day |
| Placebo | 772.4 ± 63.1 | 886.0 ± 86.6 | 966.6 ± 153.4 | 864.2 ± 43.8 |
| 5 μg/dose | 647.4 ± 117.5 | 785.2 ± 109.4 | 872.6 ± 107.1 | 762.6 ± 71.0* |
| 15 μg/dose | 702.6 ± 33.4 | 734.6 ± 157.2 | 831.4 ± 77.2 | 748.4 ± 72.3* |
| 45 μg/dose | 689.0 ± 66.5 (−11%) | 743.0 ± 66.2* (−16%) | 820.5 ± 61.9 (−15%) | 719.8 ± 84.1* (−17%) |
| 150 μg/dose | 676.4 ± 64.1* (−12%) | 718.2 ± 86.5* (−19%) | 764.8 ± 35.4* (−21%) | 697.4 ± 59.8** (−19%) |

*$p < 0.05$
**$p < 0.01$

TABLE 17B

| | Formulation with ADJU-PHOS/CpG | | | |
|---|---|---|---|---|
| Group | 7 day | 14 day | 21 day | 28 day |
| Placebo | 770.6 ± 7.6 | 863.0 ± 62.4 | 920.0 ± 62.9 | 849.8 ± 100.4 |
| 5 μg/dose | 722.8 ± 31.4 | 833.2 ± 90.3 | 846.6 ± 75.9 | 767.3 ± 38.8 |
| 15 μg/dose | 718.6 ± 63.1 | 843.2 ± 34.1 | 886.0 ± 45.2* | 721.6 ± 51.8* |
| 45 μg/dose | 715.8 ± 68.1 (−7%) | 761.6 ± 27.4* (−12%) | 723.0 ± 98.4** (−21%) | 718.0 ± 21.6* (−16%) |
| 150 μg/dose | 663.4 ± 83.2 (−14%) | 708.6 ± 47.3** (−18%) | 718.0 ± 27.7*** (−22%) | 715.0 ± 39.6* (−16%) |

*$p < 0.05$
**$p < 0.01$
***$p < 0.001$

Tables 18A-18B

AST of CIA Rats Immunized with Vaccine Formulations Containing IL-6 Derived Peptide Construct (SEQ ID NO: 148) at Different Dose Levels

TABLE 18A

| | Formulation with ISA 51/CpG | | | |
|---|---|---|---|---|
| Group | 7 day | 14 day | 21 day | 28 day |
| Placebo | 132.3 ± 23.8 | 133.0 ± 14.9 | 146.2 ± 9.3 | 139.8 ± 16.6 |
| 5 μg/dose | 131.5 ± 5.2 | 128.4 ± 20.4 | 141.5 ± 21.5 | 137.5 ± 3.9 |
| 15 μg/dose | 122.0 ± 8.0 | 114.6 ± 22.9 | 133.5 ± 16.6 | 134.6 ± 36.2 |
| 45 μg/dose | 102.2 ± 21.9 (−23%) | 109.7 ± 20.7 (−18%) | 131.1 ± 5.0 (−11%) | 130.9 ± 28.9 (−7%) |
| 150 μg/dose | 100.2 ± 10.8* (−24%) | 93.9 ± 12.1** (−29%) | 121.5 ± 9.4* (−17%) | 100.1 ± 8.7** (−29%) |

*$p < 0.05$
**$p < 0.01$

TABLE 18B

| | Formulation with ADJU-PHOS/CpG | | | |
|---|---|---|---|---|
| Group | 7 day | 14 day | 21 day | 28 day |
| Placebo | 131.7 ± 15.6 | 135.4 ± 10.4 | 140.5 ± 19.2 | 134.8 ± 20.7 |
| 5 μg/dose | 124.3 ± 7.5 | 125.9 ± 8.4 | 134.8 ± 29.1 | 119.4 ± 9.2 |

TABLE 18B-continued

Formulation with ADJU-PHOS/CpG

| Group | 7 day | 14 day | 21 day | 28 day |
|---|---|---|---|---|
| 15 μg/dose | 117.5 ± 5.8 | 123.0 ± 7.1 | 122.9 ± 14.3 | 118.8 ± 22.8 |
| 45 μg/dose | 113.9 ± 5.5* (−14%) | 120.0 ± 9.8* (−11%) | 118.3 ± 7.9* (−16%) | 106.4 ± 18.2* (−22%) |
| 150 μg/dose | 108.1 ± 6.9* (−18%) | 107.6 ± 12.1** (−21%) | 110.0 ± 11.6* (−22%) | 103.6 ± 17.8* (−24%) |

*p < 0.05
**p < 0.01

Cross-reactivity of IgGs from Immune Sera Targeting Human IL-6R Binding Site Peptide Immunogen Constructs with Macaque and Rodent IL-6 Proteins

| | Immunogen | |
|---|---|---|
| | UBITh ®1-εK-KKK-IL-6$_{73-83}$ | UBITh ®1-εK-IL-6$_{73-83}$ |
| SEQ ID NO | 119 | 122 |
| Formulation | ADJU-PHOS | ADJU-PHOS + CpG3 |
| Human IL-6 | 2.497 | 3.226 |
| Macaque IL-6 | 1.478 | 5.635 |
| Rodent IL-6 | — | 1.653 |

Tables 20A-20B

Neutralizing Activity of IgGs Induced by IL-6 Peptide Immunogen Constructs for Cis/Trans-Binding

TABLE 20A

IC$_{50}$ for inhibitory effect on cis-binding

| Immunogen | SEQ ID NO | IC50 (μg/mL) |
|---|---|---|
| UBITh ®1-εK-IL-6$_{62-83}$ | 124 | 37.4 |
| UBITh ®1-εK-IL-6$_{58-83}$ | 125 | 120.8 |
| UBITh ®1-εK-IL-6$_{52-83}$ | 126 | 271.4 |
| UBITh ®1-εK-IL-6$_{52-72}$ | 127 | 160 |
| UBITh ®1-εK-IL-6$_{42-72}$ | 128 | 508.6 |
| IL-6$_{42-72}$-εK-UBITh ®1 | 129 | 2343 |
| UBITh ®1-εK-IL-6$_{50-67}$ | 130 | >10000 |
| UBITh ®3-εK-KKK-IL-6$_{73-83}$ | 107 | 296.5 |
| IL6$_{144-166}$-KKK-εK-UBITh ®1 | 116 | 56.54 |
| UBITh ®1-εK-KKK-IL6$_{73-83}$-KKK-εK-UBITh ®1 | 118 | 144.8 |
| TCZ | | 0.935 |

TABLE 20B

IC$_{50}$ for inhibitory effect on trans-binding

| Immunogen | SEQ ID NO | IC50 (μg/mL) |
|---|---|---|
| UBITh ®1-εK-IL-6$_{42-72}$ | 128 | 6.971 |
| IL-6$_{42-72}$-εK-UBITh ®1 | 129 | 3.277 |
| UBITh ®1-εK-IL-6$_{50-67}$ | 130 | >10000 |
| TCZ | | 0.1 |

TABLE 21

Neutralizing Activity of IgGs Induced by IL-6 Peptide Immunogen Constructs for IL-6 Induced TF-1 Proliferation

| Immunogen | SEQ ID NO | IC$_{50}$ (μg/mL) |
|---|---|---|
| UBITh ®1-εK-IL-6$_{62-83}$ | 124 | 2.659 |
| UBITh ®1-εK-IL-6$_{58-83}$ | 125 | 1.905 |
| UBITh ®1-εK-IL-6$_{52-83}$ | 126 | 1.956 |
| UBITh ®1-εK-IL-6$_{52-72}$ | 127 | 2.191 |
| UBITh ®1-εK-IL-6$_{42-72}$ | 128 | 2.360 |
| IL-6$_{42-72}$-εK-UBITh ®1 | 129 | 4.321 |
| UBITh ®1-εK-IL-6$_{50-67}$ | 130 | 2.742 |
| UBITh ®3-εK-KKK-IL-6$_{73-83}$ | 107 | 66.940 |
| IL6$_{144-166}$-KKK-εK-UBITh ®1 | 116 | 12.250 |
| UBITh ®1-εK-KKK-IL6$_{73-83}$-KKK-εK-UBITh ®1 | 118 | 5.396 |
| Non GP IgG | | >100 |
| TCZ | | 0.365 |
| ALD518 | | 0.629 |

TABLE 22

Cross-reactivity to Human, Monkey and Rodent IL-6 of IgGs Induced by IL-6 Peptide Immunogen Constructs

| SEQ ID NO | EC$_{50}$ (μg/mL) | | |
|---|---|---|---|
| | Human IL-6 | Monkey IL-6 | Rat IL-6 |
| 107 | 0.118 | 0.131 | 2.401 |
| 116 | 0.173 | 0.146 | 7.941 |
| 118 | 0.028 | 0.032 | 0.416 |
| 124 | 0.287 | 0.334 | 1.234 |
| 125 | 0.270 | 0.313 | 2.454 |
| 126 | 0.323 | 0.356 | 2.224 |
| 127 | 0.434 | 0.409 | 14.82 |
| 128 | 0.434 | 0.377 | 9.277 |
| 129 | 0.184 | 0.214 | 1.263 |
| 130 | 0.219 | 0.230 | 6.397 |
| 131 | 0.118 | 0.646 | 6.362 |
| 132 | 0.173 | 0.285 | 2.406 |
| 133 | 0.410 | 0.276 | 3.888 |

The invention claimed is:

1. An IL-6 peptide immunogen construct represented by the formulae:

(Th)$_m$-(A)$_n$-(IL-6R binding region of IL-6 or a fragment thereof)-X or (IL-6R binding region of IL-6 or a fragment thereof)-(A)$_n$-(Th)$_m$-X or (Th)$_m$-(A)$_n$-(IL-6R binding region of IL-6 or a fragment thereof)-(A)$_n$-(Th)$_m$-X wherein Th is a heterologous T helper epitope selected from the group consisting of SEQ ID NOs: 89 and 91;
A is a heterologous spacer;
IL-6R binding region of IL-6 or a fragment thereof is selected from the group consisting of SEQ ID NOs: 5 to 19;
X is an α-COOH or α-CONH$_2$ of an amino acid;
m is from 1 to 4; and
n is from 0 to about b 10.

2. The IL-6 peptide immunogen construct according to claim 1, wherein the peptide immunogen construct is selected from the group consisting of SEQ ID NOs: 107, 112-118, 124-129, and 131-145.

3. The IL-6 peptide immunogen construct of claim 1, wherein the heterologous spacer is (α, ε-N) Lys, ε-N-Lys-Lys-Lys-Lys (SEQ ID NO: 77), Lys-Lys-Lys-ε-N-Lys (SEQ ID NO: 231), or Pro-Pro-Xaa-Pro-Xaa-Pro (SEQ ID NO: 76), and any combination thereof.

4. A composition comprising the IL-6 peptide immunogen construct according to claim 1.

5. A pharmaceutical composition comprising:
 a. the IL-6 peptide immunogen construct according to claim 1; and
 b. a pharmaceutically acceptable delivery vehicle and/or adjuvant.

6. The pharmaceutical composition of claim 5, wherein the IL-6 peptide immunogen construct is mixed with a CpG oligodeoxynucleotide (ODN) to form a stabilized immunostimulatory complex.

7. The pharmaceutical composition of claim 5, wherein the IL-6 peptide immunogen construct is selected from the group consisting of SEQ ID NOs: 107, 112-118, 124-129, and 131-145; and
 wherein the IL-6 peptide immunogen construct is mixed with a CpG oligodeoxynucleotide (ODN) to form a stabilized immunostimulatory complex.

8. A method of attenuating the severity of rheumatoid arthritis in an animal comprising administering an effective amount of the pharmaceutical composition according to claim 5 to the animal.

* * * * *

SEQUENCE LISTING

<160> NUMBER OF SEQ ID NOS: 236

<210> SEQ ID NO 1
<211> LENGTH: 184
<212> TYPE: PRT
<213> ORGANISM: Homo sapiens
<220> FEATURE:
<221> NAME/KEY: PEPTIDE
<222> LOCATION: (1)..(184)
<223> OTHER INFORMATION: Human IL-6 1-184

<400> SEQUENCE: 1

Pro Val Pro Pro Gly Glu Asp Ser Lys Asp Val Ala Ala Pro His Arg
1               5                   10                  15

Gln Pro Leu Thr Ser Ser Glu Arg Ile Asp Lys Gln Ile Arg Tyr Ile
            20                  25                  30

Leu Asp Gly Ile Ser Ala Leu Arg Lys Glu Thr Cys Asn Lys Ser Asn
        35                  40                  45

Met Cys Glu Ser Ser Lys Glu Ala Leu Ala Glu Asn Asn Leu Asn Leu
    50                  55                  60

Pro Lys Met Ala Glu Lys Asp Gly Cys Phe Gln Ser Gly Phe Asn Glu
65                  70                  75                  80

Glu Thr Cys Leu Val Lys Ile Ile Thr Gly Leu Leu Glu Phe Glu Val
                85                  90                  95

Tyr Leu Glu Tyr Leu Gln Asn Arg Phe Glu Ser Ser Glu Glu Gln Ala
            100                 105                 110

Arg Ala Val Gln Met Ser Thr Lys Val Leu Ile Gln Phe Leu Gln Lys
        115                 120                 125

Lys Ala Lys Asn Leu Asp Ala Ile Thr Thr Pro Asp Pro Thr Thr Asn
130                 135                 140

Ala Ser Leu Leu Thr Lys Leu Gln Ala Gln Asn Gln Trp Leu Gln Asp
145                 150                 155                 160

Met Thr Thr His Leu Ile Leu Arg Ser Phe Lys Glu Phe Leu Gln Ser
                165                 170                 175

Ser Leu Arg Ala Leu Arg Gln Met
            180

<210> SEQ ID NO 2
<211> LENGTH: 184
<212> TYPE: PRT
<213> ORGANISM: Macaca fascicularis
<220> FEATURE:
<221> NAME/KEY: PEPTIDE
<222> LOCATION: (1)..(184)
<223> OTHER INFORMATION: Macaque IL-6 1-184

<400> SEQUENCE: 2

Pro Val Leu Pro Gly Glu Asp Ser Lys Asp Val Ala Ala Pro His Ser
1               5                   10                  15

Gln Pro Leu Thr Ser Ser Glu Arg Ile Asp Lys His Ile Arg Tyr Ile
            20                  25                  30

Leu Asp Gly Ile Ser Ala Leu Arg Lys Glu Thr Cys Asn Arg Ser Asn
        35                  40                  45

Met Cys Glu Ser Ser Lys Glu Ala Leu Ala Glu Asn Asn Leu Asn Leu
    50                  55                  60

Pro Lys Met Ala Glu Lys Asp Gly Cys Phe Gln Ser Gly Phe Asn Glu
65                  70                  75                  80

Asp Thr Cys Leu Val Lys Ile Ile Thr Gly Leu Leu Glu Phe Glu Val
                85                  90                  95

```
Tyr Leu Glu Tyr Leu Gln Asn Arg Phe Glu Ser Ser Glu Glu Gln Ala
            100                 105                 110

Arg Ala Val Gln Met Ser Thr Lys Val Leu Ile Gln Phe Leu Gln Lys
            115                 120                 125

Lys Ala Lys Asn Leu Asp Ala Ile Thr Thr Pro Glu Pro Thr Thr Asn
            130                 135                 140

Ala Ser Leu Leu Thr Lys Leu Gln Ala Gln Asn Gln Trp Leu Gln Asp
145                 150                 155                 160

Met Thr Thr His Leu Ile Leu Arg Ser Phe Lys Glu Phe Leu Gln Ser
                165                 170                 175

Ser Leu Arg Ala Leu Arg Gln Met
            180

<210> SEQ ID NO 3
<211> LENGTH: 184
<212> TYPE: PRT
<213> ORGANISM: Mus musculus
<220> FEATURE:
<221> NAME/KEY: PEPTIDE
<222> LOCATION: (1)..(184)
<223> OTHER INFORMATION: Mouse IL-6 1-184

<400> SEQUENCE: 3

Ser Gln Val Arg Arg Gly Asp Phe Thr Glu Asp Thr Thr Pro Asn Arg
1               5                   10                  15

Pro Val Tyr Thr Thr Ser Gln Val Gly Gly Leu Ile Thr His Val Leu
            20                  25                  30

Trp Glu Ile Val Glu Met Arg Lys Glu Leu Cys Asn Gly Asn Ser Asp
        35                  40                  45

Cys Met Asn Asn Asp Asp Ala Leu Ala Glu Asn Asn Leu Lys Leu Pro
    50                  55                  60

Glu Ile Gln Arg Asn Asp Gly Cys Tyr Gln Thr Gly Tyr Asn Gln Glu
65                  70                  75                  80

Ile Cys Leu Leu Lys Ile Ser Ser Gly Leu Leu Glu Tyr His Ser Tyr
                85                  90                  95

Leu Glu Tyr Met Lys Asn Asn Leu Lys Asp Asn Lys Lys Asp Lys Ala
            100                 105                 110

Arg Val Leu Gln Arg Asp Thr Glu Thr Leu Ile His Ile Phe Asn Gln
            115                 120                 125

Glu Val Lys Asp Leu His Lys Ile Val Leu Pro Thr Pro Ile Ser Asn
            130                 135                 140

Ala Leu Leu Thr Asp Lys Leu Glu Ser Gln Lys Glu Trp Leu Arg Thr
145                 150                 155                 160

Lys Thr Ile Gln Phe Ile Leu Lys Ser Leu Glu Glu Phe Leu Lys Val
                165                 170                 175

Thr Leu Arg Ser Thr Arg Gln Thr
            180

<210> SEQ ID NO 4
<211> LENGTH: 184
<212> TYPE: PRT
<213> ORGANISM: Rattus norvegicus
<220> FEATURE:
<221> NAME/KEY: PEPTIDE
<222> LOCATION: (1)..(184)
<223> OTHER INFORMATION: Rat IL-6 1-184
```

<400> SEQUENCE: 4

Ser Gln Val Arg Arg Gly Asp Phe Thr Glu Asp Thr Thr His Asn Arg
1               5                   10                  15

Pro Val Tyr Thr Thr Ser Gln Val Gly Gly Leu Ile Thr Tyr Val Leu
            20                  25                  30

Arg Glu Ile Leu Glu Met Arg Lys Glu Leu Cys Asn Gly Asn Ser Asp
        35                  40                  45

Cys Met Asn Ser Asp Asp Ala Leu Ser Glu Asn Asn Leu Lys Leu Pro
50                  55                  60

Glu Ile Gln Arg Asn Asp Gly Cys Phe Gln Thr Gly Tyr Asn Gln Glu
65                  70                  75                  80

Ile Cys Leu Leu Lys Ile Cys Ser Gly Leu Leu Glu Phe Arg Phe Tyr
                85                  90                  95

Leu Glu Phe Val Lys Asn Asn Leu Gln Asp Asn Lys Lys Asp Lys Ala
            100                 105                 110

Arg Val Ile Gln Ser Asn Thr Glu Thr Leu Val His Ile Phe Lys Gln
        115                 120                 125

Glu Ile Lys Asp Ser Tyr Lys Ile Val Leu Pro Thr Pro Thr Ser Asn
130                 135                 140

Ala Leu Leu Met Glu Lys Leu Glu Ser Gln Lys Glu Trp Leu Arg Thr
145                 150                 155                 160

Lys Thr Ile Gln Leu Ile Leu Lys Ala Leu Glu Glu Phe Leu Lys Val
                165                 170                 175

Thr Met Arg Ser Thr Arg Gln Thr
            180

<210> SEQ ID NO 5
<211> LENGTH: 11
<212> TYPE: PRT
<213> ORGANISM: Homo sapiens
<220> FEATURE:
<221> NAME/KEY: PEPTIDE
<222> LOCATION: (1)..(11)
<223> OTHER INFORMATION: IL-6 73-83

<400> SEQUENCE: 5

Cys Phe Gln Ser Gly Phe Asn Glu Glu Thr Cys
1               5                   10

<210> SEQ ID NO 6
<211> LENGTH: 22
<212> TYPE: PRT
<213> ORGANISM: Homo sapiens
<220> FEATURE:
<221> NAME/KEY: PEPTIDE
<222> LOCATION: (1)..(22)
<223> OTHER INFORMATION: IL-6 62-83

<400> SEQUENCE: 6

Leu Asn Leu Pro Lys Met Ala Glu Lys Asp Gly Cys Phe Gln Ser Gly
1               5                   10                  15

Phe Asn Glu Glu Thr Cys
            20

<210> SEQ ID NO 7
<211> LENGTH: 26
<212> TYPE: PRT
<213> ORGANISM: Homo sapiens
<220> FEATURE:
<221> NAME/KEY: PEPTIDE

```
<222> LOCATION: (1)..(26)
<223> OTHER INFORMATION: IL-6 58-83

<400> SEQUENCE: 7

Ala Glu Asn Asn Leu Asn Leu Pro Lys Met Ala Glu Lys Asp Gly Cys
1               5                   10                  15

Phe Gln Ser Gly Phe Asn Glu Glu Thr Cys
            20                  25

<210> SEQ ID NO 8
<211> LENGTH: 32
<212> TYPE: PRT
<213> ORGANISM: Homo sapiens
<220> FEATURE:
<221> NAME/KEY: PEPTIDE
<222> LOCATION: (1)..(32)
<223> OTHER INFORMATION: IL-6 52-83

<400> SEQUENCE: 8

Ser Ser Lys Glu Ala Leu Ala Glu Asn Asn Leu Asn Leu Pro Lys Met
1               5                   10                  15

Ala Glu Lys Asp Gly Cys Phe Gln Ser Gly Phe Asn Glu Glu Thr Cys
            20                  25                  30

<210> SEQ ID NO 9
<211> LENGTH: 21
<212> TYPE: PRT
<213> ORGANISM: Homo sapiens
<220> FEATURE:
<221> NAME/KEY: PEPTIDE
<222> LOCATION: (1)..(21)
<223> OTHER INFORMATION: IL-6 52-72

<400> SEQUENCE: 9

Ser Ser Lys Glu Ala Leu Ala Glu Asn Asn Leu Asn Leu Pro Lys Met
1               5                   10                  15

Ala Glu Lys Asp Gly
            20

<210> SEQ ID NO 10
<211> LENGTH: 31
<212> TYPE: PRT
<213> ORGANISM: Homo sapiens
<220> FEATURE:
<221> NAME/KEY: PEPTIDE
<222> LOCATION: (1)..(31)
<223> OTHER INFORMATION: IL-6  42-72

<400> SEQUENCE: 10

Glu Thr Cys Asn Lys Ser Asn Met Cys Glu Ser Ser Lys Glu Ala Leu
1               5                   10                  15

Ala Glu Asn Asn Leu Asn Leu Pro Lys Met Ala Glu Lys Asp Gly
            20                  25                  30

<210> SEQ ID NO 11
<211> LENGTH: 18
<212> TYPE: PRT
<213> ORGANISM: Homo sapiens
<220> FEATURE:
<221> NAME/KEY: PEPTIDE
<222> LOCATION: (1)..(18)
<223> OTHER INFORMATION: IL-6 50-67, C67 substitute M67
```

<400> SEQUENCE: 11

Cys Glu Ser Ser Lys Glu Ala Leu Ala Glu Asn Asn Leu Asn Leu Pro
1               5                   10                  15

Lys Cys

<210> SEQ ID NO 12
<211> LENGTH: 16
<212> TYPE: PRT
<213> ORGANISM: Homo sapiens
<220> FEATURE:
<221> NAME/KEY: PEPTIDE
<222> LOCATION: (1)..(16)
<223> OTHER INFORMATION: IL-6 42-57

<400> SEQUENCE: 12

Glu Thr Cys Asn Lys Ser Asn Met Cys Glu Ser Ser Lys Glu Ala Leu
1               5                   10                  15

<210> SEQ ID NO 13
<211> LENGTH: 15
<212> TYPE: PRT
<213> ORGANISM: Homo sapiens
<220> FEATURE:
<221> NAME/KEY: PEPTIDE
<222> LOCATION: (1)..(15)
<223> OTHER INFORMATION: IL-6 61-75, S73 substitute C73

<400> SEQUENCE: 13

Asn Leu Asn Leu Pro Lys Met Ala Glu Lys Asp Gly Ser Phe Gln
1               5                   10                  15

<210> SEQ ID NO 14
<211> LENGTH: 12
<212> TYPE: PRT
<213> ORGANISM: Homo sapiens
<220> FEATURE:
<221> NAME/KEY: PEPTIDE
<222> LOCATION: (1)..(12)
<223> OTHER INFORMATION: IL-6 61-72

<400> SEQUENCE: 14

Asn Leu Asn Leu Pro Lys Met Ala Glu Lys Asp Gly
1               5                   10

<210> SEQ ID NO 15
<211> LENGTH: 7
<212> TYPE: PRT
<213> ORGANISM: Homo sapiens
<220> FEATURE:
<221> NAME/KEY: PEPTIDE
<222> LOCATION: (1)..(7)
<223> OTHER INFORMATION: IL-6 44-50

<400> SEQUENCE: 15

Cys Asn Lys Ser Asn Met Cys
1               5

<210> SEQ ID NO 16
<211> LENGTH: 42
<212> TYPE: PRT
<213> ORGANISM: Homo sapiens
<220> FEATURE:
<221> NAME/KEY: PEPTIDE
<222> LOCATION: (1)..(42)
<223> OTHER INFORMATION: IL-6 44-83

<400> SEQUENCE: 16

Glu Thr Cys Asn Lys Ser Asn Met Cys Glu Ser Ser Lys Glu Ala Leu
1               5                   10                  15

Ala Glu Asn Asn Leu Asn Leu Pro Lys Met Ala Glu Lys Asp Gly Cys
            20                  25                  30

Phe Gln Ser Gly Phe Asn Glu Glu Thr Cys
            35                  40

<210> SEQ ID NO 17
<211> LENGTH: 40
<212> TYPE: PRT
<213> ORGANISM: Homo sapiens
<220> FEATURE:
<221> NAME/KEY: PEPTIDE
<222> LOCATION: (1)..(40)
<223> OTHER INFORMATION: IL-6 44-83

<400> SEQUENCE: 17

Cys Asn Lys Ser Asn Met Cys Glu Ser Ser Lys Glu Ala Leu Ala Glu
1               5                   10                  15

Asn Asn Leu Asn Leu Pro Lys Met Ala Glu Lys Asp Gly Cys Phe Gln
            20                  25                  30

Ser Gly Phe Asn Glu Glu Thr Cys
            35                  40

<210> SEQ ID NO 18
<211> LENGTH: 13
<212> TYPE: PRT
<213> ORGANISM: Homo sapiens
<220> FEATURE:
<221> NAME/KEY: PEPTIDE
<222> LOCATION: (1)..(13)
<223> OTHER INFORMATION: IL-6 150-162, C150 substitute K150, C162
      substitute T162

<400> SEQUENCE: 18

Cys Leu Gln Ala Gln Asn Gln Trp Leu Gln Asp Met Cys
1               5                   10

<210> SEQ ID NO 19
<211> LENGTH: 23
<212> TYPE: PRT
<213> ORGANISM: Homo sapiens
<220> FEATURE:
<221> NAME/KEY: PEPTIDE
<222> LOCATION: (1)..(23)
<223> OTHER INFORMATION: IL-6 144-166, C144 substitute N144, C166
      substitute I166

<400> SEQUENCE: 19

Cys Ala Ser Leu Leu Thr Lys Leu Gln Ala Gln Asn Gln Trp Leu Gln
1               5                   10                  15

Asp Met Thr Thr His Leu Cys
            20

<210> SEQ ID NO 20
<211> LENGTH: 11
<212> TYPE: PRT
<213> ORGANISM: Mus musculus
<220> FEATURE:
<221> NAME/KEY: PEPTIDE
<222> LOCATION: (1)..(11)
<223> OTHER INFORMATION: mouse IL-6 72-82

```
<400> SEQUENCE: 20

Cys Tyr Gln Thr Gly Tyr Asn Gln Glu Ile Cys
1               5                   10

<210> SEQ ID NO 21
<211> LENGTH: 10
<212> TYPE: PRT
<213> ORGANISM: Homo sapiens
<220> FEATURE:
<221> NAME/KEY: PEPTIDE
<222> LOCATION: (1)..(10)
<223> OTHER INFORMATION: IL-6 32-41

<400> SEQUENCE: 21

Ile Leu Asp Gly Ile Ser Ala Leu Arg Lys
1               5                   10

<210> SEQ ID NO 22
<211> LENGTH: 10
<212> TYPE: PRT
<213> ORGANISM: Homo sapiens
<220> FEATURE:
<221> NAME/KEY: PEPTIDE
<222> LOCATION: (1)..(10)
<223> OTHER INFORMATION: IL-6 33-42

<400> SEQUENCE: 22

Leu Asp Gly Ile Ser Ala Leu Arg Lys Glu
1               5                   10

<210> SEQ ID NO 23
<211> LENGTH: 10
<212> TYPE: PRT
<213> ORGANISM: Homo sapiens
<220> FEATURE:
<221> NAME/KEY: PEPTIDE
<222> LOCATION: (1)..(10)
<223> OTHER INFORMATION: IL-6 34-43

<400> SEQUENCE: 23

Asp Gly Ile Ser Ala Leu Arg Lys Glu Thr
1               5                   10

<210> SEQ ID NO 24
<211> LENGTH: 10
<212> TYPE: PRT
<213> ORGANISM: Homo sapiens
<220> FEATURE:
<221> NAME/KEY: PEPTIDE
<222> LOCATION: (1)..(10)
<223> OTHER INFORMATION: IL-6 35-44

<400> SEQUENCE: 24

Gly Ile Ser Ala Leu Arg Lys Glu Thr Cys
1               5                   10

<210> SEQ ID NO 25
<211> LENGTH: 10
<212> TYPE: PRT
<213> ORGANISM: Homo sapiens
<220> FEATURE:
<221> NAME/KEY: PEPTIDE
<222> LOCATION: (1)..(10)
<223> OTHER INFORMATION: IL-6 36-45
```

<400> SEQUENCE: 25

Ile Ser Ala Leu Arg Lys Glu Thr Cys Asn
1               5                   10

<210> SEQ ID NO 26
<211> LENGTH: 10
<212> TYPE: PRT
<213> ORGANISM: Homo sapiens
<220> FEATURE:
<221> NAME/KEY: PEPTIDE
<222> LOCATION: (1)..(10)
<223> OTHER INFORMATION: IL-6 37-46

<400> SEQUENCE: 26

Ser Ala Leu Arg Lys Glu Thr Cys Asn Lys
1               5                   10

<210> SEQ ID NO 27
<211> LENGTH: 10
<212> TYPE: PRT
<213> ORGANISM: Homo sapiens
<220> FEATURE:
<221> NAME/KEY: PEPTIDE
<222> LOCATION: (1)..(10)
<223> OTHER INFORMATION: IL-6 38-47

<400> SEQUENCE: 27

Ala Leu Arg Lys Glu Thr Cys Asn Lys Ser
1               5                   10

<210> SEQ ID NO 28
<211> LENGTH: 10
<212> TYPE: PRT
<213> ORGANISM: Homo sapiens
<220> FEATURE:
<221> NAME/KEY: PEPTIDE
<222> LOCATION: (1)..(10)
<223> OTHER INFORMATION: IL-6 39-48

<400> SEQUENCE: 28

Leu Arg Lys Glu Thr Cys Asn Lys Ser Asn
1               5                   10

<210> SEQ ID NO 29
<211> LENGTH: 10
<212> TYPE: PRT
<213> ORGANISM: Homo sapiens
<220> FEATURE:
<221> NAME/KEY: PEPTIDE
<222> LOCATION: (1)..(10)
<223> OTHER INFORMATION: IL-6 40-49

<400> SEQUENCE: 29

Arg Lys Glu Thr Cys Asn Lys Ser Asn Met
1               5                   10

<210> SEQ ID NO 30
<211> LENGTH: 10
<212> TYPE: PRT
<213> ORGANISM: Homo sapiens
<220> FEATURE:
<221> NAME/KEY: PEPTIDE
<222> LOCATION: (1)..(10)
<223> OTHER INFORMATION: IL-6 41-50

```
<400> SEQUENCE: 30

Lys Glu Thr Cys Asn Lys Ser Asn Met Cys
1               5                   10

<210> SEQ ID NO 31
<211> LENGTH: 10
<212> TYPE: PRT
<213> ORGANISM: Homo sapiens
<220> FEATURE:
<221> NAME/KEY: PEPTIDE
<222> LOCATION: (1)..(10)
<223> OTHER INFORMATION: IL-6 42-51

<400> SEQUENCE: 31

Glu Thr Cys Asn Lys Ser Asn Met Cys Glu
1               5                   10

<210> SEQ ID NO 32
<211> LENGTH: 10
<212> TYPE: PRT
<213> ORGANISM: Homo sapiens
<220> FEATURE:
<221> NAME/KEY: PEPTIDE
<222> LOCATION: (1)..(10)
<223> OTHER INFORMATION: IL-6 43-52

<400> SEQUENCE: 32

Thr Cys Asn Lys Ser Asn Met Cys Glu Ser
1               5                   10

<210> SEQ ID NO 33
<211> LENGTH: 10
<212> TYPE: PRT
<213> ORGANISM: Homo sapiens
<220> FEATURE:
<221> NAME/KEY: PEPTIDE
<222> LOCATION: (1)..(10)
<223> OTHER INFORMATION: IL-6 44-53

<400> SEQUENCE: 33

Cys Asn Lys Ser Asn Met Cys Glu Ser Ser
1               5                   10

<210> SEQ ID NO 34
<211> LENGTH: 10
<212> TYPE: PRT
<213> ORGANISM: Homo sapiens
<220> FEATURE:
<221> NAME/KEY: PEPTIDE
<222> LOCATION: (1)..(10)
<223> OTHER INFORMATION: IL-6 45-54

<400> SEQUENCE: 34

Asn Lys Ser Asn Met Cys Glu Ser Ser Lys
1               5                   10

<210> SEQ ID NO 35
<211> LENGTH: 10
<212> TYPE: PRT
<213> ORGANISM: Homo sapiens
<220> FEATURE:
<221> NAME/KEY: PEPTIDE
<222> LOCATION: (1)..(10)
<223> OTHER INFORMATION: IL-6 46-55
```

```
<400> SEQUENCE: 35

Lys Ser Asn Met Cys Glu Ser Ser Lys Glu
1               5                   10

<210> SEQ ID NO 36
<211> LENGTH: 10
<212> TYPE: PRT
<213> ORGANISM: Homo sapiens
<220> FEATURE:
<221> NAME/KEY: PEPTIDE
<222> LOCATION: (1)..(10)
<223> OTHER INFORMATION: IL-6 47-56

<400> SEQUENCE: 36

Ser Asn Met Cys Glu Ser Ser Lys Glu Ala
1               5                   10

<210> SEQ ID NO 37
<211> LENGTH: 10
<212> TYPE: PRT
<213> ORGANISM: Homo sapiens
<220> FEATURE:
<221> NAME/KEY: PEPTIDE
<222> LOCATION: (1)..(10)
<223> OTHER INFORMATION: IL-6 48-57

<400> SEQUENCE: 37

Asn Met Cys Glu Ser Ser Lys Glu Ala Leu
1               5                   10

<210> SEQ ID NO 38
<211> LENGTH: 10
<212> TYPE: PRT
<213> ORGANISM: Homo sapiens
<220> FEATURE:
<221> NAME/KEY: PEPTIDE
<222> LOCATION: (1)..(10)
<223> OTHER INFORMATION: IL-6 49-58

<400> SEQUENCE: 38

Met Cys Glu Ser Ser Lys Glu Ala Leu Ala
1               5                   10

<210> SEQ ID NO 39
<211> LENGTH: 10
<212> TYPE: PRT
<213> ORGANISM: Homo sapiens
<220> FEATURE:
<221> NAME/KEY: PEPTIDE
<222> LOCATION: (1)..(10)
<223> OTHER INFORMATION: IL-6 50-59

<400> SEQUENCE: 39

Cys Glu Ser Ser Lys Glu Ala Leu Ala Glu
1               5                   10

<210> SEQ ID NO 40
<211> LENGTH: 10
<212> TYPE: PRT
<213> ORGANISM: Homo sapiens
<220> FEATURE:
<221> NAME/KEY: PEPTIDE
<222> LOCATION: (1)..(10)
<223> OTHER INFORMATION: IL-6 51-60
```

```
<400> SEQUENCE: 40

Glu Ser Ser Lys Glu Ala Leu Ala Glu Asn
1               5                   10

<210> SEQ ID NO 41
<211> LENGTH: 10
<212> TYPE: PRT
<213> ORGANISM: Homo sapiens
<220> FEATURE:
<221> NAME/KEY: PEPTIDE
<222> LOCATION: (1)..(10)
<223> OTHER INFORMATION: IL6- 52-61

<400> SEQUENCE: 41

Ser Ser Lys Glu Ala Leu Ala Glu Asn Asn
1               5                   10

<210> SEQ ID NO 42
<211> LENGTH: 10
<212> TYPE: PRT
<213> ORGANISM: Homo sapiens
<220> FEATURE:
<221> NAME/KEY: PEPTIDE
<222> LOCATION: (1)..(10)
<223> OTHER INFORMATION: IL-6 53-62

<400> SEQUENCE: 42

Ser Lys Glu Ala Leu Ala Glu Asn Asn Leu
1               5                   10

<210> SEQ ID NO 43
<211> LENGTH: 10
<212> TYPE: PRT
<213> ORGANISM: Homo sapiens
<220> FEATURE:
<221> NAME/KEY: PEPTIDE
<222> LOCATION: (1)..(10)
<223> OTHER INFORMATION: IL-6 54-63

<400> SEQUENCE: 43

Lys Glu Ala Leu Ala Glu Asn Asn Leu Asn
1               5                   10

<210> SEQ ID NO 44
<211> LENGTH: 10
<212> TYPE: PRT
<213> ORGANISM: Homo sapiens
<220> FEATURE:
<221> NAME/KEY: PEPTIDE
<222> LOCATION: (1)..(10)
<223> OTHER INFORMATION: IL-6 55-64

<400> SEQUENCE: 44

Glu Ala Leu Ala Glu Asn Asn Leu Asn Leu
1               5                   10

<210> SEQ ID NO 45
<211> LENGTH: 10
<212> TYPE: PRT
<213> ORGANISM: Homo sapiens
<220> FEATURE:
<221> NAME/KEY: PEPTIDE
<222> LOCATION: (1)..(10)
<223> OTHER INFORMATION: IL-6 56-65
```

```
<400> SEQUENCE: 45

Ala Leu Ala Glu Asn Asn Leu Asn Leu Pro
1               5                   10

<210> SEQ ID NO 46
<211> LENGTH: 10
<212> TYPE: PRT
<213> ORGANISM: Homo sapiens
<220> FEATURE:
<221> NAME/KEY: PEPTIDE
<222> LOCATION: (1)..(10)
<223> OTHER INFORMATION: IL-6 57-66

<400> SEQUENCE: 46

Leu Ala Glu Asn Asn Leu Asn Leu Pro Lys
1               5                   10

<210> SEQ ID NO 47
<211> LENGTH: 10
<212> TYPE: PRT
<213> ORGANISM: Homo sapiens
<220> FEATURE:
<221> NAME/KEY: PEPTIDE
<222> LOCATION: (1)..(10)
<223> OTHER INFORMATION: IL-6 58-67

<400> SEQUENCE: 47

Ala Glu Asn Asn Leu Asn Leu Pro Lys Met
1               5                   10

<210> SEQ ID NO 48
<211> LENGTH: 10
<212> TYPE: PRT
<213> ORGANISM: Homo sapiens
<220> FEATURE:
<221> NAME/KEY: PEPTIDE
<222> LOCATION: (1)..(10)
<223> OTHER INFORMATION: IL-6 59-68

<400> SEQUENCE: 48

Glu Asn Asn Leu Asn Leu Pro Lys Met Ala
1               5                   10

<210> SEQ ID NO 49
<211> LENGTH: 10
<212> TYPE: PRT
<213> ORGANISM: Homo sapiens
<220> FEATURE:
<221> NAME/KEY: PEPTIDE
<222> LOCATION: (1)..(10)
<223> OTHER INFORMATION: IL-6 60-69

<400> SEQUENCE: 49

Asn Asn Leu Asn Leu Pro Lys Met Ala Glu
1               5                   10

<210> SEQ ID NO 50
<211> LENGTH: 10
<212> TYPE: PRT
<213> ORGANISM: Homo sapiens
<220> FEATURE:
<221> NAME/KEY: PEPTIDE
<222> LOCATION: (1)..(10)
<223> OTHER INFORMATION: IL-6 61-70
```

```
<400> SEQUENCE: 50

Asn Leu Asn Leu Pro Lys Met Ala Glu Lys
1               5                   10

<210> SEQ ID NO 51
<211> LENGTH: 10
<212> TYPE: PRT
<213> ORGANISM: Homo sapiens
<220> FEATURE:
<221> NAME/KEY: PEPTIDE
<222> LOCATION: (1)..(10)
<223> OTHER INFORMATION: IL-6 62-71

<400> SEQUENCE: 51

Leu Asn Leu Pro Lys Met Ala Glu Lys Asp
1               5                   10

<210> SEQ ID NO 52
<211> LENGTH: 10
<212> TYPE: PRT
<213> ORGANISM: Homo sapiens
<220> FEATURE:
<221> NAME/KEY: PEPTIDE
<222> LOCATION: (1)..(10)
<223> OTHER INFORMATION: IL-6 63-72

<400> SEQUENCE: 52

Asn Leu Pro Lys Met Ala Glu Lys Asp Gly
1               5                   10

<210> SEQ ID NO 53
<211> LENGTH: 10
<212> TYPE: PRT
<213> ORGANISM: Homo sapiens
<220> FEATURE:
<221> NAME/KEY: PEPTIDE
<222> LOCATION: (1)..(10)
<223> OTHER INFORMATION: IL-6 64-73

<400> SEQUENCE: 53

Leu Pro Lys Met Ala Glu Lys Asp Gly Cys
1               5                   10

<210> SEQ ID NO 54
<211> LENGTH: 10
<212> TYPE: PRT
<213> ORGANISM: Homo sapiens
<220> FEATURE:
<221> NAME/KEY: PEPTIDE
<222> LOCATION: (1)..(10)
<223> OTHER INFORMATION: IL-6 65-74

<400> SEQUENCE: 54

Pro Lys Met Ala Glu Lys Asp Gly Cys Phe
1               5                   10

<210> SEQ ID NO 55
<211> LENGTH: 10
<212> TYPE: PRT
<213> ORGANISM: Homo sapiens
<220> FEATURE:
<221> NAME/KEY: PEPTIDE
<222> LOCATION: (1)..(10)
<223> OTHER INFORMATION: IL-6 66-75
```

```
<400> SEQUENCE: 55

Lys Met Ala Glu Lys Asp Gly Cys Phe Gln
1               5                   10

<210> SEQ ID NO 56
<211> LENGTH: 10
<212> TYPE: PRT
<213> ORGANISM: Homo sapiens
<220> FEATURE:
<221> NAME/KEY: PEPTIDE
<222> LOCATION: (1)..(10)
<223> OTHER INFORMATION: IL-6 67-76

<400> SEQUENCE: 56

Met Ala Glu Lys Asp Gly Cys Phe Gln Ser
1               5                   10

<210> SEQ ID NO 57
<211> LENGTH: 10
<212> TYPE: PRT
<213> ORGANISM: Homo sapiens
<220> FEATURE:
<221> NAME/KEY: PEPTIDE
<222> LOCATION: (1)..(10)
<223> OTHER INFORMATION: IL-6 68-77

<400> SEQUENCE: 57

Ala Glu Lys Asp Gly Cys Phe Gln Ser Gly
1               5                   10

<210> SEQ ID NO 58
<211> LENGTH: 10
<212> TYPE: PRT
<213> ORGANISM: Homo sapiens
<220> FEATURE:
<221> NAME/KEY: PEPTIDE
<222> LOCATION: (1)..(10)
<223> OTHER INFORMATION: IL-6 69-78

<400> SEQUENCE: 58

Glu Lys Asp Gly Cys Phe Gln Ser Gly Phe
1               5                   10

<210> SEQ ID NO 59
<211> LENGTH: 10
<212> TYPE: PRT
<213> ORGANISM: Homo sapiens
<220> FEATURE:
<221> NAME/KEY: PEPTIDE
<222> LOCATION: (1)..(10)
<223> OTHER INFORMATION: IL-6 70-79

<400> SEQUENCE: 59

Lys Asp Gly Cys Phe Gln Ser Gly Phe Asn
1               5                   10

<210> SEQ ID NO 60
<211> LENGTH: 10
<212> TYPE: PRT
<213> ORGANISM: Homo sapiens
<220> FEATURE:
<221> NAME/KEY: PEPTIDE
<222> LOCATION: (1)..(10)
<223> OTHER INFORMATION: IL-6 71-80
```

```
<400> SEQUENCE: 60

Asp Gly Cys Phe Gln Ser Gly Phe Asn Glu
1               5                   10

<210> SEQ ID NO 61
<211> LENGTH: 10
<212> TYPE: PRT
<213> ORGANISM: Homo sapiens
<220> FEATURE:
<221> NAME/KEY: PEPTIDE
<222> LOCATION: (1)..(10)
<223> OTHER INFORMATION: IL-6 72-81

<400> SEQUENCE: 61

Gly Cys Phe Gln Ser Gly Phe Asn Glu Glu
1               5                   10

<210> SEQ ID NO 62
<211> LENGTH: 10
<212> TYPE: PRT
<213> ORGANISM: Homo sapiens
<220> FEATURE:
<221> NAME/KEY: PEPTIDE
<222> LOCATION: (1)..(10)
<223> OTHER INFORMATION: IL-6 73-82

<400> SEQUENCE: 62

Cys Phe Gln Ser Gly Phe Asn Glu Glu Thr
1               5                   10

<210> SEQ ID NO 63
<211> LENGTH: 10
<212> TYPE: PRT
<213> ORGANISM: Homo sapiens
<220> FEATURE:
<221> NAME/KEY: PEPTIDE
<222> LOCATION: (1)..(10)
<223> OTHER INFORMATION: IL-6 74-83

<400> SEQUENCE: 63

Phe Gln Ser Gly Phe Asn Glu Glu Thr Cys
1               5                   10

<210> SEQ ID NO 64
<211> LENGTH: 10
<212> TYPE: PRT
<213> ORGANISM: Homo sapiens
<220> FEATURE:
<221> NAME/KEY: PEPTIDE
<222> LOCATION: (1)..(10)
<223> OTHER INFORMATION: IL-6 75-84

<400> SEQUENCE: 64

Gln Ser Gly Phe Asn Glu Glu Thr Cys Leu
1               5                   10

<210> SEQ ID NO 65
<211> LENGTH: 10
<212> TYPE: PRT
<213> ORGANISM: Homo sapiens
<220> FEATURE:
<221> NAME/KEY: PEPTIDE
<222> LOCATION: (1)..(10)
<223> OTHER INFORMATION: IL-6 76-85
```

```
<400> SEQUENCE: 65

Ser Gly Phe Asn Glu Glu Thr Cys Leu Val
1               5                   10

<210> SEQ ID NO 66
<211> LENGTH: 10
<212> TYPE: PRT
<213> ORGANISM: Homo sapiens
<220> FEATURE:
<221> NAME/KEY: PEPTIDE
<222> LOCATION: (1)..(10)
<223> OTHER INFORMATION: IL-6 77-86

<400> SEQUENCE: 66

Gly Phe Asn Glu Glu Thr Cys Leu Val Lys
1               5                   10

<210> SEQ ID NO 67
<211> LENGTH: 10
<212> TYPE: PRT
<213> ORGANISM: Homo sapiens
<220> FEATURE:
<221> NAME/KEY: PEPTIDE
<222> LOCATION: (1)..(10)
<223> OTHER INFORMATION: IL-6 78-87

<400> SEQUENCE: 67

Phe Asn Glu Glu Thr Cys Leu Val Lys Ile
1               5                   10

<210> SEQ ID NO 68
<211> LENGTH: 10
<212> TYPE: PRT
<213> ORGANISM: Homo sapiens
<220> FEATURE:
<221> NAME/KEY: PEPTIDE
<222> LOCATION: (1)..(10)
<223> OTHER INFORMATION: IL-6 79-88

<400> SEQUENCE: 68

Asn Glu Glu Thr Cys Leu Val Lys Ile Ile
1               5                   10

<210> SEQ ID NO 69
<211> LENGTH: 10
<212> TYPE: PRT
<213> ORGANISM: Homo sapiens
<220> FEATURE:
<221> NAME/KEY: PEPTIDE
<222> LOCATION: (1)..(10)
<223> OTHER INFORMATION: IL-6 80-89

<400> SEQUENCE: 69

Glu Glu Thr Cys Leu Val Lys Ile Ile Thr
1               5                   10

<210> SEQ ID NO 70
<211> LENGTH: 10
<212> TYPE: PRT
<213> ORGANISM: Homo sapiens
<220> FEATURE:
<221> NAME/KEY: PEPTIDE
<222> LOCATION: (1)..(10)
<223> OTHER INFORMATION: IL-6 81-90
```

<400> SEQUENCE: 70

Glu Thr Cys Leu Val Lys Ile Ile Thr Gly
1               5                   10

<210> SEQ ID NO 71
<211> LENGTH: 10
<212> TYPE: PRT
<213> ORGANISM: Homo sapiens
<220> FEATURE:
<221> NAME/KEY: PEPTIDE
<222> LOCATION: (1)..(10)
<223> OTHER INFORMATION: IL-6 82-91

<400> SEQUENCE: 71

Thr Cys Leu Val Lys Ile Ile Thr Gly Leu
1               5                   10

<210> SEQ ID NO 72
<211> LENGTH: 14
<212> TYPE: PRT
<213> ORGANISM: Rattus norvegicus
<220> FEATURE:
<221> NAME/KEY: PEPTIDE
<222> LOCATION: (1)..(14)
<223> OTHER INFORMATION: Rat IL-6 150-162, C150 substitute K150, C162
      substitute T162

<400> SEQUENCE: 72

Cys Leu Glu Ser Gln Lys Glu Trp Leu Arg Thr Lys Thr Cys
1               5                   10

<210> SEQ ID NO 73
<211> LENGTH: 23
<212> TYPE: PRT
<213> ORGANISM: Rattus norvegicus
<220> FEATURE:
<221> NAME/KEY: PEPTIDE
<222> LOCATION: (1)..(23)
<223> OTHER INFORMATION: rat IL-6 144-166
<220> FEATURE:
<221> NAME/KEY: PEPTIDE
<222> LOCATION: (1)..(23)
<223> OTHER INFORMATION: rat IL-6 144-166, C144 substitute N144, C166
      substitute I162

<400> SEQUENCE: 73

Asn Ala Leu Leu Met Glu Lys Leu Glu Ser Gln Lys Glu Trp Leu Arg
1               5                   10                  15

Thr Lys Thr Ile Gln Leu Ile
            20

<210> SEQ ID NO 74
<211> LENGTH: 11
<212> TYPE: PRT
<213> ORGANISM: Rattus norvegicus
<220> FEATURE:
<221> NAME/KEY: PEPTIDE
<222> LOCATION: (1)..(11)
<223> OTHER INFORMATION: rat IL-6 72-82

<400> SEQUENCE: 74

Cys Phe Gln Thr Gly Tyr Asn Gln Glu Ile Cys
1               5                   10

<210> SEQ ID NO 75
<211> LENGTH: 11
<212> TYPE: PRT

```
<213> ORGANISM: Macaca fascicularis
<220> FEATURE:
<221> NAME/KEY: PEPTIDE
<222> LOCATION: (1)..(11)
<223> OTHER INFORMATION: macaque IL-6 73-83

<400> SEQUENCE: 75

Cys Phe Gln Ser Gly Phe Asn Glu Asp Thr Cys
1               5                   10

<210> SEQ ID NO 76
<211> LENGTH: 6
<212> TYPE: PRT
<213> ORGANISM: Artificial Sequence
<220> FEATURE:
<223> OTHER INFORMATION: Synthetic peptide
<220> FEATURE:
<221> NAME/KEY: PEPTIDE
<222> LOCATION: (1)..(6)
<223> OTHER INFORMATION: Spacer1
<220> FEATURE:
<221> NAME/KEY: SITE
<222> LOCATION: (3)..(3)
<223> OTHER INFORMATION: Any amino acid, preferably aspartic acid
<220> FEATURE:
<221> NAME/KEY: SITE
<222> LOCATION: (5)..(5)
<223> OTHER INFORMATION: Any amino acid, preferably aspartic acid

<400> SEQUENCE: 76

Pro Pro Xaa Pro Xaa Pro
1               5

<210> SEQ ID NO 77
<211> LENGTH: 4
<212> TYPE: PRT
<213> ORGANISM: Artificial Sequence
<220> FEATURE:
<223> OTHER INFORMATION: Synthetic peptide
<220> FEATURE:
<221> NAME/KEY: PEPTIDE
<222> LOCATION: (1)..(4)
<223> OTHER INFORMATION: epsilon K-KKK as spacer
<220> FEATURE:
<221> NAME/KEY: SITE
<222> LOCATION: (1)..(1)
<223> OTHER INFORMATION: epsilon-K

<400> SEQUENCE: 77

Lys Lys Lys Lys
1

<210> SEQ ID NO 78
<211> LENGTH: 17
<212> TYPE: PRT
<213> ORGANISM: Clostridium tetani
<220> FEATURE:
<221> NAME/KEY: PEPTIDE
<222> LOCATION: (1)..(17)
<223> OTHER INFORMATION: Clostridium tetani 1 Th

<400> SEQUENCE: 78

Lys Lys Gln Tyr Ile Lys Ala Asn Ser Lys Phe Ile Gly Ile Thr Glu
1               5                   10                  15

Leu

<210> SEQ ID NO 79
<211> LENGTH: 15
<212> TYPE: PRT
<213> ORGANISM: Measles virus
```

```
<220> FEATURE:
<221> NAME/KEY: PEPTIDE
<222> LOCATION: (1)..(15)
<223> OTHER INFORMATION: MvF1 Th

<400> SEQUENCE: 79

Leu Ser Glu Ile Lys Gly Val Ile Val His Arg Leu Glu Gly Val
1               5                   10                  15

<210> SEQ ID NO 80
<211> LENGTH: 24
<212> TYPE: PRT
<213> ORGANISM: Bordetella pertussis
<220> FEATURE:
<221> NAME/KEY: PEPTIDE
<222> LOCATION: (1)..(24)
<223> OTHER INFORMATION: Bordetella pertussis Th

<400> SEQUENCE: 80

Gly Ala Tyr Ala Arg Cys Pro Asn Gly Thr Arg Ala Leu Thr Val Ala
1               5                   10                  15

Glu Leu Arg Gly Asn Ala Glu Leu
            20

<210> SEQ ID NO 81
<211> LENGTH: 17
<212> TYPE: PRT
<213> ORGANISM: Clostridium tetani
<220> FEATURE:
<221> NAME/KEY: PEPTIDE
<222> LOCATION: (1)..(17)
<223> OTHER INFORMATION: Clostridium tetani 2 Th

<400> SEQUENCE: 81

Trp Val Arg Asp Ile Ile Asp Asp Phe Thr Asn Glu Ser Ser Gln Lys
1               5                   10                  15

Thr

<210> SEQ ID NO 82
<211> LENGTH: 23
<212> TYPE: PRT
<213> ORGANISM: diphtheria bacilli
<220> FEATURE:
<221> NAME/KEY: PEPTIDE
<222> LOCATION: (1)..(23)
<223> OTHER INFORMATION: Diphtheria Th

<400> SEQUENCE: 82

Asp Ser Glu Thr Ala Asp Asn Leu Glu Lys Thr Val Ala Ala Leu Ser
1               5                   10                  15

Ile Leu Pro Gly His Gly Cys
            20

<210> SEQ ID NO 83
<211> LENGTH: 21
<212> TYPE: PRT
<213> ORGANISM: Plasmodium falciparum
<220> FEATURE:
<221> NAME/KEY: PEPTIDE
<222> LOCATION: (1)..(21)
<223> OTHER INFORMATION: Plasmodium falciparum Th
```

<400> SEQUENCE: 83

Asp His Glu Lys Lys His Ala Lys Met Glu Lys Ala Ser Ser Val Phe
1               5                   10                  15

Asn Val Val Asn Ser
            20

<210> SEQ ID NO 84
<211> LENGTH: 17
<212> TYPE: PRT
<213> ORGANISM: Schistosoma mansoni
<220> FEATURE:
<221> NAME/KEY: PEPTIDE
<222> LOCATION: (1)..(17)
<223> OTHER INFORMATION: Schistosoma mansoni Th

<400> SEQUENCE: 84

Lys Trp Phe Lys Thr Asn Ala Pro Asn Gly Val Asp Glu Lys His Arg
1               5                   10                  15

His

<210> SEQ ID NO 85
<211> LENGTH: 25
<212> TYPE: PRT
<213> ORGANISM: Cholera Toxin
<220> FEATURE:
<221> NAME/KEY: PEPTIDE
<222> LOCATION: (1)..(25)
<223> OTHER INFORMATION: Cholera Toxin Th

<400> SEQUENCE: 85

Ala Leu Asn Ile Trp Asp Arg Phe Asp Val Phe Cys Thr Leu Gly Ala
1               5                   10                  15

Thr Thr Gly Tyr Leu Lys Gly Asn Ser
            20                  25

<210> SEQ ID NO 86
<211> LENGTH: 15
<212> TYPE: PRT
<213> ORGANISM: Measles virus
<220> FEATURE:
<221> NAME/KEY: PEPTIDE
<222> LOCATION: (1)..(15)
<223> OTHER INFORMATION: MvF 2 Th

<400> SEQUENCE: 86

Ile Ser Glu Ile Lys Gly Val Ile Val His Lys Ile Glu Gly Ile
1               5                   10                  15

<210> SEQ ID NO 87
<211> LENGTH: 22
<212> TYPE: PRT
<213> ORGANISM: Measles virus
<220> FEATURE:
<221> NAME/KEY: PEPTIDE
<222> LOCATION: (1)..(22)
<223> OTHER INFORMATION: KKKMvF 3 Th
<220> FEATURE:
<221> NAME/KEY: SITE
<222> LOCATION: (7)..(7)
<223> OTHER INFORMATION: S or T
<220> FEATURE:
<221> NAME/KEY: SITE
<222> LOCATION: (10)..(10)
<223> OTHER INFORMATION: K or R
<220> FEATURE:
<221> NAME/KEY: SITE
<222> LOCATION: (11)..(11)

```
<223> OTHER INFORMATION: G or T
<220> FEATURE:
<221> NAME/KEY: SITE
<222> LOCATION: (15)..(15)
<223> OTHER INFORMATION: H or T
<220> FEATURE:
<221> NAME/KEY: SITE
<222> LOCATION: (16)..(16)
<223> OTHER INFORMATION: K or R
<220> FEATURE:
<221> NAME/KEY: SITE
<222> LOCATION: (19)..(19)
<223> OTHER INFORMATION: G or T

<400> SEQUENCE: 87

Lys Lys Lys Ile Ser Ile Xaa Glu Ile Xaa Xaa Val Ile Val Xaa Xaa
1               5                   10                  15

Ile Glu Xaa Ile Leu Phe
            20

<210> SEQ ID NO 88
<211> LENGTH: 18
<212> TYPE: PRT
<213> ORGANISM: Hepatitis B virus
<220> FEATURE:
<221> NAME/KEY: PEPTIDE
<222> LOCATION: (1)..(18)
<223> OTHER INFORMATION: HBsAg 1 Th
<220> FEATURE:
<221> NAME/KEY: SITE
<222> LOCATION: (1)..(1)
<223> OTHER INFORMATION: K or R
<220> FEATURE:
<221> NAME/KEY: SITE
<222> LOCATION: (2)..(2)
<223> OTHER INFORMATION: K or R
<220> FEATURE:
<221> NAME/KEY: SITE
<222> LOCATION: (3)..(3)
<223> OTHER INFORMATION: K or R
<220> FEATURE:
<221> NAME/KEY: SITE
<222> LOCATION: (4)..(4)
<223> OTHER INFORMATION: L or I or V or F
<220> FEATURE:
<221> NAME/KEY: SITE
<222> LOCATION: (5)..(5)
<223> OTHER INFORMATION: F or K or R
<220> FEATURE:
<221> NAME/KEY: SITE
<222> LOCATION: (6)..(6)
<223> OTHER INFORMATION: L or I or V or F
<220> FEATURE:
<221> NAME/KEY: SITE
<222> LOCATION: (7)..(7)
<223> OTHER INFORMATION: L or I or V or F
<220> FEATURE:
<221> NAME/KEY: SITE
<222> LOCATION: (9)..(9)
<223> OTHER INFORMATION: K or R
<220> FEATURE:
<221> NAME/KEY: SITE
<222> LOCATION: (10)..(10)
<223> OTHER INFORMATION: L or I or V or F
<220> FEATURE:
<221> NAME/KEY: SITE
<222> LOCATION: (11)..(11)
<223> OTHER INFORMATION: L or I or V or F
<220> FEATURE:
<221> NAME/KEY: SITE
<222> LOCATION: (13)..(13)
<223> OTHER INFORMATION: L or I or V or F
<220> FEATURE:
<221> NAME/KEY: SITE
<222> LOCATION: (15)..(15)
<223> OTHER INFORMATION: Q or L or I or V or F
```

-continued

```
<220> FEATURE:
<221> NAME/KEY: SITE
<222> LOCATION: (17)..(17)
<223> OTHER INFORMATION: L or I or V or F
<220> FEATURE:
<221> NAME/KEY: SITE
<222> LOCATION: (18)..(18)
<223> OTHER INFORMATION: D or R

<400> SEQUENCE: 88

Xaa Xaa Xaa Xaa Xaa Xaa Xaa Thr Xaa Xaa Xaa Thr Xaa Pro Xaa Ser
1               5                   10                  15

Xaa Xaa

<210> SEQ ID NO 89
<211> LENGTH: 19
<212> TYPE: PRT
<213> ORGANISM: Measles virus
<220> FEATURE:
<221

```
<221> NAME/KEY: SITE
<222> LOCATION: (11)..(11)
<223> OTHER INFORMATION: I or L
<220> FEATURE:
<221> NAME/KEY: SITE
<222> LOCATION: (14)..(14)
<223> OTHER INFORMATION: P or I
<220> FEATURE:
<221> NAME/KEY: SITE
<222> LOCATION: (15)..(15)
<223> OTHER INFORMATION: Q or T
<220> FEATURE:
<221> NAME/KEY: SITE
<222> LOCATION: (16)..(16)
<223> OTHER INFORMATION: S or T
<220> FEATURE:
<221> NAME/KEY: SITE
<222> LOCATION: (17)..(17)
<223> OTHER INFORMATION: L or I

<400> SEQUENCE: 90

Lys Lys Lys Xaa Xaa Xaa Xaa Thr Arg Ile Xaa Thr Ile Xaa Xaa Xaa
1               5                   10                  15

Xaa Asp

<210> SEQ ID NO 91
<211> LENGTH: 19
<212> TYPE: PRT
<213> ORGANISM: Measles virus
<220> FEATURE:
<221> NAME/KEY: PEPTIDE
<222> LOCATION: (1)..(19)
<223> OTHER INFORMATION: MvF 5 Th (UBITh1)

<400> SEQUENCE: 91

Ile Ser Ile Thr Glu Ile Lys Gly Val Ile Val His Arg Ile Glu Thr
1               5                   10                  15

```
<212> TYPE: PRT
<213> ORGANISM: Influenza virus
<220> FEATURE:
<221> NAME/KEY: PEPTIDE
<222> LOCATION: (1)..(15)
<223> OTHER INFORMATION: Influenza MP1_2 Th

<400> SEQUENCE: 94

Ser Gly Pro Leu Lys Ala Glu Ile Ala Gln Arg Leu Glu Asp Val
1               5                   10                  15

<210> SEQ ID NO 95
<211> LENGTH: 9
<212> TYPE: PRT
<213> ORGANISM: Influenza virus
<220> FEATURE:
<221> NAME/KEY: PEPTIDE
<222> LOCATION: (1)..(9)
<223> OTHER INFORMATION: Influenza NSP1 Th

<400> SEQUENCE: 95

Asp Arg Leu Arg Arg Asp Gln Lys Ser
1               5

<210> SEQ ID NO 96
<211> LENGTH: 19
<212> TYPE: PRT
<213> ORGANISM: Epstein-Barr virus
<220> FEATURE:
<221> NAME/KEY: PEPTIDE
<222> LOCATION: (1)..(19)
<223> OTHER INFORMATION: EBV BHRF1 Th

<400> SEQUENCE: 96

Ala Gly Leu Thr Leu Ser Leu Leu Val Ile Cys Ser Tyr Leu Phe Ile
1               5                   10                  15

Ser Arg Gly

<210> SEQ ID NO 97
<211> LENGTH: 15
<212> TYPE: PRT
<213> ORGANISM: Clostridium tetani
<220> FEATURE:
<221> NAME/KEY: PEPTIDE
<222> LOCATION: (1)..(15)
<223> OTHER INFORMATION: Clostridium tetani TT1 Th

<400> SEQUENCE: 97

Gln Tyr Ile Lys Ala Asn Ser Lys Phe Ile Gly Ile Thr Glu Leu
1               5                   10                  15

<210> SEQ ID NO 98
<211> LENGTH: 20
<212> TYPE: PRT
<213> ORGANISM: Epstein-Barr virus
<220> FEATURE:
<221> NAME/KEY: PEPTIDE
<222> LOCATION: (1)..(20)
<223> OTHER INFORMATION: EBV EBNA-1 Th

<400> SEQUENCE: 98

Pro Gly Pro Leu Arg Glu Ser Ile Val Cys Tyr Phe Met Val Phe Leu
1               5                   10                  15

Gln Thr His Ile
            20

<210> SEQ ID NO 99
```

```
<211> LENGTH: 21
<212> TYPE: PRT
<213> ORGANISM: Clostridium tetani
<220> FEATURE:
<221> NAME/KEY: PEPTIDE
<222> LOCATION: (1)..(21)
<223> OTHER INFORMATION: Clostridium tetani TT2 Th

<400> SEQUENCE: 99

Phe Asn Asn Phe Thr Val Ser Phe Trp Leu Arg Val Pro Lys Val Ser
1 5 10 15

Ala Ser His Leu Glu
20

<210> SEQ ID NO 100
<211> LENGTH: 16
<212> TYPE: PRT
<213> ORGANISM: Clostridium tetani
<220> FEATURE:
<221> NAME/KEY: PEPTIDE
<222> LOCATION: (1)..(16)
<223> OTHER INFORMATION: Clostridium tetani TT3 Th

<400> SEQUENCE: 100

Lys Phe Ile Ile Lys Arg Tyr Thr Pro Asn Asn Glu Ile Asp Ser Phe
1 5 10 15

<210> SEQ ID NO 101
<211> LENGTH: 16
<212> TYPE: PRT
<213> ORGANISM: Clostridium tetani
<220> FEATURE:
<221> NAME/KEY: PEPTIDE
<222> LOCATION: (1)..(16)
<223> OTHER INFORMATION: Clostridium tetani TT4 Th

<400> SEQUENCE: 101

Val Ser Ile Asp Lys Phe Arg Ile Phe Cys Lys Ala Leu Asn Pro Lys
1 5 10 15

<210> SEQ ID NO 102
<211> LENGTH: 18
<212> TYPE: PRT
<213> ORGANISM: Epstein-Barr virus
<220> FEATURE:
<221> NAME/KEY: PEPTIDE
<222> LOCATION: (1)..(18)
<223> OTHER INFORMATION: EBV CP Th

<400> SEQUENCE: 102

Val Pro Gly Leu Tyr Ser Pro Cys Arg Ala Phe Phe Asn Lys Glu Glu
1 5 10 15

Leu Leu

<210> SEQ ID NO 103
<211> LENGTH: 14
<212> TYPE: PRT
<213> ORGANISM: Human cytomegalovirus
<220> FEATURE:
<221> NAME/KEY: PEPTIDE
<222> LOCATION: (1)..(14)
<223> OTHER INFORMATION: HCMV IE1 Th

<400> SEQUENCE: 103

Asp Lys Arg Glu Met Trp Met Ala Cys Ile Lys Glu Leu His
1 5 10

```
<210> SEQ ID NO 104
<211> LENGTH: 15
<212> TYPE: PRT
<213> ORGANISM: Epstein-Barr virus
<220> FEATURE:
<221> NAME/KEY: PEPTIDE
<222> LOCATION: (1)..(15)
<223> OTHER INFORMATION: EBV GP340 Th

<400> SEQUENCE: 104

Thr Gly His Gly Ala Arg Thr Ser Thr Glu Pro Thr Thr Asp Tyr
1               5                   10                  15

<210> SEQ ID NO 105
<211> LENGTH: 13
<212> TYPE: PRT
<213> ORGANISM: Epstein-Barr virus
<220> FEATURE:
<221> NAME/KEY: PEPTIDE
<222> LOCATION: (1)..(13)
<223> OTHER INFORMATION: EBV BPLF1 Th

<400> SEQUENCE: 105

Lys Glu Leu Lys Arg Gln Tyr Glu Lys Lys Leu Arg Gln
1               5                   10

<210> SEQ ID NO 106
<211> LENGTH: 11
<212> TYPE: PRT
<213> ORGANISM: Epstein-Barr virus
<220> FEATURE:
<221> NAME/KEY: PEPTIDE
<222> LOCATION: (1)..(11)
<223> OTHER INFORMATION: EBV EBNA-2 Th

<400> SEQUENCE: 106

Thr Val Phe Tyr Asn Ile Pro Pro Met Pro Leu
1               5                   10

<210> SEQ ID NO 107
<211> LENGTH: 34
<212> TYPE: PRT
<213> ORGANISM: Homo sapiens
<220> FEATURE:
<221> NAME/KEY: PEPTIDE
<222> LOCATION: (1)..(19)
<223> OTHER INFORMATION: MvF 4 Th (UBITh3)
<220> FEATURE:
<221> NAME/KEY: SITE
<222> LOCATION: (4)..(4)
<223> OTHER INFORMATION: S or T
<220> FEATURE:
<221> NAME/KEY: SITE
<222> LOCATION: (7)..(7)
<223> OTHER INFORMATION: K or R
<220> FEATURE:
<221> NAME/KEY: SITE
<222> LOCATION: (8)..(8)
<223> OTHER INFORMATION: G or T
<220> FEATURE:
<221> NAME/KEY: SITE
<222> LOCATION: (12)..(12)
<223> OTHER INFORMATION: H or T
<220> FEATURE:
<221> NAME/KEY: SITE
<222> LOCATION: (13)..(13)
<223> OTHER INFORMATION: K or R
<220> FEATURE:
<221> NAME/KEY: PEPTIDE
<222> LOCATION: (20)..(23)
<223> OTHER INFORMATION: epsilon K-KKK as a spacer
<220> FEATURE:
<221> NAME/KEY: SITE
```

```
<222> LOCATION: (20)..(20)
<223> OTHER INFORMATION: epsilon-K
<220> FEATURE:
<221> NAME/KEY: PEPTIDE
<222> LOCATION: (24)..(34)
<223> OTHER INFORMATION: IL-6 73-83 cyclized

<400> SEQUENCE: 107

Ile Ser Ile Xaa Glu Ile Xaa Xaa Val Ile Val Xaa Xaa Ile Glu Thr
1               5                   10                  15

Ile Leu Phe Lys Lys Lys Lys Cys Phe Gln Ser Gly Phe Asn Glu Glu
            20                  25                  30

Thr Cys

<210> SEQ ID NO 108
<211> LENGTH: 34
<212> TYPE: PRT
<213> ORGANISM: Homo sapiens
<220> FEATURE:
<221> NAME/KEY: PEPTIDE
<222> LOCATION: (1)..(11)
<223> OTHER INFORMATION: IL-6 73-83 cyclized
<220> FEATURE:
<221> NAME/KEY: PEPTIDE
<222> LOCATION: (12)..(15)
<223> OTHER INFORMATION: epsilon K-KKK as a spacer
<220> FEATURE:
<221> NAME/KEY: SITE
<222> LOCATION: (15)..(15)
<223> OTHER INFORMATION: epsilon-K
<220> FEATURE:
<221> NAME/KEY: PEPTIDE
<222> LOCATION: (16)..(34)
<223> OTHER INFORMATION: MvF4 Th (UBITh3)
<220> FEATURE:
<221> NAME/KEY: SITE
<222> LOCATION: (19)..(19)
<223> OTHER INFORMATION: S or T
<220> FEATURE:
<221> NAME/KEY: SITE
<222> LOCATION: (22)..(22)
<223> OTHER INFORMATION: K or R
<220> FEATURE:
<221> NAME/KEY: SITE
<222> LOCATION: (23)..(23)
<223> OTHER INFORMATION: G or T
<220> FEATURE:
<221> NAME/KEY: SITE
<222> LOCATION: (27)..(27)
<223> OTHER INFORMATION: H or T
<220> FEATURE:
<221> NAME/KEY: SITE
<222> LOCATION: (28)..(28)
<223> OTHER INFORMATION: K or R

<400> SEQUENCE: 108

Cys Phe Gln Ser Gly Phe Asn Glu Glu Thr Cys Lys Lys Lys Lys Ile
1               5                   10                  15

Ser Ile Xaa Glu Ile Xaa Xaa Val Ile Val Xaa Xaa Ile Glu Thr Ile
            20                  25                  30

Leu Phe

<210> SEQ ID NO 109
<211> LENGTH: 54
<212> TYPE: PRT
<213> ORGANISM: Homo sapiens
<220> FEATURE:
<221> NAME/KEY: PEPTIDE
<222> LOCATION: (1)..(19)
<223> OTHER INFORMATION: MvF4 Th (UBITh3)
<220> FEATURE:
```

```
<221> NAME/KEY: SITE
<222> LOCATION: (4)..(4)
<223> OTHER INFORMATION: S or T
<220> FEATURE:
<221> NAME/KEY: SITE
<222> LOCATION: (7)..(7)
<223> OTHER INFORMATION: K or R
<220> FEATURE:
<221> NAME/KEY: SITE
<222> LOCATION: (8)..(8)
<223> OTHER INFORMATION: G or T
<220> FEATURE:
<221> NAME/KEY: SITE
<222> LOCATION: (12)..(12)
<223> OTHER INFORMATION: H or T
<220> FEATURE:
<221> NAME/KEY: SITE
<222> LOCATION: (13)..(13)
<223> OTHER INFORMATION: K or R
<220> FEATURE:
<221> NAME/KEY: SITE
<222> LOCATION: (20)..(20)
<223> OTHER INFORMATION: epsilon-K
<220> FEATURE:
<221> NAME/KEY: PEPTIDE
<222> LOCATION: (20)..(23)
<223> OTHER INFORMATION: epsilon K-KKK as a spacer
<220> FEATURE:
<221> NAME/KEY: PEPTIDE
<222> LOCATION: (24)..(54)
<223> OTHER INFORMATION: IL-6 154-184

<400> SEQUENCE: 109

Ile Ser Ile Xaa Glu Ile Xaa Xaa Val Ile Val Xaa Xaa Ile Glu Thr
1               5                   10                  15

Ile Leu Phe Lys Lys Lys Lys Gln Asn Gln Trp Leu Gln Asp Met Thr
            20                  25                  30

Thr His Leu Ile Leu Arg Ser Phe Lys Glu Phe Leu Gln Ser Ser Leu
        35                  40                  45

Arg Ala Leu Arg Gln Met
    50

<210> SEQ ID NO 110
<211> LENGTH: 58
<212> TYPE: PRT
<213> ORGANISM: Homo sapiens
<220> FEATURE:
<221> NAME/KEY: PEPTIDE
<222> LOCATION: (1)..(31)
<223> OTHER INFORMATION: (IL-6 154-184) x 6 as branched peptide
<220> FEATURE:
<221> NAME/KEY: SITE
<222> LOCATION: (32)..(33)
<223> OTHER INFORMATION: (epsilon K-K) x 4 as a linker
<220> FEATURE:
<221> NAME/KEY: SITE
<222> LOCATION: (34)..(35)
<223> OTHER INFORMATION: (epsilon K-K) x 2 as a linker
<220> FEATURE:
<221> NAME/KEY: PEPTIDE
<222> LOCATION: (36)..(39)
<223> OTHER INFORMATION: epsilon K-KKK as a spacer
<220> FEATURE:
<221> NAME/KEY: PEPTIDE
<222> LOCATION: (40)..(58)
<223> OTHER INFORMATION: MvF4 Th  (UBITh3)
<220> FEATURE:
<221> NAME/KEY: SITE
<222> LOCATION: (43)..(43)
<223> OTHER INFORMATION: S or T
<220> FEATURE:
<221> NAME/KEY: SITE
<222> LOCATION: (46)..(46)
<223> OTHER INFORMATION: K or R
```

```
<220> FEATURE:
<221> NAME/KEY: SITE
<222> LOCATION: (47)..(47)
<223> OTHER INFORMATION: G or T
<220> FEATURE:
<221> NAME/KEY: SITE
<222> LOCATION: (51)..(51)
<223> OTHER INFORMATION: H or T
<220> FEATURE:
<221> NAME/KEY: SITE
<222> LOCATION: (52)..(52)
<223> OTHER INFORMATION: K or R

<400> SEQUENCE: 110

Gln Asn Gln Trp Leu Gln Asp Met Thr Thr His Leu Ile Leu Arg Ser
1               5                   10                  15

Phe Lys Glu Phe Leu Gln Ser Ser Leu Arg Ala Leu Arg Gln Met Lys
            20                  25                  30

Lys Lys Lys Lys Lys Lys Ile Ser Ile Xaa Glu Ile Xaa Xaa Val
        35                  40                  45

Ile Val Xaa Xaa Ile Glu Thr Ile Leu Phe
    50                  55

<210> SEQ ID NO 111
<211> LENGTH: 60
<212> TYPE: PRT
<213> ORGANISM: Homo sapiens
<220> FEATURE:
<221> NAME/KEY: PEPTIDE
<222> LOCATION: (1)..(33)
<223> OTHER INFORMATION: (KK- IL-6 154-184) x 6 as branched peptide
<220> FEATURE:
<221> NAME/KEY: SITE
<222> LOCATION: (34)..(35)
<223> OTHER INFORMATION: (epsilon K-K) x 4 as a linker
<220> FEATURE:
<221> NAME/KEY: SITE
<222> LOCATION: (36)..(37)
<223> OTHER INFORMATION: (epsilon K-K) x 2 as a linker
<220> FEATURE:
<221> NAME/KEY: PEPTIDE
<222> LOCATION: (38)..(41)
<223> OTHER INFORMATION: epsilon K-KKK as a spacer
<220> FEATURE:
<221> NAME/KEY: PEPTIDE
<222> LOCATION: (42)..(60)
<223> OTHER INFORMATION: MvF4 Th  (UBITh3)
<220> FEATURE:
<221> NAME/KEY: SITE
<222> LOCATION: (45)..(45)
<223> OTHER INFORMATION: S or T
<220> FEATURE:
<221> NAME/KEY: SITE
<222> LOCATION: (48)..(48)
<223> OTHER INFORMATION: K or R
<220> FEATURE:
<221> NAME/KEY: SITE
<222> LOCATION: (49)..(49)
<223> OTHER INFORMATION: G or T
<220> FEATURE:
<221> NAME/KEY: SITE
<222> LOCATION: (53)..(53)
<223> OTHER INFORMATION: H or T
<220> FEATURE:
<221> NAME/KEY: SITE
<222> LOCATION: (54)..(54)
<223> OTHER INFORMATION: K or R

<400> SEQUENCE: 111

Lys Lys Gln Asn Gln Trp Leu Gln Asp Met Thr Thr His Leu Ile Leu
1               5                   10                  15
```

```
Arg Ser Phe Lys Glu Phe Leu Gln Ser Ser Leu Arg Ala Leu Arg Gln
            20                  25                  30

Met Lys Lys Lys Lys Lys Lys Lys Ile Ser Ile Xaa Glu Ile Xaa
        35                  40                  45

Xaa Val Ile Val Xaa Xaa Ile Glu Thr Ile Leu Phe
 50                  55                  60

<210> SEQ ID NO 112
<211> LENGTH: 36
<212> TYPE: PRT
<213> ORGANISM: Homo sapiens
<220> FEATURE:
<221> NAME/KEY: PEPTIDE
<222> LOCATION: (1)..(19)
<223> OTHER INFORMATION: MvF5 Th (UBITh1)
<220> FEATURE:
<221> NAME/KEY: SITE
<222> LOCATION: (20)..(20)
<223> OTHER INFORMATION: epsilon-K
<220> FEATURE:
<221> NAME/KEY: PEPTIDE
<222> LOCATION: (20)..(23)
<223> OTHER INFORMATION: epsilon K-KKK as a spacer
<220> FEATURE:
<221> NAME/KEY: PEPTIDE
<222> LOCATION: (24)..(36)
<223> OTHER INFORMATION: IL-6 150-162 cyclized

<400> SEQUENCE: 112

Ile Ser Ile Thr Glu Ile Lys Gly Val Ile Val His Arg Ile Glu Thr
 1               5                  10                  15

Ile Leu Phe Lys Lys Lys Lys Cys Leu Gln Ala Gln Asn Gln Trp Leu
            20                  25                  30

Gln Asp Met Cys
        35

<210> SEQ ID NO 113
<211> LENGTH: 36
<212> TYPE: PRT
<213> ORGANISM: Homo sapiens
<220> FEATURE:
<221> NAME/KEY: PEPTIDE
<222> LOCATION: (1)..(13)
<223> OTHER INFORMATION: IL-6 150-162 cyclized
<220> FEATURE:
<221> NAME/KEY: PEPTIDE
<222> LOCATION: (14)..(17)
<223> OTHER INFORMATION: epsilon K-KKK as spacer
<220> FEATURE:
<221> NAME/KEY: SITE
<222> LOCATION: (17)..(17)
<223> OTHER INFORMATION: epsilon-K
<220> FEATURE:
<221> NAME/KEY: PEPTIDE
<222> LOCATION: (18)..(36)
<223> OTHER INFORMATION: MvF5 Th (UBITh1)

<400> SEQUENCE: 113

Cys Leu Gln Ala Gln Asn Gln Trp Leu Gln Asp Met Cys Lys Lys Lys
 1               5                  10                  15

Lys Ile Ser Ile Thr Glu Ile Lys Gly Val Ile Val His Arg Ile Glu
            20                  25                  30

Thr Ile Leu Phe
        35

<210> SEQ ID NO 114
<211> LENGTH: 59
```

```
<212> TYPE: PRT
<213> ORGANISM: Homo sapiens
<220> FEATURE:
<221> NAME/KEY: PEPTIDE
<222> LOCATION: (1)..(19)
<223> OTHER INFORMATION: MvF5 Th (UBITh1)
<220> FEATURE:
<221> NAME/KEY: SITE
<222> LOCATION: (20)..(20)
<223> OTHER INFORMATION: epsilon-K
<220> FEATURE:
<221> NAME/KEY: PEPTIDE
<222> LOCATION: (20)..(23)
<223> OTHER INFORMATION: epsilon K-KKK as a spacer
<220> FEATURE:
<221> NAME/KEY: PEPTIDE
<222> LOCATION: (24)..(36)
<223> OTHER INFORMATION: IL-6 150-162 cyclized
<220> FEATURE:
<221> NAME/KEY: PEPTIDE
<222> LOCATION: (37)..(40)
<223> OTHER INFORMATION: epsilon K-KKK as a spacer
<220> FEATURE:
<221> NAME/KEY: SITE
<222> LOCATION: (40)..(40)
<223> OTHER INFORMATION: epsilon K
<220> FEATURE:
<221> NAME/KEY: PEPTIDE
<222> LOCATION: (41)..(59)
<223> OTHER INFORMATION: MvF5 Th (UBITh1)

<400> SEQUENCE: 114

Ile Ser Ile Thr Glu Ile Lys Gly Val Ile Val His Arg Ile Glu Thr
1               5                   10                  15
Ile Leu Phe Lys Lys Lys Lys Cys Leu Gln Ala Gln Asn Gln Trp Leu
            20                  25                  30
Gln Asp Met Cys Lys Lys Lys Lys Ile Ser Ile Thr Glu Ile Lys Gly
        35                  40                  45
Val Ile Val His Arg Ile Glu Thr Ile Leu Phe
    50                  55

<210> SEQ ID NO 115
<211> LENGTH: 46
<212> TYPE: PRT
<213> ORGANISM: Homo sapiens
<220> FEATURE:
<221> NAME/KEY: PEPTIDE
<222> LOCATION: (1)..(19)
<223> OTHER INFORMATION: MvF5 Th (UBITh1)
<220> FEATURE:
<221> NAME/KEY: SITE
<222> LOCATION: (20)..(20)
<223> OTHER INFORMATION: epsilon-K
<220> FEATURE:
<221> NAME/KEY: PEPTIDE
<222> LOCATION: (20)..(23)
<223> OTHER INFORMATION: epsilon K-KKK as a spacer
<220> FEATURE:
<221> NAME/KEY: PEPTIDE
<222> LOCATION: (24)..(46)
<223> OTHER INFORMATION: IL-6 144-166 cyclized

<400> SEQUENCE: 115

Ile Ser Ile Thr Glu Ile Lys Gly Val Ile Val His Arg Ile Glu Thr
1               5                   10                  15
Ile Leu Phe Lys Lys Lys Lys Cys Ala Ser Leu Leu Thr Lys Leu Gln
            20                  25                  30
Ala Gln Asn Gln Trp Leu Gln Asp Met Thr Thr His Leu Cys
        35                  40                  45
```

-continued

```
<210> SEQ ID NO 116
<211> LENGTH: 46
<212> TYPE: PRT
<213> ORGANISM: Homo sapiens
<220> FEATURE:
<221> NAME/KEY: PEPTIDE
<222> LOCATION: (1)..(23)
<223> OTHER INFORMATION: IL-6 144-166 cyclized
<220> FEATURE:
<221> NAME/KEY: PEPTIDE
<222> LOCATION: (24)..(27)
<223> OTHER INFORMATION: epsilon K-KKK as spacer
<220> FEATURE:
<221> NAME/KEY: SITE
<222> LOCATION: (27)..(27)
<223> OTHER INFORMATION: epsilon-K
<220> FEATURE:
<221> NAME/KEY: PEPTIDE
<222> LOCATION: (28)..(46)
<223> OTHER INFORMATION: MvF5 Th (UBITh1)

<400> SEQUENCE: 116

Cys Ala Ser Leu Leu Thr Lys Leu Gln Ala Gln Asn Gln Trp Leu Gln
 1               5                  10                  15

Asp Met Thr Thr His Leu Cys Lys Lys Lys Lys Ile Ser Ile Thr Glu
             20                  25                  30

Ile Lys Gly Val Ile Val His Arg Ile Glu Thr Ile Leu Phe
         35                  40                  45

<210> SEQ ID NO 117
<211> LENGTH: 69
<212> TYPE: PRT
<213> ORGANISM: Homo sapiens
<220> FEATURE:
<221> NAME/KEY: PEPTIDE
<222> LOCATION: (1)..(19)
<223> OTHER INFORMATION: MvF5 Th (UBITh1)
<220> FEATURE:
<221> NAME/KEY: SITE
<222> LOCATION: (20)..(20)
<223> OTHER INFORMATION: epsilon-K
<220> FEATURE:
<221> NAME/KEY: PEPTIDE
<222> LOCATION: (20)..(23)
<223> OTHER INFORMATION: epsilon K-KKK as a spacer
<220> FEATURE:
<221> NAME/KEY: PEPTIDE
<222> LOCATION: (24)..(46)
<223> OTHER INFORMATION: IL-6 144-166 cyclized
<220> FEATURE:
<221> NAME/KEY: PEPTIDE
<222> LOCATION: (47)..(50)
<223> OTHER INFORMATION: epsilon K-KKK as a spacer
<220> FEATURE:
<221> NAME/KEY: SITE
<222> LOCATION: (50)..(50)
<223> OTHER INFORMATION: epsilon K
<220> FEATURE:
<221> NAME/KEY: PEPTIDE
<222> LOCATION: (51)..(69)
<223> OTHER INFORMATION: MvF5 Th (UBITh1)

<400> SEQUENCE: 117

Ile Ser Ile Thr Glu Ile Lys Gly Val Ile Val His Arg Ile Glu Thr
 1               5                  10                  15

Ile Leu Phe Lys Lys Lys Lys Cys Ala Ser Leu Leu Thr Lys Leu Gln
             20                  25                  30

Ala Gln Asn Gln Trp Leu Gln Asp Met Thr Thr His Leu Cys Lys Lys
         35                  40                  45

Lys Lys Ile Ser Ile Thr Glu Ile Lys Gly Val Ile Val His Arg Ile
     50                  55                  60
```

Glu Thr Ile Leu Phe
65

<210> SEQ ID NO 118
<211> LENGTH: 57
<212> TYPE: PRT
<213> ORGANISM: Homo sapiens
<220> FEATURE:
<221> NAME/KEY: PEPTIDE
<222> LOCATION: (1)..(19)
<223> OTHER INFORMATION: MvF5 Th (UBITh1)
<220> FEATURE:
<221> NAME/KEY: SITE
<222> LOCATION: (20)..(20)
<223> OTHER INFORMATION: epsilon-K
<220> FEATURE:
<221> NAME/KEY: PEPTIDE
<222> LOCATION: (20)..(23)
<223> OTHER INFORMATION: epsilon K-KKK as a spacer
<220> FEATURE:
<221> NAME/KEY: PEPTIDE
<222> LOCATION: (24)..(34)
<223> OTHER INFORMATION: IL-6 73-83 cyclized
<220> FEATURE:
<221> NAME/KEY: PEPTIDE
<222> LOCATION: (35)..(38)
<223> OTHER INFORMATION: epsilon K-KKK as a spacer
<220> FEATURE:
<221> NAME/KEY: SITE
<222> LOCATION: (38)..(38)
<223> OTHER INFORMATION: epsilon K
<220> FEATURE:
<221> NAME/KEY: PEPTIDE
<222> LOCATION: (39)..(57)
<223> OTHER INFORMATION: MvF5 Th (UBITh1)

<400> SEQUENCE: 118

Ile Ser Ile Thr Glu Ile Lys Gly Val Ile Val His Arg Ile Glu Thr
1               5                   10                  15

Ile Leu Phe Lys Lys Lys Lys Cys Phe Gln Ser Gly Phe Asn Glu Glu
            20                  25                  30

Thr Cys Lys Lys Lys Lys Ile Ser Ile Thr Glu Ile Lys Gly Val Ile
        35                  40                  45

Val His Arg Ile Glu Thr Ile Leu Phe
    50                  55

<210> SEQ ID NO 119
<211> LENGTH: 34
<212> TYPE: PRT
<213> ORGANISM: Homo sapiens
<220> FEATURE:
<221> NAME/KEY: PEPTIDE
<222> LOCATION: (1)..(19)
<223> OTHER INFORMATION: MvF5 Th (UBITh1)
<220> FEATURE:
<221> NAME/KEY: SITE
<222> LOCATION: (20)..(20)
<223> OTHER INFORMATION: epsilon-K
<220> FEATURE:
<221> NAME/KEY: PEPTIDE
<222> LOCATION: (20)..(23)
<223> OTHER INFORMATION: epsilon K-KKK as a spacer
<220> FEATURE:
<221> NAME/KEY: PEPTIDE
<222> LOCATION: (24)..(34)
<223> OTHER INFORMATION: IL-6 73-83 cyclized

<400> SEQUENCE: 119

Ile Ser Ile Thr Glu Ile Lys Gly Val Ile Val His Arg Ile Glu Thr
1               5                   10                  15

```
Ile Leu Phe Lys Lys Lys Lys Cys Phe Gln Ser Gly Phe Asn Glu Glu
            20                  25                  30

Thr Cys

<210> SEQ ID NO 120
<211> LENGTH: 33
<212> TYPE: PRT
<213> ORGANISM: Homo sapiens
<220> FEATURE:
<221> NAME/KEY: PEPTIDE
<222> LOCATION: (1)..(18)
<223> OTHER INFORMATION: HBsAg3 Th (UBITh2)
<220> FEATURE:
<221> NAME/KEY: SITE
<222> LOCATION: (19)..(19)
<223> OTHER INFORMATION: epsilon-K
<220> FEATURE:
<221> NAME/KEY: PEPTIDE
<222> LOCATION: (19)..(22)
<223> OTHER INFORMATION: epsilon K-KKK as a spacer
<220> FEATURE:
<221> NAME/KEY: PEPTIDE
<222> LOCATION: (23)..(33)
<223> OTHER INFORMATION: IL-6 73-83 cyclized

<400> SEQUENCE: 120

Lys Lys Lys Ile Ile Thr Ile Thr Arg Ile Ile Thr Ile Ile Thr Thr
1               5                   10                  15

Ile Asp Lys Lys Lys Lys Cys Phe Gln Ser Gly Phe Asn Glu Glu Thr
            20                  25                  30

Cys

<210> SEQ ID NO 121
<211> LENGTH: 45
<212> TYPE: PRT
<213> ORGANISM: Homo sapiens
<220> FEATURE:
<221> NAME/KEY: PEPTIDE
<222> LOCATION: (1)..(23)
<223> OTHER INFORMATION: IL-6 144-166 cyclized
<220> FEATURE:
<221> NAME/KEY: PEPTIDE
<222> LOCATION: (24)..(27)
<223> OTHER INFORMATION: epsilon K-KKK as a spacer
<220> FEATURE:
<221> NAME/KEY: SITE
<222> LOCATION: (27)..(27)
<223> OTHER INFORMATION: epsilon K
<220> FEATURE:
<221> NAME/KEY: PEPTIDE
<222> LOCATION: (28)..(45)
<223> OTHER INFORMATION: HBsAg3 Th (UBITh2)

<400> SEQUENCE: 121

Cys Ala Ser Leu Leu Thr Lys Leu Gln Ala Gln Asn Gln Trp Leu Gln
1               5                   10                  15

Asp Met Thr Thr His Leu Cys Lys Lys Lys Lys Lys Lys Lys Ile Ile
            20                  25                  30

Thr Ile Thr Arg Ile Ile Thr Ile Thr Thr Ile Asp
            35                  40                  45

<210> SEQ ID NO 122
<211> LENGTH: 31
<212> TYPE: PRT
<213> ORGANISM: Homo sapiens
<220> FEATURE:
<221> NAME/KEY: PEPTIDE
<222> LOCATION: (1)..(19)
<223> OTHER INFORMATION: MvF5 Th (UBITh1)
```

```
<220> FEATURE:
<221> NAME/KEY: SITE
<222> LOCATION: (20)..(20)
<223> OTHER INFORMATION: epsilon-K as a spacer
<220> FEATURE:
<221> NAME/KEY: PEPTIDE
<222> LOCATION: (21)..(31)
<223> OTHER INFORMATION: IL-6 73-83 cyclized

<400> SEQUENCE: 122

Ile Ser Ile Thr Glu Ile Lys Gly Val Ile Val His Arg Ile Glu Thr
1               5                   10                  15

Ile Leu Phe Lys Cys Phe Gln Ser Gly Phe Asn Glu Glu Thr Cys
            20                  25                  30

<210> SEQ ID NO 123
<211> LENGTH: 30
<212> TYPE: PRT
<213> ORGANISM: Homo sapiens
<220> FEATURE:
<221> NAME/KEY: PEPTIDE
<222> LOCATION: (1)..(18)
<223> OTHER INFORMATION: HBsAg3 Th (UBITh2)
<220> FEATURE:
<221> NAME/KEY: SITE
<222> LOCATION: (19)..(19)
<223> OTHER INFORMATION: epsilon-K as a spacer
<220> FEATURE:
<221> NAME/KEY: PEPTIDE
<222> LOCATION: (20)..(30)
<223> OTHER INFORMATION: IL-6 73-83 cyclized

<400> SEQUENCE: 123

Lys Lys Lys Ile Ile Thr Ile Thr Arg Ile Ile Thr Ile Ile Thr Thr
1               5                   10                  15

Ile Asp Lys Cys Phe Gln Ser Gly Phe Asn Glu Glu Thr Cys
            20                  25                  30

<210> SEQ ID NO 124
<211> LENGTH: 42
<212> TYPE: PRT
<213> ORGANISM: Homo sapiens
<220> FEATURE:
<221> NAME/KEY: PEPTIDE
<222> LOCATION: (1)..(19)
<223> OTHER INFORMATION: MvF5 Th (UBITh1)
<220> FEATURE:
<221> NAME/KEY: SITE
<222> LOCATION: (20)..(20)
<223> OTHER INFORMATION: epsilon-K as a spacer
<220> FEATURE:
<221> NAME/KEY: PEPTIDE
<222> LOCATION: (21)..(42)
<223> OTHER INFORMATION: IL-6 62-83 cyclized

<400> SEQUENCE: 124

Ile Ser Ile Thr Glu Ile Lys Gly Val Ile Val His Arg Ile Glu Thr
1               5                   10                  15

Ile Leu Phe Lys Leu Asn Leu Pro Lys Met Ala Glu Lys Asp Gly Cys
            20                  25                  30

Phe Gln Ser Gly Phe Asn Glu Glu Thr Cys
        35                  40

<210> SEQ ID NO 125
<211> LENGTH: 46
<212> TYPE: PRT
<213> ORGANISM: Homo sapiens
<220> FEATURE:
<221> NAME/KEY: PEPTIDE
```

```
<222> LOCATION: (1)..(19)
<223> OTHER INFORMATION: MvF5 Th (UBITh1)
<220> FEATURE:
<221> NAME/KEY: SITE
<222> LOCATION: (20)..(20)
<223> OTHER INFORMATION: epsilon-K as a spacer
<220> FEATURE:
<221> NAME/KEY: PEPTIDE
<222> LOCATION: (21)..(46)
<223> OTHER INFORMATION: IL-6 58-83 cyclized

<400> SEQUENCE: 125

Ile Ser Ile Thr Glu Ile Lys Gly Val Ile Val His Arg Ile Glu Thr
1               5                   10                  15

Ile Leu Phe Lys Ala Glu Asn Asn Leu Asn Leu Pro Lys Met Ala Glu
            20                  25                  30

Lys Asp Gly Cys Phe Gln Ser Gly Phe Asn Glu Glu Thr Cys
        35                  40                  45

<210> SEQ ID NO 126
<211> LENGTH: 52
<212> TYPE: PRT
<213> ORGANISM: Homo sapiens
<220> FEATURE:
<221> NAME/KEY: PEPTIDE
<222> LOCATION: (1)..(19)
<223> OTHER INFORMATION: MvF5 Th (UBITh1)
<220> FEATURE:
<221> NAME/KEY: SITE
<222> LOCATION: (20)..(20)
<223> OTHER INFORMATION: epsilon-K as a spacer
<220> FEATURE:
<221> NAME/KEY: PEPTIDE
<222> LOCATION: (21)..(52)
<223> OTHER INFORMATION: IL-6 52-83 cyclized

<400> SEQUENCE: 126

Ile Ser Ile Thr Glu Ile Lys Gly Val Ile Val His Arg Ile Glu Thr
1               5                   10                  15

Ile Leu Phe Lys Ser Ser Lys Glu Ala Leu Ala Glu Asn Asn Leu Asn
            20                  25                  30

Leu Pro Lys Met Ala Glu Lys Asp Gly Cys Phe Gln Ser Gly Phe Asn
        35                  40                  45

Glu Glu Thr Cys
    50

<210> SEQ ID NO 127
<211> LENGTH: 41
<212> TYPE: PRT
<213> ORGANISM: Homo sapiens
<220> FEATURE:
<221> NAME/KEY: PEPTIDE
<222> LOCATION: (1)..(19)
<223> OTHER INFORMATION: MvF5 Th (UBITh1)
<220> FEATURE:
<221> NAME/KEY: SITE
<222> LOCATION: (20)..(20)
<223> OTHER INFORMATION: epsilon-K as a spacer
<220> FEATURE:
<221> NAME/KEY: PEPTIDE
<222> LOCATION: (21)..(41)
<223> OTHER INFORMATION: IL-6 52-72

<400> SEQUENCE: 127

Ile Ser Ile Thr Glu Ile Lys Gly Val Ile Val His Arg Ile Glu Thr
1               5                   10                  15

Ile Leu Phe Lys Ser Ser Lys Glu Ala Leu Ala Glu Asn Asn Leu Asn
            20                  25                  30
```

-continued

```
Leu Pro Lys Met Ala Glu Lys Asp Gly
        35                  40

<210> SEQ ID NO 128
<211> LENGTH: 51
<212> TYPE: PRT
<213> ORGANISM: Homo sapiens
<220> FEATURE:
<221> NAME/KEY: PEPTIDE
<222> LOCATION: (1)..(19)
<223> OTHER INFORMATION: MvF5 Th (UBITh1)
<220> FEATURE:
<221> NAME/KEY: SITE
<222> LOCATION: (20)..(20)
<223> OTHER INFORMATION: epsilon-K as a spacer
<220> FEATURE:
<221> NAME/KEY: PEPTIDE
<222> LOCATION: (21)..(51)
<223> OTHER INFORMATION: IL-6 42-72 cyclized

<400> SEQUENCE: 128

Ile Ser Ile Thr Glu Ile Lys Gly Val Ile Val His Arg Ile Glu Thr
1               5                   10                  15

Ile Leu Phe Lys Glu Thr Cys Asn Lys Ser Asn Met Cys Glu Ser Ser
            20                  25                  30

Lys Glu Ala Leu Ala Glu Asn Asn Leu Asn Leu Pro Lys Met Ala Glu
        35                  40                  45

Lys Asp Gly
    50

<210> SEQ ID NO 129
<211> LENGTH: 51
<212> TYPE: PRT
<213> ORGANISM: Homo sapiens
<220> FEATURE:
<221> NAME/KEY: PEPTIDE
<222> LOCATION: (1)..(31)
<223> OTHER INFORMATION: IL-6 42-72 cyclized
<220> FEATURE:
<221> NAME/KEY: SITE
<222> LOCATION: (32)..(32)
<223> OTHER INFORMATION: epsilon-K as spacer
<220> FEATURE:
<221> NAME/KEY: PEPTIDE
<222> LOCATION: (33)..(51)
<223> OTHER INFORMATION: MvF5 Th (UBITh1)

<400> SEQUENCE: 129

Glu Thr Cys Asn Lys Ser Asn Met Cys Glu Ser Ser Lys Glu Ala Leu
1               5                   10                  15

Ala Glu Asn Asn Leu Asn Leu Pro Lys Met Ala Glu Lys Asp Gly Lys
            20                  25                  30

Ile Ser Ile Thr Glu Ile Lys Gly Val Ile Val His Arg Ile Glu Thr
        35                  40                  45

Ile Leu Phe
    50

<210> SEQ ID NO 130
<211> LENGTH: 38
<212> TYPE: PRT
<213> ORGANISM: Homo sapiens
<220> FEATURE:
<221> NAME/KEY: PEPTIDE
<222> LOCATION: (1)..(19)
<223> OTHER INFORMATION: MvF5 Th (UBITh1)
<220> FEATURE:
<221> NAME/KEY: SITE
```

```
<222> LOCATION: (20)..(20)
<223> OTHER INFORMATION: epsilon-K as a spacer
<220> FEATURE:
<221> NAME/KEY: PEPTIDE
<222> LOCATION: (21)..(38)
<223> OTHER INFORMATION: IL-6 50-67 cyclized

<400> SEQUENCE: 130

Ile Ser Ile Thr Glu Ile Lys Gly Val Ile Val His Arg Ile Glu Thr
1               5                   10                  15

Ile Leu Phe Lys Cys Glu Ser Ser Lys Glu Ala Leu Ala Glu Asn Asn
            20                  25                  30

Leu Asn Leu Pro Lys Cys
        35

<210> SEQ ID NO 131
<211> LENGTH: 27
<212> TYPE: PRT
<213> ORGANISM: Homo sapiens
<220> FEATURE:
<221> NAME/KEY: PEPTIDE
<222> LOCATION: (1)..(19)
<223> OTHER INFORMATION: MvF5 Th (UBITh1)
<220> FEATURE:
<221> NAME/KEY: SITE
<222> LOCATION: (20)..(20)
<223> OTHER INFORMATION: epsilon-K as a spacer
<220> FEATURE:
<221> NAME/KEY: PEPTIDE
<222> LOCATION: (21)..(27)
<223> OTHER INFORMATION: IL-6 44-50 cyclized

<400> SEQUENCE: 131

Ile Ser Ile Thr Glu Ile Lys Gly Val Ile Val His Arg Ile Glu Thr
1               5                   10                  15

Ile Leu Phe Lys Cys Asn Lys Ser Asn Met Cys
            20                  25

<210> SEQ ID NO 132
<211> LENGTH: 60
<212> TYPE: PRT
<213> ORGANISM: Homo sapiens
<220> FEATURE:
<221> NAME/KEY: PEPTIDE
<222> LOCATION: (1)..(19)
<223> OTHER INFORMATION: MvF5 Th (UBITh1)
<220> FEATURE:
<221> NAME/KEY: SITE
<222> LOCATION: (20)..(20)
<223> OTHER INFORMATION: epsilon-K as a spacer
<220> FEATURE:
<221> NAME/KEY: PEPTIDE
<222> LOCATION: (21)..(60)
<223> OTHER INFORMATION: IL-6 44-83 cyclized

<400> SEQUENCE: 132

Ile Ser Ile Thr Glu Ile Lys Gly Val Ile Val His Arg Ile Glu Thr
1               5                   10                  15

Ile Leu Phe Lys Cys Asn Lys Ser Asn Met Cys Glu Ser Ser Lys Glu
            20                  25                  30

Ala Leu Ala Glu Asn Asn Leu Asn Leu Pro Lys Met Ala Glu Lys Asp
        35                  40                  45

Gly Cys Phe Gln Ser Gly Phe Asn Glu Glu Thr Cys
        50                  55                  60

<210> SEQ ID NO 133
<211> LENGTH: 60
```

-continued

```
<212> TYPE: PRT
<213> ORGANISM: Homo sapiens
<220> FEATURE:
<221> NAME/KEY: PEPTIDE
<222> LOCATION: (1)..(19)
<223> OTHER INFORMATION: MvF5 Th (UBITh1)
<220> FEATURE:
<221> NAME/KEY: SITE
<222> LOCATION: (20)..(20)
<223> OTHER INFORMATION: epsilon-K as a spacer
<220> FEATURE:
<221> NAME/KEY: PEPTIDE
<222> LOCATION: (21)..(60)
<223> OTHER INFORMATION: IL-6 44-83

<400> SEQUENCE: 133

Ile Ser Ile Thr Glu Ile Lys Gly Val Ile Val His Arg Ile Glu Thr
1               5                   10                  15

Ile Leu Phe Lys Cys Asn Lys Ser Asn Met Cys Glu Ser Ser Lys Glu
            20                  25                  30

Ala Leu Ala Glu Asn Asn Leu Asn Leu Pro Lys Met Ala Glu Lys Asp
        35                  40                  45

Gly Cys Phe Gln Ser Gly Phe Asn Glu Glu Thr Cys
    50                  55                  60

<210> SEQ ID NO 134
<211> LENGTH: 39
<212> TYPE: PRT
<213> ORGANISM: Homo sapiens
<220> FEATURE:
<221> NAME/KEY: PEPTIDE
<222> LOCATION: (1)..(19)
<223> OTHER INFORMATION: MvF5 Th (UBITh1)
<220> FEATURE:
<221> NAME/KEY: SITE
<222> LOCATION: (20)..(20)
<223> OTHER INFORMATION: epsilon-K
<220> FEATURE:
<221> NAME/KEY: PEPTIDE
<222> LOCATION: (20)..(23)
<223> OTHER INFORMATION: epsilon K-KKK as a spacer
<220> FEATURE:
<221> NAME/KEY: PEPTIDE
<222> LOCATION: (24)..(39)
<223> OTHER INFORMATION: IL-6 42-57 cyclized

<400> SEQUENCE: 134

Ile Ser Ile Thr Glu Ile Lys Gly Val Ile Val His Arg Ile Glu Thr
1               5                   10                  15

Ile Leu Phe Lys Lys Lys Lys Glu Thr Cys Asn Lys Ser Asn Met Cys
            20                  25                  30

Glu Ser Ser Lys Glu Ala Leu
        35

<210> SEQ ID NO 135
<211> LENGTH: 39
<212> TYPE: PRT
<213> ORGANISM: Homo sapiens
<220> FEATURE:
<221> NAME/KEY: PEPTIDE
<222> LOCATION: (1)..(16)
<223> OTHER INFORMATION: IL-6 42-57 cyclized
<220> FEATURE:
<221> NAME/KEY: PEPTIDE
<222> LOCATION: (17)..(20)
<223> OTHER INFORMATION: epsilon K-KKK as spacer
<220> FEATURE:
<221> NAME/KEY: SITE
<222> LOCATION: (20)..(20)
<223> OTHER INFORMATION: epsilon-K
```

```
<220> FEATURE:
<221> NAME/KEY: PEPTIDE
<222> LOCATION: (21)..(39)
<223> OTHER INFORMATION: MvF5 Th (UBITh1)

<400> SEQUENCE: 135

Glu Thr Cys Asn Lys Ser Asn Met Cys Glu Ser Ser Lys Glu Ala Leu
1               5                   10                  15

Lys Lys Lys Lys Ile Ser Ile Thr Glu Ile Lys Gly Val Ile Val His
            20                  25                  30

Arg Ile Glu Thr Ile Leu Phe
                35

<210> SEQ ID NO 136
<211> LENGTH: 36
<212> TYPE: PRT
<213> ORGANISM: Homo sapiens
<220> FEATURE:
<221> NAME/KEY: PEPTIDE
<222> LOCATION: (1)..(19)
<223> OTHER INFORMATION: MvF5 Th (UBITh1)
<220> FEATURE:
<221> NAME/KEY: SITE
<222> LOCATION: (20)..(20)
<223> OTHER INFORMATION: epsilon-K as a spacer
<220> FEATURE:
<221> NAME/KEY: PEPTIDE
<222> LOCATION: (21)..(36)
<223> OTHER INFORMATION: IL-6 42-57 cyclized

<400> SEQUENCE: 136

Ile Ser Ile Thr Glu Ile Lys Gly Val Ile Val His Arg Ile Glu Thr
1               5                   10                  15

Ile Leu Phe Lys Glu Thr Cys Asn Lys Ser Asn Met Cys Glu Ser Ser
            20                  25                  30

Lys Glu Ala Leu
            35

<210> SEQ ID NO 137
<211> LENGTH: 36
<212> TYPE: PRT
<213> ORGANISM: Homo sapiens
<220> FEATURE:
<221> NAME/KEY: PEPTIDE
<222> LOCATION: (1)..(16)
<223> OTHER INFORMATION: IL-6 42-57 cyclized
<220> FEATURE:
<221> NAME/KEY: SITE
<222> LOCATION: (17)..(17)
<223> OTHER INFORMATION: epsilon-K as spacer
<220> FEATURE:
<221> NAME/KEY: PEPTIDE
<222> LOCATION: (18)..(36)
<223> OTHER INFORMATION: MvF5 Th (UBITh1)

<400> SEQUENCE: 137

Glu Thr Cys Asn Lys Ser Asn Met Cys Glu Ser Ser Lys Glu Ala Leu
1               5                   10                  15

Lys Ile Ser Ile Thr Glu Ile Lys Gly Val Ile Val His Arg Ile Glu
            20                  25                  30

Thr Ile Leu Phe
            35

<210> SEQ ID NO 138
<211> LENGTH: 38
<212> TYPE: PRT
<213> ORGANISM: Homo sapiens
```

```
<220> FEATURE:
<221> NAME/KEY: PEPTIDE
<222> LOCATION: (1)..(19)
<223> OTHER INFORMATION: MvF5 Th (UBITh1)
<220> FEATURE:
<221> NAME/KEY: SITE
<222> LOCATION: (20)..(20)
<223> OTHER INFORMATION: epsilon-K
<220> FEATURE:
<221> NAME/KEY: PEPTIDE
<222> LOCATION: (20)..(23)
<223> OTHER INFORMATION: epsilon K-KKK as a spacer
<220> FEATURE:
<221> NAME/KEY: PEPTIDE
<222> LOCATION: (24)..(38)
<223> OTHER INFORMATION: IL-6 61-75

<400> SEQUENCE: 138

Ile Ser Ile Thr Glu Ile Lys Gly Val Ile Val His Arg Ile Glu Thr
1               5                   10                  15

Ile Leu Phe Lys Lys Lys Lys Asn Leu Asn Leu Pro Lys Met Ala Glu
            20                  25                  30

Lys Asp Gly Ser Phe Gln
            35

<210> SEQ ID NO 139
<211> LENGTH: 38
<212> TYPE: PRT
<213> ORGANISM: Homo sapiens
<220> FEATURE:
<221> NAME/KEY: PEPTIDE
<222> LOCATION: (1)..(15)
<223> OTHER INFORMATION: IL-6 61-75
<220> FEATURE:
<221> NAME/KEY: PEPTIDE
<222> LOCATION: (16)..(19)
<223> OTHER INFORMATION: epsilon K-KKK as spacer
<220> FEATURE:
<221> NAME/KEY: SITE
<222> LOCATION: (19)..(19)
<223> OTHER INFORMATION: epsilon-K
<220> FEATURE:
<221> NAME/KEY: PEPTIDE
<222> LOCATION: (20)..(38)
<223> OTHER INFORMATION: MvF5 Th (UBITh1)

<400> SEQUENCE: 139

Asn Leu Asn Leu Pro Lys Met Ala Glu Lys Asp Gly Ser Phe Gln Lys
1               5                   10                  15

Lys Lys Lys Ile Ser Ile Thr Glu Ile Lys Gly Val Ile Val His Arg
            20                  25                  30

Ile Glu Thr Ile Leu Phe
            35

<210> SEQ ID NO 140
<211> LENGTH: 35
<212> TYPE: PRT
<213> ORGANISM: Homo sapiens
<220> FEATURE:
<221> NAME/KEY: PEPTIDE
<222> LOCATION: (1)..(19)
<223> OTHER INFORMATION: MvF5 Th (UBITh1)
<220> FEATURE:
<221> NAME/KEY: SITE
<222> LOCATION: (20)..(20)
<223> OTHER INFORMATION: epsilon-K as a spacer
<220> FEATURE:
<221> NAME/KEY: PEPTIDE
<222> LOCATION: (21)..(35)
<223> OTHER INFORMATION: IL-6 61-75
```

```
<400> SEQUENCE: 140

Ile Ser Ile Thr Glu Ile Lys Gly Val Ile Val His Arg Ile Glu Thr
1               5                   10                  15

Ile Leu Phe Lys Asn Leu Asn Leu Pro Lys Met Ala Glu Lys Asp Gly
            20                  25                  30

Ser Phe Gln
        35

<210> SEQ ID NO 141
<211> LENGTH: 35
<212> TYPE: PRT
<213> ORGANISM: Homo sapiens
<220> FEATURE:
<221> NAME/KEY: PEPTIDE
<222> LOCATION: (1)..(15)
<223> OTHER INFORMATION: IL-6 61-75
<220> FEATURE:
<221> NAME/KEY: SITE
<222> LOCATION: (16)..(16)
<223> OTHER INFORMATION: epsilon-K as a spacer
<220> FEATURE:
<221> NAME/KEY: PEPTIDE
<222> LOCATION: (17)..(35)
<223> OTHER INFORMATION: MvF5 Th (UBITh1)

<400> SEQUENCE: 141

Asn Leu Asn Leu Pro Lys Met Ala Glu Lys Asp Gly Ser Phe Gln Lys
1               5                   10                  15

Ile Ser Ile Thr Glu Ile Lys Gly Val Ile Val His Arg Ile Glu Thr
            20                  25                  30

Ile Leu Phe
        35

<210> SEQ ID NO 142
<211> LENGTH: 35
<212> TYPE: PRT
<213> ORGANISM: Homo sapiens
<220> FEATURE:
<221> NAME/KEY: PEPTIDE
<222> LOCATION: (1)..(19)
<223> OTHER INFORMATION: MvF5 Th (UBITh1)
<220> FEATURE:
<221> NAME/KEY: SITE
<222> LOCATION: (20)..(20)
<223> OTHER INFORMATION: epsilon-K
<220> FEATURE:
<221> NAME/KEY: PEPTIDE
<222> LOCATION: (20)..(23)
<223> OTHER INFORMATION: epsilon K-KKK as a spacer
<220> FEATURE:
<221> NAME/KEY: PEPTIDE
<222> LOCATION: (24)..(35)
<223> OTHER INFORMATION: IL-6 61-72

<400> SEQUENCE: 142

Ile Ser Ile Thr Glu Ile Lys Gly Val Ile Val His Arg Ile Glu Thr
1               5                   10                  15

Ile Leu Phe Lys Lys Lys Lys Asn Leu Asn Leu Pro Lys Met Ala Glu
            20                  25                  30

Lys Asp Gly
        35

<210> SEQ ID NO 143
<211> LENGTH: 35
<212> TYPE: PRT
<213> ORGANISM: Homo sapiens
<220> FEATURE:
```

```
<221> NAME/KEY: PEPTIDE
<222> LOCATION: (1)..(12)
<223> OTHER INFORMATION: IL-6 61-72
<220> FEATURE:
<221> NAME/KEY: PEPTIDE
<222> LOCATION: (13)..(16)
<223> OTHER INFORMATION: epsilon K-KKK as spacer
<220> FEATURE:
<221> NAME/KEY: SITE
<222> LOCATION: (16)..(16)
<223> OTHER INFORMATION: epsilon-K
<220> FEATURE:
<221> NAME/KEY: PEPTIDE
<222> LOCATION: (17)..(35)
<223> OTHER INFORMATION: MvF5 Th (UBITh1)

<400> SEQUENCE: 143

Asn Leu Asn Leu Pro Lys Met Ala Glu Lys Asp Gly Lys Lys Lys
1               5                   10                  15

Ile Ser Ile Thr Glu Ile Lys Gly Val Ile Val His Arg Ile Glu Thr
                20                  25                  30

Ile Leu Phe
        35

<210> SEQ ID NO 144
<211> LENGTH: 32
<212> TYPE: PRT
<213> ORGANISM: Homo sapiens
<220> FEATURE:
<221> NAME/KEY: PEPTIDE
<222> LOCATION: (1)..(19)
<223> OTHER INFORMATION: MvF5 Th (UBITh1)
<220> FEATURE:
<221> NAME/KEY: SITE
<222> LOCATION: (20)..(20)
<223> OTHER INFORMATION: epsilon-K as a spacer
<220> FEATURE:
<221> NAME/KEY: PEPTIDE
<222> LOCATION: (21)..(32)
<223> OTHER INFORMATION: IL-6 61-72

<400> SEQUENCE: 144

Ile Ser Ile Thr Glu Ile Lys Gly Val Ile Val His Arg Ile Glu Thr
1               5                   10                  15

Ile Leu Phe Lys Asn Leu Asn Leu Pro Lys Met Ala Glu Lys Asp Gly
                20                  25                  30

<210> SEQ ID NO 145
<211> LENGTH: 32
<212> TYPE: PRT
<213> ORGANISM: Homo sapiens
<220> FEATURE:
<221> NAME/KEY: PEPTIDE
<222> LOCATION: (1)..(12)
<223> OTHER INFORMATION: IL-6 61-72
<220> FEATURE:
<221> NAME/KEY: SITE
<222> LOCATION: (13)..(13)
<223> OTHER INFORMATION: epsilon-K as a spacer
<220> FEATURE:
<221> NAME/KEY: PEPTIDE
<222> LOCATION: (14)..(32)
<223> OTHER INFORMATION: MvF5 Th (UBITh1)

<400> SEQUENCE: 145

Asn Leu Asn Leu Pro Lys Met Ala Glu Lys Asp Gly Lys Ile Ser Ile
1               5                   10                  15

Thr Glu Ile Lys Gly Val Ile Val His Arg Ile Glu Thr Ile Leu Phe
                20                  25                  30
```

```
<210> SEQ ID NO 146
<211> LENGTH: 34
<212> TYPE: PRT
<213> ORGANISM: Mus musculus
<220> FEATURE:
<221> NAME/KEY: PEPTIDE
<222> LOCATION: (1)..(19)
<223> OTHER INFORMATION: MvF 4 Th (UBITh3)
<220> FEATURE:
<221> NAME/KEY: SITE
<222> LOCATION: (4)..(4)
<223> OTHER INFORMATION: S or T
<220> FEATURE:
<221> NAME/KEY: SITE
<222> LOCATION: (7)..(7)
<223> OTHER INFORMATION: K or R
<220> FEATURE:
<221> NAME/KEY: SITE
<222> LOCATION: (8)..(8)
<223> OTHER INFORMATION: G or T
<220> FEATURE:
<221> NAME/KEY: SITE
<222> LOCATION: (12)..(12)
<223> OTHER INFORMATION: H or T
<220> FEATURE:
<221> NAME/KEY: SITE
<222> LOCATION: (13)..(13)
<223> OTHER INFORMATION: K or R
<220> FEATURE:
<221> NAME/KEY: PEPTIDE
<222> LOCATION: (20)..(23)
<223> OTHER INFORMATION: epsilon K-KKK as a spacer
<220> FEATURE:
<221> NAME/KEY: SITE
<222> LOCATION: (20)..(20)
<223> OTHER INFORMATION: epsilon-K
<220> FEATURE:
<221> NAME/KEY: PEPTIDE
<222> LOCATION: (24)..(34)
<223> OTHER INFORMATION: mouse counterpart IL-6 72-82 cyclized

<400> SEQUENCE: 146

Ile Ser Ile Xaa Glu Ile Xaa Xaa Val Ile Val Xaa Xaa Ile Glu Thr
1               5                   10                  15

Ile Leu Phe Lys Lys Lys Lys Cys Tyr Gln Thr Gly Tyr Asn Gln Glu
            20                  25                  30

Ile Cys

<210> SEQ ID NO 147
<211> LENGTH: 54
<212> TYPE: PRT
<213> ORGANISM: Mus musculus
<220> FEATURE:
<221> NAME/KEY: PEPTIDE
<222> LOCATION: (1)..(19)
<223> OTHER INFORMATION: MvF4 Th (UBITh3)
<220> FEATURE:
<221> NAME/KEY: SITE
<222> LOCATION: (4)..(4)
<223> OTHER INFORMATION: S or T
<220> FEATURE:
<221> NAME/KEY: SITE
<222> LOCATION: (7)..(7)
<223> OTHER INFORMATION: K or R
<220> FEATURE:
<221> NAME/KEY: SITE
<222> LOCATION: (8)..(8)
<223> OTHER INFORMATION: G or T
<220> FEATURE:
<221> NAME/KEY: SITE
<222> LOCATION: (12)..(12)
<223> OTHER INFORMATION: H or T
<220> FEATURE:
<221> NAME/KEY: SITE
```

```
<222> LOCATION: (13)..(13)
<223> OTHER INFORMATION: K or R
<220> FEATURE:
<221> NAME/KEY: SITE
<222> LOCATION: (20)..(20)
<223> OTHER INFORMATION: epsilon-K
<220> FEATURE:
<221> NAME/KEY: PEPTIDE
<222> LOCATION: (20)..(23)
<223> OTHER INFORMATION: epsilon K-KKK as a spacer
<220> FEATURE:
<221> NAME/KEY: PEPTIDE
<222> LOCATION: (24)..(54)
<223> OTHER INFORMATION: mouse counterpart IL-6 154-184

<400> SEQUENCE: 147

Ile Ser Ile Xaa Glu Ile Xaa Xaa Val Ile Val Xaa Xaa Ile Glu Thr
1               5                   10                  15

Ile Leu Phe Lys Lys Lys Lys Gln Lys Glu Trp Leu Arg Thr Lys Thr
            20                  25                  30

Ile Gln Phe Ile Leu Lys Ser Leu Glu Glu Phe Leu Lys Val Thr Leu
        35                  40                  45

Arg Ser Thr Arg Gln Thr
    50

<210> SEQ ID NO 148
<211> LENGTH: 34
<212> TYPE: PRT
<213> ORGANISM: Rattus norvegicus
<220> FEATURE:
<221> NAME/KEY: PEPTIDE
<222> LOCATION: (1)..(19)
<223> OTHER INFORMATION: MvF 4 Th (UBITh3)
<220> FEATURE:
<221> NAME/KEY: SITE
<222> LOCATION: (4)..(4)
<223> OTHER INFORMATION: S or T
<220> FEATURE:
<221> NAME/KEY: SITE
<222> LOCATION: (7)..(7)
<223> OTHER INFORMATION: K or R
<220> FEATURE:
<221> NAME/KEY: SITE
<222> LOCATION: (8)..(8)
<223> OTHER INFORMATION: G or T
<220> FEATURE:
<221> NAME/KEY: SITE
<222> LOCATION: (12)..(12)
<223> OTHER INFORMATION: H or T
<220> FEATURE:
<221> NAME/KEY: SITE
<222> LOCATION: (13)..(13)
<223> OTHER INFORMATION: K or R
<220> FEATURE:
<221> NAME/KEY: PEPTIDE
<222> LOCATION: (20)..(23)
<223> OTHER INFORMATION: epsilon K-KKK as a spacer
<220> FEATURE:
<221> NAME/KEY: SITE
<222> LOCATION: (20)..(20)
<223> OTHER INFORMATION: epsilon-K
<220> FEATURE:
<221> NAME/KEY: PEPTIDE
<222> LOCATION: (24)..(34)
<223> OTHER INFORMATION: rat counterpart IL-6 72-82 cyclized

<400> SEQUENCE: 148

Ile Ser Ile Xaa Glu Ile Xaa Xaa Val Ile Val Xaa Xaa Ile Glu Thr
1               5                   10                  15
```

Ile Leu Phe Lys Lys Lys Lys Cys Phe Gln Thr Gly Tyr Asn Gln Glu
                20                  25                  30

Ile Cys

```
<210> SEQ ID NO 149
<211> LENGTH: 57
<212> TYPE: PRT
<213> ORGANISM: Rattus norvegicus
<220> FEATURE:
<221> NAME/KEY: PEPTIDE
<222> LOCATION: (1)..(19)
<223> OTHER INFORMATION: MvF 4 Th (UBITh3)
<220> FEATURE:
<221> NAME/KEY: SITE
<222> LOCATION: (4)..(4)
<223> OTHER INFORMATION: S or T
<220> FEATURE:
<221> NAME/KEY: SITE
<222> LOCATION: (7)..(7)
<223> OTHER INFORMATION: K or R
<220> FEATURE:
<221> NAME/KEY: SITE
<222> LOCATION: (8)..(8)
<223> OTHER INFORMATION: G or T
<220> FEATURE:
<221> NAME/KEY: SITE
<222> LOCATION: (12)..(12)
<223> OTHER INFORMATION: H or T
<220> FEATURE:
<221> NAME/KEY: SITE
<222> LOCATION: (13)..(13)
<223> OTHER INFORMATION: K or R
<220> FEATURE:
<221> NAME/KEY: PEPTIDE
<222> LOCATION: (20)..(23)
<223> OTHER INFORMATION: epsilon K-KKK as a spacer
<220> FEATURE:
<221> NAME/KEY: SITE
<222> LOCATION: (20)..(20)
<223> OTHER INFORMATION: epsilon-K
<220> FEATURE:
<221> NAME/KEY: PEPTIDE
<222> LOCATION: (24)..(34)
<223> OTHER INFORMATION: rat counterpart IL-6 72-82 cyclized
<220> FEATURE:
<221> NAME/KEY: PEPTIDE
<222> LOCATION: (35)..(38)
<223> OTHER INFORMATION: epsilon K-KKK as a spacer
<220> FEATURE:
<221> NAME/KEY: SITE
<222> LOCATION: (38)..(38)
<223> OTHER INFORMATION: epsilon-K
<220> FEATURE:
<221> NAME/KEY: PEPTIDE
<222> LOCATION: (39)..(57)
<223> OTHER INFORMATION: MvF 4 Th (UBITh3)
<220> FEATURE:
<221> NAME/KEY: SITE
<222> LOCATION: (42)..(42)
<223> OTHER INFORMATION: S or T
<220> FEATURE:
<221> NAME/KEY: SITE
<222> LOCATION: (45)..(45)
<223> OTHER INFORMATION: K or R
<220> FEATURE:
<221> NAME/KEY: SITE
<222> LOCATION: (46)..(46)
<223> OTHER INFORMATION: G or T
<220> FEATURE:
<221> NAME/KEY: SITE
<222> LOCATION: (50)..(50)
<223> OTHER INFORMATION: H or T
<220> FEATURE:
<221> NAME/KEY: SITE
<222> LOCATION: (51)..(51)
<223> OTHER INFORMATION: K or R
```

<400> SEQUENCE: 149

Ile Ser Ile Xaa Glu Ile Xaa Xaa Val Ile Val Xaa Xaa Ile Glu Thr
1               5                   10                  15

Ile Leu Phe Lys Lys Lys Lys Cys Phe Gln Thr Gly Tyr Asn Gln Glu
            20                  25                  30

Ile Cys Lys Lys Lys Lys Ile Ser Ile Xaa Glu Ile Xaa Xaa Val Ile
        35                  40                  45

Val Xaa Xaa Ile Glu Thr Ile Leu Phe
    50                  55

<210> SEQ ID NO 150
<211> LENGTH: 34
<212> TYPE: PRT
<213> ORGANISM: Rattus norvegicus
<220> FEATURE:
<221> NAME/KEY: PEPTIDE
<222> LOCATION: (1)..(19)
<223> OTHER INFORMATION: MvF5 Th (UBITh1)
<220> FEATURE:
<221> NAME/KEY: SITE
<222> LOCATION: (20)..(20)
<223> OTHER INFORMATION: epsilon-K
<220> FEATURE:
<221> NAME/KEY: PEPTIDE
<222> LOCATION: (20)..(23)
<223> OTHER INFORMATION: epsilon K-KKK as a spacer
<220> FEATURE:
<221> NAME/KEY: PEPTIDE
<222> LOCATION: (24)..(34)
<223> OTHER INFORMATION: rat counterpart IL-6 72-82 cyclized

<400> SEQUENCE: 150

Ile Ser Ile Thr Glu Ile Lys Gly Val Ile Val His Arg Ile Glu Thr
1               5                   10                  15

Ile Leu Phe Lys Lys Lys Lys Cys Phe Gln Thr Gly Tyr Asn Gln Glu
                20                  25                  30

Ile Cys

<210> SEQ ID NO 151
<211> LENGTH: 57
<212> TYPE: PRT
<213> ORGANISM: Rattus norvegicus
<220> FEATURE:
<221> NAME/KEY: PEPTIDE
<222> LOCATION: (1)..(19)
<223> OTHER INFORMATION: MvF5 Th (UBITh1)
<220> FEATURE:
<221> NAME/KEY: SITE
<222> LOCATION: (20)..(20)
<223> OTHER INFORMATION: epsilon-K
<220> FEATURE:
<221> NAME/KEY: PEPTIDE
<222> LOCATION: (20)..(23)
<223> OTHER INFORMATION: epsilon K-KKK as a spacer
<220> FEATURE:
<221> NAME/KEY: PEPTIDE
<222> LOCATION: (24)..(34)
<223> OTHER INFORMATION: rat counterpart IL-6 72-82 cyclized
<220> FEATURE:
<221> NAME/KEY: PEPTIDE
<222> LOCATION: (35)..(38)
<223> OTHER INFORMATION: epsilon K-KKK as a spacer
<220> FEATURE:
<221> NAME/KEY: SITE
<222> LOCATION: (38)..(38)
<223> OTHER INFORMATION: epsilon K
<220> FEATURE:
<221> NAME/KEY: PEPTIDE
<222> LOCATION: (39)..(57)

<223> OTHER INFORMATION: MvF5 Th (UBITh1)

<400> SEQUENCE: 151

Ile Ser Ile Thr Glu Ile Lys Gly Val Ile Val His Arg Ile Glu Thr
1               5                   10                  15

Ile Leu Phe Lys Lys Lys Cys Phe Gln Thr Gly Tyr Asn Gln Glu
            20                  25                  30

Ile Cys Lys Lys Lys Lys Ile Ser Thr Glu Ile Lys Gly Val Ile
        35                  40                  45

Val His Arg Ile Glu Thr Ile Leu Phe
    50                  55

<210> SEQ ID NO 152
<211> LENGTH: 36
<212> TYPE: PRT
<213> ORGANISM: Rattus norvegicus
<220> FEATURE:
<221> NAME/KEY: PEPTIDE
<222> LOCATION: (1)..(13)
<223> OTHER INFORMATION: rat counterpart IL-6 150-162 cyclized
<220> FEATURE:
<221> NAME/KEY: PEPTIDE
<222> LOCATION: (14)..(17)
<223> OTHER INFORMATION: epsilon K-KKK as spacer
<220> FEATURE:
<221> NAME/KEY: SITE
<222> LOCATION: (17)..(17)
<223> OTHER INFORMATION: epsilon-K
<220> FEATURE:
<221> NAME/KEY: PEPTIDE
<222> LOCATION: (18)..(36)
<223> OTHER INFORMATION: MvF5 Th (UBITh1)

<400> SEQUENCE: 152

Cys Leu Glu Ser Gln Lys Glu Trp Leu Arg Thr Lys Cys Lys Lys Lys
1               5                   10                  15

Lys Ile Ser Ile Thr Glu Ile Lys Gly Val Ile Val His Arg Ile Glu
            20                  25                  30

Thr Ile Leu Phe
        35

<210> SEQ ID NO 153
<211> LENGTH: 59
<212> TYPE: PRT
<213> ORGANISM: Rattus norvegicus
<220> FEATURE:
<221> NAME/KEY: PEPTIDE
<222> LOCATION: (1)..(19)
<223> OTHER INFORMATION: MvF5 Th (UBITh1)
<220> FEATURE:
<221> NAME/KEY: SITE
<222> LOCATION: (20)..(20)
<223> OTHER INFORMATION: epsilon-K
<220> FEATURE:
<221> NAME/KEY: PEPTIDE
<222> LOCATION: (20)..(23)
<223> OTHER INFORMATION: epsilon K-KKK as a spacer
<220> FEATURE:
<221> NAME/KEY: PEPTIDE
<222> LOCATION: (24)..(36)
<223> OTHER INFORMATION: rat counterpart IL-6 150-162 cyclized
<220> FEATURE:
<221> NAME/KEY: PEPTIDE
<222> LOCATION: (37)..(40)
<223> OTHER INFORMATION: epsilon K-KKK as a spacer
<220> FEATURE:
<221> NAME/KEY: SITE
<222> LOCATION: (40)..(40)
<223> OTHER INFORMATION: epsilon K
<220> FEATURE:

```
<221> NAME/KEY: PEPTIDE
<222> LOCATION: (41)..(59)
<223> OTHER INFORMATION: MvF5 Th (UBITh1)

<400> SEQUENCE: 153

Ile Ser Ile Thr Glu Ile Lys Gly Val Ile Val His Arg Ile Glu Thr
1               5                   10                  15

Ile Leu Phe Lys Lys Lys Lys Cys Leu Glu Ser Gln Lys Glu Trp Leu
            20                  25                  30

Arg Thr Lys Cys Lys Lys Lys Ile Ser Ile Thr Glu Ile Lys Gly
            35                  40                  45

Val Ile Val His Arg Ile Glu Thr Ile Leu Phe
    50                  55

<210> SEQ ID NO 154
<211> LENGTH: 46
<212> TYPE: PRT
<213> ORGANISM: Rattus norvegicus
<220> FEATURE:
<221> NAME/KEY: PEPTIDE
<222> LOCATION: (1)..(23)
<223> OTHER INFORMATION: rat counterpart IL-6 144-166 cyclized
<220> FEATURE:
<221> NAME/KEY: PEPTIDE
<222> LOCATION: (24)..(27)
<223> OTHER INFORMATION: epsilon K-KKK as spacer
<220> FEATURE:
<221> NAME/KEY: SITE
<222> LOCATION: (27)..(27)
<223> OTHER INFORMATION: epsilon-K
<220> FEATURE:
<221> NAME/KEY: PEPTIDE
<222> LOCATION: (28)..(46)
<223> OTHER INFORMATION: MvF5 Th (UBITh1)

<400> SEQUENCE: 154

Cys Ala Leu Leu Met Glu Lys Leu Glu Ser Gln Lys Glu Trp Leu Arg
1               5                   10                  15

Thr Lys Thr Ile Gln Leu Cys Lys Lys Lys Ile Ser Ile Thr Glu
            20                  25                  30

Ile Lys Gly Val Ile Val His Arg Ile Glu Thr Ile Leu Phe
            35                  40                  45

<210> SEQ ID NO 155
<211> LENGTH: 36
<212> TYPE: PRT
<213> ORGANISM: Rattus norvegicus
<220> FEATURE:
<221> NAME/KEY: PEPTIDE
<222> LOCATION: (1)..(13)
<223> OTHER INFORMATION: rat counterpart IL-6 150-162 cyclized
<220> FEATURE:
<221> NAME/KEY: PEPTIDE
<222> LOCATION: (14)..(17)
<223> OTHER INFORMATION: epsilon K-KKK as a spacer
<220> FEATURE:
<221> NAME/KEY: SITE
<222> LOCATION: (17)..(17)
<223> OTHER INFORMATION: epsilon-K
<220> FEATURE:
<221> NAME/KEY: PEPTIDE
<222> LOCATION: (18)..(36)
<223> OTHER INFORMATION: MvF4 Th (UBITh3)
<220> FEATURE:
<221> NAME/KEY: SITE
<222> LOCATION: (21)..(21)
<223> OTHER INFORMATION: S or T
<220> FEATURE:
<221> NAME/KEY: SITE
<222> LOCATION: (24)..(24)
```

<223> OTHER INFORMATION: K or R
<220> FEATURE:
<221> NAME/KEY: SITE
<222> LOCATION: (25)..(25)
<223> OTHER INFORMATION: G or T
<220> FEATURE:
<221> NAME/KEY: SITE
<222> LOCATION: (29)..(29)
<223> OTHER INFORMATION: H or T
<220> FEATURE:
<221> NAME/KEY: SITE
<222> LOCATION: (30)..(30)
<223> OTHER INFORMATION: K or R

<400> SEQUENCE: 155

Cys Leu Glu Ser Gln Lys Glu Trp Leu Arg Thr Lys Cys Lys Lys Lys
1               5                   10                  15

Lys Ile Ser Ile Xaa Glu Ile Xaa Xaa Val Ile Val Xaa Xaa Ile Glu
            20                  25                  30

Thr Ile Leu Phe
        35

<210> SEQ ID NO 156
<211> LENGTH: 59
<212> TYPE: PRT
<213> ORGANISM: Rattus norvegicus
<220> FEATURE:
<221> NAME/KEY: PEPTIDE
<222> LOCATION: (1)..(19)
<223> OTHER INFORMATION: MvF 4 Th (UBITh3)
<220> FEATURE:
<221> NAME/KEY: SITE
<222> LOCATION: (4)..(4)
<223> OTHER INFORMATION: S or T
<220> FEATURE:
<221> NAME/KEY: SITE
<222> LOCATION: (7)..(7)
<223> OTHER INFORMATION: K or R
<220> FEATURE:
<221> NAME/KEY: SITE
<222> LOCATION: (8)..(8)
<223> OTHER INFORMATION: G or T
<220> FEATURE:
<221> NAME/KEY: SITE
<222> LOCATION: (12)..(12)
<223> OTHER INFORMATION: H or T
<220> FEATURE:
<221> NAME/KEY: SITE
<222> LOCATION: (13)..(13)
<223> OTHER INFORMATION: K or R
<220> FEATURE:
<221> NAME/KEY: PEPTIDE
<222> LOCATION: (20)..(23)
<223> OTHER INFORMATION: epsilon K-KKK as a spacer
<220> FEATURE:
<221> NAME/KEY: SITE
<222> LOCATION: (20)..(20)
<223> OTHER INFORMATION: epsilon-K
<220> FEATURE:
<221> NAME/KEY: PEPTIDE
<222> LOCATION: (24)..(36)
<223> OTHER INFORMATION: rat counterpart IL-6 150-162 cyclized
<220> FEATURE:
<221> NAME/KEY: PEPTIDE
<222> LOCATION: (37)..(40)
<223> OTHER INFORMATION: epsilon K-KKK as a spacer
<220> FEATURE:
<221> NAME/KEY: SITE
<222> LOCATION: (40)..(40)
<223> OTHER INFORMATION: epsilon-K
<220> FEATURE:
<221> NAME/KEY: PEPTIDE
<222> LOCATION: (41)..(59)
<223> OTHER INFORMATION: MvF 4 Th (UBITh3)
<220> FEATURE:

```
<221> NAME/KEY: SITE
<222> LOCATION: (44)..(44)
<223> OTHER INFORMATION: S or T
<220> FEATURE:
<221> NAME/KEY: SITE
<222> LOCATION: (47)..(47)
<223> OTHER INFORMATION: K or R
<220> FEATURE:
<221> NAME/KEY: SITE
<222> LOCATION: (48)..(48)
<223> OTHER INFORMATION: G or T
<220> FEATURE:
<221> NAME/KEY: SITE
<222> LOCATION: (52)..(52)
<223> OTHER INFORMATION: H or T
<220> FEATURE:
<221> NAME/KEY: SITE
<222> LOCATION: (53)..(53)
<223> OTHER INFORMATION: K or R

<400> SEQUENCE: 156

Ile Ser Ile Xaa Glu Ile Xaa Xaa Val Ile Val Xaa Xaa Ile Glu Thr
1               5                   10                  15

Ile Leu Phe Lys Lys Lys Lys Cys Leu Glu Ser Gln Lys Glu Trp Leu
            20                  25                  30

Arg Thr Lys Cys Lys Lys Lys Lys Ile Ser Ile Xaa Glu Ile Xaa Xaa
        35                  40                  45

Val Ile Val Xaa Xaa Ile Glu Thr Ile Leu Phe
    50                  55

<210> SEQ ID NO 157
<211> LENGTH: 46
<212> TYPE: PRT
<213> ORGANISM: Rattus norvegicus
<220> FEATURE:
<221> NAME/KEY: PEPTIDE
<222> LOCATION: (1)..(23)
<223> OTHER INFORMATION: rat counterpart IL-6 144-166 cyclized
<220> FEATURE:
<221> NAME/KEY: PEPTIDE
<222> LOCATION: (24)..(27)
<223> OTHER INFORMATION: epsilon K-KKK as a spacer
<220> FEATURE:
<221> NAME/KEY: SITE
<222> LOCATION: (27)..(27)
<223> OTHER INFORMATION: epsilon-K
<220> FEATURE:
<221> NAME/KEY: PEPTIDE
<222> LOCATION: (28)..(46)
<223> OTHER INFORMATION: MvF4 Th (UBITh3)
<220> FEATURE:
<221> NAME/KEY: SITE
<222> LOCATION: (31)..(31)
<223> OTHER INFORMATION: S or T
<220> FEATURE:
<221> NAME/KEY: SITE
<222> LOCATION: (34)..(34)
<223> OTHER INFORMATION: K or R
<220> FEATURE:
<221> NAME/KEY: SITE
<222> LOCATION: (34)..(35)
<223> OTHER INFORMATION: G or T
<220> FEATURE:
<221> NAME/KEY: SITE
<222> LOCATION: (39)..(39)
<223> OTHER INFORMATION: H or T
<220> FEATURE:
<221> NAME/KEY: SITE
<222> LOCATION: (40)..(40)
<223> OTHER INFORMATION: K or R
```

<400> SEQUENCE: 157

Cys Ala Leu Leu Met Glu Lys Leu Glu Ser Gln Lys Glu Trp Leu Arg
1               5                   10                  15

Thr Lys Thr Ile Gln Leu Cys Lys Lys Lys Lys Ile Ser Ile Xaa Glu
            20                  25                  30

Ile Xaa Xaa Val Ile Val Xaa Xaa Ile Glu Thr Ile Leu Phe
        35                  40                  45

<210> SEQ ID NO 158
<211> LENGTH: 34
<212> TYPE: PRT
<213> ORGANISM: Macaca fascicularis
<220> FEATURE:
<221> NAME/KEY: PEPTIDE
<222> LOCATION: (1)..(19)
<223> OTHER INFORMATION: MvF 4 Th (UBITh3)
<220> FEATURE:
<221> NAME/KEY: SITE
<222> LOCATION: (4)..(4)
<223> OTHER INFORMATION: S or T
<220> FEATURE:
<221> NAME/KEY: SITE
<222> LOCATION: (7)..(7)
<223> OTHER INFORMATION: K or R
<220> FEATURE:
<221> NAME/KEY: SITE
<222> LOCATION: (8)..(8)
<223> OTHER INFORMATION: G or T
<220> FEATURE:
<221> NAME/KEY: SITE
<222> LOCATION: (12)..(12)
<223> OTHER INFORMATION: H or T
<220> FEATURE:
<221> NAME/KEY: SITE
<222> LOCATION: (13)..(13)
<223> OTHER INFORMATION: K or R
<220> FEATURE:
<221> NAME/KEY: PEPTIDE
<222> LOCATION: (20)..(23)
<223> OTHER INFORMATION: epsilon K-KKK as a spacer
<220> FEATURE:
<221> NAME/KEY: SITE
<222> LOCATION: (20)..(20)
<223> OTHER INFORMATION: epsilon-K
<220> FEATURE:
<221> NAME/KEY: PEPTIDE
<222> LOCATION: (24)..(34)
<223> OTHER INFORMATION: macaque counterpart IL-6 73-83 cyclized

<400> SEQUENCE: 158

Ile Ser Ile Xaa Glu Ile Xaa Xaa Val Ile Val Xaa Xaa Ile Glu Thr
1               5                   10                  15

Ile Leu Phe Lys Lys Lys Lys Cys Phe Gln Ser Gly Phe Asn Glu Asp
            20                  25                  30

Thr Cys

<210> SEQ ID NO 159
<211> LENGTH: 34
<212> TYPE: PRT
<213> ORGANISM: Macaca fascicularis
<220> FEATURE:
<221> NAME/KEY: PEPTIDE
<222> LOCATION: (1)..(19)
<223> OTHER INFORMATION: MvF5 Th (UBITh1)
<220> FEATURE:
<221> NAME/KEY: SITE
<222> LOCATION: (20)..(20)
<223> OTHER INFORMATION: epsilon-K
<220> FEATURE:
<221> NAME/KEY: PEPTIDE

```
<222> LOCATION: (20)..(23)
<223> OTHER INFORMATION: epsilon K-KKK as a spacer
<220> FEATURE:
<221> NAME/KEY: PEPTIDE
<222> LOCATION: (24)..(34)
<223> OTHER INFORMATION: macaque counterpart IL-6 73-83 cyclized

<400> SEQUENCE: 159

Ile Ser Ile Thr Glu Ile Lys Gly Val Ile Val His Arg Ile Glu Thr
1               5                   10                  15

Ile Leu Phe Lys Lys Lys Lys Cys Phe Gln Ser Gly Phe Asn Glu Asp
            20                  25                  30

Thr Cys

<210> SEQ ID NO 160
<211> LENGTH: 33
<212> TYPE: PRT
<213> ORGANISM: Macaca fascicularis
<220> FEATURE:
<221> NAME/KEY: PEPTIDE
<222> LOCATION: (1)..(18)
<223> OTHER INFORMATION: HBsAg3 Th (UBITh2)
<220> FEATURE:
<221> NAME/KEY: SITE
<222> LOCATION: (19)..(19)
<223> OTHER INFORMATION: epsilon-K
<220> FEATURE:
<221> NAME/KEY: PEPTIDE
<222> LOCATION: (19)..(22)
<223> OTHER INFORMATION: epsilon K-KKK as a spacer
<220> FEATURE:
<221> NAME/KEY: PEPTIDE
<222> LOCATION: (23)..(33)
<223> OTHER INFORMATION: macaque counterpart IL-6 73-83 cyclized

<400> SEQUENCE: 160

Lys Lys Lys Ile Ile Thr Ile Thr Arg Ile Ile Thr Ile Ile Thr Thr
1               5                   10                  15

Ile Asp Lys Lys Lys Lys Cys Phe Gln Ser Gly Phe Asn Glu Asp Thr
            20                  25                  30

Cys

<210> SEQ ID NO 161
<211> LENGTH: 32
<212> TYPE: PRT
<213> ORGANISM: Homo sapiens
<220> FEATURE:
<221> NAME/KEY: PEPTIDE
<222> LOCATION: (1)..(17)
<223> OTHER INFORMATION: Clostridium tetani1 Th
<220> FEATURE:
<221> NAME/KEY: PEPTIDE
<222> LOCATION: (18)..(21)
<223> OTHER INFORMATION: epsilon K-KKK as a spacer
<220> FEATURE:
<221> NAME/KEY: SITE
<222> LOCATION: (21)..(21)
<223> OTHER INFORMATION: epsilon-K
<220> FEATURE:
<221> NAME/KEY: PEPTIDE
<222> LOCATION: (22)..(32)
<223> OTHER INFORMATION: IL-6 73-83

<400> SEQUENCE: 161

Lys Lys Gln Tyr Ile Lys Ala Asn Ser Lys Phe Ile Gly Ile Thr Glu
1               5                   10                  15

Leu Lys Lys Lys Lys Cys Phe Gln Ser Gly Phe Asn Glu Glu Thr Cys
            20                  25                  30
```

```
<210> SEQ ID NO 162
<211> LENGTH: 30
<212> TYPE: PRT
<213> ORGANISM: Homo sapiens
<220> FEATURE:
<221> NAME/KEY: PEPTIDE
<222> LOCATION: (1)..(15)
<223> OTHER INFORMATION: MvF1 Th
<220> FEATURE:
<221> NAME/KEY: PEPTIDE
<222> LOCATION: (16)..(19)
<223> OTHER INFORMATION: epsilon K-KKK as a spacer
<220> FEATURE:
<221> NAME/KEY: SITE
<222> LOCATION: (19)..(19)
<223> OTHER INFORMATION: epsilon-K
<220> FEATURE:
<221> NAME/KEY: PEPTIDE
<222> LOCATION: (20)..(30)
<223> OTHER INFORMATION: IL-6 73-83

<400> SEQUENCE: 162

Leu Ser Glu Ile Lys Gly Val Ile Val His Arg Leu Glu Gly Val Lys
1               5                   10                  15

Lys Lys Lys Cys Phe Gln Ser Gly Phe Asn Glu Glu Thr Cys
            20                  25                  30

<210> SEQ ID NO 163
<211> LENGTH: 39
<212> TYPE: PRT
<213> ORGANISM: Homo sapiens
<220> FEATURE:
<221> NAME/KEY: PEPTIDE
<222> LOCATION: (1)..(24)
<223> OTHER INFORMATION: Bordetella pertussis Th
<220> FEATURE:
<221> NAME/KEY: PEPTIDE
<222> LOCATION: (25)..(28)
<223> OTHER INFORMATION: epsilon K-KKK as a spacer
<220> FEATURE:
<221> NAME/KEY: SITE
<222> LOCATION: (28)..(28)
<223> OTHER INFORMATION: epsilon-K
<220> FEATURE:
<221> NAME/KEY: PEPTIDE
<222> LOCATION: (29)..(39)
<223> OTHER INFORMATION: IL-6 73-83

<400> SEQUENCE: 163

Gly Ala Tyr Ala Arg Cys Pro Asn Gly Thr Arg Ala Leu Thr Val Ala
1               5                   10                  15

Glu Leu Arg Gly Asn Ala Glu Leu Lys Lys Lys Lys Cys Phe Gln Ser
            20                  25                  30

Gly Phe Asn Glu Glu Thr Cys
        35

<210> SEQ ID NO 164
<211> LENGTH: 32
<212> TYPE: PRT
<213> ORGANISM: Homo sapiens
<220> FEATURE:
<221> NAME/KEY: PEPTIDE
<222> LOCATION: (1)..(17)
<223> OTHER INFORMATION: Clostridium tetani2 Th
<220> FEATURE:
<221> NAME/KEY: PEPTIDE
<222> LOCATION: (18)..(21)
<223> OTHER INFORMATION: epsilon K-KKK as a spacer
<220> FEATURE:
<221> NAME/KEY: SITE
<222> LOCATION: (21)..(21)
```

<223> OTHER INFORMATION: epsilon-K
<220> FEATURE:
<221> NAME/KEY: PEPTIDE
<222> LOCATION: (22)..(32)
<223> OTHER INFORMATION: IL-6 73-83

<400> SEQUENCE: 164

Trp Val Arg Asp Ile Ile Asp Asp Phe Thr Asn Glu Ser Ser Gln Lys
1               5                   10                  15

Thr Lys Lys Lys Lys Cys Phe Gln Ser Gly Phe Asn Glu Glu Thr Cys
            20                  25                  30

<210> SEQ ID NO 165
<211> LENGTH: 38
<212> TYPE: PRT
<213> ORGANISM: Homo sapiens
<220> FEATURE:
<221> NAME/KEY: PEPTIDE
<222> LOCATION: (1)..(23)
<223> OTHER INFORMATION: Diphtheria Th
<220> FEATURE:
<221> NAME/KEY: PEPTIDE
<222> LOCATION: (24)..(27)
<223> OTHER INFORMATION: epsilon K-KKK as a spacer
<220> FEATURE:
<221> NAME/KEY: SITE
<222> LOCATION: (27)..(27)
<223> OTHER INFORMATION: epsilon-K
<220> FEATURE:
<221> NAME/KEY: PEPTIDE
<222> LOCATION: (28)..(38)
<223> OTHER INFORMATION: IL-6 73-83

<400> SEQUENCE: 165

Asp Ser Glu Thr Ala Asp Asn Leu Glu Lys Thr Val Ala Ala Leu Ser
1               5                   10                  15

Ile Leu Pro Gly His Gly Cys Lys Lys Lys Cys Phe Gln Ser Gly
            20                  25                  30

Phe Asn Glu Glu Thr Cys
            35

<210> SEQ ID NO 166
<211> LENGTH: 36
<212> TYPE: PRT
<213> ORGANISM: Homo sapiens
<220> FEATURE:
<221> NAME/KEY: PEPTIDE
<222> LOCATION: (1)..(21)
<223> OTHER INFORMATION: Plasmodium falciparum Th
<220> FEATURE:
<221> NAME/KEY: PEPTIDE
<222> LOCATION: (22)..(25)
<223> OTHER INFORMATION: epsilon K-KKK as a spacer
<220> FEATURE:
<221> NAME/KEY: SITE
<222> LOCATION: (25)..(25)
<223> OTHER INFORMATION: epsilon-K
<220> FEATURE:
<221> NAME/KEY: PEPTIDE
<222> LOCATION: (26)..(36)
<223> OTHER INFORMATION: IL-6 73-83

<400> SEQUENCE: 166

Asp His Glu Lys Lys His Ala Lys Met Glu Lys Ala Ser Ser Val Phe
1               5                   10                  15

Asn Val Val Asn Ser Lys Lys Lys Cys Phe Gln Ser Gly Phe Asn
            20                  25                  30

Glu Glu Thr Cys
            35

```
<210> SEQ ID NO 167
<211> LENGTH: 32
<212> TYPE: PRT
<213> ORGANISM: Homo sapiens
<220> FEATURE:
<221> NAME/KEY: PEPTIDE
<222> LOCATION: (1)..(17)
<223> OTHER INFORMATION: Schistosoma mansoni Th
<220> FEATURE:
<221> NAME/KEY: PEPTIDE
<222> LOCATION: (18)..(21)
<223> OTHER INFORMATION: epsilon K-KKK as a spacer
<220> FEATURE:
<221> NAME/KEY: SITE
<222> LOCATION: (21)..(21)
<223> OTHER INFORMATION: epsilon-K
<220> FEATURE:
<221> NAME/KEY: PEPTIDE
<222> LOCATION: (22)..(32)
<223> OTHER INFORMATION: IL-6 73-83

<400> SEQUENCE: 167

Lys Trp Phe Lys Thr Asn Ala Pro Asn Gly Val Asp Glu Lys His Arg
1               5                   10                  15

His Lys Lys Lys Lys Cys Phe Gln Ser Gly Phe Asn Glu Glu Thr Cys
            20                  25                  30

<210> SEQ ID NO 168
<211> LENGTH: 40
<212> TYPE: PRT
<213> ORGANISM: Homo sapiens
<220> FEATURE:
<221> NAME/KEY: PEPTIDE
<222> LOCATION: (1)..(25)
<223> OTHER INFORMATION: Cholera Toxin Th
<220> FEATURE:
<221> NAME/KEY: PEPTIDE
<222> LOCATION: (26)..(29)
<223> OTHER INFORMATION: epsilon K-KKK as a spacer
<220> FEATURE:
<221> NAME/KEY: SITE
<222> LOCATION: (29)..(29)
<223> OTHER INFORMATION: epsilon-K
<220> FEATURE:
<221> NAME/KEY: PEPTIDE
<222> LOCATION: (30)..(40)
<223> OTHER INFORMATION: IL-6 73-83

<400> SEQUENCE: 168

Ala Leu Asn Ile Trp Asp Arg Phe Asp Val Phe Cys Thr Leu Gly Ala
1               5                   10                  15

Thr Thr Gly Tyr Leu Lys Gly Asn Ser Lys Lys Lys Cys Phe Gln
            20                  25                  30

Ser Gly Phe Asn Glu Glu Thr Cys
            35                  40

<210> SEQ ID NO 169
<211> LENGTH: 30
<212> TYPE: PRT
<213> ORGANISM: Homo sapiens
<220> FEATURE:
<221> NAME/KEY: PEPTIDE
<222> LOCATION: (1)..(15)
<223> OTHER INFORMATION: MvF2 Th
<220> FEATURE:
<221> NAME/KEY: PEPTIDE
<222> LOCATION: (16)..(19)
<223> OTHER INFORMATION: epsilon K-KKK as a spacer
<220> FEATURE:
<221> NAME/KEY: SITE
```

```
<222> LOCATION: (19)..(19)
<223> OTHER INFORMATION: epsilon-K
<220> FEATURE:
<221> NAME/KEY: PEPTIDE
<222> LOCATION: (20)..(30)
<223> OTHER INFORMATION: IL-6 73-83

<400> SEQUENCE: 169

Ile Ser Glu Ile Lys Gly Val Ile Val His Lys Ile Glu Gly Ile Lys
1               5                   10                  15

Lys Lys Lys Cys Phe Gln Ser Gly Phe Asn Glu Glu Thr Cys
            20                  25                  30

<210> SEQ ID NO 170
<211> LENGTH: 37
<212> TYPE: PRT
<213> ORGANISM: Homo sapiens
<220> FEATURE:
<221> NAME/KEY: PEPTIDE
<222> LOCATION: (1)..(22)
<223> OTHER INFORMATION: KKKMvF3 Th
<220> FEATURE:
<221> NAME/KEY: SITE
<222> LOCATION: (7)..(7)
<223> OTHER INFORMATION: S or T
<220> FEATURE:
<221> NAME/KEY: SITE
<222> LOCATION: (10)..(10)
<223> OTHER INFORMATION: K or R
<220> FEATURE:
<221> NAME/KEY: SITE
<222> LOCATION: (11)..(11)
<223> OTHER INFORMATION: G or T
<220> FEATURE:
<221> NAME/KEY: SITE
<222> LOCATION: (15)..(15)
<223> OTHER INFORMATION: H or T
<220> FEATURE:
<221> NAME/KEY: SITE
<222> LOCATION: (16)..(16)
<223> OTHER INFORMATION: K or R
<220> FEATURE:
<221> NAME/KEY: SITE
<222> LOCATION: (19)..(19)
<223> OTHER INFORMATION: G or T
<220> FEATURE:
<221> NAME/KEY: PEPTIDE
<222> LOCATION: (23)..(26)
<223> OTHER INFORMATION: epsilon K-KKK as a spacer
<220> FEATURE:
<221> NAME/KEY: SITE
<222> LOCATION: (26)..(26)
<223> OTHER INFORMATION: epsilon-K
<220> FEATURE:
<221> NAME/KEY: PEPTIDE
<222> LOCATION: (27)..(37)
<223> OTHER INFORMATION: IL-6 73-83

<400> SEQUENCE: 170

Lys Lys Lys Ile Ser Ile Xaa Glu Ile Xaa Xaa Val Ile Val Xaa Xaa
1               5                   10                  15

Ile Glu Xaa Ile Leu Phe Lys Lys Lys Cys Phe Gln Ser Gly Phe
            20                  25                  30

Asn Glu Glu Thr Cys
        35

<210> SEQ ID NO 171
<211> LENGTH: 33
<212> TYPE: PRT
<213> ORGANISM: Hepatitis B virus
<220> FEATURE:
<221> NAME/KEY: PEPTIDE
```

```
<222> LOCATION: (1)..(18)
<223> OTHER INFORMATION: HBsAg 1 Th
<220> FEATURE:
<221> NAME/KEY: SITE
<222> LOCATION: (1)..(1)
<223> OTHER INFORMATION: K or R
<220> FEATURE:
<221> NAME/KEY: SITE
<222> LOCATION: (2)..(2)
<223> OTHER INFORMATION: K or R
<220> FEATURE:
<221> NAME/KEY: SITE
<222> LOCATION: (3)..(3)
<223> OTHER INFORMATION: K or R
<220> FEATURE:
<221> NAME/KEY: SITE
<222> LOCATION: (4)..(4)
<223> OTHER INFORMATION: L or I or V or F
<220> FEATURE:
<221> NAME/KEY: SITE
<222> LOCATION: (5)..(5)
<223> OTHER INFORMATION: F or K or R
<220> FEATURE:
<221> NAME/KEY: SITE
<222> LOCATION: (6)..(6)
<223> OTHER INFORMATION: L or I or V or F
<220> FEATURE:
<221> NAME/KEY: SITE
<222> LOCATION: (7)..(7)
<223> OTHER INFORMATION: L or I or V or F
<220> FEATURE:
<221> NAME/KEY: SITE
<222> LOCATION: (9)..(9)
<223> OTHER INFORMATION: K or R
<220> FEATURE:
<221> NAME/KEY: SITE
<222> LOCATION: (10)..(10)
<223> OTHER INFORMATION: L or I or V or F
<220> FEATURE:
<221> NAME/KEY: SITE
<222> LOCATION: (11)..(11)
<223> OTHER INFORMATION: L or I or V or F
<220> FEATURE:
<221> NAME/KEY: SITE
<222> LOCATION: (13)..(13)
<223> OTHER INFORMATION: L or I or V or F
<220> FEATURE:
<221> NAME/KEY: SITE
<222> LOCATION: (15)..(15)
<223> OTHER INFORMATION: Q or L or I or V or F
<220> FEATURE:
<221> NAME/KEY: SITE
<222> LOCATION: (17)..(17)
<223> OTHER INFORMATION: L or I or V or F
<220> FEATURE:
<221> NAME/KEY: SITE
<222> LOCATION: (18)..(18)
<223> OTHER INFORMATION: D or R
<220> FEATURE:
<221> NAME/KEY: PEPTIDE
<222> LOCATION: (19)..(22)
<223> OTHER INFORMATION: epsilon K-KKK as a spacer
<220> FEATURE:
<221> NAME/KEY: SITE
<222> LOCATION: (22)..(22)
<223> OTHER INFORMATION: epsilon-K
<220> FEATURE:
<221> NAME/KEY: PEPTIDE
<222> LOCATION: (23)..(33)
<223> OTHER INFORMATION: IL-6 73-83

<400> SEQUENCE: 171

Xaa Xaa Xaa Xaa Xaa Xaa Xaa Thr Xaa Xaa Xaa Thr Xaa Pro Xaa Ser
1               5                   10                  15

Xaa Xaa Lys Lys Lys Lys Cys Phe Gln Ser Gly Phe Asn Glu Glu Thr
            20                  25                  30
```

Cys

```
<210> SEQ ID NO 172
<211> LENGTH: 33
<212> TYPE: PRT
<213> ORGANISM: Hepatitis B virus
<220> FEATURE:
<221> NAME/KEY: PEPTIDE
<222> LOCATION: (1)..(18)
<223> OTHER INFORMATION: HBsAg 2 Th
<220> FEATURE:
<221> NAME/KEY: SITE
<222> LOCATION: (4)..(4)
<223> OTHER INFORMATION: I or F
<220> FEATURE:
<221> NAME/KEY: SITE
<222> LOCATION: (5)..(5)
<223> OTHER INFORMATION: I or F
<220> FEATURE:
<221> NAME/KEY: SITE
<222> LOCATION: (6)..(6)
<223> OTHER INFORMATION: T or L
<220> FEATURE:
<221> NAME/KEY: SITE
<222> LOCATION: (7)..(7)
<223> OTHER INFORMATION: I or L
<220> FEATURE:
<221> NAME/KEY: SITE
<222> LOCATION: (11)..(11)
<223> OTHER INFORMATION: I or L
<220> FEATURE:
<221> NAME/KEY: SITE
<222> LOCATION: (14)..(14)
<223> OTHER INFORMATION: P or I
<220> FEATURE:
<221> NAME/KEY: SITE
<222> LOCATION: (15)..(15)
<223> OTHER INFORMATION: Q or T
<220> FEATURE:
<221> NAME/KEY: SITE
<222> LOCATION: (16)..(16)
<223> OTHER INFORMATION: S or T
<220> FEATURE:
<221> NAME/KEY: SITE
<222> LOCATION: (17)..(17)
<223> OTHER INFORMATION: L or I
<220> FEATURE:
<221> NAME/KEY: PEPTIDE
<222> LOCATION: (19)..(22)
<223> OTHER INFORMATION: epsilon K-KKK as a spacer
<220> FEATURE:
<221> NAME/KEY: SITE
<222> LOCATION: (22)..(22)
<223> OTHER INFORMATION: epsilon-K
<220> FEATURE:
<221> NAME/KEY: PEPTIDE
<222> LOCATION: (23)..(33)
<223> OTHER INFORMATION: IL-6 73-83

<400> SEQUENCE: 172

Lys Lys Lys Xaa Xaa Xaa Xaa Thr Arg Ile Xaa Thr Ile Xaa Xaa Xaa
1               5                   10                  15

Xaa Asp Lys Lys Lys Lys Cys Phe Gln Ser Gly Phe Asn Glu Glu Thr
            20                  25                  30

Cys

<210> SEQ ID NO 173
<211> LENGTH: 26
<212> TYPE: PRT
<213> ORGANISM: Homo sapiens
<220> FEATURE:
<221> NAME/KEY: PEPTIDE
<222> LOCATION: (1)..(11)
<223> OTHER INFORMATION: Influenza MP1_1 Th
```

```
<220> FEATURE:
<221> NAME/KEY: PEPTIDE
<222> LOCATION: (12)..(15)
<223> OTHER INFORMATION: epsilon K-KKK as a spacer
<220> FEATURE:
<221> NAME/KEY: SITE
<222> LOCATION: (15)..(15)
<223> OTHER INFORMATION: epsilon-K
<220> FEATURE:
<221> NAME/KEY: PEPTIDE
<222> LOCATION: (16)..(26)
<223> OTHER INFORMATION: IL-6 73-83

<400> SEQUENCE: 173

Phe Val Phe Thr Leu Thr Val Pro Ser Glu Arg Lys Lys Lys Lys Cys
1               5                   10                  15

Phe Gln Ser Gly Phe Asn Glu Glu Thr Cys
            20                  25

<210> SEQ ID NO 174
<211> LENGTH: 30
<212> TYPE: PRT
<213> ORGANISM: Homo sapiens
<220> FEATURE:
<221> NAME/KEY: PEPTIDE
<222> LOCATION: (1)..(15)
<223> OTHER INFORMATION: Influenza MP1_2 Th
<220> FEATURE:
<221> NAME/KEY: PEPTIDE
<222> LOCATION: (16)..(19)
<223> OTHER INFORMATION: epsilon K-KKK as a spacer
<220> FEATURE:
<221> NAME/KEY: SITE
<222> LOCATION: (19)..(19)
<223> OTHER INFORMATION: epsilon-K
<220> FEATURE:
<221> NAME/KEY: PEPTIDE
<222> LOCATION: (30)..(30)
<223> OTHER INFORMATION: IL-6 73-83

<400> SEQUENCE: 174

Ser Gly Pro Leu Lys Ala Glu Ile Ala Gln Arg Leu Glu Asp Val Lys
1               5                   10                  15

Lys Lys Lys Cys Phe Gln Ser Gly Phe Asn Glu Glu Thr Cys
            20                  25                  30

<210> SEQ ID NO 175
<211> LENGTH: 24
<212> TYPE: PRT
<213> ORGANISM: Homo sapiens
<220> FEATURE:
<221> NAME/KEY: PEPTIDE
<222> LOCATION: (1)..(9)
<223> OTHER INFORMATION: Influenza NSP1 Th
<220> FEATURE:
<221> NAME/KEY: PEPTIDE
<222> LOCATION: (10)..(13)
<223> OTHER INFORMATION: epsilon K-KKK as a spacer
<220> FEATURE:
<221> NAME/KEY: SITE
<222> LOCATION: (13)..(13)
<223> OTHER INFORMATION: epsilon-K
<220> FEATURE:
<221> NAME/KEY: PEPTIDE
<222> LOCATION: (14)..(24)
<223> OTHER INFORMATION: IL-6 73-83

<400> SEQUENCE: 175

Asp Arg Leu Arg Arg Asp Gln Lys Ser Lys Lys Lys Cys Phe Gln
1               5                   10                  15
```

```
Ser Gly Phe Asn Glu Glu Thr Cys
            20

<210> SEQ ID NO 176
<211> LENGTH: 34
<212> TYPE: PRT
<213> ORGANISM: Homo sapiens
<220> FEATURE:
<221> NAME/KEY: PEPTIDE
<222> LOCATION: (1)..(19)
<223> OTHER INFORMATION: EBV BHRF1 Th
<220> FEATURE:
<221> NAME/KEY: PEPTIDE
<222> LOCATION: (20)..(23)
<223> OTHER INFORMATION: epsilon K-KKK as a spacer
<220> FEATURE:
<221> NAME/KEY: SITE
<222> LOCATION: (23)..(23)
<223> OTHER INFORMATION: epsilon-K
<220> FEATURE:
<221> NAME/KEY: PEPTIDE
<222> LOCATION: (24)..(34)
<223> OTHER INFORMATION: IL-6 73-83

<400> SEQUENCE: 176

Ala Gly Leu Thr Leu Ser Leu Leu Val Ile Cys Ser Tyr Leu Phe Ile
1               5                   10                  15

Ser Arg Gly Lys Lys Lys Lys Cys Phe Gln Ser Gly Phe Asn Glu Glu
            20                  25                  30

Thr Cys

<210> SEQ ID NO 177
<211> LENGTH: 30
<212> TYPE: PRT
<213> ORGANISM: Homo sapiens
<220> FEATURE:
<221> NAME/KEY: PEPTIDE
<222> LOCATION: (1)..(15)
<223> OTHER INFORMATION: Clostridium tetani TT1 Th
<220> FEATURE:
<221> NAME/KEY: PEPTIDE
<222> LOCATION: (16)..(19)
<223> OTHER INFORMATION: epsilon K-KKK as a spacer
<220> FEATURE:
<221> NAME/KEY: SITE
<222> LOCATION: (19)..(19)
<223> OTHER INFORMATION: epsilon-K
<220> FEATURE:
<221> NAME/KEY: PEPTIDE
<222> LOCATION: (20)..(30)
<223> OTHER INFORMATION: IL-6 73-83

<400> SEQUENCE: 177

Gln Tyr Ile Lys Ala Asn Ser Lys Phe Ile Gly Ile Thr Glu Leu Lys
1               5                   10                  15

Lys Lys Lys Cys Phe Gln Ser Gly Phe Asn Glu Glu Thr Cys
            20                  25                  30

<210> SEQ ID NO 178
<211> LENGTH: 35
<212> TYPE: PRT
<213> ORGANISM: Homo sapiens
<220> FEATURE:
<221> NAME/KEY: PEPTIDE
<222> LOCATION: (1)..(20)
<223> OTHER INFORMATION: EBV EBNA-1 Th
<220> FEATURE:
<221> NAME/KEY: PEPTIDE
<222> LOCATION: (21)..(24)
<223> OTHER INFORMATION: epsilon K-KKK as a spacer
```

```
<220> FEATURE:
<221> NAME/KEY: SITE
<222> LOCATION: (24)..(24)
<223> OTHER INFORMATION: epsilon-K
<220> FEATURE:
<221> NAME/KEY: PEPTIDE
<222> LOCATION: (25)..(35)
<223> OTHER INFORMATION: IL-6 73-83

<400> SEQUENCE: 178

Pro Gly Pro Leu Arg Glu Ser Ile Val Cys Tyr Phe Met Val Phe Leu
1               5                   10                  15

Gln Thr His Ile Lys Lys Lys Lys Cys Phe Gln Ser Gly Phe Asn Glu
            20                  25                  30

Glu Thr Cys
        35

<210> SEQ ID NO 179
<211> LENGTH: 36
<212> TYPE: PRT
<213> ORGANISM: Homo sapiens
<220> FEATURE:
<221> NAME/KEY: PEPTIDE
<222> LOCATION: (1)..(21)
<223> OTHER INFORMATION: Clostridium tetani  TT2 Th
<220> FEATURE:
<221> NAME/KEY: PEPTIDE
<222> LOCATION: (22)..(25)
<223> OTHER INFORMATION: epsilon K-KKK as a spacer
<220> FEATURE:
<221> NAME/KEY: SITE
<222> LOCATION: (25)..(25)
<223> OTHER INFORMATION: epsilon-K
<220> FEATURE:
<221> NAME/KEY: PEPTIDE
<222> LOCATION: (26)..(36)
<223> OTHER INFORMATION: IL-6 73-83

<400> SEQUENCE: 179

Phe Asn Asn Phe Thr Val Ser Phe Trp Leu Arg Val Pro Lys Val Ser
1               5                   10                  15

Ala Ser His Leu Glu Lys Lys Lys Lys Cys Phe Gln Ser Gly Phe Asn
            20                  25                  30

Glu Glu Thr Cys
        35

<210> SEQ ID NO 180
<211> LENGTH: 31
<212> TYPE: PRT
<213> ORGANISM: Homo sapiens
<220> FEATURE:
<221> NAME/KEY: PEPTIDE
<222> LOCATION: (1)..(16)
<223> OTHER INFORMATION: Clostridium tetani TT3 Th
<220> FEATURE:
<221> NAME/KEY: PEPTIDE
<222> LOCATION: (17)..(20)
<223> OTHER INFORMATION: epsilon K-KKK as a spacer
<220> FEATURE:
<221> NAME/KEY: SITE
<222> LOCATION: (20)..(20)
<223> OTHER INFORMATION: epsilon-K
<220> FEATURE:
<221> NAME/KEY: PEPTIDE
<222> LOCATION: (21)..(31)
<223> OTHER INFORMATION: IL-6 73-83

<400> SEQUENCE: 180

Lys Phe Ile Ile Lys Arg Tyr Thr Pro Asn Asn Glu Ile Asp Ser Phe
1               5                   10                  15
```

```
Lys Lys Lys Lys Cys Phe Gln Ser Gly Phe Asn Glu Glu Thr Cys
            20                  25                  30

<210> SEQ ID NO 181
<211> LENGTH: 31
<212> TYPE: PRT
<213> ORGANISM: Homo sapiens
<220> FEATURE:
<221> NAME/KEY: PEPTIDE
<222> LOCATION: (1)..(16)
<223> OTHER INFORMATION: Clostridium tetani  TT4 Th
<220> FEATURE:
<221> NAME/KEY: PEPTIDE
<222> LOCATION: (17)..(20)
<223> OTHER INFORMATION: epsilon K-KKK as a spacer
<220> FEATURE:
<221> NAME/KEY: SITE
<222> LOCATION: (20)..(20)
<223> OTHER INFORMATION: epsilon-K
<220> FEATURE:
<221> NAME/KEY: PEPTIDE
<222> LOCATION: (21)..(31)
<223> OTHER INFORMATION: IL-6 73-83

<400> SEQUENCE: 181

Val Ser Ile Asp Lys Phe Arg Ile Phe Cys Lys Ala Leu Asn Pro Lys
1               5                   10                  15

Lys Lys Lys Lys Cys Phe Gln Ser Gly Phe Asn Glu Glu Thr Cys
            20                  25                  30

<210> SEQ ID NO 182
<211> LENGTH: 33
<212> TYPE: PRT
<213> ORGANISM: Homo sapiens
<220> FEATURE:
<221> NAME/KEY: PEPTIDE
<222> LOCATION: (1)..(18)
<223> OTHER INFORMATION: EBV CP Th
<220> FEATURE:
<221> NAME/KEY: PEPTIDE
<222> LOCATION: (19)..(22)
<223> OTHER INFORMATION: epsilon K-KKK as a spacer
<220> FEATURE:
<221> NAME/KEY: SITE
<222> LOCATION: (22)..(22)
<223> OTHER INFORMATION: epsilon-K
<220> FEATURE:
<221> NAME/KEY: PEPTIDE
<222> LOCATION: (23)..(33)
<223> OTHER INFORMATION: IL-6 73-83

<400> SEQUENCE: 182

Val Pro Gly Leu Tyr Ser Pro Cys Arg Ala Phe Phe Asn Lys Glu Glu
1               5                   10                  15

Leu Leu Lys Lys Lys Lys Cys Phe Gln Ser Gly Phe Asn Glu Glu Thr
            20                  25                  30

Cys

<210> SEQ ID NO 183
<211> LENGTH: 29
<212> TYPE: PRT
<213> ORGANISM: Homo sapiens
<220> FEATURE:
<221> NAME/KEY: PEPTIDE
<222> LOCATION: (1)..(14)
<223> OTHER INFORMATION: HCMV IE1 Th
<220> FEATURE:
<221> NAME/KEY: PEPTIDE
<222> LOCATION: (15)..(18)
<223> OTHER INFORMATION: epsilon K-KKK as a spacer
```

```
<220> FEATURE:
<221> NAME/KEY: SITE
<222> LOCATION: (18)..(18)
<223> OTHER INFORMATION: epsilon-K
<220> FEATURE:
<221> NAME/KEY: PEPTIDE
<222> LOCATION: (19)..(29)
<223> OTHER INFORMATION: IL-6 73-83

<400> SEQUENCE: 183

Asp Lys Arg Glu Met Trp Met Ala Cys Ile Lys Glu Leu His Lys Lys
1               5                   10                  15

Lys Lys Cys Phe Gln Ser Gly Phe Asn Glu Glu Thr Cys
            20                  25

<210> SEQ ID NO 184
<211> LENGTH: 30
<212> TYPE: PRT
<213> ORGANISM: Homo sapiens
<220> FEATURE:
<221> NAME/KEY: PEPTIDE
<222> LOCATION: (1)..(15)
<223> OTHER INFORMATION: EBV GP340 Th
<220> FEATURE:
<221> NAME/KEY: PEPTIDE
<222> LOCATION: (16)..(19)
<223> OTHER INFORMATION: epsilon K-KKK as a spacer
<220> FEATURE:
<221> NAME/KEY: SITE
<222> LOCATION: (19)..(19)
<223> OTHER INFORMATION: epsilon-K
<220> FEATURE:
<221> NAME/KEY: PEPTIDE
<222> LOCATION: (20)..(30)
<223> OTHER INFORMATION: IL-6 73-83

<400> SEQUENCE: 184

Thr Gly His Gly Ala Arg Thr Ser Thr Glu Pro Thr Thr Asp Tyr Lys
1               5                   10                  15

Lys Lys Lys Cys Phe Gln Ser Gly Phe Asn Glu Glu Thr Cys
            20                  25                  30

<210> SEQ ID NO 185
<211> LENGTH: 28
<212> TYPE: PRT
<213> ORGANISM: Homo sapiens
<220> FEATURE:
<221> NAME/KEY: PEPTIDE
<222> LOCATION: (1)..(13)
<223> OTHER INFORMATION: EBV BPLF1 Th
<220> FEATURE:
<221> NAME/KEY: PEPTIDE
<222> LOCATION: (14)..(17)
<223> OTHER INFORMATION: epsilon K-KKK as a spacer
<220> FEATURE:
<221> NAME/KEY: SITE
<222> LOCATION: (17)..(17)
<223> OTHER INFORMATION: epsilon-K
<220> FEATURE:
<221> NAME/KEY: PEPTIDE
<222> LOCATION: (18)..(28)
<223> OTHER INFORMATION: IL-6 73-83

<400> SEQUENCE: 185

Lys Glu Leu Lys Arg Gln Tyr Glu Lys Lys Leu Arg Gln Lys Lys Lys
1               5                   10                  15

Lys Cys Phe Gln Ser Gly Phe Asn Glu Glu Thr Cys
            20                  25

<210> SEQ ID NO 186
```

```
<211> LENGTH: 26
<212> TYPE: PRT
<213> ORGANISM: Homo sapiens
<220> FEATURE:
<221> NAME/KEY: PEPTIDE
<222> LOCATION: (1)..(11)
<223> OTHER INFORMATION: EBV EBNA-2 Th
<220> FEATURE:
<221> NAME/KEY: PEPTIDE
<222> LOCATION: (12)..(15)
<223> OTHER INFORMATION: epsilon K-KKK as a spacer
<220> FEATURE:
<221> NAME/KEY: SITE
<222> LOCATION: (15)..(15)
<223> OTHER INFORMATION: epsilon-K
<220> FEATURE:
<221> NAME/KEY: PEPTIDE
<222> LOCATION: (16)..(26)
<223> OTHER INFORMATION: IL-6 73-83

<400> SEQUENCE: 186

Thr Val Phe Tyr Asn Ile Pro Pro Met Pro Leu Lys Lys Lys Lys Cys
1               5                   10                  15
Phe Gln Ser Gly Phe Asn Glu Glu Thr Cys
            20                  25

<210> SEQ ID NO 187
<211> LENGTH: 49
<212> TYPE: PRT
<213> ORGANISM: Artificial Sequence
<220> FEATURE:
<223> OTHER INFORMATION: Synthetic peptide
<220> FEATURE:
<221> NAME/KEY: PEPTIDE
<222> LOCATION: (1)..(31)
<223> OTHER INFORMATION: IL-6 42-72, cyclized
<220> FEATURE:
<221> NAME/KEY: SITE
<222> LOCATION: (32)..(32)
<223> OTHER INFORMATION: epsilon-K as a spacer
<220> FEATURE:
<221> NAME/KEY: PEPTIDE
<222> LOCATION: (33)..(49)
<223> OTHER INFORMATION: Clostridium tetani 1 Th

<400> SEQUENCE: 187

Glu Thr Cys Asn Lys Ser Asn Met Cys Glu Ser Ser Lys Glu Ala Leu
1               5                   10                  15
Ala Glu Asn Asn Leu Asn Leu Pro Lys Met Ala Glu Lys Asp Gly Lys
            20                  25                  30
Lys Lys Gln Tyr Ile Lys Ala Asn Ser Lys Phe Ile Gly Ile Thr Glu
        35                  40                  45
Leu

<210> SEQ ID NO 188
<211> LENGTH: 47
<212> TYPE: PRT
<213> ORGANISM: Artificial Sequence
<220> FEATURE:
<223> OTHER INFORMATION: Synthetic peptide
<220> FEATURE:
<221> NAME/KEY: PEPTIDE
<222> LOCATION: (1)..(31)
<223> OTHER INFORMATION: IL-6 42-72, cyclized
<220> FEATURE:
<221> NAME/KEY: SITE
<222> LOCATION: (32)..(32)
<223> OTHER INFORMATION: epsilon-K as a spacer
<220> FEATURE:
<221> NAME/KEY: PEPTIDE
<222> LOCATION: (33)..(47)
```

<223> OTHER INFORMATION: MvF1 Th

<400> SEQUENCE: 188

Glu Thr Cys Asn Lys Ser Asn Met Cys Glu Ser Ser Lys Glu Ala Leu
1               5                   10                  15

Ala Glu Asn Asn Leu Asn Leu Pro Lys Met Ala Glu Lys Asp Gly Lys
            20                  25                  30

Leu Ser Glu Ile Lys Gly Val Ile Val His Arg Leu Glu Gly Val
        35                  40                  45

<210> SEQ ID NO 189
<211> LENGTH: 56
<212> TYPE: PRT
<213> ORGANISM: Artificial Sequence
<220> FEATURE:
<223> OTHER INFORMATION: Synthetic peptide
<220> FEATURE:
<221> NAME/KEY: PEPTIDE
<222> LOCATION: (1)..(31)
<223> OTHER INFORMATION: IL-6 42-72, cyclized
<220> FEATURE:
<221> NAME/KEY: SITE
<222> LOCATION: (32)..(32)
<223> OTHER INFORMATION: epsilon-K as a spacer
<220> FEATURE:
<221> NAME/KEY: PEPTIDE
<222> LOCATION: (33)..(56)
<223> OTHER INFORMATION: Bordetella pertussis Th

<400> SEQUENCE: 189

Glu Thr Cys Asn Lys Ser Asn Met Cys Glu Ser Ser Lys Glu Ala Leu
1               5                   10                  15

Ala Glu Asn Asn Leu Asn Leu Pro Lys Met Ala Glu Lys Asp Gly Lys
            20                  25                  30

Gly Ala Tyr Ala Arg Cys Pro Asn Gly Thr Arg Ala Leu Thr Val Ala
        35                  40                  45

Glu Leu Arg Gly Asn Ala Glu Leu
    50                  55

<210> SEQ ID NO 190
<211> LENGTH: 49
<212> TYPE: PRT
<213> ORGANISM: Artificial Sequence
<220> FEATURE:
<223> OTHER INFORMATION: Synthetic peptide
<220> FEATURE:
<221> NAME/KEY: PEPTIDE
<222> LOCATION: (1)..(31)
<223> OTHER INFORMATION: IL-6 42-72, cyclized
<220> FEATURE:
<221> NAME/KEY: SITE
<222> LOCATION: (32)..(32)
<223> OTHER INFORMATION: epsilon-K as a spacer
<220> FEATURE:
<221> NAME/KEY: PEPTIDE
<222> LOCATION: (33)..(49)
<223> OTHER INFORMATION: Clostridium tetani 2 Th

<400> SEQUENCE: 190

Glu Thr Cys Asn Lys Ser Asn Met Cys Glu Ser Ser Lys Glu Ala Leu
1               5                   10                  15

Ala Glu Asn Asn Leu Asn Leu Pro Lys Met Ala Glu Lys Asp Gly Lys
            20                  25                  30

Trp Val Arg Asp Ile Ile Asp Asp Phe Thr Asn Glu Ser Ser Gln Lys
        35                  40                  45

Thr

<210> SEQ ID NO 191
<211> LENGTH: 55
<212> TYPE: PRT
<213> ORGANISM: Artificial Sequence
<220> FEATURE:
<223> OTHER INFORMATION: Synthetic peptide
<220> FEATURE:
<221> NAME/KEY: PEPTIDE
<222> LOCATION: (1)..(31)
<223> OTHER INFORMATION: IL-6 42-72, cyclized
<220> FEATURE:
<221> NAME/KEY: SITE
<222> LOCATION: (32)..(32)
<223> OTHER INFORMATION: epsilon-K as a spacer
<220> FEATURE:
<221> NAME/KEY: PEPTIDE
<222> LOCATION: (33)..(55)
<223> OTHER INFORMATION: Diphtheria Th

<400> SEQUENCE: 191

Glu Thr Cys Asn Lys Ser Asn Met Cys Glu Ser Ser Lys Glu Ala Leu
1               5                   10                  15

Ala Glu Asn Asn Leu Asn Leu Pro Lys Met Ala Glu Lys Asp Gly Lys
            20                  25                  30

Asp Ser Glu Thr Ala Asp Asn Leu Glu Lys Thr Val

```
<223> OTHER INFORMATION: IL-6 42-72, cyclized
<220> FEATURE:
<221> NAME/KEY: SITE
<222> LOCATION: (32)..(32)
<223> OTHER INFORMATION: epsilon-K as a spacer
<220> FEATURE:
<221> NAME/KEY: PEPTIDE
<222> LOCATION: (33)..(49)
<223> OTHER INFORMATION: Schistosoma mansoni Th

<400> SEQUENCE: 193

Glu Thr Cys Asn Lys Ser Asn Met Cys Glu Ser Ser Lys Glu Ala Leu
1               5                   10                  15

Ala Glu Asn Asn Leu Asn Leu Pro Lys Met Ala Glu Lys Asp Gly Lys
            20                  25                  30

Lys Trp Phe Lys Thr Asn Ala Pro Asn Gly Val Asp Glu Lys His Arg
        35                  40                  45

His

<210> SEQ ID NO 194
<211> LENGTH: 25
<212> TYPE: PRT
<213> ORGANISM: Artificial Sequence
<220> FEATURE:
<223> OTHER INFORMATION: Synthetic peptide
<220> FEATURE:
<221> NAME/KEY: PEPTIDE
<222> LOCATION: (1)..(25)
<223> OTHER INFORMATION: Cholera Toxin Th

<400> SEQUENCE: 194

Ala Leu Asn Ile Trp Asp Arg Phe Asp Val Phe Cys Thr Leu Gly Ala
1               5                   10                  15

Thr Thr Gly Tyr Leu Lys Gly Asn Ser
            20                  25

<210> SEQ ID NO 195
<211> LENGTH: 47
<212> TYPE: PRT
<213> ORGANISM: Artificial Sequence
<220> FEATURE:
<223> OTHER INFORMATION: Synthetic peptide
<220> FEATURE:
<221> NAME/KEY: PEPTIDE
<222> LOCATION: (1)..(31)
<223> OTHER INFORMATION: IL-6 42-72, cyclized
<220> FEATURE:
<221> NAME/KEY: SITE
<222> LOCATION: (32)..(32)
<223> OTHER INFORMATION: epsilon-K as a spacer
<220> FEATURE:
<221> NAME/KEY: PEPTIDE
<222> LOCATION: (33)..(47)
<223> OTHER INFORMATION: MvF 2 Th

<400> SEQUENCE: 195

Glu Thr Cys Asn Lys Ser Asn Met Cys Glu Ser Ser Lys Glu Ala Leu
1               5                   10                  15

Ala Glu Asn Asn Leu Asn Leu Pro Lys Met Ala Glu Lys Asp Gly Lys
            20                  25                  30

Ile Ser Glu Ile Lys Gly Val Ile Val His Lys Ile Glu Gly Ile
        35                  40                  45

<210> SEQ ID NO 196
<211> LENGTH: 54
<212> TYPE: PRT
<213> ORGANISM: Artificial Sequence
```

```
<220> FEATURE:
<223> OTHER INFORMATION: Synthetic peptide
<220> FEATURE:
<221> NAME/KEY: PEPTIDE
<222> LOCATION: (1)..(31)
<223> OTHER INFORMATION: IL-6 42-72, cyclized
<220> FEATURE:
<221> NAME/KEY: SITE
<222> LOCATION: (32)..(32)
<223> OTHER INFORMATION: epsilon-K as a spacer
<220> FEATURE:
<221> NAME/KEY: PEPTIDE
<222> LOCATION: (33)..(54)
<223> OTHER INFORMATION: KKKMvF 3 Th
<220> FEATURE:
<221> NAME/KEY: SITE
<222> LOCATION: (39)..(39)
<223> OTHER INFORMATION: S or T
<220> FEATURE:
<221> NAME/KEY: SITE
<222> LOCATION: (42)..(42)
<223> OTHER INFORMATION: K or R
<220> FEATURE:
<221> NAME/KEY: SITE
<222> LOCATION: (43)..(43)
<223> OTHER INFORMATION: G or T
<220> FEATURE:
<221> NAME/KEY: SITE
<222> LOCATION: (47)..(47)
<223> OTHER INFORMATION: H or T
<220> FEATURE:
<221> NAME/KEY: SITE
<222> LOCATION: (48)..(48)
<223> OTHER INFORMATION: K or R
<220> FEATURE:
<221> NAME/KEY: SITE
<222> LOCATION: (51)..(51)
<223> OTHER INFORMATION: G or T

<400> SEQUENCE: 196

Glu Thr Cys Asn Lys Ser Asn Met Cys Glu Ser Ser Lys Glu Ala Leu
1               5                   10                  15

Ala Glu Asn Asn Leu Asn Leu Pro Lys Met Ala Glu Lys Asp Gly Lys
            20                  25                  30

Lys Lys Lys Ile Ser Ile Xaa Glu Ile Xaa Xaa Val Ile Val Xaa Xaa
        35                  40                  45

Ile Glu Xaa Ile Leu Phe
    50

<210> SEQ ID NO 197
<211> LENGTH: 50
<212> TYPE: PRT
<213> ORGANISM: Artificial Sequence
<220> FEATURE:
<223> OTHER INFORMATION: Synthetic peptide
<220> FEATURE:
<221> NAME/KEY: PEPTIDE
<222> LOCATION: (1)..(31)
<223> OTHER INFORMATION: IL-6 42-72, cyclized
<220> FEATURE:
<221> NAME/KEY: SITE
<222> LOCATION: (32)..(32)
<223> OTHER INFORMATION: epsilon-K as a spacer
<220> FEATURE:
<221> NAME/KEY: PEPTIDE
<222> LOCATION: (33)..(50)
<223> OTHER INFORMATION: HBsAg 1 Th
<220> FEATURE:
<221> NAME/KEY: SITE
<222> LOCATION: (33)..(33)
<223> OTHER INFORMATION: K or R
<220> FEATURE:
<221> NAME/KEY: SITE
<222> LOCATION: (34)..(34)
```

```
<223> OTHER INFORMATION: K or R
<220> FEATURE:
<221> NAME/KEY: SITE
<222> LOCATION: (35)..(35)
<223> OTHER INFORMATION: K or R
<220> FEATURE:
<221> NAME/KEY: SITE
<222> LOCATION: (36)..(36)
<223> OTHER INFORMATION: L or I or V or F
<220> FEATURE:
<221> NAME/KEY: SITE
<222> LOCATION: (37)..(37)
<223> OTHER INFORMATION: F or K or R
<220> FEATURE:
<221> NAME/KEY: SITE
<222> LOCATION: (38)..(38)
<223> OTHER INFORMATION: L or I or V or F
<220> FEATURE:
<221> NAME/KEY: SITE
<222> LOCATION: (39)..(39)
<223> OTHER INFORMATION: L or I or V or F
<220> FEATURE:
<221> NAME/KEY: SITE
<222> LOCATION: (41)..(41)
<223> OTHER INFORMATION: K or R
<220> FEATURE:
<221> NAME/KEY: SITE
<222> LOCATION: (42)..(42)
<223> OTHER INFORMATION: L or I or V or F
<220> FEATURE:
<221> NAME/KEY: SITE
<222> LOCATION: (43)..(43)
<223> OTHER INFORMATION: L or I or V or F
<220> FEATURE:
<221> NAME/KEY: SITE
<222> LOCATION: (45)..(45)
<223> OTHER INFORMATION: L or I or V or F
<220> FEATURE:
<221> NAME/KEY: SITE
<222> LOCATION: (47)..(47)
<223> OTHER INFORMATION: Q or L or I or V or F
<220> FEATURE:
<221> NAME/KEY: SITE
<222> LOCATION: (49)..(49)
<223> OTHER INFORMATION: L or I or V or F
<220> FEATURE:
<221> NAME/KEY: SITE
<222> LOCATION: (50)..(50)
<223> OTHER INFORMATION: D or R

<400> SEQUENCE: 197

Glu Thr Cys Asn Lys Ser Asn Met Cys Glu Ser Ser Lys Glu Ala Leu
1               5                   10                  15

Ala Glu Asn Asn Leu Asn Leu Pro Lys Met Ala Glu Lys Asp Gly Lys
                20                  25                  30

Xaa Xaa Xaa Xaa Xaa Xaa Thr Xaa Xaa Xaa Thr Xaa Pro Xaa Ser
            35                  40                  45

Xaa Xaa
    50

<210> SEQ ID NO 198
<211> LENGTH: 50
<212> TYPE: PRT
<213> ORGANISM: Artificial Sequence
<220> FEATURE:
<223> OTHER INFORMATION: Synthetic peptide
<220> FEATURE:
<221> NAME/KEY: PEPTIDE
<222> LOCATION: (1)..(31)
<223> OTHER INFORMATION: IL-6 42-72, cyclized
<220> FEATURE:
<221> NAME/KEY: SITE
<222> LOCATION: (32)..(32)
<223> OTHER INFORMATION: epsilon-K as a spacer
```

```
<220> FEATURE:
<221> NAME/KEY: PEPTIDE
<222> LOCATION: (33)..(50)
<223> OTHER INFORMATION: HBsAg 2 Th
<220> FEATURE:
<221> NAME/KEY: SITE
<222> LOCATION: (36)..(36)
<223> OTHER INFORMATION: I or F
<220> FEATURE:
<221> NAME/KEY: SITE
<222> LOCATION: (37)..(37)
<223> OTHER INFORMATION: I or F
<220> FEATURE:
<221> NAME/KEY: SITE
<222> LOCATION: (38)..(38)
<223> OTHER INFORMATION: T or L
<220> FEATURE:
<221> NAME/KEY: SITE
<222> LOCATION: (39)..(39)
<223> OTHER INFORMATION: I or L
<220> FEATURE:
<221> NAME/KEY: SITE
<222> LOCATION: (43)..(43)
<223> OTHER INFORMATION: I or L
<220> FEATURE:
<221> NAME/KEY: SITE
<222> LOCATION: (46)..(46)
<223> OTHER INFORMATION: P or I
<220> FEATURE:
<221> NAME/KEY: SITE
<222> LOCATION: (47)..(47)
<223> OTHER INFORMATION: Q or T
<220> FEATURE:
<221> NAME/KEY: SITE
<222> LOCATION: (48)..(48)
<223> OTHER INFORMATION: S or T
<220> FEATURE:
<221> NAME/KEY: SITE
<222> LOCATION: (49)..(49)
<223> OTHER INFORMATION: L or I

<400> SEQUENCE: 198

Glu Thr Cys Asn Lys Ser Asn Met Cys Glu Ser Ser Lys Glu Ala Leu
1               5                   10                  15

Ala Glu Asn Asn Leu Asn Leu Pro Lys Met Ala Glu Lys Asp Gly Lys
                20                  25                  30

Lys Lys Lys Xaa Xaa Xaa Xaa Thr Arg Ile Xaa Thr Ile Xaa Xaa Xaa
            35                  40                  45

Xaa Asp
    50

<210> SEQ ID NO 199
<211> LENGTH: 50
<212> TYPE: PRT
<213> ORGANISM: Artificial Sequence
<220> FEATURE:
<223> OTHER INFORMATION: Synthetic peptide
<220> FEATURE:
<221> NAME/KEY: PEPTIDE
<222> LOCATION: (1)..(18)
<223> OTHER INFORMATION: HBsAg 3 Th (UBITh2)
<220> FEATURE:
<221> NAME/KEY: PEPTIDE
<222> LOCATION: (1)..(31)
<223> OTHER INFORMATION: IL-6 42-72, cyclized
<220> FEATURE:
<221> NAME/KEY: SITE
<222> LOCATION: (32)..(32)
<223> OTHER INFORMATION: epsilon-K as a spacer
<220> FEATURE:
<221> NAME/KEY: PEPTIDE
<222> LOCATION: (33)..(50)
<223> OTHER INFORMATION: HBsAg 3 Th (UBITh2)
```

<400> SEQUENCE: 199

Glu Thr Cys Asn Lys Ser Asn Met Cys Glu Ser Ser Lys Glu Ala Leu
1               5                   10                  15

Ala Glu Asn Asn Leu Asn Leu Pro Lys Met Ala Glu Lys Asp Gly Lys
            20                  25                  30

Lys Lys Lys Ile Ile Thr Ile Thr Arg Ile Ile Thr Ile Ile Thr Thr
        35                  40                  45

Ile Asp
    50

<210> SEQ ID NO 200
<211> LENGTH: 43
<212> TYPE: PRT
<213> ORGANISM: Artificial Sequence
<220> FEATURE:
<223> OTHER INFORMATION: Synthetic peptide
<220> FEATURE:
<221> NAME/KEY: PEPTIDE
<222> LOCATION: (1)..(11)
<223> OTHER INFORMATION: Influenza MP1_1 Th
<220> FEATURE:
<221> NAME/KEY: PEPTIDE
<222> LOCATION: (1)..(11)
<223> OTHER INFORMATION: Influenza MP1_1 Th
<220> FEATURE:
<221> NAME/KEY: PEPTIDE
<222> LOCATION: (1)..(31)
<223> OTHER INFORMATION: IL-6 42-72, cyclized
<220> FEATURE:
<221> NAME/KEY: SITE
<222> LOCATION: (32)..(32)
<223> OTHER INFORMATION: epsilon-K as a spacer
<220> FEATURE:
<221> NAME/KEY: PEPTIDE
<222> LOCATION: (33)..(43)
<223> OTHER INFORMATION: Influenza MP1_1 Th

<400> SEQUENCE: 200

Glu Thr Cys Asn Lys Ser Asn Met Cys Glu Ser Ser Lys Glu Ala Leu
1               5                   10                  15

Ala Glu Asn Asn Leu Asn Leu Pro Lys Met Ala Glu Lys Asp Gly Lys
            20                  25                  30

Phe Val Phe Thr Leu Thr Val Pro Ser Glu Arg
            35                  40

<210> SEQ ID NO 201
<211> LENGTH: 47
<212> TYPE: PRT
<213> ORGANISM: Artificial Sequence
<220> FEATURE:
<223> OTHER INFORMATION: Synthetic peptide
<220> FEATURE:
<221> NAME/KEY: PEPTIDE
<222> LOCATION: (1)..(31)
<223> OTHER INFORMATION: IL-6 42-72, cyclized
<220> FEATURE:
<221> NAME/KEY: SITE
<222> LOCATION: (32)..(32)
<223> OTHER INFORMATION: epsilon-K as a spacer
<220> FEATURE:
<221> NAME/KEY: PEPTIDE
<222> LOCATION: (33)..(47)
<223> OTHER INFORMATION: Influenza MP1_2 Th

<400> SEQUENCE: 201

Glu Thr Cys Asn Lys Ser Asn Met Cys Glu Ser Ser Lys Glu Ala Leu
1               5                   10                  15

Ala Glu Asn Asn Leu Asn Leu Pro Lys Met Ala Glu Lys Asp Gly Lys
            20                  25                  30

Ser Gly Pro Leu Lys Ala Glu Ile Ala Gln Arg Leu Glu Asp Val
        35                  40                  45

<210> SEQ ID NO 202
<211> LENGTH: 41
<212> TYPE: PRT
<213> ORGANISM: Artificial Sequence
<220> FEATURE:
<223> OTHER INFORMATION: Synthetic peptide
<220> FEATURE:
<221> NAME/KEY: PEPTIDE
<222> LOCATION: (1)..(31)
<223> OTHER INFORMATION: IL-6 42-72, cyclized
<220> FEATURE:
<221> NAME/KEY: SITE
<222> LOCATION: (32)..(32)
<223> OTHER INFORMATION: epsilon-K as a spacer
<220> FEATURE:
<221> NAME/KEY: PEPTIDE
<222> LOCATION: (33)..(41)
<223> OTHER INFORMATION: Influenza NSP1 Th

<400> SEQUENCE: 202

Glu Thr Cys Asn Lys Ser Asn Met Cys Glu Ser Ser Lys Glu Ala Leu
1               5                   10                  15

Ala Glu Asn Asn Leu Asn Leu Pro Lys Met Ala Glu Lys Asp Gly Lys
            20                  25                  30

Asp Arg Leu Arg Arg Asp Gln Lys Ser
        35                  40

<210> SEQ ID NO 203
<211> LENGTH: 51
<212> TYPE: PRT
<213> ORGANISM: Artificial Sequence
<220> FEATURE:
<223> OTHER INFORMATION: Synthetic peptide
<220> FEATURE:
<221> NAME/KEY: PEPTIDE
<222> LOCATION: (1)..(31)
<223> OTHER INFORMATION: IL-6 42-72, cyclized
<220> FEATURE:
<221> NAME/KEY: SITE
<222> LOCATION: (32)..(32)
<223> OTHER INFORMATION: epsilon-K as a spacer
<220> FEATURE:
<221> NAME/KEY: PEPTIDE
<222> LOCATION: (33)..(51)
<223> OTHER INFORMATION: EBV BHRF1 Th

<400> SEQUENCE: 203

Glu Thr Cys Asn Lys Ser Asn Met Cys Glu Ser Ser Lys Glu Ala Leu
1               5                   10                  15

Ala Glu Asn Asn Leu Asn Leu Pro Lys Met Ala Glu Lys Asp Gly Lys
            20                  25                  30

Ala Gly Leu Thr Leu Ser Leu Leu Val Ile Cys Ser Tyr Leu Phe Ile
        35                  40                  45

Ser Arg Gly
    50

<210> SEQ ID NO 204
<211> LENGTH: 47
<212> TYPE: PRT
<213> ORGANISM: Artificial Sequence
<220> FEATURE:
<223> OTHER INFORMATION: Synthetic peptide

```
<220> FEATURE:
<221> NAME/KEY: PEPTIDE
<222> LOCATION: (1)..(31)
<223> OTHER INFORMATION: IL-6 42-72, cyclized
<220> FEATURE:
<221> NAME/KEY: SITE
<222> LOCATION: (32)..(32)
<223> OTHER INFORMATION: epsilon-K as a spacer
<220> FEATURE:
<221> NAME/KEY: PEPTIDE
<222> LOCATION: (33)..(47)
<223> OTHER INFORMATION: Clostridium tetani TT1 Th

<400> SEQUENCE: 204

Glu Thr Cys Asn Lys Ser Asn Met Cys Glu Ser Ser Lys Glu Ala Le

<400> SEQUENCE: 206

Glu Thr Cys Asn Lys Ser Asn Met Cys Glu Ser Ser Lys Glu Ala Leu
1               5                   10                  15

Ala Glu Asn Asn Leu Asn Leu Pro Lys Met Ala Glu Lys Asp Gly Lys
            20                  25                  30

Phe Asn Asn Phe Thr Val Ser Phe Trp Leu Arg Val Pro Lys Val Ser
        35                  40                  45

Ala Ser His Leu Glu
    50

<210> SEQ ID NO 207
<211> LENGTH: 48
<212> TYPE: PRT
<213> ORGANISM: Artificial Sequence
<220> FEATURE:
<223> OTHER INFORMATION: Synthetic peptide
<220> FEATURE:
<221> NAME/KEY: PEPTIDE
<222> LOCATION: (1)..(31)
<223> OTHER INFORMATION: IL-6 42-72, cyclized
<220> FEATURE:
<221> NAME/KEY: SITE
<222> LOCATION: (32)..(32)
<223> OTHER INFORMATION: epsilon-K as a spacer
<220> FEATURE:
<221> NAME/KEY: PEPTIDE
<222> LOCATION: (33)..(48)
<223> OTHER INFORMATION: Clostridium tetani TT3 Th

<400> SEQUENCE: 207

Glu Thr Cys Asn Lys Ser Asn Met Cys Glu Ser Ser Lys Glu Ala Leu
1               5                   10                  15

Ala Glu Asn Asn Leu Asn Leu Pro Lys Met Ala Glu Lys Asp Gly Lys
            20                  25                  30

Lys Phe Ile Ile Lys Arg Tyr Thr Pro Asn Asn Glu Ile Asp Ser Phe
        35                  40                  45

<210> SEQ ID NO 208
<211> LENGTH: 48
<212> TYPE: PRT
<213> ORGANISM: Artificial Sequence
<220> FEATURE:
<223> OTHER INFORMATION: Synthetic peptide
<220> FEATURE:
<221> NAME/KEY: PEPTIDE
<222> LOCATION: (1)..(31)
<223> OTHER INFORMATION: IL-6 42-72, cyclized
<220> FEATURE:
<221> NAME/KEY: SITE
<222> LOCATION: (32)..(32)
<223> OTHER INFORMATION: epsilon-K as a spacer
<220> FEATURE:
<221> NAME/KEY: PEPTIDE
<222> LOCATION: (33)..(48)
<223> OTHER INFORMATION: Clostridium tetani  TT4 Th

<400> SEQUENCE: 208

Glu Thr Cys Asn Lys Ser Asn Met Cys Glu Ser Ser Lys Glu Ala Leu
1               5                   10                  15

Ala Glu Asn Asn Leu Asn Leu Pro Lys Met Ala Glu Lys Asp Gly Lys
            20                  25                  30

Val Ser Ile Asp Lys Phe Arg Ile Phe Cys Lys Ala Leu Asn Pro Lys
        35                  40                  45

<210> SEQ ID NO 209

```
<211> LENGTH: 50
<212> TYPE: PRT
<213> ORGANISM: Artificial Sequence
<220> FEATURE:
<223> OTHER INFORMATION: Synthetic peptide
<220> FEATURE:
<221> NAME/KEY: PEPTIDE
<222> LOCATION: (1)..(31)
<223> OTHER INFORMATION: IL-6 42-72, cyclized
<220> FEATURE:
<221> NAME/KEY: SITE
<222> LOCATION: (32)..(32)
<223> OTHER INFORMATION: epsilon-K as a spacer
<220> FEATURE:
<221> NAME/KEY: PEPTIDE
<222> LOCATION: (33)..(50)
<223> OTHER INFORMATION: EBV CP Th

<400> SEQUENCE: 209

Glu Thr Cys Asn Lys Ser Asn Met Cys Glu Ser Ser Lys Glu Ala Leu
1               5                   10                  15

Ala Glu Asn Asn Leu Asn Leu Pro Lys Met Ala Glu Lys Asp Gly Lys
            20                  25                  30

Val Pro Gly Leu Tyr Ser Pro Cys Arg Ala Phe Phe Asn Lys Glu Glu
        35                  40                  45

Leu Leu
    50

<210> SEQ ID NO 210
<211> LENGTH: 46
<212> TYPE: PRT
<213> ORGANISM: Artificial Sequence
<220> FEATURE:
<223> OTHER INFORMATION: Synthetic peptide
<220> FEATURE:
<221> NAME/KEY: PEPTIDE
<222> LOCATION: (1)..(31)
<223> OTHER INFORMATION: IL-6 42-72, cyclized
<220> FEATURE:
<221> NAME/KEY: SITE
<222> LOCATION: (32)..(32)
<223> OTHER INFORMATION: epsilon-K as a spacer
<220> FEATURE:
<221> NAME/KEY: PEPTIDE
<222> LOCATION: (33)..(46)
<223> OTHER INFORMATION: HCMV IE1 Th

<400> SEQUENCE: 210

Glu Thr Cys Asn Lys Ser Asn Met Cys Glu Ser Ser Lys Glu Ala Leu
1               5                   10                  15

Ala Glu Asn Asn Leu Asn Leu Pro Lys Met Ala Glu Lys Asp Gly Lys
            20                  25                  30

Asp Lys Arg Glu Met Trp Met Ala Cys Ile Lys Glu Leu His
        35                  40                  45

<210> SEQ ID NO 211
<211> LENGTH: 47
<212> TYPE: PRT
<213> ORGANISM: Artificial Sequence
<220> FEATURE:
<223> OTHER INFORMATION: Synthetic peptide
<220> FEATURE:
<221> NAME/KEY: PEPTIDE
<222> LOCATION: (1)..(31)
<223> OTHER INFORMATION: IL-6 42-72, cyclized
<220> FEATURE:
<221> NAME/KEY: SITE
<222> LOCATION: (32)..(32)
<223> OTHER INFORMATION: epsilon-K as a spacer
<220> FEATURE:
```

```
<221> NAME/KEY: PEPTIDE
<222> LOCATION: (33)..(47)
<223> OTHER INFORMATION: EBV GP340 Th

<400> SEQUENCE: 211

Glu Thr Cys Asn Lys Ser Asn Met Cys Glu Ser Ser Lys Glu Ala Leu
1               5                   10                  15

Ala Glu Asn Asn Leu Asn Leu Pro Lys Met Ala Glu Lys Asp Gly Lys
            20                  25                  30

Thr Gly His Gly Ala Arg Thr Ser Thr Glu Pro Thr Thr Asp Tyr
        35                  40                  45

<210> SEQ ID NO 212
<211> LENGTH: 45
<212> TYPE: PRT
<213> ORGANISM: Artificial Sequence
<220> FEATURE:
<223> OTHER INFORMATION: Synthetic peptide
<220> FEATURE:
<221> NAME/KEY: PEPTIDE
<222> LOCATION: (1)..(31)
<223> OTHER INFORMATION: IL-6 42-72, cyclized
<220> FEATURE:
<221> NAME/KEY: SITE
<222> LOCATION: (32)..(32)
<223> OTHER INFORMATION: epsilon-K as a spacer
<220> FEATURE:
<221> NAME/KEY: PEPTIDE
<222> LOCATION: (33)..(45)
<223> OTHER INFORMATION: EBV BPLF1 Th

<400> SEQUENCE: 212

Glu Thr Cys Asn Lys Ser Asn Met Cys Glu Ser Ser Lys Glu Ala Leu
1               5                   10                  15

Ala Glu Asn Asn Leu Asn Leu Pro Lys Met Ala Glu Lys Asp Gly Lys
            20                  25                  30

Lys Glu Leu Lys Arg Gln Tyr Glu Lys Leu Arg Gln
        35                  40                  45

<210> SEQ ID NO 213
<211> LENGTH: 43
<212> TYPE: PRT
<213> ORGANISM: Artificial Sequence
<220> FEATURE:
<223> OTHER INFORMATION: Synthetic peptide
<220> FEATURE:
<221> NAME/KEY: PEPTIDE
<222> LOCATION: (1)..(31)
<223> OTHER INFORMATION: IL-6 42-72, cyclized
<220> FEATURE:
<221> NAME/KEY: SITE
<222> LOCATION: (32)..(32)
<223> OTHER INFORMATION: epsilon-K as a spacer
<220> FEATURE:
<221> NAME/KEY: PEPTIDE
<222> LOCATION: (33)..(43)
<223> OTHER INFORMATION: EBV EBNA-2 Th

<400> SEQUENCE: 213

Glu Thr Cys Asn Lys Ser Asn Met Cys Glu Ser Ser Lys Glu Ala Leu
1               5                   10                  15

Ala Glu Asn Asn Leu Asn Leu Pro Lys Met Ala Glu Lys Asp Gly Lys
            20                  25                  30

Thr Val Phe Tyr Asn Ile Pro Pro Met Pro Leu
        35                  40

<210> SEQ ID NO 214
```

```
<211> LENGTH: 47
<212> TYPE: PRT
<213> ORGANISM: Artificial Sequence
<220> FEATURE:
<223> OTHER INFORMATION: Synthetic peptide
<220> FEATURE:
<221> NAME/KEY: PEPTIDE
<222> LOCATION: (1)..(31)
<223> OTHER INFORMATION: IL-6 42-72, cyclized
<220> FEATURE:
<221> NAME/KEY: SITE
<222> LOCATION: (32)..(32)
<223> OTHER INFORMATION: epsilon-K as a spacer
<220> FEATURE:
<221> NAME/KEY: PEPTIDE
<222> LOCATION: (33)..(47)
<223> OTHER INFORMATION: HBsAg4 Th (UBITh4)

<400> SEQUENCE: 214

Glu Thr Cys Asn Lys Ser Asn Met Cys Glu Ser Ser Lys Glu Ala Leu
1               5                   10                  15

Ala Glu Asn Asn Leu Asn Leu Pro Lys Met Ala Glu Lys Asp Gly Lys
            20                  25                  30

Phe Phe Leu Leu Thr Arg Ile Leu Thr Ile Pro Gln Ser Leu Asp
        35                  40                  45

<210> SEQ ID NO 215
<211> LENGTH: 48
<212> TYPE: PRT
<213> ORGANISM: Artificial Sequence
<220> FEATURE:
<223> OTHER INFORMATION: Synthetic peptide
<220> FEATURE:
<221> NAME/KEY: PEPTIDE
<222> LOCATION: (1)..(31)
<223> OTHER INFORMATION: IL-6 42-72, cyclized
<220> FEATURE:
<221> NAME/KEY: SITE
<222> LOCATION: (32)..(32)
<223> OTHER INFORMATION: epsilon-K as a spacer
<220> FEATURE:
<221> NAME/KEY: PEPTIDE
<222> LOCATION: (33)..(48)
<223> OTHER INFORMATION: Yersinia Invasin (Inv) Th

<400> SEQUENCE: 215

Glu Thr Cys Asn Lys Ser Asn Met Cys Glu Ser Ser Lys Glu Ala Leu
1               5                   10                  15

Ala Glu Asn Asn Leu Asn Leu Pro Lys Met Ala Glu Lys Asp Gly Lys
            20                  25                  30

Thr Ala Lys Ser Lys Lys Phe Pro Ser Tyr Thr Ala Thr Tyr Gln Phe
        35                  40                  45

<210> SEQ ID NO 216
<211> LENGTH: 22
<212> TYPE: PRT
<213> ORGANISM: Artificial Sequence
<220> FEATURE:
<223> OTHER INFORMATION: KKKMvF3 Th (individual)

<400> SEQUENCE: 216

Lys Lys Lys Ile Ser Ile Ser Glu Ile Lys Gly Val Ile Val His Lys
1               5                   10                  15

Ile Glu Gly Ile Leu Phe
            20

<210> SEQ ID NO 217
<211> LENGTH: 22
```

```
<212> TYPE: PRT
<213> ORGANISM: Artificial Sequence
<220> FEATURE:
<223> OTHER INFORMATION: KKKMvF3 Th (individual)

<400> SEQUENCE: 217

Lys Lys Lys Ile Ser Ile Thr Glu Ile Arg Thr Val Ile Val Thr Arg
1               5                   10                  15

Ile Glu Thr Ile Leu Phe
            20

<210> SEQ ID NO 218
<211> LENGTH: 18
<212> TYPE: PRT
<213> ORGANISM: Artificial Sequence
<220> FEATURE:
<223> OTHER INFORMATION: HBsAg1 Th (individual)

<400> SEQUENCE: 218

Lys Lys Lys Leu Phe Leu Leu Thr Lys Leu Leu Thr Leu Pro Gln Ser
1               5                   10                  15

Leu Asp

<210> SEQ ID NO 219
<211> LENGTH: 18
<212> TYPE: PRT
<213> ORGANISM: Artificial Sequence
<220> FEATURE:
<223> OTHER INFORMATION: HBsAg1 Th (individual)

<400> SEQUENCE: 219

Arg Arg Arg Ile Lys Ile Ile Thr Arg Ile Ile Thr Ile Pro Leu Ser
1               5                   10                  15

Ile Arg

<210> SEQ ID NO 220
<211> LENGTH: 18
<212> TYPE: PRT
<213> ORGANISM: Artificial Sequence
<220> FEATURE:
<223> OTHER INFORMATION: HBsAg1 Th (individual)

<400> SEQUENCE: 220

Lys Lys Lys Val Arg Val Val Thr Lys Val Val Thr Val Pro Ile Ser
1               5                   10                  15

Val Asp

<210> SEQ ID NO 221
<211> LENGTH: 18
<212> TYPE: PRT
<213> ORGANISM: Artificial Sequence
<220> FEATURE:
<223> OTHER INFORMATION: HBsAg1 Th (individual)

<400> SEQUENCE: 221

Lys Lys Lys Phe Phe Phe Phe Thr Lys Phe Phe Thr Phe Pro Val Ser
1               5                   10                  15

Phe Asp

<210> SEQ ID NO 222
<211> LENGTH: 18
<212> TYPE: PRT
<213> ORGANISM: Artificial Sequence
<220> FEATURE:
```

<223> OTHER INFORMATION: HBsAg1 Th (individual)

<400> SEQUENCE: 222

Lys Lys Lys Leu Phe Leu Leu Thr Lys Leu Leu Thr Leu Pro Phe Ser
1               5                   10                  15

Leu Asp

<210> SEQ ID NO 223
<211> LENGTH: 19
<212> TYPE: PRT
<213> ORGANISM: Artificial Sequence
<220> FEATURE:
<223> OTHER INFORMATION: MvF4 Th (individual)

<400> SEQUENCE: 223

Ile Ser Ile Ser Glu Ile Lys Gly Val Ile Val His Lys Ile Glu Thr
1               5                   10                  15

Ile Leu Phe

<210> SEQ ID NO 224
<211> LENGTH: 19
<212> TYPE: PRT
<213> ORGANISM: Artificial Sequence
<220> FEATURE:
<223> OTHER INFORMATION: MvF4 Th (individual)

<400> SEQUENCE: 224

Ile Ser Ile Thr Glu Ile Arg Thr Val Ile Val Thr Arg Ile Glu Thr
1               5                   10                  15

Ile Leu Phe

<210> SEQ ID NO 225
<211> LENGTH: 18
<212> TYPE: PRT
<213> ORGANISM: Artificial Sequence
<220> FEATURE:
<223> OTHER INFORMATION: HBsAg2 Th (individual)

<400> SEQUENCE: 225

Lys Lys Lys Ile Ile Thr Ile Thr Arg Ile Ile Thr Ile Pro Gln Ser
1               5                   10                  15

Leu Asp

<210> SEQ ID NO 226
<211> LENGTH: 18
<212> TYPE: PRT
<213> ORGANISM: Artificial Sequence
<220> FEATURE:
<223> OTHER INFORMATION: HBsAg2 Th (individual)

<400> SEQUENCE: 226

Lys Lys Lys Phe Phe Leu Leu Thr Arg Ile Leu Thr Ile Ile Thr Thr
1               5                   10                  15

Ile Asp

<210> SEQ ID NO 227
<211> LENGTH: 212
<212> TYPE: PRT
<213> ORGANISM: Homo sapiens
<220> FEATURE:
<221> NAME/KEY: PEPTIDE
<222> LOCATION: (1)..(212)
<223> OTHER INFORMATION: IL-6 Protein -continued

```
<400> SEQUENCE: 227

Met Asn Ser Phe Ser Thr Ser Ala Phe Gly Pro Val Ala Phe Ser Leu
1               5                   10                  15

Gly Leu Leu Leu Val Leu Pro Ala Ala Phe Pro Ala Pro Val Pro Pro
            20                  25                  30

Gly Glu Asp Ser Lys Asp Val Ala Ala Pro His Arg Gln Pro Leu Thr
        35                  40                  45

Ser Ser Glu Arg Ile Asp Lys Gln Ile Arg Tyr Ile Leu Asp Gly Ile
    50                  55                  60

Ser Ala Leu Arg Lys Glu Thr Cys Asn Lys Ser Asn Met Cys Glu Ser
65                  70                  75                  80

Ser Lys Glu Ala Leu Ala Glu Asn Asn Leu Asn Leu Pro Lys Met Ala
                85                  90                  95

Glu Lys Asp Gly Cys Phe Gln Ser Gly Phe Asn Glu Glu Thr Cys Leu
            100                 105                 110

Val Lys Ile Ile Thr Gly Leu Leu Glu Phe Glu Val Tyr Leu Glu Tyr
        115                 120                 125

Leu Gln Asn Arg Phe Glu Ser Ser Glu Glu Gln Ala Arg Ala Val Gln
    130                 135                 140

Met Ser Thr Lys Val Leu Ile Gln Phe Leu Gln Lys Lys Ala Lys Asn
145                 150                 155                 160

Leu Asp Ala Ile Thr Thr Pro Asp Pro Thr Thr Asn Ala Ser Leu Leu
                165                 170                 175

Thr Lys Leu Gln Ala Gln Asn Gln Trp Leu Gln Asp Met Thr Thr His
            180                 185                 190

Leu Ile Leu Arg Ser Phe Lys Glu Phe Leu Gln Ser Ser Leu Arg Ala
        195                 200                 205

Leu Arg Gln Met
    210

<210> SEQ ID NO 228
<211> LENGTH: 212
<212> TYPE: PRT
<213> ORGANISM: Macaca fascicularis
<220> FEATURE:
<221> NAME/KEY: PEPTIDE
<222> LOCATION: (1)..(212)
<223> OTHER INFORMATION: IL-6 Protein

<400> SEQUENCE: 228

Met Asn Ser Phe Ser Thr Ser Ala Phe Gly Pro Val Ala Phe Ser Leu
1               5                   10                  15

Gly Leu Leu Leu Val Leu Pro Ala Ala Phe Pro Ala Pro Val Leu Pro
            20                  25                  30

Gly Glu Asp Ser Lys Asn Val Ala Ala Pro His Ser Gln Pro Leu Thr
        35                  40                  45

Ser Ser Glu Arg Ile Asp Lys His Ile Arg Tyr Ile Leu Asp Gly Ile
    50                  55                  60

Ser Ala Leu Arg Lys Glu Thr Cys Asn Arg Ser Asn Met Cys Glu Ser
65                  70                  75                  80

Ser Lys Glu Ala Leu Ala Glu Asn Asn Leu Asn Leu Pro Lys Met Ala
                85                  90                  95

Glu Lys Asp Gly Cys Phe Gln Ser Gly Phe Asn Glu Asp Thr Cys Leu
            100                 105                 110

Val Lys Ile Ile Thr Gly Leu Leu Glu Phe Glu Val Tyr Leu Glu Tyr
        115                 120                 125
```

-continued

Leu Gln Asn Arg Phe Glu Ser Glu Glu Gln Ala Arg Ala Val Gln
    130                 135                 140

Met Ser Thr Lys Val Leu Ile Gln Phe Leu Gln Lys Ala Lys Asn
145                 150                 155                 160

Leu Asp Ala Ile Thr Thr Pro Glu Pro Thr Thr Asn Ala Ser Leu Leu
                165                 170                 175

Thr Lys Leu Gln Ala Gln Asn Gln Trp Leu Gln Asp Met Thr Thr His
                180                 185                 190

Leu Ile Leu Arg Ser Phe Lys Glu Phe Leu Gln Ser Asn Leu Arg Ala
                195                 200                 205

Leu Arg Gln Met
    210

<210> SEQ ID NO 229
<211> LENGTH: 211
<212> TYPE: PRT
<213> ORGANISM: Mus musculus
<220> FEATURE:
<221> NAME/KEY: PEPTIDE
<222> LOCATION: (1)..(211)
<223> OTHER INFORMATION: IL-6 Protein

<400> SEQUENCE: 229

Met Lys Phe Leu Ser Ala Arg Asp Phe His Pro Val Ala Phe Leu Gly
1               5                   10                  15

Leu Met Leu Val Thr Thr Thr Ala Phe Pro Thr Ser Gln Val Arg Arg
                20                  25                  30

Gly Asp Phe Thr Glu Asp Thr Thr Pro Asn Arg Pro Val Tyr Thr Thr
                35                  40                  45

Ser Gln Val Gly Gly Leu Ile Thr His Val Leu Trp Glu Ile Val Glu
    50                  55                  60

Met Arg Lys Glu Leu Cys Asn Gly Asn Ser Asp Cys Met Asn Asn Asp
65                  70                  75                  80

Asp Ala Leu Ala Glu Asn Asn Leu Lys Leu Pro Glu Ile Gln Arg Asn
                85                  90                  95

Asp Gly Cys Tyr Gln Thr Gly Tyr Asn Gln Glu Ile Cys Leu Leu Lys
                100                 105                 110

Ile Ser Ser Gly Leu Leu Glu Tyr His Ser Tyr Leu Glu Tyr Met Lys
                115                 120                 125

Asn Asn Leu Lys Asp Asn Lys Lys Asp Lys Ala Arg Val Leu Gln Arg
    130                 135                 140

Asp Thr Glu Thr Leu Ile His Ile Phe Asn Gln Glu Val Lys Asp Leu
145                 150                 155                 160

His Lys Ile Val Leu Pro Thr Pro Ile Ser Asn Ala Leu Leu Thr Asp
                165                 170                 175

Lys Leu Glu Ser Gln Lys Glu Trp Leu Arg Thr Lys Thr Ile Gln Phe
                180                 185                 190

Ile Leu Lys Ser Leu Glu Glu Phe Leu Lys Val Thr Leu Arg Ser Thr
                195                 200                 205

Arg Gln Thr
    210

<210> SEQ ID NO 230
<211> LENGTH: 211
<212> TYPE: PRT
<213> ORGANISM: Rattus norvegicus
<220> FEATURE:

```
<221> NAME/KEY: PEPTIDE
<222> LOCATION: (1)..(211)
<223> OTHER INFORMATION: IL-6 Protein

<400> SEQUENCE: 230

Met Lys Phe Leu Ser Ala Arg Asp Phe Gln Pro Val Ala Phe Leu Gly
1               5                   10                  15

Leu Met Leu Leu Thr Ala Thr Ala Phe Pro Thr Ser Gln Val Arg Arg
            20                  25                  30

Gly Asp Phe Thr Glu Asp Thr Thr His Asn Arg Pro Val Tyr Thr Thr
            35                  40                  45

Ser Gln Val Gly Gly Leu Ile Thr Tyr Val Leu Arg Glu Ile Leu Glu
    50                  55                  60

Met Arg Lys Glu Leu Cys Asn Gly Asn Ser Asp Cys Met Asn Ser Asp
65                  70                  75                  80

Asp Ala Leu Ser Glu Asn Asn Leu Lys Leu Pro Glu Ile Gln Arg Asn
                85                  90                  95

Asp Gly Cys Phe Gln Thr Gly Tyr Asn Gln Glu Ile Cys Leu Leu Lys
            100                 105                 110

Ile Cys Ser Gly Leu Leu Glu Phe Arg Phe Tyr Leu Glu Phe Val Lys
        115                 120                 125

Asn Asn Leu Gln Asp Asn Lys Lys Asp Lys Ala Arg Val Ile Gln Ser
130                 135                 140

Asn Thr Glu Thr Leu Val His Ile Phe Lys Gln Glu Ile Lys Asp Ser
145                 150                 155                 160

Tyr Lys Ile Val Leu Pro Thr Pro Thr Ser Asn Ala Leu Leu Met Glu
                165                 170                 175

Lys Leu Glu Ser Gln Lys Glu Trp Leu Arg Thr Lys Thr Ile Gln Leu
            180                 185                 190

Ile Leu Lys Ala Leu Glu Glu Phe Leu Lys Val Thr Met Arg Ser Thr
        195                 200                 205

Arg Gln Thr
    210

<210> SEQ ID NO 231
<211> LENGTH: 4
<212> TYPE: PRT
<213> ORGANISM: Artificial Sequence
<220> FEATURE:
<223> OTHER INFORMATION: KKK-epsilon-K spacer
<220> FEATURE:
<221> NAME/KEY: PEPTIDE
<222> LOCATION: (1)..(4)
<223> OTHER INFORMATION: KKK-epsilon-K as spacer
<220> FEATURE:
<221> NAME/KEY: SITE
<222> LOCATION: (4)..(4)
<223> OTHER INFORMATION: epsilon-K

<400> SEQUENCE: 231

Lys Lys Lys Lys
1

<210> SEQ ID NO 232
<211> LENGTH: 32
<212> TYPE: DNA
<213> ORGANISM: Artificial Sequence
<220> FEATURE:
<223> OTHER INFORMATION: CpG1 oligonucleotide ODN
```

<400> SEQUENCE: 232
tcgtcgtttt gtcgttttgt cgttttgtcg tt                32

<210> SEQ ID NO 233
<211> LENGTH: 24
<212> TYPE: DNA
<213> ORGANISM: Artificial Sequence
<220> FEATURE:
<223> OTHER INFORMATION: CpG2 oligonucleotide ODN
<220> FEATURE:
<221> NAME/KEY: misc_feature
<222> LOCATION: (1)..(1)
<223> OTHER INFORMATION: phosphorothioate group

<400> SEQUENCE: 233
tcgtcgtttt gtcgttttgt cgtt                24

<210> SEQ ID NO 234
<211> LENGTH: 24
<212> TYPE: DNA
<213> ORGANISM: Artificial Sequence
<220> FEATURE:
<223> OTHER INFORMATION: CpG3 Oligonucleotide ODN

<400> SEQUENCE: 234
tcgtcgtttt gtcgttttgt cgtt                24

<210> SEQ ID NO 235
<211> LENGTH: 60
<212> TYPE: PRT
<213> ORGANISM: Homo sapiens
<220> FEATURE:
<221> NAME/KEY: PEPTIDE
<222> LOCATION: (1)..(60)
<223> OTHER INFORMATION: IL-6 (32-91)

<400> SEQUENCE: 235

Ile Leu Asp Gly Ile Ser Ala Leu Arg Lys Glu Thr Cys Asn Lys Ser
1               5                   10                  15

Asn Met Cys Glu Ser Ser Lys Glu Ala Leu Ala Glu Asn Asn Leu Asn
            20                  25                  30

Leu Pro Lys Met Ala Glu Lys Asp Gly Cys Phe Gln Ser Gly Phe Asn
        35                  40                  45

Glu Glu Thr Cys Leu Val Lys Ile Ile Thr Gly Leu
    50                  55                  60

<210> SEQ ID NO 236
<211> LENGTH: 31
<212> TYPE: PRT
<213> ORGANISM: Mus musculus
<220> FEATURE:
<221> NAME/KEY: PEPTIDE
<222> LOCATION: (1)..(31)
<223> OTHER INFORMATION: IL-6 (154-184)

<400> SEQUENCE: 236

Gln Lys Glu Trp Leu Arg Thr Lys Thr Ile Gln Phe Ile Leu Lys Ser
1               5                   10                  15

Leu Glu Glu Phe Leu Lys Val Thr Leu Arg Ser Thr Arg Gln Thr
            20                  25                  30